United States Patent
Langan et al.

(10) Patent No.: US 12,304,927 B2
(45) Date of Patent: May 20, 2025

(54) DE NOVO DESIGN OF PROTEIN SWITCHES

(71) Applicant: UNIVERSITY OF WASHINGTON, Seattle, WA (US)

(72) Inventors: Robert A. Langan, Seattle, WA (US); Scott Boyken, Seattle, WA (US); David Baker, Seattle, WA (US); Walter Novak, Seattle, WA (US); Marc Joseph Lajoie, Seattle, WA (US); Alfredo Quijano Rubio, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 0 days.

(21) Appl. No.: 17/077,692

(22) Filed: Oct. 22, 2020

(65) Prior Publication Data

US 2021/0115090 A1   Apr. 22, 2021

Related U.S. Application Data

(63) Continuation of application No. 16/796,009, filed on Feb. 20, 2020, now Pat. No. 10,851,135, which is a continuation of application No. PCT/US2019/042651, filed on Jul. 19, 2019.

(60) Provisional application No. 62/788,398, filed on Jan. 4, 2019, provisional application No. 62/785,537, filed on Dec. 27, 2018, provisional application No. 62/700,681, filed on Jul. 19, 2018.

(51) Int. Cl.
*C07K 14/00* (2006.01)
*A61K 47/69* (2017.01)

(52) U.S. Cl.
CPC ........ *C07K 14/001* (2013.01); *A61K 47/6949* (2017.08); *C07K 2319/40* (2013.01); *C07K 2319/60* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 6,217,864 B1 | 4/2001 | Coffino et al. | |
| 7,223,556 B1 | 5/2007 | Zhou et al. | |
| 9,765,019 B2 | 9/2017 | Hedstrom et al. | |
| 10,851,135 B2 * | 12/2020 | Langan | A61K 47/6949 |
| 2003/0153727 A1 | 8/2003 | Kenten et al. | |
| 2004/0018625 A1 | 9/2004 | Struhl et al. | |

FOREIGN PATENT DOCUMENTS

WO   WO 2015/138711   9/2015

OTHER PUBLICATIONS

Krumm, Brian E. and Grisshammer, Reinhard; "Peptide ligand recognition by g protein coupled receptors." Front. Pharmacol. (2015) 6 (48).*
Van der Kant, Rob and Vreind, Gert: "alpha bulges in g protein coupled receptors." Int. J. Mol. Sci. (2014) 15 p. 7841-7864.*
Howes, Laura; "Deepmine ai predicts protein structures." C&ENews, Dec. 1, 2020.*
Jordan, Allan M.; "ARtificial intelligence in drug design—the storm before the calm?" Med. Chem. Lett (2018) 9 p. 1150-1152.*
Peltomaa, Riikka et al; "Phage display in the quest for new selective recognition elements for biosensors." ACS Omega (2019) 4 p. 11569-11580.*
Yampolsky, Lev Y. and Stoltzfus, Arlin; "THe exchangeability of amino acids in proteins." Genetics (2005) 170 p. 1459-1472.*
NCBI Reference Sequence NP_002522, downloaded Mar. 1, 2022.*
The introduction to the Oct. 2010 issue of the journal Pharmaceuticals (2010) 3(11).*
Wess, Jurgen et al; "Conformational changes invovled in g protein coupled receptor activation." Trends PHarmacol. Sci. (2008) 29(12) p. 616-625.*
Rocha-Resende, Cibele et al; "Moving pieces in a crytomic puzzle: cryptide from tityus serrulatus ts2 nav toxin as a potent agonist of muscarinic receptors." Peptides (2017) 98 p. 70-77.*
Szczepek, Michal et al; "Crystal structure of a common gpcr binding interface for g protein and arrestin." Nat. Comm. (2014) 5 (480).*
Lowe, Derek; "Not alphafold's fault." Blog, In the Pipeline, entry of Sep. 7, 2022.*
Ambroggio et al., "Design of protein conformational switches," Curr. Opin. Struct. Biol. 16, 525-530 (2006).
Aranda-Diaz et al., "Robust synthetic circuits for two-dimensional control of gene expression in yeast," ACS Synth. Biol. 6, 545-554 (2017).
Berger et al., "Computationally designed high specificity inhibitors delineate the roles of BCL2 family proteins in cancer," eLife 5, e20352 1422 (2016).
Boyken et al., "De novo design of protein homo-oligomers with modularhydrogen-bond network-mediated specificity," Science 352, 680-687 (2016).
Brunette et al., "Exploring the repeat protein universe through computational protein design," Nature 528, 580-584 (2015).
Choi et al., "Design of protein switches based on an ensemble model of allostery," Nat. Commun. 6, 6968 (2015).
Chothia et al., "Principles of protein-protein recognition," Nature 256, 705-708 (1975).
Clift et al., "A Method for the Acute and Rapid Degradation of Endogenous Proteins," Cell vol. 171 Issue: 7 p. 1692-1706 (2017).
Crick, "The packing of [alpha]-helices: simple coiled-coils," Acta Cryst (1953). Q6,30 689-697 (1953).
Crick, "The Fourier transform of a coiled-coil," Acta Crystallogr. 6, 685-689 (1953).
Davey et al., "Rational design of proteins that exchange on functional timescales," Nat. Chem. Biol. 13, 1280-1285 (2017).

(Continued)

*Primary Examiner* — Fred H Reynolds
(74) *Attorney, Agent, or Firm* — McDonnell Boehnen Hulbert & Berghoff

(57) ABSTRACT

Disclosed are protein switches that can sequester bioactive peptides and/or binding domains, holding them in an inactive ("off") state, until combined with a

(56) References Cited

OTHER PUBLICATIONS

Delgado-Soler et al., "Molecular determinants of Bim(BH3) peptide binding to pro-survival proteins," J. Chem. Inf. Model. 52, 2107-2118 (2012).
Dou et al., "De novo design of a fluorescence-activating β-barrel," Nature 561,485-491 (2018).
Dueber et al., "A Engineering synthetic signaling proteins with ultrasensitive input/output control," 25, 660-662 (2007).
Dueber et al., "Rewiring cell signaling: the logic and plasticity of eukaryotic protein circuitry," Curr. Opin. Struct. Biol. 14, 690-699 (2004).
Dyer et al., "High-throughput SAXS for the characterization of biomolecules in solution: a practical approach," Methods Mol. Biol. 1091, 245-258 (2014).
Fleming et al., "Do all backbone polar groups in proteins form hydrogen bonds?," Protein Sci. 14, 1911-1917 (2005).
Gardner et al., "Construction of a genetic toggle switch in *Escherichia coli*," Nature 403, 339-342 (2000).
Giesecke et al., "Synthetic protein-protein interactiondomains created by shuffling Cys2His2 zinc-fingers," Mol. Syst. Biol. 2,2006.0011 (2006).
Glantz et al., "Functional and topological diversity of LOV domain photoreceptors," Proc Natl Acad Sci USA 113, EI442-51 (2016).
Grigoryan et al., "Probing designability via a generalized model of helical bundle geometry," J. Mol. Biol. 405, 1079-1100 (2011).
Güttler et al., "NES consensus redefined by structures of PKI-type and Rev-type nuclear export signals bound to CRM1." Nat. Struct. Mol. Biol. 17(11):1367-76 (2010).
Ha et al., "Protein conformational switches: from nature to design," Chemistry 18, 7984-7999 (2012).
Harrigan et al., "Real time genetic compensation operationally defines the dynamic demands of feedback control," bioRxiv 244020 (2018).
Huang et al., "High thermodynamic stability of parametrically designed helical bundles," Science 346, 481-485 (2014).
Huang et al., "RosettaRemodel: A Generalized Framework for Flexible Backbone Protein Design," PLoS One 6, e24109 (2011).
Ikeda et al., "Molecular interaction and synergistic activation of a promoter by Six, Eya, and Dach proteins mediated through CREB binding protein," Mol. Cell. Biol. 22, 6759-6766 (2002).
Isaacs et al., "RNA synthetic biology," Nat. Biotechnol. 24 545-554 (2006).
Joh et al., "De novo design of a transmembrane Zn2+-transporting four-helix bundle," Science 346, 1520-1524 (2014).
Khalil et al., "A synthetic biology framework for programming eukaryotic transcription functions," Cell 150, 647-658 (2012).
Kosugi et al., "Six classes of nuclear localization signals specific to different binding grooves of importin α" J. Biol. Chem. 284, 478-485 (2009).
Kuhlman et al., "Native protein sequences are close to optimal for their structures," Proc. Natl Acad. Sci. USA 97, 10383-10388 (2000).
Leaver-Fay et al., "ROSETTA3: an object-oriented software suite for the simulation and design of macromolecules," Meth Enzymol 487, 545-574 (2011).
Lee et al., "A highly characterized yeast toolkit for modular, multipart assembly," ACS Synth. Biol. 4, 975-986 (2015).
Linko et al., "The enabled state of DNA nanotechnology," Curr. Opin. Biotechnol. 24, 555-561 (2013).
Liu, "Allostery: an overview of its history, concepts, methods, and application," PLoS Comput. Biol. 12, e1004966 (2016).
Maguire et al., "Rapid Sampling of Hydrogen Bond Networks for Computational Protein Design," J Chem. Theory Comput 14, 2751-2760 (2018).
Matsuzawa et al., "Method for targeting protein destruction by using a ubiquitin-independent, proteasome-mediated degradation pathway," PNAS 102(42):14982-87 (2005).
Moreira et al., "Hot spots—a review of the protein-protein interface determinant amino-acid residues," Proteins 68, 803-812 (2007).
Natsume et al., "Rapid Protein Depletion in Human Cells by Auxin-Inducible Degron Tagging with Short Homology Donors," Cell Reports vol. 15 Issue: 1 p. 210-218 (2016).
Ng et al., "Modular and tunable biological feedback control using a de novo protein switch," Nature 572:265-271 (2019)—with supplemental materials.
Nielsen et al., "Genetic circuit design automation," Science 352, aac7341 (2016).
Perez-Pinera et al., "RNA-guided gene activation by CRISPR-Cas9-based transcripion factors," Nat. Methods 10, 973-976 (2013).
Perkins et al., "Transient protein-protein interactions: structural, functional, and network properties," Structure 18, 1233-1243 (2010).
Prehoda et al., "Integration of multiple signals through cooperative regulation of the N-WASP-Arp2/3 complex," Science 290, 801-806 (2000).
Raman et al., "Engineering allostery," Trends Genet. 30, 521-528 (2014).
Rehtanz et al., "Direct interaction between nucleosome assembly protein 1 and the papillomavirus E2 proteins involved in activation of transcription," Mol. Cell. Biol. 24, 2153-2168 (2004).
Renicke et al., "A LOV2 Domain-Based Optogenetic Tool to Control Protein Degradation and Cellular Function," Chemistry & Biology vol. 20 Issue 4, p. 458-460.
Rocklin et al., "Global analysis of protein folding using massively parallel design, synthesis, and testing," Science 357, 168-175 (2017).
Schneidman-Duhovny et al., "FoXS: a web server for rapid computation and fitting of SAXS profiles," Nucleic Acids Res 38, W540-4 (2010).
Singh et al., "Role of intrinsic disorder in transient interactions of hub proteins," Proteins 66, 761-765 (2007).
Stein et al., "Synthetic protein switches: design principles and applications," Trends Biotechnol. 33, 101-110 (2015).
Takeuchi et al., "Structural elements of the ubiquitin-independent proteasome degron of ornithine decarboxylase" Biochem J. 410, 401-407 (2008).
Westphal et al., "Molecular biology of Bax and Bak activation and action. Biochim," Biophys. Acta 1813, 521-531 (2011).
Wilmington et al., "An Inducible System for Rapid Degradation of Specific Cellular Proteins Using Proteasome Adaptors," PLOS Onevol. 11 Issue: 4 (2016).
Wittman et al., "Engineered riboswitches: expanding researchers' toolbox with synthetic RNA regulators," FEBS Lett. 586, 2076-2083 (2012).
Zhang et al., "Control of DNA strand displacement kinetics using toehold exchange," J. Am. Chem. Soc. 131, 17303-17314 (2009).
Dueber et al., "Reprogramming control of an allosteric signaling switch through modular recombination," Science, 301(5641):1904-08 (2003).
Huang et al., "The coming of age of de novo protein design," Nature 537, 320-327 (2016).
Langan et al., "De novo design of bioactive protein switches," Nature 572(7768):205-10 (2019).
UniProt: UPI0006AB52F2—RefSeq Identifier XP_013725879 first seen Sep. 1, 2015, one page.
The International Search Report (ISR) with Written Opinion for PCT/US2019/042651 dated Jan. 17, 2020, pp. 1-24.

* cited by examiner

Cage only

Cage with naked Key

Spycatcher/Spytag linked

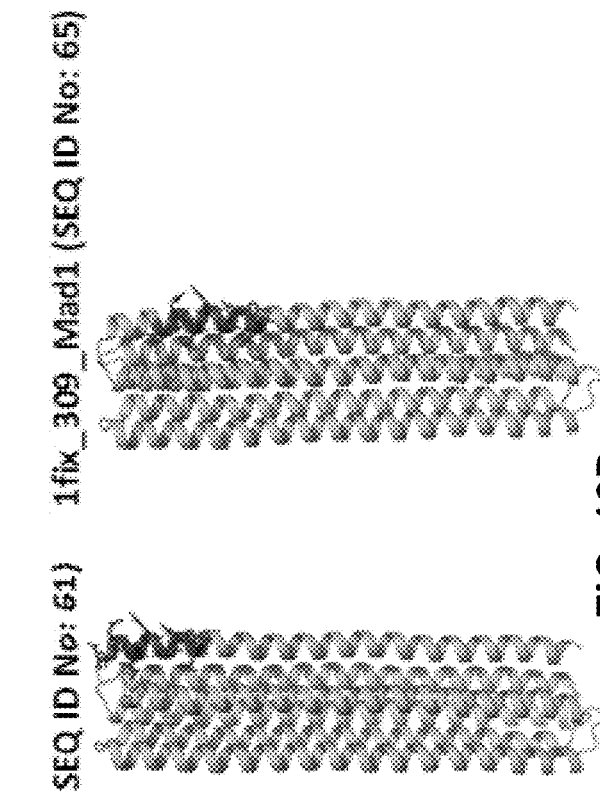
FIG. 12A
FIG. 12B
FIG. 12D
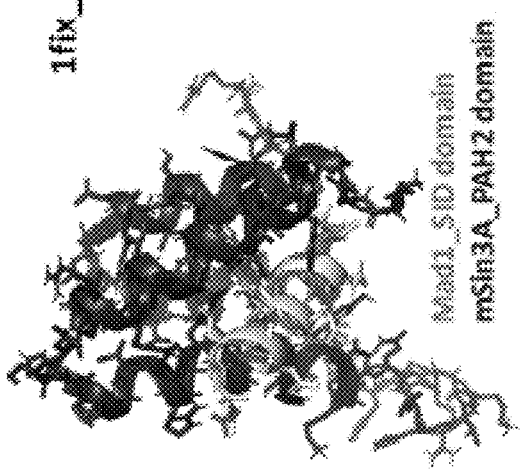
FIG. 12C

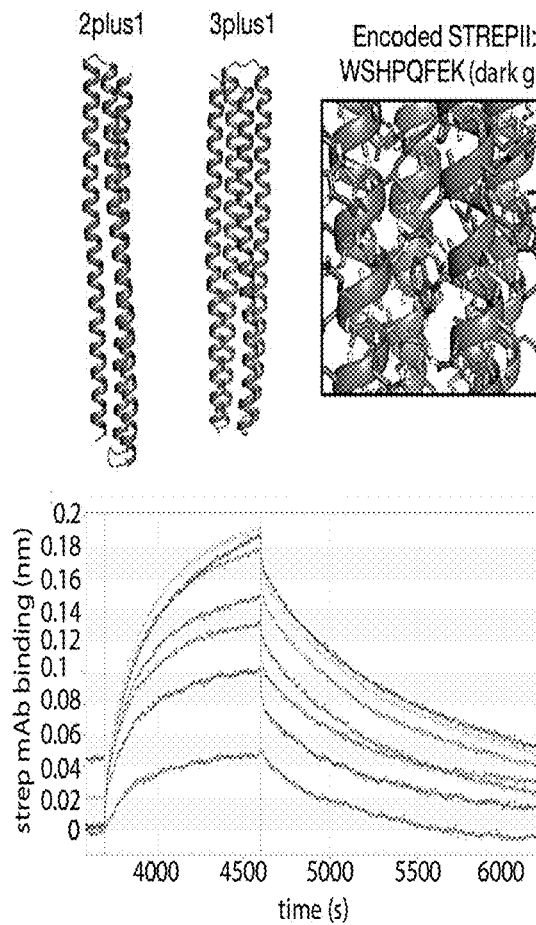
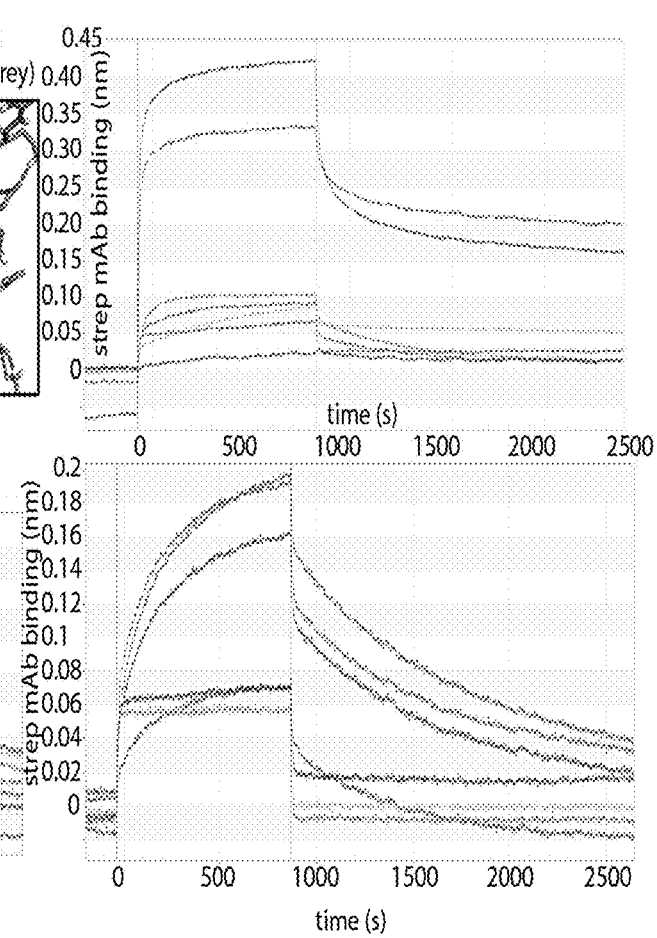
FIG. 13A  FIG. 13B
FIG. 13C  FIG. 13D

DE NOVO DESIGN OF PROTEIN SWITCHES

CROSS REFERENCE TO EARLIER FILED APPLICATIONS

This application is a Continuation of U.S. patent application Ser. No. 16/796,009, filed Feb. 20, 2020, which is a Continuation of International Application No. PCT/US2019/042651, filed Jul. 19, 2019, which claims priority to U.S. Provisional Application No. 62/700,681, filed Jul. 19, 2018; U.S. Provisional Application No. 62/785,537, filed Dec. 27, 2018; and U.S. Provisional Application No. 62/788,398, filed Jan. 4, 2019, the disclosures of which are hereby incorporated by reference in their entirety.

REFERENCE TO SEQUENCE LISTING SUBMITTED ELECTRONICALLY VIA EFS-WEB

The content of the electronically submitted sequence listing in ASCII text file (Name: 18-1054-PCT_Sequence-Listing_ST25.txt; Size: 32,278 kb; and Date of Creation: Jul. 19, 2019) filed with the application is herein incorporated by reference in its entirety.

BACKGROUND

There has been considerable progress in the de novo design of stable protein structures based on the principle that proteins fold into their lowest free energy state. These efforts have focused on maximizing the free energy gap between the desired folded structure and all other structures. Designing proteins that can switch conformations is more challenging, as multiple states must have sufficiently low free energies to be populated relative to the unfolded state, and the free energy differences between the states must be small enough that the state occupancies can be toggled by an external input. The de novo design of a protein system which switches conformational state in the presence of an external input has not been achieved.

SUMMARY

In a first aspect are disclosed non-naturally occurring polypeptides comprising:
(a) a helical bundle, comprising between 2 and 7 alpha-helices; and
(b) amino acid linkers connecting each alpha helix.

In one embodiment, each helix is independently 18-60, 18-55, 18-50, 18-45, 22-60, 22-55, 22-50, 22-45, 25-60, 25-55, 25-50, 25-45, 28-60, 28-55, 28-50, 28-45, 32-60, 32-55, 32-50, 32-45, 35-60, 35-55, 35-50, 35-45, 38-60, 38-55, 38-50, 38-45, 40-60, 40-58, 40-55, 40-50, or 40-45 amino acids in length. In another embodiment, each amino acid linker is independently between 3-10, 4-10, 5-10, 6-10, 7-10, 8-10, 9-10, 2-9, 3-9, 4-9, 5-9, 6-9, 7-9, 8-9, 2-8, 3-8, 4-8, 5-8, 6-8, 7-8, 2-7, 3-7, 4-7, 5-7, 6-7, 2-6, 3-6, 4-6, 5-6, 2-5, 3-5, 4-5, 2-4, 3-4, 2-3, or 2, 3, 4, 5, 6, 7, 8, 9, or 10 amino acids in length, not including any further functional sequences that may be fused to the linker. In a further embodiment, the polypeptide comprises one or more bioactive peptide in at least one of the alpha helices, wherein the one or more bioactive peptides are capable of selectively binding to a defined target, wherein the one or more bioactive peptides may comprise one or more bioactive peptide selected from the non-limiting group consisting of SEQ ID NO:60, 62-64, 66, 27052-27093, and 27118-27119.

In another aspect, the disclosure provides non-naturally occurring polypeptides comprising the polypeptide having at least 40% sequence identity along its length to the amino acid sequence of a cage polypeptide disclosed herein, or selected from the group consisting of SEQ ID NOS: 1-49, 51-52, 54-59, 61, 65, 67-14317, 27094-27117, 27120-27125, 27,278 to 27,321, and cage polypeptides listed in Table 2, Table 3, and/or Table 4, wherein the N-terminal and/or C-terminal 60 amino acids of the polypeptides are optional, wherein the sequence identity requirement does not include optional amino acid residues. In one aspect, the disclosure provides non-naturally occurring polypeptide comprising the polypeptide having at least 40% sequence identity along its length to the amino acid sequence of a cage polypeptide listed in Table 2, Table 3, and/or Table 4, not including optional amino acid residues. In one embodiment, of each of these aspects, the polypeptide comprises the amino acid sequence having an amino acid sequence having at least 45%, 50%, 55%, 60%, 65%, 70%, 75%, 80%, 85%, 90%, 91%, 92%, 93%, 94%, 95%, 96%, 97%, 98%, 99%, or 100% sequence identity, not including optional amino acid residues, along its length to the amino acid sequence elected from the group consisting of SEQ ID NOS:1-91, SEQ ID NOS: 1-49, 51-52, 54-59, 61, 65, 67-14317, 27094-27117, 27120-27125, 27,278 to 27,321, and cage polypeptide listed in Table 2, Table 3, and/or Table 4.

In one embodiment of any of the aspects of the disclosure, the non-naturally occurring polypeptide further comprises one or more bioactive peptides within or replacing the latch region of the polypeptide, wherein the one or more bioactive peptides may comprise one or more bioactive peptide selected from the non-limiting group consisting of SEQ ID NO:60, 62-64, 66, 27052-27093, and 27118-27119.

In another aspect are provided non-naturally occurring polypeptides comprising a polypeptide having at least 40%, 45%, 50%, 55%, 60%, 65%, 70%, 75%, 80%, 85%, 90%, 91%, 92%, 93%, 94%, 95%, 96%, 97%, 98%, 99%, or 100% sequence identity, not including optional amino acid residues, along its length to the amino acid sequence of a key polypeptide disclosed herein, or a key polypeptide selected from the group consisting of SEQ ID NOS:14318-26601, 26602-27015, and 27016-27051, and key polypeptides listed in Table. In one embodiment, the polypeptide comprises an amino acid sequence having an amino acid sequence having at least 45%, 50%, 55%, 60%, 65%, 70%, 75%, 80%, 85%, 90%, 91%, 92%, 93%, 94%, 95%, 96%, 97%, 98%, 99%, or 100% sequence identity, not including optional amino acid residues, along its length to the amino acid sequence of a key protein selected from the group consisting of key polypeptides listed in Table 2, Table 3, and/or Table 4.

In another embodiment, the disclosure provides fusion proteins comprising the cage polypeptide of any embodiment or combination of embodiments of the disclosure fused to the key polypeptide of any embodiment or combination of embodiments of the disclosure.

In other aspects, the disclosure provides nucleic acids encoding the cage polypeptide, key polypeptide, of fusion protein of any embodiment or combination of embodiments of the disclosure; expression vectors comprising the nucleic acids operatively linked to a promoter, and/or host cells comprising the nucleic acids and/or expression vectors. In one embodiment, the nucleic acid or the expression vector is integrated into a host cell chromosome. In another embodiment, the nucleic acid or the expression vector is episomal. In another embodiment, the host cell comprises (a) a first nucleic acid encoding the cage polypeptide of any embodiment or combination of embodiments of the disclosure operatively linked to a first promoter; and (b) a second nucleic acid encoding the key polypeptide o of any embodiment or combination of embodiments of the disclosure operatively linked to a second promoter, wherein the second nucleic acid encodes a key polypeptide capable of binding to a structural region of the cage polypeptide encoded by the first nucleic acid, and wherein binding of the key polypeptide to the structural region of the cage polypeptide induces a conformational change in the cage polypeptide.

In a further embodiment of the host cells of the disclosure, the first nucleic acid comprises a plurality of first nucleic acids encoding a plurality of different cage polypeptides. In one embodiment, the second nucleic acid comprises a plurality of second nucleic acids encoding a plurality of different key polypeptides, wherein the plurality of different key polypeptides comprise one or more key polypeptides that are capable of binding to and inducing a conformational change in only a subset of the plurality of different cage polypeptides. In another embodiment, the second nucleic acid encodes a single key polypeptide that is capable of binding to and inducing a conformational change in each different cage polypeptide.

In another embodiment, the host cell may comprise
(a) a first nucleic acid encoding a fusion protein according to any embodiment or combination of embodiments of the disclosure operatively linked to a first promoter; and
(b) a second nucleic acid encoding a fusion protein according to any embodiment or combination of embodiments of the disclosure operatively linked to a second promoter, wherein:
   (i) the cage polypeptide encoded by the first nucleic acid is activated by the key polypeptide encoded by the second nucleic acid;
   (ii) the cage polypeptide encoded by the first nucleic acid is not activated by the key polypeptide encoded by the first nucleic acid;
   (iii) the cage polypeptide encoded by the second nucleic acid is activated by the key polypeptide encoded by the first nucleic acid; and
   (iv) the cage polypeptide encoded by the second nucleic acid is not activated by the key polypeptide encoded by the second nucleic acid.

In another aspect, the disclosure provides kits comprising
(a) one or more cage polypeptides according to any embodiment or combination of embodiments of the disclosure;
(b) one or more key polypeptides according to any embodiment or combination of embodiments of the disclosure; and
(c) optionally, one or more fusion proteins according to any embodiment or combination of embodiments of the disclosure.

In one aspect, the disclosure provides kits, comprising:
(a) a first nucleic acid encoding one or more cage polypeptides according to any embodiment or combination of embodiments of the disclosure;
(b) a second nucleic acid encoding one or more key polypeptides according to any embodiment or combination of embodiments of the disclosure; and
(c) optionally, a third nucleic acid encoding one or more fusion proteins according to any embodiment or combination of embodiments of the disclosure.

In various embodiments, the first nucleic acid, the second nucleic acid, and/or the third nucleic acid comprise expression vectors.

In another aspect, the disclosure provides LOCKR switches comprising
(a) a cage polypeptide comprising a structural region and a latch region further comprising one or more bioactive peptides, wherein the structural region interacts with the latch region to prevent activity of the one or more bioactive peptides;
(b) an optional key polypeptide that binds to the cage structural region, thereby displacing the latch region and activating the one or more bioactive peptides; and
(c) optionally, one or more effector polypeptide(s) that bind to the one or more bioactive peptides when the one or more bioactive peptides are activated.

In one embodiment, the effector polypeptide is present, and wherein the effector polypeptide comprises an effector polypeptide that selectively binds to the bioactive peptide, including but not limited to Bcl2, GFP1-10, and a protease.

In various embodiments, the host cells, kits, or LOCKR according to any embodiment or combination of embodiments of the disclosure comprise one or more cage polypeptide and one or more key polypeptide having an amino acid sequence having at least 40%, 45%, 50%, 55%, 60%, 65%, 70%, 75%, 80%, 85%, 90%, 91%, 92%, 93%, 94%, 95%, 96%, 97%, 98%, 99%, or 100% sequence identity, not including optional residues, along its length to a cage polypeptide and a key polypeptide, respectively, in the same row of Table 1, Table 2, Table 3, and/or Table 4, or to a cage polypeptide and a key polypeptide, respectively, in the same row of Table 2, Table 3, and/or Table 4. In further embodiments, the one or more bioactive peptides may comprise one or more bioactive peptide selected from the non-limiting group consisting of SEQ ID NO:60, 62-64, 66, 27052-27093, and 27118-27119.

In other embodiments, the host cells, kits, or LOCKR according to any embodiment or combination of embodiments of the disclosure comprise
(a) the one or more cage polypeptide comprise one or more cage polypeptides having at least 40%, 45%, 50%, 55%, 60%, 65%, 70%, 75%, 80%, 85%, 90%, 91%, 92%, 93%, 94%, 95%, 96%, 97%, 98%, 99%, or 100% sequence identity, not including optional amino acid residues, along its length to the amino acid sequence of a cage polypeptide selected from the group consisting of SEQ ID NOS: 1-49, 51-52, 54-59, 61, 65, 67-14317, 27094-27117, 27120-27125, 27,278 to 27,321, and cage polypeptides listed in Table 2, Table 3, and/or Table 4, wherein the N-terminal and/or C-terminal 60 amino acids of the polypeptides are optional; and
(b) the one or more key polypeptide comprise one or more polypeptides selected from the group consisting of a polypeptide having at least 40%, 45%, 50%, 55%, 60%, 65%, 70%, 75%, 80%, 85%, 90%, 91%, 92%, 93%, 94%, 95%, 96%, 97%, 98%, 99%, or 100% sequence identity, not including optional amino acid residues, along its length to the amino acid sequence of a key polypeptide selected from the group consisting of SEQ ID NOS:14318-26601, 26602-27015, 27016-27051, and key polypeptides listed in Table 2, Table 3, and/or Table 4.

In another aspect, the disclosure provides use of the polypeptides, fusion proteins, nucleic acids, expression vectors, host cells, kits, and/or LOCKR switches disclosed herein to sequester bioactive peptide in the cage polypeptide, holding them in an inactive ("off") state, until combined with the key polypeptide to induce a conformational change that activates ("on") the bioactive peptide.

DESCRIPTION OF THE FIGURES

FIG. 1A shows thermodynamic model describing our design goal. The structural region and latch region in cage form the switch with some equilibrium in the open and closed states. The key can bind the cage to promote the open state to allow target binding to the latch. FIG. 1B shows plots from the model in (a) for two values of $K_{LT}$ showing how fraction target bound is affected by addition of key ($K_{CK}$=1 nM); the different colored curves show the effect of log-decreasing values of $K_{open}$=[open]/[closed]. FIG. 1C shows loops were added to homotrimer 5L6HC3_1[5] to form monomeric five- and six-helix frameworks; double mutant V217S/I232S weakens the Latch allowing it to be displaced by key, resulting in a LOCKR system able to bind an exogenous key. FIG. 1D shows chemical denaturation with guanidinium chloride (Gdm) monitoring mean residue ellipticity (MRE) at 222 nm. FIG. 1E shows small-angle x-ray scattering (SAXS) shows that the monomeric frameworks exhibit spectra that are in close agreement to each other and the original homotrimer. FIG. 1F, Pulldown assay showing that Key binds to the truncated five-helix framework and LOCKR (V217S/I232S), but not the six-helix monomer; free GFP-Key was added to monomeric frameworks immobilized onto a plate via a hexahistidine tag; after a series of wash steps, binding was measured by GFP fluorescence (n=2, error bars indicate standard deviation).

FIG. 2A. the free energy of the latch-cage interface was tuned through sub-optimal Bim-cage interactions (left, shown as altered hydrophobic packing and a buried hydrogen bond) and by exposing hydrophobic residues at the end of the interface (right) as a toehold. FIG. 2B) Introduction of the toehold allows activation of 250 nM BimLOCKR with addition of 5 µM key ('on' bar) via Bio-layer interferometry. FIG. 2C) Bio-layer interferometry shows key-dependent binding to Bcl2 with 250 nM BimLOCKR. Association from 0-500 s, then dissociation from 500-1700 s. FIG. 2D) Each point is a result of fitting data in I and extracting the response at equilibrium. The curves show similar data with shorter keys demonstrating the ability to tune $K_{CK}$ of LOCKR and effect its range of activation.

FIG. 3A) Left: LOCKR in cartoon representation. Cage with three different latches superimposed and hydrogen bond networks marked by markers. Right: Hydrogen-bond networks across the orthogonal LOCKR interfaces FIG. 3B) BimLOCKR binding to Bcl2 in response to its cognate key on Octet. One replicate FIG. 3C) Response on Octet after 500 seconds for each switch (250 nM) and key (5 µM) pair. Average of two replicates.

(FIG. 4A) Crystal structure of design 1-fix-short-BIM-t0, which contains the encoded BIM peptide. (FIG. 4B) Crystal structure of design 1fix-short-noBim(AYYA)-t0 is in very close agreement with the design model with respect to (left) Backbone, (middle) hydrogen bond network, and (right) hydrophobic packing; the region of the Latch where Bim and Gfp11 would be encoded is shown; the electron density map is shown for the network and hydrophobic cross-sections (middle and right).

FIG. 5A. Crystal structure of GFP (pdb 2y0g) with strand 11 shown. FIG. 5B. Crystal structure of prototype switch with GFP11 stabilized as a helix (mesh is electron density). FIG. 5C. The computational design model matches the crystal structure with a root-mean-square deviation of 0.87 Å. Experimentally determined x-ray crystal structure of designed LOCKR switch 1fix-short-GFP-t0, showing the encoded the $11^{th}$ strand of GFP (GFP11) is an alpha helix and in very close agreement to the design model. FIG. 5D. GFP fluorescence is only observed in the presence of the Key peptide, demonstrating the switch is function (OFF in the absence of Key, and ON in the presence of Key).

(FIG. 6A) Schematic of test system, where colocalization-dependence is controlled by linked Spycatcher™/Spytag™ fusions. In this model, the Key should only activate the LOCKR switch (yield fluorescence) when fused to Spytag, which will colocalizing the Key to the Cage (right). When Key alone is added, it should not be able to activate the LOCKR switch (middle). (FIG. 6B and FIG. 6C) Fluorescence data demonstrating colocalization-dependence of designed LOCKR switches following the schematic in (A). Designs 1fix-latch and 1fix-short fused to Spycatcher™ show more activation when mixed with their cognate Keys fused to Spytag™; Keys lacking Spytag™ show markedly less activation.

FIG. 11A) The latch was truncated from the 6×-His tagged cage in the five redesigned LOCKR constructs (b through f). The corresponding keys were GFP tagged. Key-Cage binding was measured by Ni pulldown of the cage and measuring the resulting GFP fluorescence. Error bars are standard deviation of three replicates. FIG. 11B) Each full LOCKR construct that binds key from (a) was given a nine-residue toehold and tested for binding against all four functional keys (a through d) in the GFP pulldown assay. Error bars are standard deviation of five replicates. Key a is suspected to be promiscuous binding, but not activating, due to the pseudo-symmetric generation of LOCKR from a homotrimer. LOCKRb shows no binding to its own key, which is attributable to latch strength given results from (a) and FIG. 3b.

FIG. 12A-12D: Designed Mad1-SID LOCKR switches for key-dependent transcriptional repression. (FIG. 12A) Crystal structure of the interaction between Mad1-SID domain (white) and the PAH2 domain of the mSin3A transcriptional repressor (black) (PDB ID: 1E91). Caging of the Mad1-SID domain should enable key-dependent recruitment of the transcriptional repressor mSin3A enabling precise epigenetic regulation. (FIG. 12B) Designed Mad1-LOCKR switches, with Cage component encoding the Mad1-SID sequence at different positions (dark gray). (FIG. 12C) SDS-PAGE gel showing successfully purified 1fix_302_Mad1 (1), 1fix_309_Mad1 (2) and MBP_Mad1 (3). (FIG. 12D) Biolayer interferometry analysis of key-activated binding of the Mad1-LOCKR switches to the purified mSin3A-PAH2 domain. MBP-Mad1 is a positive control for mSin3α-PAH2 binding. 1fix_309_Mad1 (309) shows successful activation when mixed with designed Key$_a$. 1fix_302_Mad1 (302) shows very tight caging of the Mad1-SID domain, but no activation in presence of Key$_a$. Kinetic assays were performed by immobilizing 0.1 μg of Biotin-mSin3A-PAH2 protein on Streptavidin biosensor tips (ForteBio). Protein cages were tested at 50 nM in presence or absence of 500 nM Key$_a$.

FIG. 13A-13D: Caged STREPII-tag LOCKR switches; demonstration of new 2plus1 and 3plus1 LOCKR switches. (FIG. 13A) Designed 2+1 (left) and 3+1 (middle) LOCKR switches were designed to encode the STREPII sequence WSHPQFEK (SEQ ID NO:63). (FIG. 13B-FIG. 13D) Biolayerinterferometry (Octet) Data demonstrating function of the STREPII-LOCKR designs: anti-strep antibody is immobilized onto Anti-mouse FC tips to assess binding of the STREPII tag: (FIG. 13B) The designed proteins show less binding than positive control, suggesting the STREPII has been at least partially sequestered as intended. (FIG. 13C) Activation of design STREPII-3plus1_Lock_3 by 3plus1_Key_3: The curve is 250 nM of cage with no Key, compared to 250 nM Cage in the presence of increasing concentration of Key ranging from 121 nM to 6000 nM. (FIG. 13D) 250 nM STREPII-3plus1_Lock_3 in the presence of Key at 370 nM, 1111 nM, and 3333 nM; 250 nM of Cage with no Key is 250 nM, and the other plots are Key at the same concentrations (370 nM, 1111 nM, and 3333 nM) but in the absence of Cage. In all Octet plots, the left half is the association (binding) step, and the right half is the dissociation step.

DETAILED DESCRIPTION

Figure 1A:
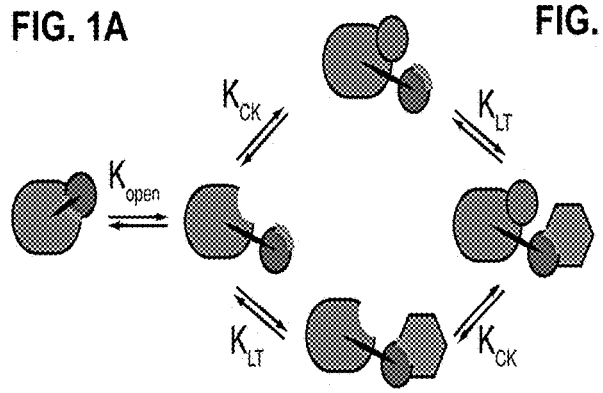
FIG. 1A-1F: Design of the LOCKR switch system.
Figure 1B:
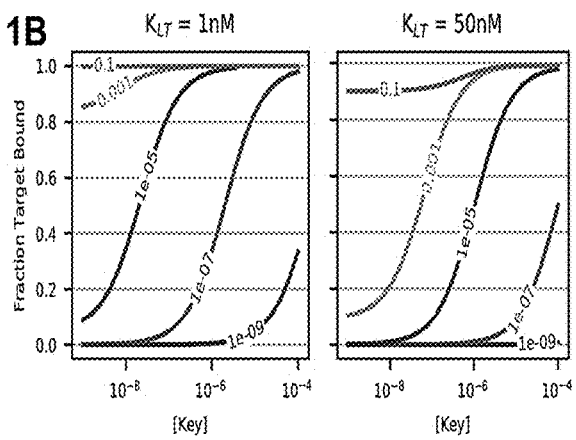

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, CA), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, CA), *Culture of Animal Cells: A Manual of Basic Technique*, 2$^{nd}$ Ed. (R. I. Freshney. 1987. Liss, Inc. New York, NY), *Gene Transfer and Expression Protocols*, pp. 109-128, ed. E. J. Murray, The Humana Press Inc., Clifton, NJ), and the Ambion 1998 Catalog (Ambion, Austin, TX).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of any aspect of the disclosure can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

In a first aspect, the disclosure provides non-naturally occurring polypeptides, comprising:
  (a) a helical bundle comprising between 2 and 7 alpha-helices; and
  (b) amino acid linkers connecting each alpha helix.

The non-naturally occurring polypeptides of this first aspect of the disclosure can be used, for example, as "cage" polypeptide component (which may also be referred to here as the "lock") of the novel protein switches disclosed in detail herein. The protein switches can be used, for example, to sequester bioactive peptides in the cage polypeptide, holding them in an inactive ("off") state, until combined with a second component (the "key" polypeptide) of the novel protein switches disclosed herein; the key polypeptide induces a conformational change that activates ("on") the bioactive peptide (see FIG. 1A). The polypeptides described herein comprise the first ever de novo designed polypeptides that can undergo conformational switching in response to protein binding. Furthermore, there are no known natural proteins that can switch in such a modular, tunable manner as the polypeptides disclosed herein.

The polypeptides are "non-naturally occurring" in that the entire polypeptide is not found in any naturally occurring polypeptide. It will be understood that components of the polypeptide may be naturally occurring, including but not limited to bioactive peptides that may be included in some embodiments.

The cage polypeptides comprise a helical bundle comprising between 2 and 7 alpha-helices. In various embodiments, the helical bundle comprises 3-7, 4-7, 5-7, 6-7, 2-6, 3-6, 4-6, 5-6, 2-5, 3-5, 4-5, 2-4, 3-4, 2-3, 2, 3, 4, 5, 6, or 7 alpha helices.

Design of the helical bundle cage polypeptides of the disclosure may be carried out by any suitable means. In one non-limiting embodiment, a BundleGridSampler™ in the Rosetta™ program may be used to generates backbone geometry based on the Crick expression for a coiled-coil and allows efficient, parallel sampling of a regular grid of coiled-coil expression parameter values, which correspond to a continuum of peptide backbone conformations. This may be supplemented by design for hydrogen bond networks using any suitable means, including but not limited to as described in Boyken et. al, (Science 352, 680-687 (2016)), followed by Rosetta™ sidechain design. In a further non-limiting embodiment, best scoring designs, based on total score, number of unsatisfied hydrogen bonds, and lack of voids in the core of the protein may be selected for helical bundle cage polypeptide design.

Each alpha helix may be of any suitable length and amino acid composition as appropriate for an intended use. In one embodiment, each helix is independently 38 to 58 amino acids in length. In various embodiments, each helix is independently between 18-60, 18-55, 18-50, 18-45, 22-60, 22-55, 22-50, 22-45, 25-60, 25-55, 25-50, 25-45, 28-60, 28-55, 28-50, 28-45, 32-60, 32-55, 32-50, 32-45, 35-60, 35-55, 35-50, 35-45, 38-60, 38-55, 38-50, 38-45, 40-60, 40-58, 40-55, 40-50, or 40-45 amino acids in length.

The amino acid linkers connecting each alpha helix can be of any suitable length or amino acid composition as appropriate for an intended use. In one non-limiting embodiment, each amino acid linker is independently between 2 and 10 amino acids in length, not including any further functional sequences that may be fused to the linker. In various non-limiting embodiments, each amino acid linker is independently 3-10, 4-10, 5-10, 6-10, 7-10, 8-10, 9-10, 2-9, 3-9, 4-9, 5-9, 6-9, 7-9, 8-9, 2-8, 3-8, 4-8, 5-8, 6-8, 7-8, 2-7, 3-7, 4-7, 5-7, 6-7, 2-6, 3-6, 4-6, 5-6, 2-5, 3-5, 4-5, 2-4, 3-4, 2-3, 2, 3, 4, 5, 6, 7, 8, 9, or 10 amino acids in length. In all embodiments, the linkers may be structured or flexible (e.g. poly-GS). These linkers may encode further functional sequences, including but not limited to protease cleavage sites or one half of a split intein system (see sequences below).

The polypeptides of this first aspect include a region, termed the "latch region", for insertion of a bioactive peptide. The cage polypeptide thus comprises a latch region and a structural region (i.e.: the remainder of the cage polypeptide that is not the latch region). When the latch region is modified to include one or more bioactive peptides, the structural region of the cage polypeptide interacts with the latch region to prevent activity of the bioactive peptide. Upon activation by key polypeptide, the latch region dissociates from its interaction with the structural region to expose the bioactive peptide, allowing the peptide to function.

As used herein, a "bioactive peptide" is any peptide of any length or amino acid composition that is capable of selectively binding to a defined target (i.e.: capable of binding to an "effector" polypeptide). Such bioactive peptides may comprise peptides of all three types of secondary structure in an inactive conformation: alpha helix, beta strand, and loop. The polypeptides of this aspect can be used to control the activity of a wide range of functional peptides. The ability to harness these biological functions with tight, inducible control is useful, for example, in engineering cells (inducible activation of function, engineering complex logic behavior and circuits, etc.), developing sensors, developing inducible protein-based therapeutics, and creating new biomaterials.

The latch region may be present near either terminus of the cage polypeptide. In one embodiment, the latch region is placed at the C-terminal helix so as to position the bioactive peptide for maximum burial of the functional residues that need to be sequestered to maintain the bioactive peptide in an inactive state while simultaneously burying hydrophobic residues and promoting solvent exposure/compensatory hydrogen bonds of polar residues. In various embodiments, the latch region may comprise a part or all of a single alpha helix in the cage polypeptide at the N-terminal or C-terminal portions. In various other embodiments, the latch region may comprise a part or all of a first, second, third, fourth, fifth, sixth, or seventh alpha helix in the cage polypeptide. In other embodiments, the latch region may comprise all or part of two or more different alpha helices in the cage polypeptide; for example, a C-terminal part of one alpha helix and an N-terminal portion of the next alpha helix, all of two consecutive alpha helices, etc.

In another embodiment, the polypeptides of this first aspect comprise one or more bioactive peptides within the latch region. In this embodiment, the bioactive peptide(s) may replace one or more amino acids in the latch region, or may be added to the latch region without removal of any amino acid residues from the latch region. In various non-limiting embodiments, the bioactive peptides may comprise one or more of the following (all sequences in parentheses are optional), or variants thereof, of SEQ ID NO:60, 62-64, 66, 27052-27093, and 27118-27119:

```
GFP11 fluorescence peptide and binding
peptide to GFP1-10:
                                   (SEQ ID NO: 27052)
RDHMVLHEYVNAAGIT.

BIM binding peptide and apoptotic peptide
to BCL-2:
                                   (SEQ ID NO: 50)
IxxxLRxIGDxFxxxY,
where x is any amino acid; in one embodiment,
the peptide is
                                   (SEQ ID NO: 60)
EIWIAQELRRIGDEFNAYYA Designed peptide for binding to BCL-2:
                                   (SEQ ID NO: 62)
KMAQELIDKVRAASLQINGDAFYAILRAL StreptagII binding peptide to streptactin
or an antibody:
                                   (SEQ ID NO: 63)
(N)WSHPQFEK TEV protease cleavage site:
                                   (SEQ ID NO: 64)
ENLYFQ(G)-X,
wherein (G) can also be S, last position,
-X can be anything except Proline Thrombin protease cleavage site:
                                   (SEQ ID NO: 66)
LVPRGS Cathepsin cleavage site:
                                   (SEQ ID NO: 27053)
RLVGFE Spytag covalent crosslinking peptide to
spycatcher:
                                   (SEQ ID NO: 27054)
AHIVMVDAYK(PTK)

NLS peptide to target the protein to the nucleus:
                                   (SEQ ID NO: 27055)
AAAKRARTS NES1 peptide to exclude the protein from the
nucleus:
                                   (SEQ ID NO: 27056)
LALKLAGLDIN NES2 peptide to exclude the protein from the
nucleus:
                                   (SEQ ID NO: 27057)
ELAEKLAGLDIN NES3 peptide to exclude the protein from the
nucleus:
                                   (SEQ ID NO: 27058)
ELAEKLRAGLDLN EZH2 binding peptide to recruit DNA-methylases:
                                   (SEQ ID NO: 27059)
TMFSSNRQKILERTETLNQEWKQRRIQ MDM2 binding peptide to recruit p53:
                                   (SEQ ID NO: 27060)
ETFSDLWKLL CP5 binding peptide:
                                   (SEQ ID NO: 27061)
GELDELVYLLDGPGYDPIHSDVVTRGGSHLFNF 9aaTAD1 for transcriptional activation:
                                   (SEQ ID NO: 27062)
TMDDVYNYLFDD 9aaTAD2 for transcriptional activation:
                                   (SEQ ID NO: 27063)
LLTGLFVQYLFDD 9aaTAD3 for transcriptional activation:
                                   (SEQ ID NO: 27064)
DDAVVESFFSS 9aaTAD4 for transcriptional activation:
                                   (SEQ ID NO: 27065)
GDFLSDLFD 9aaTAD5 for transcriptional activation:
                                   (SEQ ID NO: 27066)
GDVLSDLVD Mad1-SID-epigenetic modification:
                                   (SEQ ID NO : 27067)
NIQMLLEAADYLE Mad1-SID (3A mutant)-epigenetic modification:
                                   (SEQ ID NO: 27068)
NIAMLLAAAAYLE RHIM Domain 1 from ZBP1:
                                   (SEQ ID NO: 27069)
IQIG RHIM Domain 2 from ZBP1:
                                   (SEQ ID NO: 27070)
VQLG nanoBit Split Luciferase:
                                   (SEQ ID NO: 27071)
VSGWRLFKKIS CC-A:
                                   (SEQ ID NO: 27072)
GLEQEIAALEKENAALEWEIAALEQGG CC-B:
                                   (SEQ ID NO: 27073)
GLKQKIAALKYKNAALKKKIAALKQGG GCN4:
                                   (SEQ ID NO: 27074)
RMKQLEDKVEELLSKNYHLENEVARLKKLVGER CC-Di:
                                   (SEQ ID NO: 27075)
GEIAALKQEIAALKKENAALKWEIAALKQG Membrane-disrupting/cell-penetrating peptides:
GALA for membrane disruption:
                                   (SEQ ID NO: 27076)
WEAALAEALAEALAEHLAEALAEALEALAA Aurein 1.2:
                                   (SEQ ID NO: 27077)
GLFDIIKKIAESF Magainin-1:
                                   (SEQ ID NO: 27078)
GIGKFLHSAGKFGKAFVGEIMKS Magainin-2:
                                   (SEQ ID NO: 27079)
GIGKFLHSAKKFGKAFVGEIMNS Melittin:
                                   (SEQ ID NO: 27080)
GIGAVLKVLTTGLPALISWIKRKRQQ Mastoparan X:
                                   (SEQ ID NO: 27081)
INWKGIAAMAKKLL Cecropin A:
                                   (SEQ ID NO: 27082)
KWKLFKKIEKVGQNIRDGIIKAGPAVAVVGQATQIAK
```

-continued

Cecropin P1:
(SEQ ID NO: 27083)
SWLSKTAKKLENSAKKRISEGIAIAIQGGPR

Citropin 1.1:
(SEQ ID NO: 27084)
GLFDVIKKVASVIGGL

Temporin-1Lb:
(SEQ ID NO: 27085)
NFLGTLINLAKKIL

HPV33 L2 peptide:
(SEQ ID NO: 27086)
SYFILRRRRKRFPYFFTDVRVAA

Adenovirus pVI membrane fusion domain:
(SEQ ID NO: 27087)
AFSWGSLWSGIKNFGSTVKNY

Gamma-1 peptide from flock house virus:
(SEQ ID NO: 27088)
ASMWERVKSIIKSSLAAASNI Poliovirus 2B pore-forming peptide:
(SEQ ID NO: 27089)
VTSTITEKLLKNLIKIISSLVIITRNYEDTTT

VLATLALLGCDASPWQWL

Rhinovirus pore-forming peptide:
(SEQ ID NO: 27090)
IAQNPVENYIDEVLNEVLVVPNIN

Influenza HA2 pore-forming peptide:
(SEQ ID NO: 27091)
FLGIAEAIDIGNGWEGMEFG

Influenza HA2 derivative:
(SEQ ID NO: 27092)
GLFGAIAGFIENGWEGMIDG

HA-derived INF6:
(SEQ ID NO: 27093)
GLFGAIAGFIENGWEGMIDGWYG.

KRAB domain-epigenetic modification:
(SEQ ID NO: 27118)
MDAKSLTAWSRTLVTFKDVFVDFTREEWKLLDTAQQIVYRNVMLEN

YKNLVSLGYQLTKPDVILRLEKGEEPWLV

Figure 10:
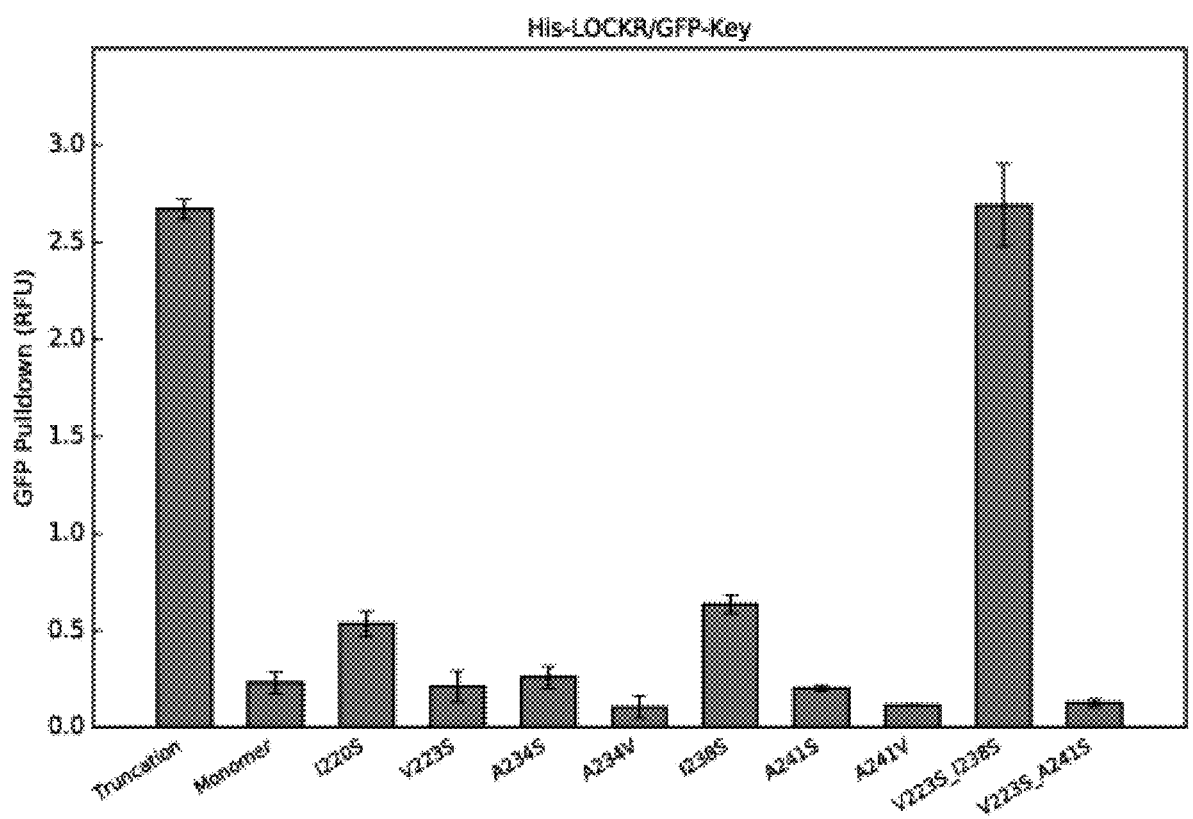
FIG. 10: GFP Plate assay to find mutations for LOCKR. Different putative LOCKR constructs were adhered via 6×-His tag to a Ni coated 96-well plate, Key-GFP was applied, and excess washed. Resulting fluorescence represents Key-GFP bound to LOCKR constructs. The truncation was used as a positive control, since the key binds to the open interface. The monomer as a negative control since it does not bind the key. Error bars represent the standard deviation of three replicates.
Figure 11A:
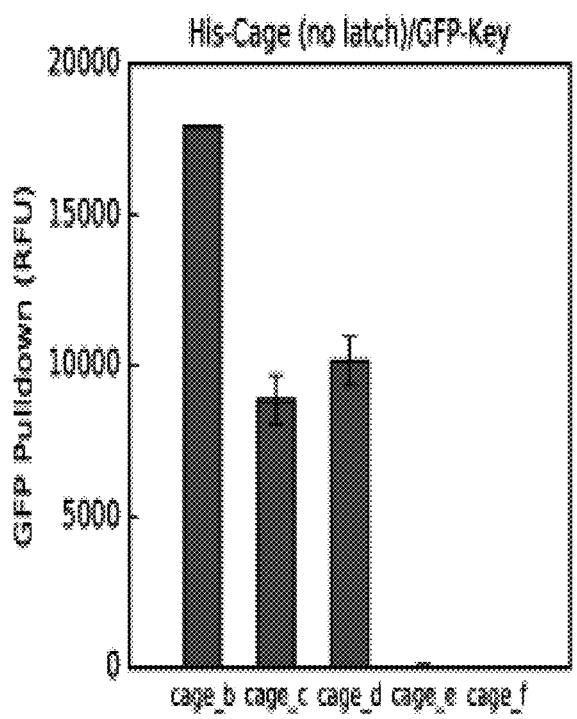
FIG. 11A-11B: Orthogonal LOCKR GFP assays.
Figure 11B:
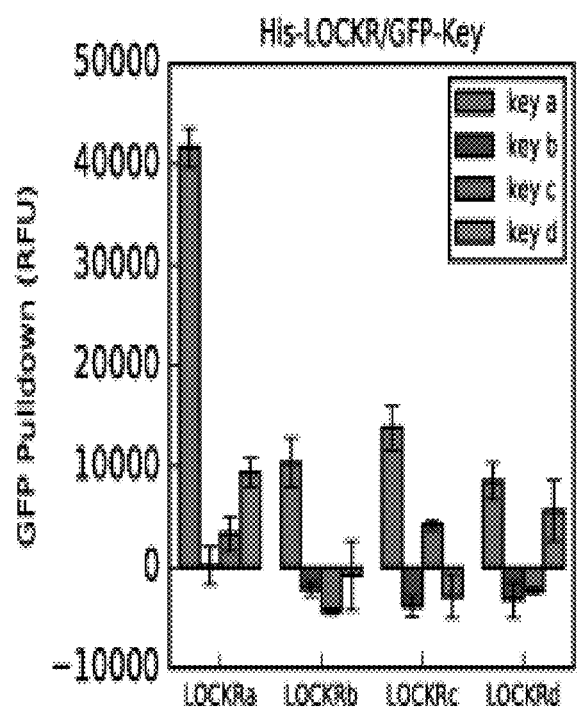

Minimal Krab domain (KOX1 11-55)-
epigenetic modification:
(SEQ ID NO: 27119)
RTLVTFKDVFVDFTREEWKLLDTAQQIVYRNVMLENYKNLVSLGY In one embodiment, the dynamic range of activation by key polypeptides can be tuned by truncating the latch region length to be shorter than the alpha-helices in the structural region, simultaneously weakening the cage polypeptide-latch region interaction and opening an exposed region on the cage polypeptide that the key polypeptide can bind to as a "toehold" (FIG. 2). Similarly, the dynamic range of activation by key polypeptides can also be tuned in a similar manner by designing mutations into the Latch that weaken the cage polypeptide-latch region interaction (FIGS. 1-2, and 10). In other embodiments, the latch region can be one or more helices totaling in length between 18-150 amino acids, between 18-100 amino acids, between 18-58 amino acids, or any range encompassed by these ranges. In other embodiments the latch region could consist of helical secondary structure, beta strand secondary structure, loop secondary structure, or combinations thereof.

In a second aspect, the disclosure provides non-naturally occurring polypeptides comprising a polypeptide having at least 40%, 45%, 50%, 55%, 60%, 65%, 70%, 75%, 80%, 85%, 90%, 91%, 92%, 93%, 94%, 95%, 96%, 97%, 98%, 99%, or 100% sequence identity along its length to the amino acid sequence of a cage polypeptide disclosed herein, not including optional amino acid residues, and optionally not including amino acid residues in the latch region, such as such SEQ ID NOS:1-49, 51-52, 54-59, 61, 65, 67-91, 92-2033 (submitted in U.S. Provisional Application Ser. No. 62/700,681 filed Jul. 19, 2018 and/or 62/785,537 filed Dec. 27, 2018 as Appendix 1), SEQ ID NOS:2034-14317 (submitted in U.S. Provisional Application Ser. No. 62/700,681 filed Jul. 19, 2018 and/or 62/785,537 filed Dec. 27, 2018 as Appendix 2), 27094-27117, 27120-27125, 27,278 to 27,321, and cage polypeptides listed in Table 2 (polypeptides with an even-numbered SEQ ID NO between SEQ ID NOS: 27126 and 27276), Table 3, and/or Table 4. In each embodiment, the N-terminal and/or C-terminal 60 amino acids of each cage polypeptides may be optional, as the terminal 60 amino acid residues may comprise a latch region that can be modified, such as by replacing all or a portion of a latch with a bioactive peptide. In one embodiment, the N-terminal 60 amino acid residues are optional; in another embodiment, the C-terminal 60 amino acid residues are optional; in a further embodiment, each of the N-terminal 60 amino acid residues and the C-terminal 60 amino acid residues are optional. In one embodiment, these optional N-terminal and/or C-terminal 60 residues are not included in determining the percent sequence identity. In another embodiment, the optional residues may be included in determining percent sequence identity.

As disclosed herein, bioactive peptides to be sequestered by the polypeptides of the disclosure are located within the latch region. The latch region is denoted by brackets in the sequence of each cage polypeptide. The bioactive peptide may be added to the latch region without removing any residues of the latch region, or may replace one or more (1, 2, 3, 4, 5, 6, 7, 8, 9, 10, or more) amino acid residues in the cage scaffold latch region to produce the final polypeptide. Thus, the latch region may be significantly modified upon inclusion of the bioactive peptide. In one embodiment, the optional residues are not included in determining percent sequence identity. In another embodiment, the latch region residues may be included in determining percent sequence identity. In a further embodiment, each of the optional residues and the latch residues may are not included in determining percent sequence identity.

In one embodiment of this second aspect, the polypeptides are polypeptides according to any embodiment or combination of embodiments of the first aspect and also having the required 40%, 45%, 50%, 55%, 60%, 65%, 70%, 75%, 80%, 85%, 90%, 91%, 92%, 93%, 94%, 95%, 96%, 97%, 98%, 99%, or 100% sequence identity along its length to the amino acid sequence of the listed reference cage polypeptides disclosed herein. In another embodiment, polypeptides further comprise a bioactive peptide within (or replacing) the latch region of the cage polypeptide.

The cage polypeptide may be a cage scaffold polypeptide (i.e.: without a bioactive peptide) For example, see SEQ ID NOS:1-17, 2034-14317, and certain cage polypeptides listed in Table 2, Table 3, and/or Table 4, or may further include a sequestered bioactive peptide (present as a fusion with the cage scaffold polypeptide) in the latch region of the cage scaffold polypeptide, as described in more detail herein (for example, see SEQ ID NOS:18-49, 51-52, 54-59, 61, 65, 67-2033, 27094-27117, 27120-27125, and certain cage polypeptides listed in Table 2, 3, and/or 4). In a specific embodiment, the cage polypeptides share 40%, 45%, 50%, 55%, 60%, 65%, 70%, 75%, 80%, 85%, 90%, 91%, 92%, 93%, 94%, 95%, 96%, 97%, 98%, 99%, or 100% sequence identity along their length to the amino acid sequence of a cage polypeptide in Table 2, Table 3, and/or Table 4.

In another specific embodiment, the cage polypeptides share 40%, 45%, 50%, 55%, 60%, 65%, 70%, 75%, 80%, 85%, 90%, 91%, 92%, 93%, 94%, 95%, 96%, 97%, 98%, 99%, or 100% sequence identity along their length to the amino acid sequence of a cage polypeptide in Table 3. In another specific embodiment, the cage polypeptides share 40%, 45%, 50%, 55%, 60%, 65%, 70%, 75%, 80%, 85%, 90%, 91%, 92%, 93%, 94%, 95%, 96%, 97%, 98%, 99%, or 100% sequence identity along their length to the amino acid sequence of a cage polypeptide in Table 4. In one embodiment of each of these embodiments, the optional N-terminal and/or C-terminal 60 residues are not included in determining the percent sequence identity. In another embodiment, the optional residues may be included in determining percent sequence identity.

As disclosed in the examples that follow, exemplary cage and key polypeptides of the disclosure have been identified and subjected to mutational analysis. Furthermore, different designs starting from the same exemplary cage and key polypeptides yield different amino acid sequences while maintaining the same intended function. In various embodiments, a given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are known. Polypeptides comprising conservative amino acid substitutions can be tested in any one of the assays described herein to confirm that the desired activity is retained. Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into H is; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Exemplary cage polypeptides (see also SEQ ID NOS: 92-14317, 27094-27117, 27120-27125, 27,728-27321, and cage polypeptides listed in Table 2, Table 3, and/or Table 4):
1) Exemplary reference cage polypeptides; latch regions denoted by brackets [ ]
    6His-MBP-TEV, 6His-TEV, and flexible linker sequences are underlined text
    fused functional domains (DARPins, componants of the split intein, and fluorescent proteins) are bolded text
    Functional peptide is italicized underlined text
    Exemplary positions that have been mutated to any amino acid to tune responsiveness are underlined bolded text. These positions are exemplary, and not an exhaustive list of residues able to tune responsiveness.
    C-terminal sequences that can be removed to tune responsiveness are contained within brackets. A range from one (1) to all residues encompassed within the brackets may be removed, starting from the C-terminus and removing successive residues therein.
    All sequences in parentheses are optional >SB76L
(SEQ ID NO: 1)
(MGSSHHHHHHSSGLVPRGSHM)SKEAVTKLQALNIKLAEKLLEALARLQELNIALVYLAVELTDPKRIADEIKK

VKDKSKEIVERAEEEIARAAAESKKILDEGSGSGSDAVAELQALNLKLAELLLEAIAKLQELNIKLVELLTKLTD

PATIREAIRKVKEDSERIVAEAERLIAAAKAESERIIREGSGSGSDPDVARLQELNIELARELLRAAAELQELNIK

LVELASELTDP[DEARKAIARVKRESKRIVEDAERLIREAAAASEKISRE]

>SB76L_17
(SEQ ID NO: 2)
(MGSSHHHHHHSSGLVPRGSHM)GSKEAVTKLMALNLKLAEKLLEAIARLQELNIALVYLATELTDPERIREEIR

KVKEESARIVEEAEEEIRRAAARSEDILREGSGSGSDAVAELQRLNLELAELLLRAAAKLQELNIDLVRLLTELT

DPKTIRDAIERVKAESERIVREAERLIREAKADSERILREGSGSGDPDVARLQELFIELARELLEALARLQELNI

DLVRLASELTDP[DTIRDAIRRVKEESARIVEDARRLIKKAAEEAEKISRE]

>SB76L_18
(SEQ ID NO: 3)
(MGSSHHHHHHSSGLVPRGSHM)GSKRAVTELQKLNIELARKLLRALAELMELNIALVYLAVELTDPRRIREEIR

KVKEKSDEIVKRAEDEIRKAAAESEKILREGSGSGSDAVAELQRLNLELAKLLLEAIAKLQALNIDLVRLLTELT

DPETIRRAIKRVKDESARIVEEAEKLIRAAKDKAREIIDKGSGSGDPDVARLQELNIELARELLEAAARLQELFI

DLVRLASELTDP[DEARKAIERVKREAERIVREAERLIREAKRASKEISDE]

```
>LOCKR_extend5
                                                      (SEQ ID NO: 4)
(MGSSHHHHHHSSGLVPRGSHM)KLLEAVTKLQALNIKLAEKLLEALARLQELNIALVYLAVELTDPKRIADEIK

KVKDKSKEIVERAEEEIARAAAESKKILDEAEEEGSGSGSELLLEAVAELQALNLKLAELLLEAIAKLQELNIKL

VELLTKLTDPATIREAIRKVKEDSERIVAEAERLIAAAKAESERIIREAERLAGSGSGSRELLRDVARLQELNIE

LARELLRAAAELQELNIKLVELASELTDP[DEARKAIARVKRESKRIVEDAERLIREAAAASEKISREAERLI]

>LOCKR_extend9
                                                      (SEQ ID NO: 5)
(MGSSHHHHHHSSGLVPRGSHM)KLAEKLLEAVTKLQALNIKLAEKLLEALARLQELNIALVYLAVELTDPKRIA

DEIKKVKDKSKEIVERAEEEIARAAAESKKILDEAEEEIARAGSGSGSLKLAELLLEAVAELQALNLKLAELLLE

AIAKLQELNIKLVELLTKLTDPATIREAIRKVKEDSERIVAEAERLIAAAKAESERIIREAERLIAAAAGSGSGS

IELARELLRDVARLQELNIELARELLRAAAELQELNIKLVELASELTDP[DEARKAIARVKRESKRIVEDAERLI

REAAAASEKISREAERLIREAA]

>LOCKR_extend18
                                                      (SEQ ID NO: 6)
(MGSSHHHHHHSSGLVPRGSHM)SKEAVTKLQALNIKLAEKLLEAVTKLQALNIKLAEKLLEALARLQELNIALV

YLAVELTDPKRIADEIKKVKDKSKEIVERAEEEIARAAAESKKILDEAEEEIARAAAESKKILDEGSGSGSDAVA

ELQALNLKLAELLLEAVAELQALNLKLAELLLEAIAKLQELNIKLVELLTKLTDPATIREAIRKVKEDSERIVAE

AERLIAAAKAESERIIREAERLIAAAKAESERIIREGSGSGDPDVARLQELNIELARELLRDVARLQELNIELAR

ELLRAAAELQELNIKLVELASELTDP[DEARKAIARVKRESKRIVEDAERLIREAAAASEKISREAERLIREAAA

ASEKISRE]

>LOCKRb
                                                      (SEQ ID NO: 7)
(MGSSHHHHHHSSGLVPRGSHM)SHAAVIKLSDLNIRLLDKLLQAVIKLTELNAELNRKLIEALQRLFDLNVALV

HLAAELTDPKRIADEIKKVKDKSKEIVERAEEEIARAAAESKKILDEAEEEIARAAAESKKILDEGSGSGSDAVA

ELQALNLKLAELLLEAVAELQALNLKLAELLLEAIAKLQELNIKLVELLTKLTDPATIREAIRKVKEDSERIVAE

AERLIAAAKAESERIIREAERLIAAAKAESERIIREGSGSNDPQVAQNQETFIELARDALRLVAENQEAFIEVAR

LTLRAAALAQEVAIKAVEAASEGGSGSG[NKEEIEKLAKEAREKLKKAEKEHKEIHDKLRKKNKKAREDLKKKAD

ELRETNKRVN]

>LOCKRc
                                                      (SEQ ID NO: 8)
(MGSSHHHHHHSSGLVPRGSHM)SLEAVLKLAELNLKLSDKLAEAVQKLAALLNKLLEKLSEALQRLFELNVALV

TLAIELTDPKRIADEIKKVKDKSKEIVERAEEEIARAAAESKKILDEAEEEIARAAAESKKILDEGSGSGSDAVA

ELQALNLKLAELLLEAVAELQALNLKLAELLLEAIAKLQELNIKLVELLTKLTDPATIREAIRKVKEDSERIVAE

AERLIAAAKAESERIIREAERLIAAAKAESERIIREGSGSNDPLVARLQELLIEHARELLRLVATSQEIFIELAR

AFLANAAQLQEAAIKAVEAASENGSGSG[SSEKVRRELKESLKENHKQNQKLLKDHKRAQEKLNRELEELKKKHK

KTLDDIRRES]

>LOCKRd
                                                      (SEQ ID NO: 9)
(MGSSHHHHHHSSGLVPRGSHM)SLEAVLKLFELNHKLSEKLLEAVLKLHALNQKLSQKLLEALARLLELNVALV

ELAIELTDPKRIADEIKKVKDKSKEIVERAEEEIARAAAESKKILDEAEEEIARAAAESKKILDEGSGSGSDAVA

ELQALNLKLAELLLEAVAELQALNLKLAELLLEAIAKLQELNIKLVELLTKLTDPATIREAIRKVKEDSERIVAE

AERLIAAAKAESERIIREAERLIAAAKAESERIIREGSGSGDPEVARLQEAFIEQAREILRNVAAAQEALIEQAR

RLLALAALAQEAAIKAVELASEHGSGSG[DTVKRILEELRRRFEKLAKDLDDIARKLLEDHKKHNKELKDKQRKI

KKEADDAARS]
```

>LOCKRe (SEQ ID NO: 10)

(MGSSHHHHHHSSGLVPRGSHM)SLEAVLKLQDLNSKLSEKLSEAQLKLQALNNKLLRKLLEALLRLQDLNQALV

NLALQLTDPKRIADEIKKVKDKSKEIVERAEEEIARAAAESKKILDEAEEEIARAAAESKKILDEGSGSGSDAVA

ELQALNLKLAELLLEAVAELQALNLKLAELLLEAIAKLQELNIKLVELLTKLTDPATIREAIRKVKEDSERIVAE

AERLIAAAKAESERIIREAERLIAAAKAESERIIREGSGSGDPDVAKSQEHLIEHARELLRQVAKSQELFIELAR

QLLRLAAKSQELAIKAVELASEAGSGSG[DDVERRLRKANKESKKEAEELTEEAKKANEKTKEDSKELTKENRKT

NKTIKDEARS]

>LOCKRf (SEQ ID NO: 11)

(MGSSHHHHHHSSGLVPRGSHM)SREAVEKLAELNHKLSHKLQQAQQKLQALNLKLLQKLLEALDRLQDLNNALV

KLAQRLTDPKRIADEIKKVKDKSKEIVERAEEEIARAAAESKKILDEAEEEIARAAAESKKILDEGSGSGSDAVA

ELQALNLKLAELLLEAVAELQALNLKLAELLLEAIAKLQELNIKLVELLTKLTDPATIREAIRKVKEDSERIVAE

AERLIAAAKAESERIIREAERLIAAAKAESERIIREGSGSGDPDVARQQETLIEQARRLLRNVAESQELFIEAAR

TVLRLAAKLQEINIKQVELASEAGSGSG[DDEERRSEKTVQDAKREIKKVEDDLQRLNEEQKKKVKKQEDENQKT

LKKHKDDARS]

>miniLOCKRa_1

(SEQ ID NO: 12)

(MGSSHHHHHHSSGLVPRGSHM)NKEDATEAQKKAIRAAEELLKDVTRIQERAIREAEKALERLARVQEEAIRRV

YEAVESKNKEELKKVKEEIEELLRRLKRELDELEREIRELLKEIKEKADRLEKEIRDLIERIRRDRNASDEVVTR

LARLNEELIRELREDVRRLAELNKELLRELERAARELARLNEKLLELADRVETE[EEARKAIARVKRESKRIVED

AERLIREAAAASEKISREAERLIREAAAASEKISRE]

>miniLOCKRa_2

(SEQ ID NO: 13)

(MGSSHHHHHHSSGLVPRGSHM)DERLKRLNERLADELDKDLERLLRLNEELARELTRAAEELRELNEKLVELAK

KLQGGRSREVAERAEKEREKIRRKLEEIKKEIKEDADRIKKRADELRRRLEKTLEDAARELEKLKREPRTEELKR

KATELQKEAIRRAEELLKEVTDVQRRAIERAEELLEKLARLQEEAIRTVYLLVELNKV[DRARKAIARVKRESKR

IVEDAERLIREAAAASEKISREAERLIREAAAASEKISRE]

>miniLOCKRc_1

(SEQ ID NO: 14)

(MGSSHHHHHHSSGLVPRGSHM)LIERLTRLEKEHVRELKRLLDTSLEILRRLVEAFETNLRQLKEALKRALEAA

NLHNEEVEEVLRKLEEDLRRLEEELRKTLDDVRKEVKRLKEELDKRIKEVEDELRKIKEKLKKGDKNEKRVLEEI

LRLAEDVLKKSDKLAKDVQERARELNEILEELSRKLQELFERVVEEVTRNVPT[TERIEKVRRELKESLKENHKQ

NQKLLKDHKRAQEKLNRELEELKKKHKKTLDDIRRES]

>miniLOCKRc_2

(SEQ ID NO: 15)

(MGSSHHHHHHSSGLVPRGSHM)SEERVLELAEEEALRLSDEAAKEIQELARRLNEELEKLSKELQDLFERIVETV

TRLIDADEETLKRAAEEIKKRLEDARKKAKEAADKAREELDRARKKLKELVDEIRKKAKDALEKAGADEELVARL

LRLLEEHARELERLLRTSARIIERLLDAFRRNLEQLKEAADKAVEAAEEAVRRVED[VRVWSEKVRRELKESLKE

NHKQNQKLLKDHKRAQEKLNRELEELKKKHKKTLDDIRRES]

>1fix-short-noBim-t0

(SEQ ID NO: 16)

(MGSHHHHHHGSGSENLYFQGSGG)SELARKLLEASTKLQRLNIRLAEALLEAIARLQELNLELVYLAVELTDPK

RIRDEIKEVKDKSKEIIRRAEKEIDDAAKESEKILEEAREAISGSGSELAKLLLKAIAETQDLNLRAAKAFLEAA

AKLQELNIRAVELLVKLTDPATIREALEHAKRRSKEIIDEAERAIRAAKRESERIIEEARRLIEKGSGSGS[ELA

RELLRAHAQLQRLNLELLRELLRALAQLQELNLDLLRLASELTDPDEARKAIARVKRESKRIVEDAERLIREAAA

ASEKISREAERLIR]

>1fix-short-noBim(AYYA)-t0

(SEQ ID NO: 17)

(MGSHHHHHGSGSENLYFQGSGG)SELARKLLEASTKLQRLNIRLAEALLEAIARLQELNLELVYLAVELTDPK
RIRDEIKEVKDKSKEIIRRAEKEIDDAAKESEKILEEAREAISGSGSELAKLLLKAIAETQDLNLRAAKAFLEAA
AKLQELNIRAVELLVKLTDPATIREALEHAKRRSKEIIDEAERAIRAAKRESERIIEEARRLIEKGSGSGS[ELA
RELLRAHAQLQRLNLELLRELLRALAQLQELNLDLLRLASELTDPDEARKAIARVKRESNAYYADAERLIREAAA
ASEKISREAERLIR]

"(3) Functional LOCKR Cage designs with bioactive peptides encoded into the Latch", >aBc12LOCKR (SEQ ID NO: 18)

(MGSSHHHHHHSSGLVPRGSHM)GSKEAVTKLQALNIKLAEKLLEALARLQELNIALVYLAVELTDPKRIADEIK
KVKDKSKEIVERAEEEIARAAAESKKILDEGSGSGSDAVAELQALNLKLAELLLEAIAKLQELNIKLVELLTKLT
DPATIREAIRKVKEDSERIVAEAERLIAAAKAESERIIREGSGSGDPDVARLQELNIELARELLRAAAELQELNI
KLVELASELT(GSGSGSG)[DPKMAQELIDKVRAASLQINGDAFYAILRALAASEKLSKE]

>pBimLOCKR (SEQ ID NO: 19)

(MGSSHHHHHHSSGLVPRGSHM)KEAVTKLQALNIKLAEKLLEALARLQELNIALVYLAVELTDPKRIADEIKKV
KDKSKEIVERAEEEIARAAAESKKILDEGSGSGSDAVAELQALNLKLAELLLEAIAKLQELNIKLVELLTKLTDP
ATIREAIRKVKEDSERIVAEAERLIAAAKAESERIIREGSGSGDPDVARLQELNIELARELLRAAAELQELNIKL
VELASEGSGSGS[EIAEALRAIGDVFNESYRIVEDAERLIREAAAASEKISRE]

>BimLOCKR_extend5

(SEQ ID NO: 20)

(MGSSHHHHHHSSGLVPRGSHM)KLLEAVTKLQALNIKLAEKLLEALARLQELNIALVYLAVELTDPKRIADEIK
KVKDKSKEIVERAEEEIARAAAESKKILDEAEEEGSGSGSELLLEAVAELQALNLKLAELLLEAIAKLQELNIKL
VELLTKLTDPATIREAIRKVKEDSERIVAEAERLIAAAKAESERIIREAERLAGSGSGSRELLRDVARLQELNIE
LARELLRAAAELQELNIKLVELASELTD[EIWIAQELRRIGDEFNAYYADAERLIREAAAASEKISREAERLI]

>BimLOCKR_extend9

(SEQ ID NO: 21)

(MGSSHHHHHHSSGLVPRGSHM)KLAEKLLEAVTKLQALNIKLAEKLLEALARLQELNIALVYLAVELTDPKRIA
DEIKKVKDKSKEIVERAEEEIARAAAESKKILDEAEEEIARAGSGSGSLKLAELLLEAVAELQALNLKLAELLLE
AIAKLQELNIKLVELLTKLTDPATIREAIRKVKEDSERIVAEAERLIAAAKAESERIIREAERLIAAAAGSGSGS
IELARELLRDVARLQELNIELARELLRAAAELQELNIKLVELASELTD[EIWIAQELRRIGDEFNAYYADAERLI
REAAAASEKISREAERLIREAA]

>BimLOCKR_extend18

(SEQ ID NO: 22)

(MGSSHHHHHHSSGLVPRGSHM)SKEAVTKLQALNIKLAEKLLEAVTKLQALNIKLAEKLLEALARLQELNIALV
YLAVELTDPKRIADEIKKVKDKSKEIVERAEEEIARAAAESKKILDEAEEEIARAAAESKKILDEGSGSGSDAVA
ELQALNLKLAELLLEAVAELQALNLKLAELLLEAIAKLQELNIKLVELLTKLTDPATIREAIRKVKEDSERIVAE
AERLIAAAKAESERIIREAERLIAAAKAESERIIREGSGSGDPDVARLQELNIELARELLRDVARLQELNIELAR
ELLRAAAELQELNIKLVELASELTD[EIWIAQELRRIGDEFNAYYADAERLIREAAAASEKISREAERLIREAAA
ASEKISRE]

>BimLOCKRb (SEQ ID NO: 23)

(MGSSHHHHHHSSGLVPRGSHM)SHAAVIKLSDLNIRLLDKLLQAVIKLTELNAELNRKLIEALQRLFDLNVALV
HLAAELTDPKRIADEIKKVKDKSKEIVERAEEEIARAAAESKKILDEAEEEIARAAAESKKILDEGSGSGSDAVA
ELQALNLKLAELLLEAVAELQALNLKLAELLLEAIAKLQELNIKLVELLTKLTDPATIREAIRKVKEDSERIVAE

AERLIAAAKAESERIIREAERLIAAAKAESERIIREGSGSNDPQVAQNQETFIELARDALRLVAENQEAFIEVAR

LTLRAAALAQEVAIKAVEAASEGGSGSG[NEIWIAQELRRIGDEFNAYYAEHKEIHDKLRKKNKKAREDLKKKAD

ELRETNKRVN]

>BimLOCKRc (SEQ ID NO: 24)

(MGSSHHHHHHSSGLVPRGSHM)SLEAVLKLAELNLKLSDKLAEAVQKLAALLNKLLEKLSEALQRLFELNVALV

TLAIELTDPKRIADEIKKVKDKSKEIVERAEEEIARAAAESKKILDEAEEEIARAAAESKKILDEGSGSGSDAVA

ELQALNLKLAELLLEAVAELQALNLKLAELLLEAIAKLQELNIKLVELLTKLTDPATIREAIRKVKEDSERIVAE

AERLIAAAKAESERIIREAERLIAAAKAESERIIREGSGSNDPLVARLQELLIEHARELLRLVATSQEIFIELAR

AFLANAAQLQEAAIKAVEAASENGSG[EIWIAQELRRIGDEFNAYYAQNQKLLKDHKRAQEKLNRELEELKKKHK

KTLDDIRRES]

>BimLOCKRd (SEQ ID NO: 25)

(MGSSHHHHHHSSGLVPRGSHM)SLEAVLKLFELNHKLSEKLLEAVLKLHALNQKLSQKLLEALARLLELNVALV

ELAIELTDPKRIADEIKKVKDKSKEIVERAEEEIARAAAESKKILDEAEEEIARAAAESKKILDEGSGSGSDAVA

ELQALNLKLAELLLEAVAELQALNLKLAELLLEAIAKLQELNIKLVELLTKLTDPATIREAIRKVKEDSERIVAE

AERLIAAAKAESERIIREAERLIAAAKAESERIIREGSGSGDPEVARLQEAFIEQAREILRNVAAAQEALIEQAR

RLLALAALAQEAAIKAVELASEHGSGS[EIWIAQELRRIGDEFNAYYADLDDIARKLLEDHKKHNKELKDKQRKI

KTIKDEARS]

>StrepLOCKRa_300

(SEQ ID NO: 26)

(MGSSHHHHHHSSGLVPRGSHM)SKEAVTKLQALNIKLAEKLLEAVTKLQALNIKLAEKLLEALARLQELNIALV

YLAVELTDPKRIADEIKKVKDKSKEIVERAEEEIARAAAESKKILDEAEEEIARAAAESKKILDEGSGSGSDAVA

ELQALNLKLAELLLEAVAELQALNLKLAELLLEAIAKLQELNIKLVELLTKLTDPATIREAIRKVKEDSERIVAE

AERLIAAAKAESERIIREAERLIAAAKAESERIIREGSGSGDPDVARLQELNIELARELLRDVARLQELNIELAR

ELLRAAAELQELNIKLVELAS(GG)[NWSHPQFEKKAIARVKRESKRIVEDAERLIREAAAASEKISREAERLIR

EAAAASEKISRE]

>strepLOCKRa_306

(SEQ ID NO: 27)

(MGSSHHHHHHSSGLVPRGSHM)SKEAVTKLQALNIKLAEKLLEAVTKLQALNIKLAEKLLEALARLQELNIALV

YLAVELTDPKRIADEIKKVKDKSKEIVERAEEEIARAAAESKKILDEAEEEIARAAAESKKILDEGSGSGSDAVA

ELQALNLKLAELLLEAVAELQALNLKLAELLLEAIAKLQELNIKLVELLTKLTDPATIREAIRKVKEDSERIVAE

AERLIAAAKAESERIIREAERLIAAAKAESERIIREGSGSGDPDVARLQELNIELARELLRDVARLQELNIELAR

ELLRAAAELQELNIKLVELASELTDPD[ENWSHPQFEKRESKRIVEDAERLIREAAAASEKISREAERLIREAAA

ASEKISRE]

>strepLOCKRa_309

(SEQ ID NO: 28)

(MGSSHHHHHHSSGLVPRGSHM)SKEAVTKLQALNIKLAEKLLEAVTKLQALNIKLAEKLLEALARLQELNIALV

YLAVELTDPKRIADEIKKVKDKSKEIVERAEEEIARAAAESKKILDEAEEEIARAAAESKKILDEGSGSGSDAVA

ELQALNLKLAELLLEAVAELQALNLKLAELLLEAIAKLQELNIKLVELLTKLTDPATIREAIRKVKEDSERIVAE

AERLIAAAKAESERIIREAERLIAAAKAESERIIREGSGSGDPDVARLQELNIELARELLRDVARLQELNIELAR

ELLRAAAELQELNIKLVELASELTDPD[EARKNWSHPQFEKKRIVEDAERLIREAAAASEKISREAERLIREAAA

ASEKISRE]

>strepLOCKRa_312 (SEQ ID NO: 29)
(MGSSHHHHHHSSGLVPRGSHM)SKEAVTKLQALNIKLAEKLLEAVTKLQALNIKLAEKLLEALARLQELNIALV
YLAVELTDPKRIADEIKKVKDKSKEIVERAEEEIARAAAESKKILDEAEEEIARAAAESKKILDEGSGSGSDAVA
ELQALNLKLAELLLEAVAELQALNLKLAELLLEAIAKLQELNIKLVELLTKLTDPATIREAIRKVKEDSERIVAE
AERLIAAAKAESERIIREAERLIAAAKAESERIIREGSGSGDPDVARLQELNIELARELLRDVARLQELNIELAR
ELLRAAAELQELNIKLVELASELTDPD[EARKAIA*NWSHPQFEK*VEDAERLIREAAAASEKISREAERLIREAAA
ASEKISRE]

>strepLOCKRa_313 (SEQ ID NO: 30)
(MGSSHHHHHHSSGLVPRGSHM)SKEAVTKLQALNIKLAEKLLEAVTKLQALNIKLAEKLLEALARLQELNIALV
YLAVELTDPKRIADEIKKVKDKSKEIVERAEEEIARAAAESKKILDEAEEEIARAAAESKKILDEGSGSGSDAVA
ELQALNLKLAELLLEAVAELQALNLKLAELLLEAIAKLQELNIKLVELLTKLTDPATIREAIRKVKEDSERIVAE
AERLIAAAKAESERIIREAERLIAAAKAESERIIREGSGSGDPDVARLQELNIELARELLRDVARLQELNIELAR
ELLRAAAELQELNIKLVELASELTDPD[EARKAIAR*NWSHPQFEK*EDAERLIREAAAASEKISREAERLIREAAA
ASEKISRE]

>strepLOCKRa_317 (SEQ ID NO: 31)
(MGSSHHHHHHSSGLVPRGSHM)SKEAVTKLQALNIKLAEKLLEAVTKLQALNIKLAEKLLEALARLQELNIALV
YLAVELTDPKRIADEIKKVKDKSKEIVERAEEEIARAAAESKKILDEAEEEIARAAAESKKILDEGSGSGSDAVA
ELQALNLKLAELLLEAVAELQALNLKLAELLLEAIAKLQELNIKLVELLTKLTDPATIREAIRKVKEDSERIVAE
AERLIAAAKAESERIIREAERLIAAAKAESERIIREGSGSGDPDVARLQELNIELARELLRDVARLQELNIELAR
ELLRAAAELQELNIKLVELASELTDPD[EARKAIARVKRE*NWSHPQFEK*RLIREAAAASEKISREAERLIREAAA
ASEKISRE]

>strepLOCKRa_320 (SEQ ID NO: 32)
(MGSSHHHHHHSSGLVPRGSHM)SKEAVTKLQALNIKLAEKLLEAVTKLQALNIKLAEKLLEALARLQELNIALV
YLAVELTDPKRIADEIKKVKDKSKEIVERAEEEIARAAAESKKILDEAEEEIARAAAESKKILDEGSGSGSDAVA
ELQALNLKLAELLLEAVAELQALNLKLAELLLEAIAKLQELNIKLVELLTKLTDPATIREAIRKVKEDSERIVAE
AERLIAAAKAESERIIREAERLIAAAKAESERIIREGSGSGDPDVARLQELNIELARELLRDVARLQELNIELAR
ELLRAAAELQELNIKLVELASELTDPD[EARKAIARVKRESKR*NWSHPQFEK*REAAAASEKISREAERLIREAAA
ASEKISRE]

>strepLOCKRa_323 (SEQ ID NO: 33)
(MGSSHHHHHHSSGLVPRGSHM)SKEAVTKLQALNIKLAEKLLEAVTKLQALNIKLAEKLLEALARLQELNIALV
YLAVELTDPKRIADEIKKVKDKSKEIVERAEEEIARAAAESKKILDEAEEEIARAAAESKKILDEGSGSGSDAVA
ELQALNLKLAELLLEAVAELQALNLKLAELLLEAIAKLQELNIKLVELLTKLTDPATIREAIRKVKEDSERIVAE
AERLIAAAKAESERIIREAERLIAAAKAESERIIREGSGSGDPDVARLQELNIELARELLRDVARLQELNIELAR
ELLRAAAELQELNIKLVELASELTDPD[EARKAIARVKRESKRIVE*NWSHPQFEK*AAASEKISREAERLIREAAA
ASEKISRE]

>strepLOCKRa_329 (SEQ ID NO: 34)
(MGSSHHHHHHSSGLVPRGSHM)SKEAVTKLQALNIKLAEKLLEAVTKLQALNIKLAEKLLEALARLQELNIALV
YLAVELTDPKRIADEIKKVKDKSKEIVERAEEEIARAAAESKKILDEAEEEIARAAAESKKILDEGSGSGSDAVA
ELQALNLKLAELLLEAVAELQALNLKLAELLLEAIAKLQELNIKLVELLTKLTDPATIREAIRKVKEDSERIVAE
AERLIAAAKAESERIIREAERLIAAAKAESERIIREGSGSGDPDVARLQELNIELARELLRDVARLQELNIELAR -continued ELLRAAAELQELNIKLVELASELTDPD[EARKAIARVKRESKRIVEDAERLI*NWSHPQFEK*ISREAERLIREAAA
ASEKISRE]

>SB13_LOCKR (SEQ ID NO: 35)

(<u>MGSSHHHHHHSSGLVPRGSHM</u>)GSKEAVTKLQALNIKLAEKLLEALARLQELNIALVYLAVELTDPKRIADEIK
KVKDKSKEIVERAEEEIARAAAESKKILDEGSGSGSDAVAELQALNLKLAELLLEAIAKLQELNIKLVELLTKLT
DPATIREAIRKVKEDSERIVAEAERLIAAAKAESERIIREGSGSGDPDVARLQELNIELARELLRAAAELQELNI
KLVELASEGSGSGSG[*YELRRALEELEKALRELKKSLDEIERSLEEIEKNPSEDALVENNRLNVENNKIIVEVLR*
*IIAEVLKINAKS*]

>ZCX12_LOCKR (SEQ ID NO: 36)

(<u>MGSSHHHHHHSSGLVPRGSHM</u>)GSKEAVTKLQALNIKLAEKLLEALARLQELNIALVYLAVELTDPKRIADEIK
KVKDKSKEIVERAEEEIARAAAESKKILDEGSGSGSDAVAELQALNLKLAELLLEAIAKLQELNIKLVELLTKLT
DPATIREAIRKVKEDSERIVAEAERLIAAAKAESERIIREGSGSGDPDVARLQELNIELARELLRAAAELQELNI
KLVELASEGSGSGSG[*KKLVEEVERALRELLKTSEDLVRKVEKALRELLELIRRGGTKDKIEEKIRRVLEEIKRE*
*LERQKRKIEDVLRQIKEELYRS*]

>SB13_LOCKR_extend18 (SEQ ID NO: 37)

(<u>MGSSHHHHHHSSGLVPRGSHM</u>)SKEAVTKLQALNIKLAEKLLEAVTKLQALNIKLAEKLLEALARLQELNIALV
YLAVELTDPKRIADEIKKVKDKSKEIVERAEEEIARAAAESKKILDEAEEEIARAAAESKKILDEGSGSGSDAVA
ELQALNLKLAELLLEAVAELQALNLKLAELLLEAIAKLQELNIKLVELLTKLTDPATIREAIRKVKEDSERIVAE
AERLIAAAKAESERIIREAERLIAAAKAESERIIREGSGSGDPDVARLQELNIELARELLRDVARLQELNIELAR
ELLRAAAELQELNIKLVELASEGSGSGSG[*YELRRALEELEKALRELKKSLDELERSLEELEKNPSEDALVENNR*
*LNVENNKIIVEVLRIIAEVLKINAKS*]

>ZCX12_LOCKR_extend18 (SEQ ID NO: 38)

(<u>MGSSHHHHHHSSGINPRGSHM</u>)SKEAVTKLQALNIKLAEKLLEAVTKLQALNIKLAEKLLEALARLQELNIALV
YLAVELTDPKRIADEIKKVKDKSKEIVERAEEEIARAAAESKKILDEAEEEIARAAAESKKILDEGSGSGSDAVA
ELQALNLKLAELLLEAVAELQALNLKLAELLLEAIAKLQELNIKLVELLTKLTDPATIREAIRKVKEDSERIVAE
AERLIAAAKAESERIIREAERLIAAAKAESERIIREGSGSGDPDVARLQELNIELARELLRDVARLQELNIELAR
ELLRAAAELQELNIKLVELASEGSGSGSG[*KKLVEEVERALRELLKTSEDLVRKVEKALRELLELIRRGGTKDKI*
*EEKIRRVLEEIKRELERQKRKIEDVLRQIKEELYRS*]

>fretLOCKRa (SEQ ID NO: 39)

(<u>GHHHHHHHHHHG</u>**VSKGEELFTGVVPILVELDGDVNGHKFSVSGEGEGDATYGKLTLKFICTTGKLPVPWPTLVT
TLSWGVQCFARYPDHMKQHDFFKSAMPEGYVQERTIFFKDDGNYKTRAEVKFEGDTLVNRIELKGIDFKEDGNIL
GHKLEYNYFSDNVYITADKQKNGIKANFKIRHNIEDGGVQLADHYQQNTPIGDGPVLLPDNHYLSTQSKLSKDPN
EKRDHMVLLEFVTAAGITLGMDELYK**<u>GSGCSLQGM</u>)SKEAVTKLQALNIKLAEKLLEAVTKLQALNIKLAEKLLE
ALARLQELNIALVYLAVELTDPKRIADEIKKVKDKSKEIVERAEEEIARAAAESKKILDEAEEEIARAAAESKKI
LDEGSGSGSDAVAELQALNLKLAELLLEAVAELQALNLKLAELLLEAIAKLQELNIKLVELLTKLTDPATIREAI
RKVKEDSERIVAEAERLIAAAKAESERIIREAERLIAAAKAESERIIREGSGSGDPDVARLQELNIELARELLRD
VARLQELNIELARELLRAAAELQELNIKLVELASELTDPD[EARKAIARVKRESKRIVEDAERLIREAAASEKI
SREAERLIREAAASEKISRE](**VSKGEELFTGVVPILVELDGDVNGHKFSVSGEGEGDATYGKLTLKLICTTGK
LPVPWPTLVTTLGYGVQCFARYPDHMKQHDFFKSAMPEGYVQERTIFFKDDGNYKTRAEVKFEGDTLVNRIELKG
IDFKEDGNILGHKLEYNYNSHNVYITADKQKNGIKANFKIRHNIEDGGVQLADHYQQNTPIGDGPVLLPDNHYLS
YQSKLSKDPNEKRDHMVLLEFVTAAGITLGMDELYK**)

-continued

>fretLOCKRb
(SEQ ID NO: 40)
(MGHHHHHHHHHHGVSKGEELFTGVVPILVELDGDVNGHKFSVSGEGEGDATYGKLTLKFICTTGKLPVPWPTLV
TTLSWGVQCFARYPDHM(QHDFFKSAMPEGYVQERTIFFKDDGNYKTRAEVKFEGDTLVNRIELKGIDFKEDGNI
LGHKLEYNYFSDNVYITADKQKNGIKANFKIRHNIEDGGVQLADHYQQNTPIGDGPVLLPDNHYLSTQSKLSKDP
NEKRDHMVLLEFVTAAGITLGMDELYKGSGCSLQGM) SHAAVIKLSDLNIRLLDKLLQAVIKLTELNAELNRKLI
EALQRLFDLNVALVHLAAELTDPKRIADEIKKVKDKSKEIVERAEEEIARAAAESKKILDEAEEEIARAAAESKK
ILDEGSGSGSDAVAELQALNLKLAELLLEAVAELQALNLKLAELLLEAIAKLQELNIKLVELLTKLTDPATIREA
IRKVKEDSERIVAEAERLIAAAKAESERIIREAERLIAAAKAESERIIREGSGSNDPQVAQNQETFIELARDALR
LVAENQEAFIEVARLTLRAAALAQEVAIKAVEAASEGGSGSG[NKEEIEKLAKEAREKLKKAEKEHKEIHDKLRK
KNKKAREDLKKKADELRETNKRVM](VSKGEELFTGVVPILVELDGDVNGHKFSVSGEGEGDATYGKLTLKLICT
TGKLPVPWPTLVTTLGYGVQCFARYPDHM(QHDFFKSAMPEGYVQERTIFFKDDGNYKTRAEVKFEGDTLVNRIE
LKGIDFKEDGNILGHKLEYNYNSHNVYITADKQKNGIKANFKIRHNIEDGGVQLADHYQQNTPIGDGPVLLPDNH
YLSYQSKLSKDPNEKRDHMVLLEFVTAAGITLGMDELYK)

>fretLOCKRc
(SEQ ID NO: 41)
(GHHHHHHHHHGVSKGEELFTGVVPILVELDGDVNGHKFSVSGEGEGDATYGKLTLKFICTTGKLPVPWPTLVT
TLSWGVQCFARYPDHMKQHDFFKSAMPEGYVQERTIFFKDDGNYKTRAEVKFEGDTLVNRIELKGIDFKEDGNIL
GHKLEYNYFSDNVYITADKQKNGIKANFKIRHNIEDGGVQLADHYQQNTPIGDGPVLLPDNHYLSTQSKLSKDPN
EKRDHMVLLEFVTAAGITLGMDELYKGSGCSLQGM) SLEAVLKLAELNLKLSDKLAEAVQKLAALLNKLLEKLSE
ALQRLFELNVALVTLAIELTDPKRIADEIKKVKDKSKEIVERAEEEIARAAAESKKILDEAEEEIARAAAESKKI
LDEGSGSGSDAVAELQALNLKLAELLLEAVAELQALNLKLAELLLEAIAKLQELNIKLVELLTKLTDPATIREAI
RKVKEDSERIVAEAERLIAAAKAESERIIREAERLIAAAKAESERIIREGSGSNDPLVARLQELLIEHARELLRL
VATSQEIFIELARAFLANAAQLQEAAIKAVEAASENGSGSGS[SEKVRRELKESLKENHKQNQKLLKDHKRAQEK
LNRELEEELKKKHKKTLDDIRRES](VSKGEELFTGVVPILVELDGDVNGHKFSVSGEGEGDATYGKLTLKLICTT
GKLPVPWPTLVTTLGYGVQCFARYPDHMKQHDFFKSAMPEGYVQERTIFFKDDGNYKTRAEVKFEGDTLVNRIEL
KGIDFKEDGNILGHKLEYNYNSHNVYITADKQKNGIKANFKIRHNIEDGGVQLADHYQQNTPIGDGPVLLPDNHY
LSYQSKLSKDPNEKRDHMVLLEFVTAAGITLGMDELYK)

>fretLOCKRd
(SEQ ID NO: 42)
(GHHHHHHHHHHGVSKGEELFTGVVPILVELDGDVNGHKFSVSGEGEGDATYGKLTLKFICTTGKLPVPWPTLVT
TLSWGVQCFARYPDHMKQHDFFKSAMPEGYVQERTIFFKDDGNYKTRAEVKFEGDTLVNRIELKGIDFKEDGNIL
GHKLEYNYFSDNVYITADKQKNGIKANFKIRHNIEDGGVQLADHYQQNTPIGDGPVLLPDNHYLSTQSKLSKDPN
EKRDHMVLLEFVTAAGITLGMDELYKGSGCSLQGM) SLEAVLKLFELNHKLSEKLLEAVLKLHALNQKLSQKLLE
ALARLLELNVALVELAIELTDPKRIADEIKKVKDKSKEIVERAEEEIARAAAESKKILDEAEEEIARAAAESKKI
LDEGSGSGSDAVAELQALNLKLAELLLEAVAELQALNLKLAELLLEAIAKLQELNIKLVELLTKLTDPATIREAI
RKVKEDSERIVAEAERLIAAAKAESERIIREAERLIAAAKAESERIIREGSGSGDPEVARLQEAFIEQAREILRN
VAAAQEALIEQARRLLALAALAQEAAIKAVELASEHGSGSG[DTVKRILEELRRRFEKLAKDLDDIARKLLEDHK
KHNKELKDKQRKIKKEADDAARS](VSKGEELFTGVVPILVELDGDVNGHKFSVSGEGEGDATYGKLTLKLICTT
GKLPVPWPTLVTTLGYGVQCFARYPDHMKQHDFFKSAMPEGYVQERTIFFKDDGNYKTRAEVKFEGDTLVNRIEL
KGIDFKEDGNILGHKLEYNYNSHNVYITADKQKNGIKANFKIRHNIEDGGVQLADHYQQNTPIGDGPVLLPDNHY
LSYQSKLSKDPNEKRDHMVLLEFVTAAGITLGMDELYK)

>tevLOCKR (SEQ ID NO: 43)

(MGSSHHHHHHSSGLVPRGSHM)SKEAVTKLQALNIKLAEKLLEAVTKLQALNIKLAEKLLEALARLQELNIALV
YLAVELTDPKRIADEIKKVKDKSKEIVERAEEEIARAAAESKKILDEAEEEIARAAAESKKILDEGSGSGSDAVA
ELQALNLKLAELLLEAVAELQALNLKLAELLLEAIAKLQELNIKLVELLTKLTDPATIREAIRKVKEDSERIVAE
AERLIAAAKAESERIIREAERLIAAAKAESERIIREGSGSGDPDVARLQELNIELARELLRDVARLQELNIELAR
ELLRAAAELQELNIKLVELASELTDPD[EARKAIARVKRESKRIVEDAE*ENLYFQG*AASEKISREAERLIREAAA
ASEKISRE]

>spyLOCKR (SEQ ID NO: 44)

(MGSSHHHHHHSSGLVPRGSHM)SKEAVTKLQALNIKLAEKLLEAVTKLQALNIKLAEKLLEALARLQELNIALV
YLAVELTDPKRIADEIKKVKDKSKEIVERAEEEIARAAAESKKILDEAEEEIARAAAESKKILDEGSGSGSDAVA
ELQALNLKLAELLLEAVAELQALNLKLAELLLEAIAKLQELNIKLVELLTKLTDPATIREAIRKVKEDSERIVAE
AERLIAAAKAESERIIREAERLIAAAKAESERIIREGSGSGDPDVARLQELNIELARELLRDVARLQELNIELAR
ELLRAAAELQELNIKLVELASELTDPD[EAR*AHIVMVDAYK*KRIVEDAERLIREAAAASEKISREAERLIREAAA
ASEKISRE]

>1_nesLOCKR (SEQ ID NO: 45)

SKEAVTKLQALNIKLAEKLLEAVTKLQALNIKLAEKLLEALARLQELNIALVYLAVELTDPKRIADEIKKVKDKS
KEIVERAEEEIARAAAESKKILDEAEEEIARAAAESKKILDEGSGSGSDAVAELQALNLKLAELLLEAVAELQAL
NLKLAELLLEAIAKLQELNIKLVELLTKLTDPATIREAIRKVKEDSERIVARAERLIAAAKAESERIIREAERLI
AAAKAESERIIREGSGSGDPDVARLQELNIELARELLRDVARLQELNIELARELLRAAAELQELNIKLVELASEL
TDPD[EARKAIARVKRESKRIVED*LALKLAGLDINS*EKISREAERLIREAAAASEKISRE]

>2_nesLOCKR (SEQ ID NO: 46)

SKEAVTKLQALNIKLAEKLLEAVTKLQALNIKLAEKLLEALARLQELNIALVYLAVELTDPKRIADEIKKVKDKS
KEIVERAEEEIARAAAESKKILDEAEEEIARAAAESKKILDEGSGSGSDAVAELQALNLKLAELLLEAVAELQAL
NLKLAELLLEAIAKLQELNIKLVELLTKLTDPATIREAIRKVKEDSERIVARAERLIAAAKAESERIIREAERLI
AAAKAESERIIREGSGSGDPDVARLQELNIELARELLRDVARLQELNIELARELLRAAAELQELNIKLVELASEL
TDPD[EARKAIARVKRESKRIVEDAERLIR*ELAEKLAGLDIN*AERLIREAAAASEKISRE]

>3_nesLOCKR (SEQ ID NO: 47)

SKEAVTKLQALNIKLAEKLLEAVTKLQALNIKLAEKLLEALARLQELNIALVYLAVELTDPKRIADEIKKVKDKS
KEIVERAEEEIARAAAESKKILDEAEEEIARAAAESKKILDEGSGSGSDAVAELQALNLKLAELLLEAVAELQAL
NLKLAELLLEAIAKLQELNIKLVELLTKLTDPATIREAIRKVKEDSERIVARAERLIAAAKAESERIIREAERLI
AAAKAESERIIREGSGSGDPDVARLQELNIELARELLRDVARLQELNIELARELLRAAAELQELNIKLVELASEL
TDPD[EARKAIARVKRESK*ELAEKLRAGLDLN*AAASEKISREAERLIREAAAASEKISRE]

>nlsLOCKR (SEQ ID NO: 48)

SKEAVTKLQALNIKLAEKLLEAVTKLQALNIKLAEKLLEALARLQELNIALVYLAVELTDPKRIADEIKKVKDKS
KEIVERAEEEIARAAAESKKILDEAEEEIARAAAESKKILDEGSGSGSDAVAELQALNLKLAELLLEAVAELQAL
NLKLAELLLEAIAKLQELNIKLVELLTKLTDPATIREAIRKVKEDSERIVARAERLIAAAKAESERIIREAERLI
AAAKAESERIIREGSGSGDPDVARLQELNIELARELLRDVARLQELNIELARELLRAAAELQELNIKLVELASEL
TDPD[EARKAIARVKRESKA*AAKRARTS*IREAAAASEKISREAERLIREAAAASEKISRE]

>ezh2LOCKR (SEQ ID NO: 49)

(MGSSHHHHHHSSGLVPRGSHM)SKEAVTKLQALNIKLAEKLLEAVTKLQALNIKLAEKLLEALARLQELNIALV
YLAVELTDPKRIADEIKKVKDKSKEIVERAEEEIARAAAESKKILDEAEEEIARAAAESKKILDEGSGSGSDAVA
ELQALNLKLAELLLEAVAELQALNLKLAELLLEAIAKLQELNIKLVELLTKLTDPATIREAIRKVKEDSERIVAE
AERLIAAAKAESERIIREAERLIAAAKAESERIIREGSGSGDPDVARLQELNIELARELLRDVARLQELNIELAR
ELLRAAAELQELNIKLVELASELTDPD[EARKAIARVK*TMFSSNRQKILERTETLNQEWKQRRIQ*AERLIREAAA
ASEKISRE]

>1fix_VMAc_C_BIMlatcht9

(SEQ ID NO: 51)

(MGSHHHHHHGSGSENLYFQG)SKKAAKKLQDLNIELARKLLEASTKLQRLNIRLAKALLEAIARLQELNLELVY
LAVELTDPKRIRDEIKEVKDKSKEIIRRAEKEIDDAAKESKKILEKARKAIRDAAEESRKILEEGSGSGSDALDE
LQKLNLELAKLL1KAIAETQDLNLRAAKAFLEAAAKLQELNIRAVELLVKLTDPATIRRALEHAKRRSKEIIDEA
ERAIRAAKRESERIIERARRLIEKAKEESERIIREGSGSGDPDIKKLQDLNIELARELLRAHAQLQRLNLELLRE
LLRALAQLQELNLDLLRLASELTGGSGGSGGS(**VLLNVLSKCAGSKKFRPAPAAAFARECRGFYFELQELKEDDY
YGITLSDDSDHQFLLANQVVVHNC**)GGSGGS[D*EIWIAQELRRIGDEFNAYY*ADAERLIREAAAASEKISREAER
LIREAA]

>sfGFP_VMAn_1fix_BIM_t0_latch (SEQ ID NO: 52)

(MGSHHHHHHGSGSENLYFQG)**HMSKGEELFTGVVPILVELDGDVNGHKFSVRGEGEGDATNGKLTLKFICTTGK
LPVPWPTLVTTLTYGVQCFARYPDHMKQHDFFKSAMPEGYVQERTISFKDDGTYKTRAEVKFEGDTLVNRIELKG
IDFKEDGNILGHKLEYNFNSHNVYITADKQKNGIKANFKIRHNVEDGSVQLADHYQQNTPIGDGPVLLPDNHYLS
TQSVLSKDPNEKRDHMVLLEFVTAAGITHGMDELYKSGSGSGCFAKGTNVLMADGSIECIENIEVGNKVMGKDGR
PREVIKLPRGRETMYSVVQKSQHRAHKSDSSREVPELLKFTCNATHELVVRTPRSVRRLSRTIKGVEYFEVITFE
MGQKKAPDGRIVELVKEVSKSYPISEGPERANELVESYRKASNKAYFEWTIEARDLSLLGSHVRKATYQTYAPIL**
YGGSGGSGGGGSGGSGSKEAAKKLQDLNIELARKLLEASTKLQRLNIRLAEALLEAIARLQELNLELVYLAVELT
DPKRIRDEIKEVKDKSKEIIRRAEKEIDDAAKESKKILEEARKAIRDAAEESRKILEEGSGSGSDALDELQKLNL
ELAKLLLKAIAETQDLNLRAAKAFLEAAAKLQELNIRAVELLVKLTDPATIRRALEHAKRRSKEIIDEAERAIRA
AKRESERIIEEARRLIEKAKEESERIIREGSGSGDPDIKKLQDLNIELARELLRAHAQLQRLNLELLRELLRALA
QLQELNLDLLRLASELT[D*EIWIAQELRRIGDEFNAYY*ADAERLSREAAAASEKISREAERSIREAAAASEKISR
E]

Asymmetrized functional Cages encoding Bim and GFP11 (i.e.: bioactive
peptides)
(6His-MBP-TEV, 6His-TEV, and flexible linker sequences are underlined text)
(Co-localization domain is bolded text)
(Functional peptide is italicized underlined text)
(Positions that can be mutated to any amino acid to tune responsiveness are
underlined bolded text)
(C-terminal sequences that can be removed to tune responsiveness are
italicized text)
(all sequences in parentheses are optional)

>1fix-long-BIM-t0

(SEQ ID NO: 54)

(MGSHHHHHHGSGSENLYFQG)SKEAAKKLQDLNIELARKLLEASTKLQRLNIRLAEALLEAIARLQELNLELVY
LAVELTDPKRIRDEIKEVKDKSKEIIRRAEKEIDDAAKESKKILEEARKAIRDAAEESRKILEEGSGSGSDALDE
LQKLNLELAKLLLKAIAETQDLNLRAAKAFLEAAAKLQELNIRAVELLVKLTDPATIRRALEHAKRRSKEIIDEA
ERAIRAAKRESERIIEEARRLIEKAKEESERIIREGSGSGDPDIKKLQDLNIELARELLRAHAQLQRLNLELLRE
LLRALAQLQELNLDLLRLASEL(TD[*EIWIAQELRRIGDEFNAYYA*)DAERLIREAAAASEKISREAERLIREAA
AASEKISRE]

```
>1fix-long-GFP-t0
                                                                    (SEQ ID NO: 55)
(MGSHHHHHHGSGSENLYFQG)SKEAAKKLQDLNIELARKLLEASTKLQRLNIRLAEALLEAIARLQELNLELVY

LAVELTDPKRIRDEIKEVKDKSKEIIRRAEKEIDDAAKESKKILEEARKAIRDAAEESRKILEEGSGSGSDALDE

LQKLNLELAKLLLKAIAETQDLNLRAAKAFLEAAAKLQELNIRAVELLVKLTDPATIRRALEHAKRRSKEIIDEA

ERAIRAAKRESERIIEEARRLIEKAKEESERIIREGSGSGDPDIKKLQDLNIELARELLRAHAQLQRLNLELLRE

LLRALAQLQELNLDLLRLASEL[(RDHMVLHEYVNAAGITFNAYYA)DAERLIREAAAASEKISREAERLIREAA

AASEKISRE]

>1fix-short-BIM-t0
                                                                    (SEQ ID NO: 56)
(MGSHHHHHHGSGSENLYFQGSGG)SELARKLLEASTKLQRLNIRLAEALLEAIARLQELNLELVYLAVELTDPK

RIRDEIKEVKDKSKEIIRRAEKEIDDAAKESEKILEEAREAISGSGSELAKLLLKAIAETQDLNLRAAKAFLEAA

AKLQELNIRAVELLVKLTDPATIREALEHAKRRSKEIIDEAERAIRAAKRESERIIEEARRLIEKGSGSGSELAR

ELLRAHAQLQRLNLELLRELLRALAQLQELNLDLLRLASEL(TD[EIWIAQELRRIGDEFNAYYA)DAERLIREA

AAASEKISREAERLIR]

>1fix-short-GFP-t0
                                                                    (SEQ ID NO: 57)
(MGSHHHHHHGSGSENLYFQGSGG)SELARKLLEASTKLQRLNIRLAEALLEAIARLQELNLELVYLAVELTDPK

RIRDEIKEVKDKSKEIIRRAEKEIDDAAKESEKILEEAREAISGSGSELAKLLLKAIAETQDLNLRAAKAFLEAA

AKLQELNIRAVELLVKLTDPATIREALEHAKRRSKEIIDEAERAIRAAKRESERIIEEARRLIEKGSGSGSELAR

ELLRAHAQLQRLNLELLRELLRALAQLQELNLDLLRLASEL[(RDHMVLHEYVNAAGITFNAYYA)DAERLIREA

AAASEKISREAERLIR]

>Spycatcher-1fix-long-GFP-t0
                                                                    (SEQ ID NO: 58)
(MGSHHHHHHGSGSENLYFQGS)AMVDTLSGLSSEQGQSGDMTIEEDSATHIKFSKRDEDGKELAGATMELRDSS

GKTISTWISDGQVKDFYLYPGKYTFVETAAPDGYEVATAITFTVNEQGQVTVNGKATKGSGGSKEAAKKLQDLNI

ELARKLLEASTKLQRLNIRLAEALLEAIARLQELNLELVYLAVELTDPKRIRDEIKEVKDKSKEIIRRAEKEIDD

AAKESKKILEEARKAIRDAAEESRKILEEGSGSGSDALDELQKLNLELAKLLLKAIAETQDLNLRAAKAFLEAAA

KLQELNIRAVELLVKLTDPATIRRALEHAKRRSKEIIDEAERAIRAAKRESERIIEEARRLIEKAKEESERIIRE

GSGSGDPDIKKLQDLNIELARELLRAHAQLQRLNLELLRELLRALAQLQELNLDLLRLASEL[(RDHMVLHEYVN

AAGITFNAYYA)DAERLIREAAAASEKISREAERLIREAAAASEKISRE]

>Spycatcher-1fix-short-GFP-t0
                                                                    (SEQ ID NO: 59)
(MGSHHHHHHGSGSENLYFQGS)AMVDTLSGLSSEQGQSGDMTIEEDSATHIKFSKRDEDGKELAGATMELRDSS

GKTISTWISDGQVKDFYLYPGKYTFVETAAPDGYEVATAITFTVNEQGQVTVNGKATKGSGGSELARKLLEASTK

LQRLNIRLAEALLEAIARLQELNLELVYLAVELTDPKRIRDEIKEVKDKSKEIIRRAEKEIDDAAKESEKILEEA

REAISGSGSELAKLLLKAIAETQDLNLRAAKAFLEAAAKLQELNIRAVELLVKLTDPATIREALEHAKRRSKEII

DEAERAIRAAKRESERIIEEARRLIEKGSGSGSELARELLRAHAQLQRLNLELLRELLRALAQLQELNLDLLRLA

SEL[(RDHMVLHEYVNAAGITFNAYYA)DAERLIREAAAASEKISREAERLIR]

>1fix-latch_Mad1SID_t0_1
                                                                    (SEQ ID NO: 61)
(MGSHHHHHHGSGSENLYFQG)SKEAAKKLQDLNIELARKLLEASTKLQRLNIRLAEALLEAIARLQELNLELVY

LAVELTDPKRIRDEIKEVKDKSKEIIRRAEKEIDDAAKESKKILEEARKAIRDAAEESRKILEEGSGSGSDALDE

LQKLNLELAKLLLKAIAETQDLNLRAAKAFLEAAAKLQELNIRAVELLVKLTDPATIRRALEHAKRRSKEIIDEA

ERAIRAAKRESERIIEEARRLIEKAKEESERIIREGSGSGDPDIKKLQDLNIELARELLRAHAQLQRLNLELLRE

LLRALAQLQELNLDLLRLASELT[(NIQMLLEAADYLE)RESKRIVEDAERLIREAAAASEKISREAERSIREAA

AASEKISRE]
```

-continued

>1fix-1atch_Mad1SID_T0_2

(SEQ ID NO: 65)

(MGSHHHHHGSGSENLYFQG)SKEAAKKLQDLNIELARKLLEASTKLQRLNIRLAEALLEAIARLQELNLELVY
LAVELTDPKRIRDEIKEVKDKSKEIIRRAEKEIDDAAKESKKILEEARKAIRDAAEESRKILEEGSGSGSDALDE
LQKLNLELAKLLLKAIAETQDLNLRAAKAFLEAAAKLQELNIRAVELLVKLTDPATIRRALEHAKRRSKEIIDEA
ERAIRAAKRESERIIEEARRLIEKAKEESERIIREGSGSGDPDIKKLQDLNIELARELLRAHAQLQRLNLELLRE
LLRALAQLQELNLDLLRLASELTDP[DEARK(*NIQMLLEAADYLE*)EDAERLIREAAAASEKISREAERLIREAA
SEKISRE]

>1fix-short-Bim-t0-relooped (SEQ ID NO: 67)

[MDEARKAIARVKRESKRI(*EIWIAQELRRIGDEFNAYYA*)EAEKLAT]DELWHRLLEASTKLQRLNIRLAEALL
EAIARLQELNLELVYLAVELTDPKRIRDEIKEVKDKSKEIIRRAEKEIDDAAKESEKILEEAREAISGSGSELAK
LLLKAIAETQDLNLRAAKAFLEAAAKLQELNIRAVELLVKLTDPATIREALEHAKRRSKEIIDEAERAIRAAKRE
SERIIEEARRLIEKGSGSGSELARELLRAHAQLQRLNLELLRELLRALAQLQELNLDLLRLASE

>1fix-short-spytag-t0_2

(SEQ ID NO: 68)

(MGSSHHHHHHSSGLVPRGSHM)SELARKLLEASTKLQRLNIRLAEALLEAIARLQELNLELVYLAVELTDPKRI
RDEIKEVKDKSKEIIRRAEKEIDDAAKESEKILEEAREAISGSGSELAKLLLKAIAETQDLNLRAAKAFLEAAAK
LQELNIRAVELLVKLTDPATIREALEHAKRRSKEIIDEAERAIRAAKRESERIIEEARRLIEKGSGSGSELAREL
LRAHAQLQRLNLELLRELLRALAQLQELNLDLLRLASELTDPD[EAR(*AHIVMVDAYK*)KRIVEDAERLIREAAA
ASEKISREAERLIR]

>1fix-short-spytag-t0_8

(SEQ ID NO: 69)

(MGSSHHHHHHSSGLVPRGSHM)SELARKLLEASTKLQRLNIRLAEALLEAIARLQELNLELVYLAVELTDPKRI
RDEIKEVKDKSKEIIRRAEKEIDDAAKESEKILEEAREAISGSGSELAKLLLKAIAETQDLNLRAAKAFLEAAAK
LQELNIRAVELLVKLTDPATIREALEHAKRRSKEIIDEAERAIRAAKRESERIIEEARRLIEKGSGSGSELAREL
LRAHAQLQRLNLELLRELLRALAQLQELNLDLLRLASELTDPD[EARKAIARVKRESK(*AHIVMVDAYK*)REAAA
ASEKISREAERLIR]

>1fix-short-TEV-t0_1

(SEQ ID NO: 70)

(MGSSHHHHHHSSGLVPRGSHM)SELARKLLEASTKLQRLNIRLAEALLEAIARLQELNLELVYLAVELTDPKRI
RDEIKEVKDKSKEIIRRAEKEIDDAAKESEKILEEAREAISGSGSELAKLLLKAIAETQDLNLRAAKAFLEAAAK
LQELNIRAVELLVKLTDPATIREALEHAKRRSKEIIDEAERAIRAAKRESERIIEEARRLIEKGSGSGSELAREL
LRAHAQLQRLNLELLRELLRALAQLQELNLDLLRLASELTDP[DEAR(*ENLYFQGS*)ESKRIVEDAERLIREAAA
ASEKISREAERLIR]

>1fix-short-TEV-t0_6

(SEQ ID NO: 71)

(MGSSHHHHHHSSGLVPRGSHM)SELARKLLEASTKLQRLNIRLAEALLEAIARLQELNLELVYLAVELTDPKRI
RDEIKEVKDKSKEIIRRAEKEIDDAAKESEKILEEAREAISGSGSELAKLLLKAIAETQDLNLRAAKAFLEAAAK
LQELNIRAVELLVKLTDPATIREALEHAKRRSKEIIDEAERAIRAAKRESERIIEEARRLIEKGSGSGSELAREL
LRAHAQLQRLNLELLRELLRALAQLQELNLDLLRLASELTDP[DEARKAIARVKRESKRIV(*ENLYFQGS*)EAAA
ASEKISREAERLIR]

>1fix-short-nanoBit-t0_1

(SEQ ID NO: 72)

(MGSSHHHHHHSSGLVPRGSHM)SELARKLLEASTKLQRLNIRLAEALLEAIARLQELNLELVYLAVELTDPKRI
RDEIKEVKDKSKEIIRRAEKEIDDAAKESEKILEEAREAISGSGSELAKLLLKAIAETQDLNLRAAKAFLEAAAK
LQELNIRAVELLVKLTDPATIREALEHAKRRSKEIIDEAERAIRAAKRESERIIEEARRLIEKGSGSGSELAREL

```
LRAHAQLQRLNLELLRELLRALAQLQELNLDLLRLASELTDP[DEAR(VSGWRLFKKIS)RIVEDAERLIREAAA

ASEKISREAERLIR]

>1fix-short-nanoBit-t0_3
                                                                    (SEQ ID NO: 73)
(MGSSHHHHHHSSGLVPRGSHM)SELARKLLEASTKLQRLNIRLAEALLEAIARLQELNLELVYLAVELTDPKRI

RDEIKEVKDKSKEIIRRAEKEIDDAAKESEKILEEAREAISGSGSELAKLLLKAIAETQDLNLRAAKAFLEAAAK

LQELNIRAVELLVKLTDPATIREALEHAKRRSKEIIDEAERAIRAAKRESERIIEEARRLIEKGSGSGSELAREL

LRAHAQLQRLNLELLRELLRALAQLQELNLDLLRLASELTDP[DEARKAIARVKRESK(VSGWRLFKKIS)EAAA

ASEKISREAERLIR]

>1fix-short-RHIM-t0_8
                                                                    (SEQ ID NO: 74)
(MGSSHHHHHHSSGLVPRGSHM)SELARKLLEASTKLQRLNIRLAEALLEAIARLQELNLELVYLAVELTDPKRI

RDEIKEVKDKSKEIIRRAEKEIDDAAKESEKILEEAREAISGSGSELAKLLLKAIAETQDLNLRAAKAFLEAAAK

LQELNIRAVELLVKLTDPATIREALEHAKRRSKEIIDEAERAIRAAKRESERIIEEARRLIEKGSGSGSELAREL

LRAHAQLQRLNLELLRELLRALAQLQELNLDLLRLASELTDP[DEARKAI(IQIG)RESKRIVEDAERLIREAAA

ASEKIS(VQLG)RLIR]

>1fix-short-RHIM-t0_19
                                                                    (SEQ ID NO: 75)
(MGSSHHHHHHSSGLVPRGSHM)SELARKLLEASTKLQRLNIRLAEALLEAIARLQELNLELVYLAVELTDPKRI

RDEIKEVKDKSKEIIRRAEKEIDDAAKESEKILEEAREAISGSGSELAKLLLKAIAETQDLNLRAAKAFLEAAAK

LQELNIRAVELLVKLTDPATIREALEHAKRRSKEIIDEAERAIRAAKRESERIIEEARRLIEKGSGSGSELAREL

LRAHAQLQRLNLELLRELLRALAQLQELNLDLLRLASELTDP[DEARKAIARVKRESKRIV(IQIG)RLI(VQLG

)AASEKISREAERLIR]

>1fix-short-RHIM-t0_22
                                                                    (SEQ ID NO: 76)
(MGSSHHHHHHSSGLVPRGSHM)SELARKLLEASTKLQRLNIRLAEALLEAIARLQELNLELVYLAVELTDPKRI

RDEIKEVKDKSKEIIRRAEKEIDDAAKESEKILEEAREAISGSGSELAKLLLKAIAETQDLNLRAAKAFLEAAAK

LQELNIRAVELLVKLTDPATIREALEHAKRRSKEIIDEAERAIRAAKRESERIIEEARRLIEKGSGSGSELAREL

LRAHAQLQRLNLELLRELLRALAQLQELNLDLLRLASELTDP[DEARKAIARVKRESKRIV(IQIG)RLIREAAA

ASEKIS(VQLG)RLIR]

>1fix-short-gcn4-t0_4
                                                                    (SEQ ID NO: 77)
(MGSSHHHHHHSSGLVPRGSHM)SELARKLLEASTKLQRLNIRLAEALLEAIARLQELNLELVYLAVELTDPKRI

RDEIKEVKDKSKEIIRRAEKEIDDAAKESEKILEEAREAISGSGSELAKLLLKAIAETQDLNLRAAKAFLEAAAK

LQELNIRAVELLVKLTDPATIREALEHAKRRSKEIIDEAERAIRAAKRESERIIEEARRLIEKGSGSGSELAREL

LRAHAQLQRLNLELLRELLRALAQLQELNLDLLRLASELTDP[DESVKE(LEDKVEELLSKNYHLENEVARLKKL

VGER)SREAERLIR]

>1fix-short-ccDi-t0_6
                                                                    (SEQ ID NO: 78)
(MGSSHHHHHHSSGLVPRGSHM)SELARKLLEASTKLQRLNIRLAEALLEAIARLQELNLELVYLAVELTDPKRI

RDEIKEVKDKSKEIIRRAEKEIDDAAKESEKILEEAREAISGSGSELAKLLLKAIAETQDLNLRAAKAFLEAAAK

LQELNIRAVELLVKLTDPATIREALEHAKRRSKEIIDEAERAIRAAKRESERIIEEARRLIEKGSGSGSELAREL

LRAHAQLQRLNLELLRELLRALAQLQELNLDLLRLASELTDP[DEARKAIA(GEIAALKQEIAALKKENAALKWE

IAALKQG)AERLIR]

>1fix-short-cc-a-t0_6
                                                                    (SEQ ID NO: 79)
(MGSSHHHHHHSSGLVPRGSHM)SELARKLLEASTKLQRLNIRLAEALLEAIARLQELNLELVYLAVELTDPKRI

RDEIKEVKDKSKEIIRRAEKEIDDAAKESEKILEEAREAISGSGSELAKLLLKAIAETQDLNLRAAKAFLEAAAK
```

-continued

LQELNIRAVELLVKLTDPATIREALEHAKRRSKEIIDEAERAIRAAKRESERIIEEARRLIEKGSGSGSELAREL
LRAHAQLQRLNLELLRELLRALAQLQELNLDLLRLASELTDP[DEARKAIARVKR(*GLEQEIAALEKENAALEWE
IAALEQGG*)ERLIR]

>1fix-short-cc-b-t0_6 (SEQ ID NO: 80)
(MGSSHHHHHHSSGLVPRGSHM)SELARKLLEASTKLQRLNIRLAEALLEAIARLQELNLELVYLAVELTDPKRI
RDEIKEVKDKSKEIIRRAEKEIDDAAKESEKILEEAREAISGSGSELAKLLLKAIAETQDLNLRAAKAFLEAAAK
LQELNIRAVELLVKLTDPATIREALEHAKRRSKEIIDEAERAIRAAKRESERIIEEARRLIEKGSGSGSELAREL
LRAHAQLQRLNLELLRELLRALAQLQELNLDLLRLASELTDP[DEARKAIARVKR(*GLKQKIAALKYKNAALKKK
IAALKQGG*)ERLIR STREPII-LOCKR functional Cages:
>STREPII-2plus1_LOCK_1 (SEQ ID NO: 81)
SRVEEIIEDLRRLLEEIRKENADSIRASKELLDRVKEINDTIIAELERLLKDIEKEVREKGSESEEVKKALRRVL
EELEKLLRRVAEINEEVLRRNSKLVEEDARRNAEVLKELKRLVEELMREIGDED[KVRKVAEVAEKVLRDIDKLD
R(*WSHPQFEK*)TNGEISKLDEDTRRVAERVKKAIEDLAK]

>STREPII-2plus1_LOCK_2 (SEQ ID NO: 82)
[SEVDEIIADNERALDEVRREVEEIDKENAERLGE(*WSHPQFEK*)GDRLAKALEEIRK]GVRSRLVDELERAIRE
VEEVIRRVLERVRRLIEEVSKIITDVLREVERLHEEVTKELRKVEDGNSREALDALRRLIEKVVEDSARLIKKVD
EALKAVNKEIEDLSREVADLVRAVAEELDARVK >STREPII-2plus1_LOCK_3 (SEQ ID NO: 83)
SSDEVLKEIEEIIRRLEAEVRRVNAEVNASTEDLAREVEEVLRATNELIEELERRVTGTEELKRVIDELRDRDRK
VRRRVERVIEESAKRDDESRKRLTRAVEKLRADLKKLADDGVPE[EALSKAIKDVRDIVKKVKDELKE(*WSHPQF
EK*)VDRLSEELKEWLKDVERVLKELTDKDR]

>STREPII-2plus1_LOCK_4C (SEQ ID NO: 84)
SDAEELLKRVADLLKASLESLEKILRDSKELMDRWRKKLEDLLRESEELVDRAEKILRRGGSDKEVLDKIAEEVR
RTNDDSRRLDEELHRLSRDTLRKLEENLRRTEKEVREMDKRAAERG[VDERVREELKKLLTRVE(*WSHPQFEK*)G
DKKILKEAHKESKEVNDRDRELLERLEESVR]

>STREPII-2plus1_LOCK_4N (SEQ ID NO: 85)
[SDAEELLKRVADLLKASLESLEKILRDSKELMDR(*WSHPQFEK*)LGESEELVDRAEKILRR]GGSDKEVLDKIA
EEVRRTNDDSRRLDEELHRLSRDTLRKLEENLRRTEKEVREMDKRAAERGVDERVREELKKLLTRVEEEHRKVLE
TDKKILKEAHKESKEVNDRDRELLERLEESVR >STREPII-3plus1_LOCK_1 (SEQ ID NO: 86)
SEAEDLLERVKRVLDELIEIVDRNHELNARVVETSARLVERLLEEVERALETLEREIPGRELLDKAIKDLRDVLR
RVAEKVKRSIEELKEVLEESRRVLEEVVRALAEVIDRVRRLVEKGVDLRDLIRELKRVLEEAVSLIERLVRLNTR
AAEKDNESLRELVRAIKEALKRAVDMVRADGL[DSRLVKKLDEIVKEVAKKLEDVVRANEEL(*WSHPQFEK*)GSS
VARLREAVERVARDLEETAR]

>STREPII-3plus1_LOCK_2 (SEQ ID NO: 87)
[SDEERLEKVVKDVIEKVRRILEK(*WSHPQFEK*)GSELRRILEEWEKIIREVLDKVRR]GSGSADALVEVLEEIL
RLAEELSKRVEEVLREILKLAKALSDELVKVLAEIVEAAKRISRDDELRKAVEDVARELEDLAAKDRKILDDVRE
ALERIAKEDKDILREAEETLRRLADEMRRSGVDERLLKRVVDILARLLELNATTIERLLRILEELLKLNKELAER
VIRVLEKLLEEIKR >STREPII-3plus1_LOCK3 (SEQ ID NO: 88)
SVLETVKKALEDSSEKIERIVEEDERVAKESSDRIRRLVEEDKRVADEILDLIEKGGDTDTLAKLVEEWSRTSKK
LLDDVLKLHKDWSDDSRRLLEEILRVHEELIRAVKEILDRGGKPEEVVRELEKVLKESLDTLEEIIRRLDEANAR
TVKRVADVIRELEDANAKVLEEIERKGD[DKDAVIKVIEELIRANAAV(*WSHPQFEK*)GDLVRVNKTVWKELLRV
NEKLARDLERVVK]

>STREPII-3plus1_LOCK_4 (SEQ ID NO: 89)
[SLVDELRKSLERNVRVSEEVARRLKEALGR(*WSHPQFEK*)GGDLIRLNEDVVRVVEKV]GVDESAIERVRRIIE
ELNRALDAVLKKNEDLVRRLTELLDKLLEENRRLVEELDEDLKRRGGTEEVIDTILELIERSIERLKRLLDELLR
IVREALKDNARVADENLKALKEILDELRKDGVSDEELKRVLEKAADLHARLKDAHRKLLEDLERIIRELKKKLDE
VVEENKRSVDELKR >STREPII-3plus1_LOCK3-relooped (SEQ ID NO: 90)
[MKDAVIKVIEELIRANAAV(*WSHPQFEK*)GDLVRVNKTVWKELLRVNEKLARDLERAL]DERDVSAWETVKKAL
EDSSEKIERIVEEDERVAKESSDRIRRLVEEDKRVADEILDLIEKGGDTDTLAKLVEEWSRTSKKLLDDVLKLHK
DWSDDSRRLLEEILRVHEELIRAVKEILDRGGAPEEVVRELEKVLKESLDTLEEIIRRLDEANARTVKRVADVIR
ELEDANAKVLEEIERK >STREPII-2plus1_LOCK3-relooped (SEQ ID NO: 91)
[MEEAASKAIKDVRDIVKKVKDELKE(*WSHPQFEK*)VDRLSEELKEWLKDVERVLKELT]DREEASEEELKRVID
ELRDRDRKVRRRVERVIEESAKRDDESRKRLTRAVEKLRADLKKLSVEGASDEVLKEIEEIIRRLEAEVRRVNAE
VNASTEDLAREVEEVLRATNELIEELERR >BimLOCKR_a_short_Nterm (SEQ ID NO: 27094)
[MDEARKAIARVKRESKRI(*EIWIAQELRRIGDEFNAYYA*)EAEKLATDEL]WHRLLEASTKLQRLNIRLAEALL
EAIARLQELNLELVYLAVELTDPKRIRDEIKEVKDKSKEIIRRAEKEIDDAAKESEKILEEAREAISGSGSELAK
LLLKAIAETQDLNLRAAKAFLEAAAKLQELNIRAVELLVKLTDPATIREALEHAKRRSKEIIDEAERAIRAAKRE
SERIIEEARRLIEKGSGSGSELARELLRAHAQLQRLNLELLRELLRALAQLQELNLDLLRLASE >BimILOCKR_g (SEQ ID NO: 27095)
[MSLVDEL(*EIWIAQELRRIGDEFNAYYA*)ALKRWVDVVRKVVEDLIRLNEDVVRVVEKV]GVDESAIERVRRII
EELNRALDAVLKKNEDLVRRLTELLDKLLEENRRLVEELDEDLKRRGGTEEVIDTILELIERSIERLKRLLDELL
RIVREALKDNARVADENLKALKEILDELRKDGVSDEELKRVLEKAADLHARLKDAHRKLLEDLERIIRELKKKLD
EVVEENKRSVDELKR >reloop_strepLOCKRh (SEQ ID NO: 27096)
[MKDAVIKVIEELIRANAAV(*WSHPQFEK*)GDLVRVNKTVWKELLRVNEKLARDLERALDER]DVSAWETVKKAL
EDSSEKIERIVEEDERVAKESSDRIRRLVEEDKRVADEILDLIEKGGDTDTLAKLVEEWSRTSKKLLDDVLKLHK
DWSDDSRRLLEEILRVHEELIRAVKEILDRGGAPEEVVRELEKVLKESLDTLEEIIRRLDEANARTVKRVADVIR
ELEDANAKVLEEIERK >reloop_strepLOCKRi (SEQ ID NO: 27097)
[MEEAASKAIKDVRDIVKKVKDELKE(*WSHPQFEK*)VDRLSEELKEWLKDVERVLKELTDREEA]SEEELKRVID
ELRDRDRKVRRRVERVIEESAKRDDESRKRLTRAVEKLRADLKKLSVEGASDEVLKEIEEIIRRLEAEVRRVNAE
VNASTEDLAREVEEVLRATNELIEELERR

```
>spyLOCKRa_2
                                                     (SEQ ID NO: 27098)
MSELARKLLEASTKLQRLNIRLAEALLEAIARLQELNLELVYLAVELTDPKRIRDEIKEVKDKSKEIIRRAEKEI

DDAAKESEKILEEAREAISGSGSELAKLLLKAIAETQDLNLRAAKAFLEAAAKLQELNIRAVELLVKLTDPATIR

EALEHAKRRSKEIIDEAERAIRAAKRESERIIEEARRLIEKGSGSGSELARELLRAHAQLQRLNLELLRELLRAL

AQLQELNLDLLRLASELTDP[DEAR(AHIVMVDAYK)KRIVEDAERLIREAAAASEKISREAERLIR]

>spyLOCKRa_8
                                                     (SEQ ID NO: 27099)
MSELARKLLEASTKLQRLNIRLAEALLEAIARLQELNLELVYLAVELTDPKRIRDEIKEVKDKSKEIIRRAEKEI

DDAAKESEKILEEAREAISGSGSELAK+32KAIAETQDLNLRAAKAFLEAAAKLQELNIRAVELLVKLTDPATIR

EALEHAKRRSKEIIDEAERAIRAAKRESERIIEEARRLIEKGSGSGSELARELLRAHAQLQRLNLELLRELLRAL

AQLQELNLDLLRLASELTDPDEARKAIARVKRESK(AHIVMVDAYK)REAAAASEKISREAERLIR]
```

>tevLOCKRa_1
                                                     (SEQ ID NO: 27100)
```
MSELARKLLEASTKLQRLNIRLAEALLEAIARLQELNLELVYLAVELTDPKRIRDEIKEVKDKSKEIIRRAEKEI

DDAAKESEKILEEAREAISGSGSELAKLLLKAIAETQDLNLRAAKAFLEAAAKLQELNIRAVELLVKLTDPATIR

EALEHAKRRSKEIIDEAERAIRAAKRESERIIEEARRLIEKGSGSGSELARELLRAHAQLQRLNLELLRELLRAL

AQLQELNLDLLRLASELTDP[DEAR(ENLYFQGS)ESKRIVEDAERLIREAAAASEKISREAERLIR]
```

>tevLOCKRa_6
                                                     (SEQ ID NO: 27101)
```
MSELARKLLEASTKLQRLNIRLAEALLEAIARLQELNLELVYLAVELTDPKRIRDEIKEVKDKSKEIIRRAEKEI

DDAAKESEKILEEAREAISGSGSELAKLLLKAIAETQDLNLRAAKAFLEAAAKLQELNIRAVELLVKLTDPATIR

EALEHAKRRSKEIIDEAERAIRAAKRESERIIEEARRLIEKGSGSGSELARELLRAHAQLQRLNLELLRELLRAL

AQLQELNLDLLRLASELTDP[DEARKAIARVKRESKRIV(ENLYFQGS)EAAAASEKISREAERLIR]
```

>lucLOCKRa_1
                                                     (SEQ ID NO: 27102)
```
MSELARKLLEASTKLQRLNIRLAEALLEAIARLQELNLELVYLAVELTDPKRIRDEIKEVKDKSKEIIRRAEKEI

DDAAKESEKILEEAREAISGSGSELAKLLLKAIAETQDLNLRAAKAFLEAAAKLQELNIRAVELLVKLTDPATIR

EALEHAKRRSKEIIDEAERAIRAAKRESERIIEEARRLIEKGSGSGSELARELLRAHAQLQRLNLELLRELLRAL

AQLQELNLDLLRLASELTDP[DEAR(VSGWRLFEKIS)RIVEDAERLIREAAAASEKISREAERLIR]
```

>lucLOCKRa_3
                                                     (SEQ ID NO: 27103)
```
MSELARKLLEASTKLQRLNIRLAEALLEAIARLQELNLELVYLAVELTDPKRIRDEIKEVKDKSKEIIRRAEKEI

DDAAKESEKILEEAREAISGSGSELAKLLLKAIAETQDLNLRAAKAFLEAAAKLQELNIRAVELLVKLTDPATIR

EALEHAKRRSKEIIDEAERAIRAAKRESERIIEEARRLIEKGSGSGSELARELLRAHAQLQRLNLELLRELLRAL

AQLQELNLDLLRLASELTDP[DEARKAIARVKRESK(VSGWRLFKKIS)EAAAASEKISREAERLIR]
```

>rhimLOCKRa_8
                                                     (SEQ ID NO: 27104)
```
MSELARKLLEASTKLQRLNIRLAEALLEAIARLQELNLELVYLAVELTDPKRIRDEIKEVKDKSKEIIRRAEKEI

DDAAKESEKILEEAREAISGSGSELAKLLLKAIAETQDLNLRAAKAFLEAAAKLQELNIRAVELLVKLTDPATIR

EALEHAKRRSKEIIDEAERAIRAAKRESERIIEEARRLIEKGSGSGSELARELLRAHAQLQRLNLELLRELLRAL

AQLQELNLDLLRLASELTDP[DEARKAI(IQIG)RESKRIVEDAERLIREAAAASEKIS(VQLG)RLIR]
```

>rhimLOCKRa_19
                                                     (SEQ ID NO: 27105)
```
MSELARKLLEASTKLQRLNIRLAEALLEAIARLQELNLELVYLAVELTDPKRIRDEIKEVKDKSKEIIRRAEKEI

DDAAKESEKILEEAREAISGSGSELAKLLLKAIAETQDLNLRAAKAFLEAAAKLQELNIRAVELLVKLTDPATIR

EALEHAKRRSKEIIDEAERAIRAAKRESERIIEEARRLIEKGSGSGSELARELLRAHAQLQRLNLELLRELLRAL

AQLQELNLDLLRLASELTDP[DEARKAIARVKRESKRIV(IQIG)RLI(VQLG)AASEKISREAERLIR]
```

```
>rhimLOCKRa_22
                                                 (SEQ ID NO: 27106)
MSELARKLLEASTKLQRLNIRLAEALLEAIARLQELNLELVYLAVELTDPKRIRDEIKEVKDKSKEIIRRAEKEI

DDAAKESEKILEEAREAISGSGSELAKLLLKAIAETQDLNLRAAKAFLEAAAKLQELNIRAVELLVKLTDPATIR

EALEHAKRRSKEIIDEAERAIRAAKRESERIIEEARRLIEKGSGSGSELARELLRAHAQLQRLNLELLRELLRAL

AQLQELNLDLLRLASELTDP[DEARKAIARVKRESKRIV(IQIG)RLIREAAAASEKIS(VQLG)RLIR]

>gcn4LOCKRa_4
                                                 (SEQ ID NO: 27107)
MSELARKLLEASTKLQRLNIRLAEALLEAIARLQELNLELVYLAVELTDPKRIRDEIKEVKDKSKEIIRRAEKEI

DDAAKESEKILEEAREAISGSGSELAKLLLKAIAETQDLNLRAAKAFLEAAAKLQELNIRAVELLVKLTDPATIR

KALEHAKRRSKEIIDEAERAIRAAKRESERIIEEARRLIEKGSGSGSELARELLRAHAQLQRLNLELLRELLRAL

AQLQELNLDLLRLASELTDP[DESVKE(LEDKVEELLSKNYHLENEVARLKKLVGER)SREAERLIR]

>cc-DiLOCKRa_6
                                                 (SEQ ID NO: 27108)
MSELARKLLEASTKLQRLNIRLAEALLEAIARLQELNLELVYLAVELTDPKRIRDEIKEVKDKSKEIIRRAEKEI

DDAAKESEKILEEAREAISGSGSELAKLLLKAIAETQDLNLRAAKAFLEAAAKLQELNIRAVELLVKLTDPATIR

KALEHAKRRSKEIIDEAERAIRAAKRESERIIEEARRLIEKGSGSGSELARELLRAHAQLQRLNLELLRELLRAL

AQLQELNLDLLRLASELTDP[DEARKAIA(GEIAALKQEIAALKKENAALKWEIAALKQG)AERLIR]

>cc-aLOCKRa_6
                                                 (SEQ ID NO: 27109)
MSELARKLLEASTKLQRLNIRLAEALLEAIARLQELNLELVYLAVELTDPKRIRDEIKEVKDKSKEIIRRAEKEI

DDAAKESEKILEEAREAISGSGSELAKLLLKAIAETQDLNLRAAKAFLEAAAKLQELNIRAVELLVKLTDPATIR

KALEHAKRRSKEIIDEAERAIRAAKRESERIIEEARRLIEKGSGSGSELARELLRAHAQLQRLNLELLRELLRAL

AQLQELNLDLLRLASELTDP[DEARKAIARVKR(GLEQEIAALEKENAALEWEIAALEQGG)ERLIR]

>cc-bLOCKRa_6
                                                 (SEQ ID NO: 27110)
MSELARKLLEASTKLQRLNIRLAEALLEAIARLQELNLELVYLAVELTDPKRIRDEIKEVKDKSKEIIRRAEKEI

DDAAKESEKILEEAREAISGSGSELAKLLLKAIAETQDLNLRAAKAFLEAAAKLQELNIRAVELLVKLTDPATIR

KALEHAKRRSKEIIDEAERAIRAAKRESERIIEEARRLIEKGSGSGSELARELLRAHAQLQRLNLELLRELLRAL

AQLQELNLDLLRLASELTDP[DEARKAIARVKR(GLKQKIAALKYRNAALKKKIAALKQGG)ERLIR]

>tev-spyLOCKRa_short_40
                                                 (SEQ ID NO: 27111)
SELARKLLEASTKLQRLNIRLAEALLEAIARLQELNLELVYLAVELTDPKRIRDEIKEVKDKSKEIIRRAEKEID

DAAKESEKILEEAREAISGSGSELAKLLLKAIAETQDLNLRAAKAFLEAAAKLQELNIRAVELLVKLTDPATIRE

ALEHAKRRSKEIIDEAERAIRAAKRESERIIEEARRLIEKGSGSGSELARELLRAHAQLQRLNLELLRELLRALA

QLQELNLDLLRLASELTDP[DEARKAI(ENLYFQGS)RIVEDAE(AHIVMVDAYK)EKISREAERLIR]

>tev-spyLOCKRa_short_57
                                                 (SEQ ID NO: 27112)
SELARKLLEASTKLQRLNIRLAEALLEAIARLQELNLELVYLAVELTDPKRIRDEIKEVKDKSKEIIRRAEKEID

DAAKESEKILEEAREAISGSGSELAKLLLKAIAETQDLNLRAAKAFLEAAAKLQELNIRAVELLVKLTDPATIRE

ALEHAKRRSKEIIDEAERAIRAAKRESERIIEEARRLIEKGSGSGSELARELLRAHAQLQRLNLELLRELLRALA

QLQELNLDLLRLASELTDP[DEARKAIARV(ENLYFQGS)EDAERLIREA(AHIVMVDAYK)AERLIR]

>tev-spyLOCKRa_short_63
                                                 (SEQ ID NO: 27113)
SELARKLLEASTKLQRLNIRLAEALLEAIARLQELNLELVYLAVELTDPKRIRDEIKEVKDKSKEIIRRAEKEID

DAAKESEKILEEAREAISGSGSELAKLLLKAIAETQDLNLRAAKAFLEAAAKLQELNIRAVELLVKLTDPATIRE

ALEHAKRRSKEIIDEAERAIRAAKRESERIIEEARRLIEKGSGSGSELARELLRAHAQLQRLNLELLRELLRALA

QLQELNLDLLRLASELTDP[DEARKAIARVK(ENLYFQGS)DAERLIREA(AHIVMVDAYK)AERLIR]
```

>tev-spyLOCKRa_29

(SEQ ID NO: 27114)

SKEAAKKLQDLNIELARKLLEASTKLQRLNIRLAEALLEAIARLQELNLELVYLAVELTDPKRIRDEIKEVKDKS

KEIIRRAEKEIDDAAKESKKILEEARKAIRDAAEESRKILEEGSGSGSDALDELQKLNLELAKLLLKAIAETQDL

NLRAAKAFLEAAAKLQELNIRAVELLVKLTDPATIRRALEHAKRRSKEIIDEAERAIRAAKRESERIIEEARRLI

EKAKEESERIIREGSGSGDP[DIKKLQDLNIELARELLRAHAQLQRLNLELLRELLRALAQLQELNLDLLRLASE

LTDPDEARKAIARVK(*ENLYFQGS*)DAERLIREAAAASE(*AHIVMVDAYK*)REAAAASEKISRE]

>tev-spyLOCKRa_32

(SEQ ID NO: 27115)

SKEAAKKLQDLNIELARKLLEASTKLQRLNIRLAEALLEAIARLQELNLELVYLAVELTDPKRIRDEIKEVKDKS

KEIIRRAEKEIDDAAKESKKILEEARKAIRDAAEESRKILEEGSGSGSDALDELQKLNLELAKLLLKAIAETQDL

NLRAAKAFLEAAAKLQELNIRAVELLVKLTDPATIRRALEHAKRRSKEIIDEAERAIRAAKRESERIIEEARRLI

EKAKEESERIIREGSGSGDP[DIKKLQDLNIELARELLRAHAQLQRLNLELLRELLRALAQLQELNLDLLRLASE

LTDPDEARKAIARVK(*ENLYFQGS*)DAERLIREAAAASEKISREAE(*AHIVMVDAYK*) EKISRE]

>Bim-fretLOCKRa_short (SEQ ID NO: 27116)

(**VSKGEELFTGVVPILVELDGDVNGHKFSVSGEGEGDATYGKLTLKFICTTGKLPVPWPTLVTTLSWGVQCFARY
PDHMKQHDFFKSAMPEGYVQERTIFFKDDGNYKTRAEVKFEGDTLVNRIELKGIDFKEDGNILGHKLEYNYFSDN
VYITADKQKNGIKANFKIRHNIEDGGVQLADHYQQNTPIGDGPVLLPDNHYLSTQSKLSKDPNEKRDHMVLLEFV
TAAGITLE**)LARKLLEASTKLQRLNIRLAEALLEAIARLQELNLELVYLAVELTDPKRIRDEIKEVKDKSKEIIR

RAEKEIDDAAKESEKILEEAREAISGSGSELAKLLLKAIAETQDLNLRAAKAFLEAAAKLQELNIRAVELLVKLT

DPATIREALEHAKRRSKEIIDEAERAIRAAKRESERIIEEARRLIEKGSGSGSELARELLRAHAQLQRLNLELLR

ELLRALAQLQELNLDLLRLASELTED(*EIWIAQELRRIGDEFNAYYA*)DAERLIREAAAASEKISREAERLIR](

**VSKGEELFTGVVPILVELDGDVNGHKFSVSGEGEGDATYGKLTLKLICTTGKLPVPWPTLVTTLGYGVQCFARYP
DHMKQHDFFKSAMPEGYVQERTIFFKDDGNYKTRAEVKFEGDTLVNRIELKGIDFKEDGNILGHKLEYNYNSHNV
YITADKQKNGIKANFKIRHNIEDGGVQLADHYQQNTPIGDGPVLLPDNHYLSYQSKLSKDPNEKRDHMVLLEFVT
AAGITLGMDELYKGSGC**)

>fretLOCKRa_short (SEQ ID NO: 27117)

(**VSKGEELFTGVVPILVELDGDVNGHKFSVSGEGEGDATYGKLTLKFICTTGKLPVPWPTLVTTLSWGVQCFARY
PDHMKQHDFFKSAMPEGYVQERTIFFKDDGNYKTRAEVKFEGDTLVNRIELKGIDFKEDGNILGHKLEYNYFSDN
VYITADKQKNGIKANFKIRHNIEDGGVQLADHYQQNTPIGDGPVLLPDNHYLSTQSKLSKDPNEKRDHMVLLEFV
TAAGITL**)ELARKLLEASTKLQRLNIRLAEALLEAIARLQELNLELVYLAVELTDPKRIRDEIKEVKDKSKEIIR

RAEKEIDDAAKESEKILEEAREAISGSGSELAKLLLKAIAETQDLNLRAAKAFLEAAAKLQELNIRAVELLVKLT

DPATIREALEHAKRRSKEIIDEAERAIRAAKRESERIIEEARRLIEKGSGSGSELARELLRAHAQLQRLNLELLR

ELLRALAQLQELNLDLLRLASELTDP[DEARKAIARVKRESNAYYADAERLIREAAAASEK](**VSKGEELFTGVV
PILVELDGDVNGHKFSVSGEGEGDATYGKLTLKLICTTGKLPVPWPTLVTTLGYGVQCFARYPDHMKQHDFFKSA
MPEGYVQERTIFFKDDGNYKTRAEVKFEGDTLVNRIELKGIDFKEDGNILGHKLEYNYNSHNVYITADKQKNGIK
ANFKIRHNIEDGGVQLADHYQQNTPIGDGPVLLPDNHYLSYQSKLSKDPNEKRDHMVLLEFVTAAGITLGMDELY
KGSGC**)

E18_KR1B_full (SEQ ID NO: 27120)

MSKEAVTKLQALNIKLAEKLLEAVTKLQALNIKLAEKLLEALARLQELNIALVYLAVELTDPKRIADEIKKVKDK

SKEIVERAEEEIARAAAESKKILDEAEEEIARAAAESKKILDEGSGSGSDAVAELQALNLKLAELLLEAVAELQA

LNLKLAELLLEAIAKLQELNIKLVELLTKLTDPATIREAIRKVKEDSERIVAEAERLIAAAKAESERIIREAERL

-continued

IAAAKAESERIIREGSGSGDPDVARLQELNIELARELLRDVARLQELNIELARELLRAAAELQELNIKLVELASE

LTGS[(*RTLVTFKDVFVDFTREEWKLLDTAQQIVYRNVMLENYKNLVSLGY*G)SDEARKAIARVKRESKRIVEDA

ERLIREAAAASEKISREAER]IIREAAAASEKISRE]

E18_KR1B_N13t (SEQ ID NO: 27121)

MSKEAVTKLQALNIKLAEKLLEAVTKLQALNIKLAEKLLEALARLQELNIALVYLAVELTDPKRIADEIKKVKDK

SKEIVERAEEEIARAAAESKKILDEAEEEIARAAAESKKILDEGSGSGSDAVAELQALNLKLAELLLEAVAELQA

LNLKLAELLLEAIAKLQELNIKLVELLTKLTDPATIREAIRKVKEDSERIVAEAERLIAAAKAESERIIREAERL

IAAAKAESERIIREGSGSGDPDVARLQELNIELARELLRDVARLQELNIELARELLRAAAELQELNIKLVELASE

LTGS[(*RTLVTFKDVFVDFTREEWKLLDTAQQIVYRNVMLENYKNLVSLGY*)GSSKRIVEDAERLIREAAAASEK

ISREAERLIREAAAASEKISRE]

E18_KR1B_C9t (SEQ ID NO: 27122)

MSKEAVTKLQALNIKLAEKLLEAVTKLQALNIKLAEKLLEALARLQELNIALVYLAVELTDPKRIADEIKKVKDK

SKEIVERAEEEIARAAAESKKILDEAEEEIARAAAESKKILDEGSGSGSDAVAELQALNLKLAELLLEAVAELQA

LNLKLAELLLEAIAKLQELNIKLVELLTKLTDPATIREAIRKVKEDSERIVAEAERLIAAAKAESERIIREAERL

IAAAKAESERIIREGSGSGDPDVARLQELNIELARELLRDVARLQELNIELARELLRAAAELQELNIKLVELASE

LTGS[(*RTLVTFKDVFVDFTREEWKLLDTAQQIVYRNVMLENYKNLVSLGY*)GSDEARKAIARVKRESKRIVEDA

ERLIREAAAASEKISREAERLIREAA]

E18_KR1B_Cterm1

(SEQ ID NO: 27123)

MSKEAVTKLQALNIKLAEKLLEAVTKLQALNIKLAEKLLEALARLQELNIALVYLAVELTDPKRIADEIKKVKDK

SKEIVERAEEEIARAAAESKKILDEAEEEIARAAAESKKILDEGSGSGSDAVAELQALNLKLAELLLEAVAELQA

LNLKLAELLLEAIAKLQELNIKLVELLTKLTDPATIREAIRKVKEDSERIVAEAERLIAAAKAESERIIREAERL

IAAAKAESERIIREGSGSGDPDVARLQELNIELARELLRDVARLQELNIELARELLRAAAELQELNIKLVELASE

LT[DEARKAIARVKRESKRIVEDAE(*RTLVTFKDVFVDFTREEWKLLDTAQQIVYRNVMLENYKNLVSLGY*)]

E18_KR1B_Cterm2

(SEQ ID NO: 27124)

MSKEAVTKLQALNIKLAEKLLEAVTKLQALNIKLAEKLLEALARLQELNIALVYLAVELTDPKRIADEIKKVKDK

SKEIVERAEEEIARAAAESKKILDEAEEEIARAAAESKKILDEGSGSGSDAVAELQALNLKLAELLLEAVAELQA

LNLKLAELLLEAIAKLQELNIKLVELLTKLTDPATIREAIRKVKEDSERIVAEAERLIAAAKAESERIIREAERL

IAAAKAESERIIREGSGSGDPDVARLQELNIELARELLRDVARLQELNIELARELLRAAAELQELNIKLVELASE

LT[DEARKAIARVKRESKRIVEDAERLI(*RTLVTFKDVFVDFTREEWKLLDTAQQIVYRNVMLENYKNLVSLGY*)]

E18_KRAB_Cterm3

(SEQ ID NO: 27125)

MSKTAVTKALNIKLAEKLLEAVTKLQALNIKLAEKLLEALARLQELNIALVYLAVELTDPKRIADEIKKVKDK

SKEIVERAEEEIARAAAESKKILDEAEEEIARAAAESKKILDEGSGSGSDAVAELQALNLKLAELLLEAVAELQA

LNLKLAELLLEAIAKLQELNIKLVELLTKLTDPATIREAIRKVKEDSERIVAEAERLIAAAKAESERIIREAERL

IAAAKAESERIIREGSGSGDPDVARLQELNIELARELLRDVARLQELNIELARELLRAAAELQELNIKLVELASE

LT[DEARKAIARVKRESKRIVEDAERLIREAAAASEKIS*RTLVTFKDVFVDFTREEWKLLDTAQQIVYRNVMLEN*

*YKNLVSLGY*)]

>3plus1_Cage_Nterm_GFP11_668

(SEQ ID NO: 27,278)

DEAKELLDEIRKAVKESEDRLEKLLRDYEKELRRDHMVLHEYVNAAGITLEELRRGSLDAKELLKTLEDLLREVL

EVARRVVETLKELNRRVLEVVREDIEANERLLRRVLDTLRRGGVDERRIKDLERLIRESLKKAEEVLREAAEKSR

EIVDEIREVLKRADEALKRIIKKIRETRGADALSRLLEELLRVVDDLIRVLKELIDKSRKVIEELLELLKRINEE

NLKVLAEIIK

```
>3plus1_Cage_Cterm_GFP11_668
                                                      (SEQ ID NO: 27,279)
DEAKELLDEIRKAVKESEDRLEKLLRDYEKELRRLEKELRDLKRRIEEKLEELRRGSLDAKELLKTLEDLLREVL

EVARRVVETLKELNRRVLEVVREDIERNERLLRRVLDTLRRGGVDERRIKDLERLIRESLKKAEEVLREAAEKSR

EIVDEIREVLKRADEALKRIIKKIRETRGADADHMVLHEYVNAAGITIRVLKELIDKSRKVIEELLELLKRINEE

NLKVLAEIIK

>3plus1_Cage_Cterm_GFP11_668
                                                      (SEQ ID NO: 27,280)
DEAKELLDEIRKAVKESEDRLEKLLRDYEKELRRLEKELRDLKRRIEEKLEELRRGSLDAKELLKTLEDLLREVL

EVARRVVETLKELNRRVLEVVREDIERNERLLRRVLDTLRRGGVDERRIKDLERLIRESLKKAEEVLREAAEKSR

EIVDEIREVLKRADEALKRIIKKIRETRGADARDHMVLHEYVNAAGITRVLKELIDKSRKVIEELLELLKRINEE

NLKVLAEIIK

>3plus1_Cage_Cterm_GFP11_668
                                                      (SEQ ID NO: 27,281)
DEAKELLDEIRKAVKESEDRLEKLLRDYEKELRRLEKELRDLKRRIEEKLEELRRGSLDAKELLKTLEDLLREVL

EVARRVVETLKELNRRVLEVVREDIERNERLLRRVLDTLRRGGVDERRIKDLERLIRESLKKAEEVLREAAEKSR

EIVDEIREVLKRADEALKRIIKKIRETRGADALSRDHMVLHEYVNAAGITLKELIDKSRKVIEELLELLKRINEE

NLKVLAEIIK

>3plus1_Cage_Cterm_GFP11_668
                                                      (SEQ ID NO: 27,282)
DEAKELLDEIRKAVKESEDRLEKLLRDYEKELRRLEKELRDLKRRIEEKLEELRRGSLDAKELLKTLEDLLREVL

EVARRVVETLKELNRRVLEVVREDIERNERLLRRVLDTLRRGGVDERRIKDLERLIRESLKKAEEVLREAAEKSR

EIVDEIREVLKRADEALKRIIKKIRDHMVLHEYVNAAGITLRVVDDLIRVLKELIDKSRKVIEELLELLKRINEE

NLKVLAEIIK

>3plus1_Cage_Nterm_GFP11_669
                                                      (SEQ ID NO: 27,283)
SEKEKLLKESEEEVRRLRRTLEELLRKYREVLERLRDHMVLHEYVNAAGITRLKEVLDRSGLDIDTIIKEVEDLL

KTVLDRLRELLDKIARLTKEAIEVVREIIERIVRHAERVKDELRKGGADKRKLDRVDRLIKENTRHLKEILDRIE

DLVRRSEKKLRDIIREVRRLIEELRKKAEEIKKDPDERLVKTLIEDVERVIKRILELITRVAEDNERVLERIIRE

LTDNLERHLKIVREIVK

>3plus1_Cage_Nterm_GFP11_670
                                                      (SEQ ID NO: 27,284)
SEKEDLARKLRKLVEELTREYEELVKKLERLIEEIERDHMVLHEYVNAAGITISEEVRKLGTDERVLKRLLERLR

RIIEEDHELNTELLKRLLDLLKEILDTSRELLKRLLDILRKGVRDEEVLRDLERTLREVLEENERAIEEAERVLR

KVLEDSERAVRDARRVLAEVDKSPTGDEALRKLVELLVEVLRRLIRVNRELVKLLREVLERLLRILRESVKKLKR

LIEKVIKDAT

>3plus1_Cage_Cterm_GFP11_670
                                                      (SEQ ID NO: 27,285)
SEKEDLARKLRKLVEELTREYEELVKKLERLIEEIEKVSEESVRKLEKLLREISEEVRKLGTDERVLKRLLERLR

RIIEEDHELNTELLKRLLDLLKEILDTSRELLKRLLDILRKGVRDEEVLRDLERTLREVLEENERAIEEAERVLR

KVLEDSERAVRDARRVLAEVDKSPTGDEARDHMVLHEYVNAAGITRVNRELVKLLREVLERLLRILRESVKKLKR

LIEKVIKDAT

>3plus1_Cage_Cterm_GFP11_670
                                                      (SEQ ID NO: 27,286)
SEKEDLARKLRKLVEELTREYEELVKKLERLIEEIEKVSEESVRKLEKLLREISEEVRKLGTDERVLKRLLERLR

RIIEEDHELNTELLKRLLDLLKEILDTSRELLKRLLDILRKGVRDEEVLRDLERTLREVLEENERAIEEAERVLR

KVLEDSERAVRDARRVLAEVDKSPTGDERDHMVLHEYVNAAGITIRVNRELVKLLREVLERLLRILRESVKKLKR

LIEKVIKDAT
```

-continued

>3plus1_Cage_Cterm_GFP11_670
(SEQ ID NO: 27,287)
SEKEDLARKLRKLVEELTREYEELVKKLERLIEEIEKVSEESVRKLEKLLREISEEVRKLGTDERVLKRLLERLR

RIIEEDHELNTELLKRLLDLLKEILDTSRELLKRLLDILRKGVRDEEVLRDLERTLREVLEENERAIEEAERVLR

KVLEDSERAVRDARRVLAEVDKSPTGRDHMVLHEYVNAAGITRLIRVNRELVKLLREVLERLLRILRESVKKLKR

LIEKVIKDAT

>3plus1_Cage_Nterm_GFP11_670
(SEQ ID NO: 27,288)
SEKEDLARKLRKLVEELTREYEELVKKLERLIEEIRDHMVLHEYVNAAGITEISEEVRKLGTDERVLKRLLERLR

RIIEEDHELNTELLKRLLDLLKEILDTSRELLKRLLDILRKGVRDEEVLRDLERTLREVLEENERAIEEAERVLR

KVLEDSERAVRDARRVLAEVDKSPTGDEALRKLVELLVEVLRRLIRVNRELVKLLREVLERLLRILRESVKKLKR

LIEKVIKDAT

>3plus1_Cage_Cterm_GFP11_670
(SEQ ID NO: 27,289)
SEKEDLARKLRKLVEELTREYEELVKKLERLIEEIEKVSEESVRKLEKLLREISEEVRKLGTDERVLKRLLERLR

RIIEEDHELNTELLKRLLDLLKEILDTSRELLKRLLDILRKGVRDEEVLRDLERTLREVLEENERAIEEAERVLR

KVLEDSERAVRDARRVLAEVDKSPTRDHMVLHEYVNAAGITRRLIRVNRELVKLLREVLERLLRILRESVKKLKR

LIEKVIKDAT

>3plus1_Cage_Nterm_GFP11_670
(SEQ ID NO: 27,290)
SEKEDLARKLRKLVEELTREYEELVKKLERLIERDHMVLHEYVNAAGITLREISEEVRKLGTDERVLKRLLERLR

RIIEEDHELNTELLKRLLDLLKEILDTSRELLKRLLDILRKGVRDEEVLRDLERTLREVLEENERAIEEAERVLR

KVLEDSERAVRDARRVLAEVDKSPTGDEALRKLVELLVEVLRRLIRVNRELVKLLREVLERLLRILRESVKKLKR

LIEKVIKDAT

>3plus1_Cage_Nterm_GFP11_670
(SEQ ID NO: 27,291)
SEKEDLARKLRKLVEELTREYEELVKKLERLIEEIEKRDHMVLHEYVNAAGITSEEVRKLGTDERVLKRLLERLR

RIIEEDHELNTELLKRLLDLLKEILDTSRELLKRLLDILRKGVRDEEVLRDLERTLREVLEENERAIEEAERVLR

KVLEDSERAVRDARRVLAEVDKSPTGDEALRKLVELLVEVLRRLIRVNRELVKLLREVLERLLRILRESVKKLKR

LIEKVIKDAT

>3plus1_Cage_Nterm_GFP11_670
(SEQ ID NO: 27,292)
SEKEDLARKLRKLVEELTREYEELVKKLERLIEEIEKVSEESRDHMVLHEYVNAAGITKLGTDERVLKRLLERLR

RIIEEDHELNTELLKRLLDLLKEILDTSRELLKRLLDILRKGVRDEEVLRDLERTLREVLEENERAIEEAERVLR

KVLEDSERAVRDARRVLAEVDKSPTGDEALRKLVELLVEVLRRLIRVNRELVKLLREVLERLLRILRESVKKLKR

LIEKVIKDAT

>3plus1_Cage_Nterm_GFP11_670
(SEQ ID NO: 27,293)
SEKEDLARKLRKLVEELTREYEELVKKLERLIEEIEKVSEESVRDHMVLHEYVNAAGITLGTDERVLKRLLERLR

RIIEEDHELNTELLKRLLDLLKEILDTSRELLKRLLDILRKGVRDEEVLRDLERTLREVLEENERAIEEAERVLR

KVLEDSERAVRDARRVLAEVDKSPTGDEALRKLVELLVEVLRRLIRVNRELVKLLREVLERLLRILRESVKKLKR

LIEKVIKDAT

>3plus1_Cage_Cterm_GFP11_671
(SEQ ID NO: 27,294)
SEEEDLLERVKRVLDELIEIVDRNHELNRRVVETSAALVERLLEEVERALETLEREIPGSSLLDKAIKDLRDVLR

RVKEKVKRSIEELKEVLEESRRVLEEVVRKLREVIDRVRRLVEKGVDLRDLIRELKRVLEEAVKLIERLVRLNTR

AAEKDNESLRELVRAIKEALKRAVDAVRKGGLDSRAVKKLDRDHMVLHEYVNAAGITNEELWRALVELNKESVRR

LREIVERVARDLEETAR

```
>3plus1_Cage_Cterm_GFP11_671
                                                    (SEQ ID NO: 27,295)
SEEEDLLERVKRVLDELIEIVDRNHELNRRVVETSAALVERLLEEVERALETLEREIPGSSLLDKAIKDLRDVLR

RVKEKVKRSIEELKEVLEESRRVLEEVVRKLREVIDRVRRLVEKGVDLRDLIRELKRVLEEAVKLIERLVRLNTR

AAEKDNESLRELVRAIKEALKRAVDAVRKGGLDSRARDHMVLHEYVNAAGITDVVRRNEELWRALVELNKESVRR

LREIVERVARDLEETAR

>3plus1_Cage_Cterm_GFP11_671
                                                    (SEQ ID NO: 27,296)
SEEEDLLERVKRVLDELIEIVDRNHELNRRVVETSAALVERLLEEVERALETLEREIPGSSLLDKAIKDLRDVLR

RVKEKVKRSIEELKEVLEESRRVLEEVVRKLREVIDRVRRLVEKGVDLRDLIRELKRVLEEAVKLIERLVRLNTR

AAEKDNESLRELVRAIKEALKRAVDAVRKGGLDSRRDHMVLHEYVNAAGITEDVVRRNEELWRALVELNKESVRR

LREIVERVARDLEETAR

>3plus1_Cage_Cterm_GFP11_671
                                                    (SEQ ID NO: 27,297)
SEEEDLLERVKRVLDELIEIVDRNHELNRRVVETSAALVERLLEEVERALETLEREIPGSSLLDKAIKDLRDVLR

RVKEKVKRSIEELKEVLEESRRVLEEVVRKLREVIDRVRRLVEKGVDLRDLIRELKRVLEEAVKLIERLVRLNTR

AAEKDNESLRELVRAIKEALKRAVDAVRKGGLRDHMVLHEYVNAAGITKKLEDVVRRNEELWRALVELNKESVRR

LREIVERVARDLEETAR

>3plus1_Cage_Cterm_GFP11_672
                                                    (SEQ ID NO: 27,298)
DETEEVIKKIAKLIDELIETLKKIVEDSAKLIKELIDLLEEIIKRSADLIRELEKVSKRGDRDRLKKLIDRMRRE

TERALEELRRVIEELKEATERALKTIEDLIREIEEAIRRELGDEDLAREILEVIRRILELLREDMELNLRALEEI

LRLLEEVIKLNKDAIDEILELLKRDHMVLHEYVNAAGITESKKLVRDVVEEAKRLLKENRDSTRKIIEDIRRLLR

KIEDSTR

>3plus1_Cage_Cterm_GFP11_672
                                                    (SEQ ID NO: 27,299)
DETEEVIKKIAKLIDELIETLKKIVEDSAKLIKELIDLLEEIIKRSADLIRELEKVSKRGDRDRLKKLIDRMRRE

TERALEELRRVIEELKEATERALKTIEDLIREIEEAIRRELGDEDLAREILEVIRRILELLREDMELNLRALEEI

LRLLEEVIKLNKDAIDEILELLKGRDHMVLHEYVNAAGITSKKLVRDVVEEAKRLLKENRDSTRKIIEDIRRLLR

KIEDSTR

>3plus1_Cage_Nterm_GFP11_67>3
                                                    (SEQ ID NO: 27,300)
SKEETLRKEAEDLLRRLEELTRRLEKKARELLERAKKLSRDLARDHMVLHEYVNAAGITEELIKVLEEVAKTSID

LNKEVIDVIRRVIEESLELNKRVLDVLRRVLDIAARKGRDKKAIRDVVREAARVIKEVIDEDEKVNRDLKRVIER

VIDDDRKALERLRKAVEEVASRGDDEAAKRLVEELLKAVTDLSRKNKRILEELLKAIETLSDENKKILTEILDAL

RRLVEKIEK

>3plus1_Cage_Nterm_GFP11_67>3
                                                    (SEQ ID NO: 27,301)
SKEETLRKEAEDLLRRLEELTRRLEKKARELLERAKKLSRRDHMVLHEYVNAAGITGVPEELIKVLEEVAKTSID

LNKEVIDVIRRVIEESLELNKRVLDVLRRVLDIAARKGRDKKAIRDVVREAARVIKEVIDEDEKVNRDLKRVIER

VIDDDRKALERLRKAVEEVASRGDDEAAKRLVEELLKAVTDLSRKNKRILEELLKAIETLSDENKKILTEILDAL

RRLVEKIEK

>3plus1_Cage_Cterm_GFP11_67>3
                                                    (SEQ ID NO: 27,302)
SKEETLRKEAEDLLRRLEELTRRLEKKARELLERAKKLSRDLAEELKRLLKELREKGVPEELIKVLEEVAKTSID

LNKEVIDVIRRVIEESLELNKRVLDVLRRVLDIAARKGRDKKAIRDVVREAARVIKEVIDEDEKVNRDLKRVIER

VIDDDRKALERLRKAVEEVASRGDDEARDHMVLHEYVNAAGITRKNKRILEELLKAIETLSDENKKILTEILDAL

RRLVEKIEK
```

-continued

>3plus1_Cage_Nterm_GFP11_67>3
(SEQ ID NO: 27,303)
SKEETLRKEAEDLLRRLEELTRRLEKKARELLERARDHMVLHEYVNAAGITELREKGVPEELIKVLEEVAKTSID

LNKEVIDVIRRVIEESLELNKRVLDVLRRVLDIAARKGRDKKAIRDVVREAARVIKEVIDEDEKVNRDLKRVIER

VIDDDRKALERLRKAVEEVASRGDDEAAKRLVEELLKAVTDLSRKNKRILEELLKAIETLSDENKKILTEILDAL

RRLVEKIEK

>3plus1_Cage_Nterm_GFP11_67>3
(SEQ ID NO: 27,304)
SKEETLRKEAEDLLRRLEELTRRLEKKARELLERAKKLSRDHMVLHEYVNAAGITKGVPEELIKVLEEVAKTSID

LNKEVIDVIRRVIEESLELNKRVLDVLRRVLDIAARKGRDKKAIRDVVREAARVIKEVIDEDEKVNRDLKRVIER

VIDDDRKALERLRKAVEEVASRGDDEAAKRLVEELLKAVTDLSRKNKRILEELLKAIETLSDENKKILTEILDAL

RRLVEKIEK

>3plus1_Cage_Nterm_GFP11_67>3
(SEQ ID NO: 27,305)
SKEETLRKEAEDLLRRLEELTRRLEKKARELLERAKKLRDHMVLHEYVNAAGITEKGVPEELIKVLEEVAKTSID

LNKEVIDVIRRVIEESLELNKRVLDVLRRVLDIAARKGRDKKAIRDVVREAARVIKEVIDEDEKVNRDLKRVIER

VIDDDRKALERLRKAVEEVASRGDDEAAKRLVEELLKAVTDLSRKNKRILEELLKAIETLSDENKKILTEILDAL

RRLVEKIEK

>3plus1_Cage_Nterm_GFP11_67>3
(SEQ ID NO: 27,306)
SKEETLRKEAEDLLRRLEELTRRLEKKARELLERAKKLSRDLRDHMVLHEYVNAAGITPEELIKVLEEVAKTSID

LNKEVIDVIRRVIEESLELNKRVLDVLRRVLDIAARKGRDKKAIRDVVREAARVIKEVIDEDEKVNRDLKRVIER

VIDDDRKALERLRKAVEEVASRGDDEAAKRLVEELLKAVTDLSRKNKRILEELLKAIETLSDENKKILTEILDAL

RRLVEKIEK

>3plus1_Cage_Nterm_GFP11_674
(SEQ ID NO: 27,307)
SEREEVKEKLDRLLEEVEKTVRELKREHDELLKEVEKLVRDLKRDHMVLHEYVNAAGITKEILDVIREHVRTNKE

ILDRVLEVVEEHLRRNKEILDKLLDDIRKVVEDAKRILGIGDDETLRRAVRRILEELRKLVEDIRKKVKDSLETL

ERALEEAEERIRRSLEDLKRVLKEAKDKTKDKDRLDKVEELVKKLLEDTKRTVDRVRELVRKILKKSRETLEELE

RLIEKILRELEKDAR

>3plus1_Cage_Cterm_GFP11_674
(SEQ ID NO: 27,308)
SEREEVKEKLDRLLEEVEKTVRELKREHDELLKEVEKLVRDLKKEHDELLKKVKDDGVPKEILDVIREHVRTNKE

ILDRVLEVVEEHLRRNKEILDKLLDDIRKVVEDAKRILGIGDDETLRRAVRRILEELRKLVEDIRKKVKDSLETL

ERALEEAEERIRRSLEDLKRVLKEAKDKTKDKDRDHMVLHEYVNAAGITKRTVDRVRELVRKILKKSRETLEELE

RLIEKILRELEKDAR

>3plus1_Cage_Nterm_GFP11_675
(SEQ ID NO: 27,309)
SERETVKRRLEELLKEVKRTLDKLKEEHDRLLEDVRRVVEELRDHMVLHEYVNAAGITPEELLRVIAKVLETNKR

ILDDLLRVVKKHVDLNKEILDRILEMIKEIVERVKRVLGDGDEKTLRDKIRDIIRRLEDAAREAEERVRRSLEEL

KKAVEKIRKKIEDSLRELEEALKRVRDKEEDDKRLEDISRLVKRLLDESRRVLRELEETIRKRAEESKRVLEEVK

RLVEKLIRELRKEAE

>3plus1_Cage_Nterm_GFP11_676
(SEQ ID NO: 27,310)
SEDEIIKKIIEDLRRVLKEVEEIHKEVEERLDKRDHMVLHEYVNAAGITDRVLDEVKRIGDVETVLRLAIEAVRR

ALEIVRKVTEDLIRVVRKLLEIVDAVNKRVKKAVEDVLKLLRDTLKGSKDVERVLDEARRLLEKLHRDSRRILKR

IAELLDELKELSERILERIKRLLEEVERRGSDDERLLEELIEELKDLIRRHIELLRRLIERLKELLKKHIEDLRR

LLEEIEKLLEEARK

-continued

>3plus1_Cage_Nterm_GFP11_677 (SEQ ID NO: 27,311)
SREEVLRELEEVIEDNRRLLEELIEKSKKVLDESLKLIDELLRRDHMVLHEYVNAAGITSKGDDEETARRIVTKI
RKELEDVLDEVRRIVKEILDRDRRVAEDLKRVVDENLEKLKKVLDELDKKLGDRRLVEILRDIVRLLIEINERAL
RELLKLHEEHTRIVAELLRELERVVEELRRLVELIARGEISEDDLKRVVDEVEKKLRELKRRYKEALERIKEKIK
ELKDRYERAVREVVAELRKTTK >3plus1_Cage_Cterm_GFP11_677 (SEQ ID NO: 27,312)
SREEVLRELEEVIEDNRRLLEELIEKSKKVLDESLKLIDELLRRLEEVLERVLRLLEELSKGDDEETARRIVTKI
RKELEDVLDEVRRIVKEILDRDRRVAEDLKRVVDENLEKLKKVLDELDKKLGDRRLVEILRDIVRLLIEINERAL
RELLKLHEEHTRIVAELLRELERVVEELRRLVELIARGEISEDDRDHMVLHEYVNAAGITRRYKEALERIKEKIK
ELKDRYERAVREVVAELRKTTK >3plus1_Cage_Cterm_GFP11_677 (SEQ ID NO: 27,313)
SREEVLRELEEVIEDNRRLLEELIEKSKKVLDESLKLIDELLRRLEEVLERVLRLLEELSKGDDEETARRIVTKI
RKELEDVLDEVRRIVKEILDRDRRVAEDLKRVVDENLEKLKKVLDELDKKLGDRRLVEILRDIVRLLIEINERAL
RELLKLHEEHTRIVAELLRELERVVEELRRLVELIARGERDHMVLHEYVNAAGITLRELKRRYKEALERIKEKIK
ELKDRYERAVREVVAELRKTTK >3plus1_Cage_Nterm_GFP11_678 (SEQ ID NO: 27,314)
SKAEEIAEKLDRLLEENRRALEEITTRLDDLLRRDHMVLHEYVNAAGITLDDLRRGGIREELLKRIADVIRDIMR
LLKELHDHTAEVIKTIKKLLKELHDINKEIIERLKRLKDGNVPKEELLKRVEELVRTSARLTTEVLKTVEKLIRD
DKRLSEEILKRVKELIEELKRGVDSERVKEILERILRVVEEAVRLNEESLRRILDVVRKAVKLDRESLKKILDVV
EEAVR >3plus1_Cage_Cterm_GFP11_678 (SEQ ID NO: 27,315)
SKAEEIAEKLDRLLEENRRALEEITTRLDDLLRRNKDALRKVMEKLKRLLDDLRRGGIREELLKRIADVIRDIMR
LLKELHDHTAEVIKTIKKLLKELHDINKEIIERLKRLKDGNVPKEELLKRVEELVRTSARLTTEVLKTVEKLIRD
DKRLSEEILKRVKELIEELRDHMVLHEYVNAAGITLRVVEEAVRLNEESLRRILDVVRKAVKLDRESLKKILDVV
EEAVR >3plus1_Cage_Nterm_GFP11_678 (SEQ ID NO: 27,316)
SKAEEIAEKLDRLLEENRRALEEITTRLDDLLRRNKDRDHMVLHEYVNAAGITRRGGIREELLKRIADVIRDIMR
LLKELHDHTAEVIKTIKKLLKELHDINKEIIERLKRLKDGNVPKEELLKRVEELVRTSARLTTEVLKTVEKLIRD
DKRLSEEILKRVKELIEELKRGVDSERVKEILERILRVVEEAVRLNEESLRRILDVVRKAVKLDRESLKKILDVV
EEAVR >3plus1_Cage_Cterm_GFP11_678 (SEQ ID NO: 27,317)
SKAEEIAEKLDRLLEENRRALEEITTRLDDLLRRNKDALRKVMEKLKRLLDDLRRGGIREELLKRIADVIRDIMR
LLKELHDHTAEVIKTIKKLLKELHDINKEIIERLKRLKDGNVPKEELLKRVEELVRTSARLTTEVLKTVEKLIRD
DKRLSEEILKRVKELIEELKRGRDHMVLHEYVNAAGITVEEAVRLNEESLRRILDVVRKAVKLDRESLKKILDVV
EEAVR >3plus1_Cage_Nterm_GFP11_678 (SEQ ID NO: 27,318)
SKAEEIAEKLDRLLEENRRALEEITTRLDDLLRRNKRDHMVLHEYVNAAGITLRRGGIREELLKRIADVIRDIMR
LLKELHDHTAEVIKTIKKLLKELHDINKEIIERLKRLKDGNVPKEELLKRVEELVRTSARLTTEVLKTVEKLIRD
DKRLSEEILKRVKELIEELKRGVDSERVKEILERILRVVEEAVRLNEESLRRILDVVRKAVKLDRESLKKILDVV
EEAVR -continued

```
>3plus1_Cage_Nterm_GFP11_678
                                                          (SEQ ID NO: 27,319)
SKAEEIAEKLDRLLEENRRALEEITTRLDDLLRRNKDALRDHMVLHEYVNAAGITGGIREELLKRIADVIRDIMR

LLKELHDHTAEVIKTIKKLLKELHDINKEIIERLKRLKDGNVPKEELLKRVEELVRTSARLTTEVLKTVEKLIRD

DKRLSEEILKRVKELIEELKRGVDSERVKEILERILRVVEEAVRLNEESLRRILDVVRKAVKLDRESLKKILDVV

EEAVR

>3plus1_Cage_Cterm_GFP11_679
                                                          (SEQ ID NO: 27,320)
SRVEELKKLIEDILRISREVVERIKRVAEDIHRINRRVLDDLRKLIEDILRTVEEILARKVGDTEIAERLRDTIA

RVVDEIAKLLEEHEKRSRELLEEIRKLLEDILRRSERAVEEIRELLKKGVSTKDVLRIIEEILREHLELLERVVR

RIEEILRELLKTIEEIVKRIKEILEELKEVLKRGRVKDDEVERDHMVLHEYVNAAGITYRRLLEEIKRKLEEILR

RVEELHRRLRRKLEEIDR

>3plus1_Cage_Nterm_GFP11_679
                                                          (SEQ ID NO: 27,321)
SRVEELKKLIEDILRISREVVERIKRVAEDIHRINRRVRDHMVLHEYVNAAGITEILARKVGDTEIAERLRDTIA

RVVDEIAKLLEEHEKRSRELLEEIRKLLEDILRRSERAVEEIRELLKKGVSTKDVLRIIEEILREHLELLERVVR

RIEEILRELLKTIEEIVKRIKEILEELKEVLKRGRVKDDEVEREIRRVKEDLDRILEEYRRLLEEIKRKLEEILR

RVEELHRRLRRKLEEIDR
```

In a fourth aspect, the disclosure provides non-naturally occurring polypeptides comprising a polypeptide having at least 40%, 45%, 50%, 55%, 60%, 65%, 70%, 75%, 80%, 85%, 90%, 91%, 92%, 93%, 94%, 95%, 96%, 97%, 98%, 99%, or 100% sequence identity along its length to the amino acid sequence of a key polypeptide disclosed herein or selected from the group consisting of SEQ ID NOS: 14318-26601 (submitted in U.S. Provisional Application Ser. No. 62/700,681 filed Jul. 19, 2018 and/or 62/785,537 filed Dec. 27, 2018 as Appendix 3), 26602-27015 (submitted in U.S. Provisional Application Ser. No. 62/700,681 filed Jul. 19, 2018 and/or 62/785,537 filed Dec. 27, 2018 as 3plus1_GFP11_Key_Cterm_1" nos. 1-67 and 97-117, 3plus1_GFP11_Key_Nterm_1" nos. 68-96 and 118-140, 2plus1_GFP11_Key_Cterm_" nos. 1-173, and GFP11_Key_Nterm_" nos. 174-274), 27016-27050, 27,322 to 27,358, and key polypeptides in Table 2 (polypeptides with an odd-numbered SEQ ID NO between SEQ ID NOS: 27127 and 27277), Table 3, and/or Table 4, not including optional amino acid residues.

As disclosed herein, the polypeptides of this aspect can be used, for example, as key polypeptides in conjunction with the cage polypeptides to displace the latch through competitive intermolecular binding that induces conformational change, exposing the encoded bioactive peptide or domain and thus activating the system (see, for example, FIG. 1).

As noted in the disclosure, key polypeptides may include residues that are optional; these residues are provided in parentheses and in one embodiment are not included in determining the percent sequence identity. In another embodiment, the optional residues may be included in determining percent sequence identity.

In another embodiment, non-naturally occurring polypeptides comprising a polypeptide having at least 40%, 45%, 50%, 55%, 60%, 65%, 70%, 75%, 80%, 85%, 90%, 91%, 92%, 93%, 94%, 95%, 96%, 97%, 98%, 99%, or 100% sequence identity along its length to the amino acid sequence of a key polypeptide selected from the group consisting of SEQ ID NOS: 26602-27050, and 27,322 to 27,358, as detailed below.

Key sequences are normal text
6His-MBP-TEV, 6His-TEV, and flexible linker sequences are underlined text
sequence in bold, italics, are optional residues necessary for biotinylation of MBP_key
all sequences in parentheses are optional
Any number of consecutive amino acids from the N or C terminus in the non-optional key sequence may be removed to tune responsiveness

```
>SB76_C-helix
                                                          (SEQ ID NO: 27016)
DEARKAIARVKRESKRIVEDAERLIREAAAASEKIS >SB76_C-helix-biotin
                                                          (SEQ ID NO: 27017)
DEARKAIARVKRESKRIVEDAERLIREAAAASEKISGSGK-Biotin >p5_MBP
                                                          (SEQ ID NO: 27018)
(MDP)DEARKAIARVKRESKRIVEDAERLIREAAAASEKISREA(SSGINPRGSHMKIEEGKLVIWINGDKGYNG

LAEVGKKFEKDTGIKVTVEHPDKLEEKFPQVAATGDGPDIIFWAHDRFGGYAQSGLLAEITPDKAFQDKLYPFTW

DAVRYNGKLIAYPIAVEALSLIYNKDLLPNPPKTWEEIPALDKELKAKGKSALMFNLQEPYFTWPLIAADGGYAF

KYENGKYDIKDVGVDNAGAKAGLTFLVDLIKNKHMNADTDYSIAEAAFNKGETAMTINGPWAWSNIDTSKVNYGV
```

TVLPTFKGQPSKPFVGVLSAGINAASPNKELAKEFLENYLLTDEGLEAVNKDKPLGAVALKSYEEELVKDPRIAA
TMENAQKGEIMPNIPQMSAFWYAVRTAVINAASGRQTVDEALKDAQTNSSGSGLNDIFEAQKIEWHELEHHHHHH)

> p9_MBP (SEQ ID NO: 27019)
(MDP)DEARKAIARVKRESKRIVEDAERLIREAAAASEKISREAERLIREAA(SSGLVPRGSHMKIEEGKLVIWI
NGDKGYNGLAEVGKKFEKDTGIKVTVEHPDKLEEKFPQVAATGDGPDIIFWAHDRFGGYAQSGLLAEITPDKAFQ
DKLYPFTWDAVRYNGKLIAYPIAVEALSLIYNKDLLPNPPKTWEEIPALDKELKAKGKSALMFNLQEPYFTWPLI
AADGGYAFKYENGKYDIKDVGVDNAGAKAGLTFLVDLIKNKHMNADTDYSIAEAAFNKGETAMTINGPWAWSNID
TSKVNYGVTVLPTFKGQPSKPFVGVLSAGINAASPNKELAKEFLENYLLTDEGLEAVNKDKPLGAVALKSYEEEL
VKDPRIAATMENAQKGEIMPNIPQMSAFWYAVRTAVINAASGRQTVDEALKDAQTNSSGSGLNDIFEAQKIEWHE
LEHHHHHH)

>p18_MBP (SEQ ID NO: 27020)
(MDP)DEARKAIARVKRESKRIVEDAERLIREAAAASEKISREAERLIREAAAASEKISRE(SSGLVPRGSHMKI
EEGKLVIWINGDKGYNGLAEVGKKFEKDTGIKVTVEHPDKLEEKFPQVAATGDGPDIIFWAHDRFGGYAQSGLLA
EITPDKAFQDKLYPFTWDAVRYNGKLIAYPIAVEALSLIYNKDLLPNPPKTWEEIPALDKELKAKGKSALMFNLQ
EPYFTWPLIAADGGYAFKYENGKYDIKDVGVDNAGAKAGLTFLVDLIKNKHMNADTDYSIAEAAFNKGETAMTIN
GPWAWSNIDTSKVNYGVTVLPTFKGQPSKPFVGVLSAGINAASPNKELAKEFLENYLLTDEGLEAVNKDKPLGAV
ALKSYEEELVKDPRIAATMENAQKGEIMPNIPQMSAFWYAVRTAVINAASGRQTVDEALKDAQTNSSGSGLNDIF
EAQKIEWHELEHHHHHH)

>MBP_p18 (aka. p76) (SEQ ID NO: 27021)
(MGSSHHHHHHSSGLVPRGSHMKIEEGKLVIWINGDKGYNGLAEVGKKFEKDTGIKVTVEHPDKLEEKFPQVAAT
GDGPDIIFWAHDRFGGYAQSGLLAEITPDKAFQDKLYPFTWDAVRYNGKLIAYPIAVEALSLIYNKDLLPNPPKT
WEEIPALDKELKAKGKSALMFNLQEPYFTWPLIAADGGYAFKYENGKYDIKDVGVDNAGAKAGLTFLVDLIKNKH
MNADTDYSIAEAAFNKGETAMTINGPWAWSNIDTSKVNYGVTVLPTFKGQPSKPFVGVLSAGINAASPNKELAKE
FLENYLLTDEGLEAVNKDKPLGAVALKSYEEELVKDPRIAATMENAQKGEIMPNIPQMSAFWYAVRTAVINAASG
RQTVDEALKDAQTNSGSGSGENLYFQ)DEARKAIARVKRESKRIVEDAERLIREAAAASEKISRE(*AERLIREAA
AASEKISRE*)

>key_b (SEQ ID NO: 27022)
(M)NKEEIEKLAKEAREKLKKAEKEHKEIHDKLRKKNKKAREDLKKKADELRETNKRVN(GSENLYFQGSGSGKI
EEGKLVIWINGDKGYNGLAEVGKKFEKDTGIKVTVEHPDKLEEKFPQVAATGDGPDIIFWAHDRFGGYAQSGLLA
EITPDKAFQDKLYPFTWDAVRYNGKLIAYPIAVEALSLIYNKDLLPNPPKTWEEIPALDKELKAKGKSALMFNLQ
EPYFTWPLIAADGGYAFKYENGKYDIKDVGVDNAGAKAGLTFLVDLIKNKHMNADTDYSIAKAAFNKGETAMTIN
GPWAWSNIDTSKVNYGVTVLPTFKGQPSKPFVGVLSAGINAASPNKELAKEFLENYLLTDEGLEAVNKDKPLGAV
ALKSYEEELVKDPRIAATMENAQKGEIMPNIPQMSAFWYAVRTAVINAASGRQTVDEALKDAQTNLEHHHHHH)

>key_c (SEQ ID NO: 27023)
(M)SSEKVRRELKESLKENHKQNQKLLKDHKRAQEKLNRELEELKKKHKKTLDDIRRES(GSENLYFQGSGSGKI
EEGKLVIWINGDKGYNGLAEVGKKFEKDTGIKVTVEHPDKLEEKFPQVAATGDGPDIIFWAHDRFGGYAQSGLLA
EITPDKAFQDKLYPFTWDAVRYNGKLIAYPIAVEALSLIYNKDLLPNPPKTWEEIPALDKELKAKGKSALMFNLQ
EPYFTWPLIAADGGYAFKYENGKYDIKDVGVDNAGAKAGLTFLVDLIKNKHMNADTDYSIAKAAFNKGETAMTIN
GPWAWSNIDTSKVNYGVTVLPTFKGQPSKPFVGVLSAGINAASPNKELAKEFLENYLLTDEGLEAVNKDKPLGAV
ALKSYEEELVKDPRIAATMENAQKGEIMPNIPQMSAFWYAVRTAVINAASGRQTVDEALKDAQTNLEHHHHHH)

```
>key_d                                                        (SEQ ID NO: 27024)
(M)DTVKRILEELRRRFEKLAKDLDDIARKLLEDHKKHNKELKDKQRKIKKEADDAARS(GSENLYFQGSGSGKI
EEGKLVIWINGDKGYNGLAEVGKKFEKDTGIKVTVEHPDKLEEKFPQVAATGDGPDIIFWAHDRFGGYAQSGLLA
EITPDKAFQDKLYPFTWDAVRYNGKLIAYPIAVEALSLIYNKDLLPNPPKTWEEIPALDKELKAKGKSALMFNLQ
EPYFTWPLIAADGGYAFKYENGKYDIKDVGVDNAGAKAGLTFLVDLIKNKHMNADTDYSIAKAAFNKGETAMTIN
GPWAWSNIDTSKVNYGVTVLPTFKGQPSKPFVGVLSAGINAASPNKELAKEFLENYLLTDEGLEAVNKDKPLGAV
ALKSYEEELVKDPRIAATMENAQKGEIMPNIPQMSAFWYAVRTAVINAASGRQTVDEALKDAQTNLEHHHHHH)

>key_e                                                        (SEQ ID NO: 27025)
(M)DDVERRLRKANKESKKEAEELTEEAKKANEKTKEDSKELTKENRKTNKTIKDEARS(GSENLYFQGSGSGKI
EEGKLVIWINGDKGYNGLAEVGKKFEKDTGIKVTVEHPDKLEEKFPQVAATGDGPDIIFWAHDRFGGYAQSGLLA
EITPDKAFQDKLYPFTWDAVRYNGKLIAYPIAVEALSLIYNKDLLPNPPKTWEEIPALDKELKAKGKSALMFNLQ
EPYFTWPLIAADGGYAFKYENGKYDIKDVGVDNAGAKAGLTFLVDLIKNKHMNADTDYSIAEAAFNKGETAMTIN
GPWAWSNIDTSKVNYGVTVLPTFKGQPSKPFVGVLSAGINAASPNKELAKEFLENYLLTDEGLEAVNKDKPLGAV
ALKSYEEELVKDPRIAATMENAQKGEIMPNIPQMSAFWYAVRTAVINAASGRQTVDEALKDAQTNLEHHHHHH)

>key_f                                                        (SEQ ID NO: 27026)
(M)DDEERRSEKTVQDAKREIKKVEDDLQRLNEEQKKKVKKQEDENQKTLKKHKDDARS(GSENLYFQGSGSGKI
EEGKLVIWINGDKGYNGLAEVGKKFEKDTGIKVTVEHPDKLEEKFPQVAATGDGPDIIFWAHDRFGGYAQSGLLA
EITPDKAFQDKLYPFTWDAVRYNGKLIAYPIAVEALSLIYNKDLLPNPPKTWEEIPALDKELKAKGKSALMFNLQ
EPYFTWPLIAADGGYAFKYENGKYDIKDVGVDNAGAKAGLTFLVDLIKNKHMNADTDYSIAEAAFNKGETAMTIN
GPWAWSNIDTSKVNYGVTVLPTFKGQPSKPFVGVLSAGINAASPNKELAKEFLENYLLTDEGLEAVNKDKPLGAV
ALKSYEEELVKDPRIAATMENAQKGEIMPNIPQMSAFWYAVRTAVINAASGRQTVDEALKDAQTNLEHHHHHH)

Additional Keys:
Key sequences are normal text
(6His-MBP-TEV, 6His-TEV, and flexible linker sequences are underlined text)
(Co-localization domain is bolded text)
(Positions that can be mutated to any amino acid to tune responsiveness are
underlined bolded text. These are exemplary but not exhaustive.)
(Any number of consecutive amino acids from the N or C terminus in the non-
optional key sequence may be removed to tune responsiveness)
(all sequences in parentheses are optional)

>p76-long                                                     (SEQ ID NO: 27027)
(MGSSHHHHHHSSGLVPRGSHMKIEEGKLVIWINGDKGYNGLAEVGKKFEKDTGIKVTVEHPDKLEEKFPQVAAT
GDGPDIIFWAHDRFGGYAQSGLLAEITPDKAFQDKLYPFTWDAVRYNGKLIAYPIAVEALSLIYNKDLLPNPPKT
WEEIPALDKELKAKGKSALMFNLQEPYFTWPLIAADGGYAFKYENGKYDIKDVGVDNAGAKAGLTFLVDLIKNKH
MNADTDYSIAEAAFNKGETAMTINGPWAWSNIDTSKVNYGVTVLPTFKGQPSKPFVGVLSAGINAASPNKELAKE
FLENYLLTDEGLEAVNKDKPLGAVALKSYEEELVKDPRIAATMENAQKGEIMPNIPQMSAFWYAVRTAVINAASG
RQTVDEALKDAQTNSGSGSGENLYFQ)DEARKAIARVKRESKRIVEDAERLIREAAAASEKISREAERLIREAAA
ASEKISRE >p76-short                                                    (SEQ ID NO: 27028)
(MGSSHHHHHHSSGLVPRGSHMKIEEGKLVIWINGDKGYNGLAEVGKKFEKDTGIKVTVEHPDKLEEKFPQVAAT
GDGPDIIFWAHDRFGGYAQSGLLAEITPDKAFQDKLYPFTWDAVRYNGKLIAYPIAVEALSLIYNKDLLPNPPKT
WEEIPALDKELKAKGKSALMFNLQEPYFTWPLIAADGGYAFKYENGKYDIKDVGVDNAGAKAGLTFLVDLIKNKH
MNADTDYSIAEAAFNKGETAMTINGPWAWSNIDTSKVNYGVTVLPTFKGQPSKPFVGVLSAGINAASPNKELAKE
FLENYLLTDEGLEAVNKDKPLGAVALKSYEEELVKDPRIAATMENAQKGEIMPNIPQMSAFWYAVRTAVINAASG
RQTVDEALKDAQTNSGSGSGENLYFQ)DEARKAIARVKRESKRIVEDAERLIREAAAASEKISREAERLIR
```

```
>k76-long                                                      (SEQ ID NO: 27029)
(MGSSHHHHHHSSGLVPRGSHMKIEEGKLVIWINGDKGYNGLAEVGKKFEKDTGIKVTVEHPDKLEEKFPQVAAT
GDGPDIIFWAHDRFGGYAQSGLLAEITPDKAFQDKLYPFTWDAVRYNGKLIAYPIAVEALSLIYNKDLLPNPPKT
WEEIPALDKELKAKGKSALMFNLQEPYFTWPLIAADGGYAFKYENGKYDIKDVGVDNAGAKAGLTFLVDLIKNKH
MNADTDYSIAEAAFNKGETAMTINGPWAWSNIDTSKVNYGVTVLPTFKGQPSKPFVGVLSAGINAASPNKELAKE
FLENYLLTDEGLEAVNKDKPLGAVALKSYEEELVKDPRIAATMENAQKGEIMPNIPQMSAFWYAVRTAVINAASG
RQTVDEALKDAQTNSGSGSGENLYFQ)DEARKAIARVKRESKRIVEDAERLIREAAQASEKISREARELIERAAQ
ASEKISRE >k76-short                                                     (SEQ ID NO: 27030)
(MGSSHHHHHHSSGLVPRGSHMKIEEGKLVIWINGDKGYNGLAEVGKKFEKDTGIKVTVEHPDKLEEKFPQVAAT
GDGPDIIFWAHDRFGGYAQSGLLAEITPDKAFQDKLYPFTWDAVRYNGKLIAYPIAVEALSLIYNKDLLPNPPKT
WEEIPALDKELKAKGKSALMFNLQEPYFTWPLIAADGGYAFKYENGKYDIKDVGVDNAGAKAGLTFLVDLIKNKH
MNADTDYSIAEAAFNKGETAMTINGPWAWSNIDTSKVNYGVTVLPTFKGQPSKPFVGVLSAGINAASPNKELAKE
FLENYLLTDEGLEAVNKDKPLGAVALKSYEEELVKDPRIAATMENAQKGEIMPNIPQMSAFWYAVRTAVINAASG
RQTVDEALKDAQTNSGSGSGENLYFQ)DEARKAIARVKRESKRIVEDAERLIREAAQASEKISREAERLIR >p76_GLISE                                                     (SEQ ID NO: 27031)
(MGSHHHHHHGSGSENLYFQGSGGS)DEARKAIARVKRESKRIVEDAEGLISEAAAASEKISREAERLIREAAAA
SEKISRE >p76_GSSEKIS                                                   (SEQ ID NO: 27032)
(MGSHHHHHHGSGSENLYFQGSGGS)DEARKAIARVKRESKRIVEDAERLIREAAGSSEKISREAERLIREAAAA
SEKISRE >p76_R26G                                                      (SEQ ID NO: 27033)
(MGSHHHHHHGSGSENLYFQGSGGS)DEARKAIARVKRESKRIVEDAERLIGEAAAASEKISREAERLIREAAAA
SEKISRE >p76-short_E19G                                                (SEQ ID NO: 27034)
(MGSHHHHHHGSGSENLYFQGSGGS)DEARKAIARVKRESKRIVGDAERLIREAAAASEKISREAERLIR >p76-short_GLISE_EO1_EGFR                                      (SEQ ID NO: 27035)
(MGSHHHHHHGSGSENLYFQGSGGS)DEARKAIARVKRESKRIVEDAEGLISEAAAASEKISREAERLIR >p76-short_AE_EGFR                                             (SEQ ID NO: 27036)
(MGSHHHHHHGSGSENLYFQGSGGS)DEARKAIARVAEESKRIVEDAERLIREAAAASEKISREAERLIR >p76-short_AAE_EGFR                                            (SEQ ID NO: 27037)
(MGSHHHHHHGSGSENLYFQGSGGS)DEAAKAIARVAEESKRIVEDAERLIREAAAASEKISREAERLIR >p76-short_EE_EGFR                                             (SEQ ID NO: 27038)
(MGSHHHHHHGSGSENLYFQGSGGS)DEARKAIARVKRESKRIVEDAERLIREAAEASEEISREAERLIR >p76-spytag                                                    (SEQ ID NO: 27039)
(MGSHHHHHHGSGSENLYFQGSGGSMKIEEGKLVIWINGDKGYNGLAEVGKKFEKDTGIKVTVEHPDKLEEKFPQ
VAATGDGPDIIFWAHDRFGGYAQSGLLAEITPDKAFQDKLYPFTWDAVRYNGKLIAYPIAVEALSLIYNKDLLPN
PPKTWEEIPALDKELKAKGKSALMFNLQEPYFTWPLIAADGGYAFKYENGKYDIKDVGVDNAGAKAGLTFLVDLI
KNKHMNADTDYSIAEAAFNKGETAMTINGPWAWSNIDTSKVNYGVTVLPTFKGQPSKPFVGVLSAGINAASPNKE
LAKEFLENYLLTDEGLEAVNKDKPLGAVALKSYEEELVKDPRIAATMENAQKGEIMPNIPQMSAFWYAVRTAVIN
```

-continued

<u>AASGRQTVDEALKDAQTNSGSGSGENLYFQ</u>)DEARKAIARVKRESKRIVEDAERLIREAAAASEKISREAERL<u>I</u>R

EAAAASEK<u>I</u>SRE(GGGSGSGSGSGKPGQASGS)AHIVMVDAYKPTK

>p76-short-spytag
(SEQ ID NO: 27040)
(<u>MGSHHHHHGSGSENLYFQGSGGSMKIEEGKLVIWINGDKGYNGLAEVGKKFEKDTGIKVTVEHPDKLEEKFPQ</u>

<u>VAATGDGPDIIFWAHDRFGGYAQSGLLAEITPDKAFQDKLYPFTWDAVRYNGKLIAYPIAVEALSLIYNKDLLPN</u>

<u>PPKTWEEIPALDKELKAKGKSALMFNLQEPYFTWPLIAADGGYAFKYENGKYDIKDVGVDNAGAKAGLTFLVDLI</u>

<u>KNKHMNADTDYSIAEAAFNKGETAMTINGPWAWSNIDTSKVNYGVTVLPTFKGQPSKPFVGVLSAGINAASPNKE</u>

<u>LAKEFLENYLLTDEGLEAVNKDKPLGAVALKSYEEELVKDPRIAATMENAQKGEIMPNIPQMSAFWYAVRTAVIN</u>

<u>AASGRQTVDEALKDAQTNSGSGSGENLYFQ</u>)DEARKAIARVKRESKRIVEDAERLIREAAAASEK<u>I</u>SREAERL<u>I</u>R (<u>GGGSGSGSGSGKPGQASGS</u>)AHIVMVDAYKPTK

>sfGFP_VMAn_p18
(SEQ ID NO: 27041)
(<u>MGSSHHHHHHSS</u>GLVPRGSHMSKGEELFTGVVPILVELDGDVNGHKFSVRGEGEGDATNGKLTLKFICTTGKLP

VPWPTLVTTLTYGVQCFARYPDHMKQHDFFKSAMPEGYVQERTISFKDDGTYKTRAEVKFEGDTLVNRIELKGID

FKEDGNILGHKLEYNFNSHNVYITADKQKNGIKANFKIRHNVEDGSVQLADHYQQNTPIGDGPVLLPDNHYLSTQ

SVLSKDPNEKRDHMVLLEFVTAAGITHGMDELYKSGSGSGCFAKGTNVLMADGSIECIENIEVGNKVMGKDGRPR

EVIKLPRGRETMYSVVQKSQHRAHKSDSSREVPELLKFTCNATHELVVRTPRSVRRLSRTIKGVEYFEVITFEMG

QKKAPDGRIVELVKEVSKSYPISEGPERANELVESYRKASNKAYFEWTIEARDLSLLGSHVRKATYQTYAPILYG

GSGGS)DEARKAIARVKRESKRIVEDAERLIREAAAASEKISREAERLIREAAAASEKISRE

>p18_VMAc_mCherry
(SEQ ID NO: 27042)
(<u>MGSHHHHHHGSGSENLYFQGSG</u>)DEARKAIARVKRESKRIVEDAERLIREAAAASEKISREAERLIREAAAASE

KISRE(GSGGSGSGGGVLLNVLSKCAGSKKFRPAPAAAFARECRGFYFELQELKEDDYYGITLSDDSDHQFLLAN

QVVVHNCGSGGSVSKGEEDNMAIIKEFMRFKVHMEGSVNGHEFEIEGEGEGRPYEGTQTAKLKVTKGGPLPFAWD

ILSPQFMYGSKAYVKHPADIPDYLKLSFPEGFKWERVMNFEDGGVVTVTQDSSLQDGEFIYKVKLRGTNFPSDGP

VMQKKTMGWEASSERMYPEDGALKGEIKQRLKLKDGGHYDAEVKTTYKAKKPVQLPGAYNVNIKLDITSHNEDYT

IVEQYERAEGRHSTGGMDELYK)

(Cognate Keys for 2plus1 and 3plus1 STREPII-LOCKR functional Cage designs):
>2plus1_KEY_100000.fasta alt_STREP_2plus1_1
(SEQ ID NO: 27043)
DKVRKVAEVAEKVLRDIDKLDRESKEAFRRTNGEISKLDEDTRRVAERVKKAIEDLAK >2plus1_KEY_2
(SEQ ID NO: 27044)
SEVDEIIADNERALDEVRREVEEIDKENAERLKEWVEEAREILDRLAKALEEIR >2plus1_KEY_3
(SEQ ID NO: 27045)
PEEALSKAIKDVRDIVKKVKDELKEWRDRNKELVDRLSEELKEWLKDVERVLKELTDKDR >2plus1_KEY_4
(SEQ ID NO: 27046)
DERVREELKKLLTRVEEEHRKVLETDKKILKEAHKESKEVNDRDRELLERLEESVR >3plus1_KEY_1
(SEQ ID NO: 27047)
SRLVKKLDEIVKEVAKKLEDVVRANEELWRKLVELNKESVARLREAVERVARDLEETAR >3plus1_KEY_2
(SEQ ID NO: 27048)
SDEERLEKVVKDVIEKVRRILEKWKKDIDKVVKELRRILEEWEKIIREVLDKVR >3plus1_KEY_3
(SEQ ID NO: 27049)
DKDAVIKVIEKLIRANAAVWDALLKINEDLVRVNKTVWKELLRVNEKLARDLERVVK -continued >3plus1_KEY_4
SLVDELRKSLERNVRVSEEVARRLKEALKRWVDVVRKVVEDLIRLNEDVVRVVEK (SEQ ID NO: 27050)

SEQ ID NOs: 26,602-27,015:

>3plus1_GFP11_Key_Cterm_1
SGSKEVLDILERAVEVVRRVIKALKEVLERHVDATREVIERVKRVNKRLLEAVREVVT (SEQ ID NO: 26602)

>3plus1_GFP11_Key_Cterm_2
GVPEEIDRELKRVVEELRRLHEEIKERLDDVARRSEEELRRIIKKLKEVVKEIRKKLK (SEQ ID NO: 26603)

>3plus1_GFP11_Key_Cterm_3
DLLRKLEEELRRIKEKLRKALEELEREHRELEKELDKLHDESRKEHERIEEELRR (SEQ ID NO: 26604)

>3plus1_GFP11_Key_Cterm_4
DEDLLEKIKRVIREHIKALEKLARDLKEILRRHIEALKELARDLAEVIRKLLEDVKR (SEQ ID NO: 26605)

>3plus1_GFP11_Key_Cterm_5
DLERLRRKVEELEDRLRRLLEKLARDSAELMRELERILDRYARESEELDRRLAE (SEQ ID NO: 26606)

>3plus1_GFP11_Key_Cterm_6
DLEDILRKNLDRLRKLLERLREILRENLEALKKTLKRLEDVVREILEDLKRERK (SEQ ID NO: 26607)

>3plus1_GFP11_Key_Cterm_7
DLERLRRKVEELEDRLRRLLEKLARDSAELMRELERILDRYARESEELDRRLAE (SEQ ID NO: 26608)

>3plus1_GFP11_Key_Cterm_8
SGSKEVLDILERAVEVVRRVIKALKEVLERHVDATREVIERVKRVNKRLLEAVREVVT (SEQ ID NO: 26609)

>3plus1_GFP11_Key_Cterm_9
DLERLRRKVEELEDRLRRLLEKLARDSAELMRELERILDRYARESEELDRRLAE (SEQ ID NO: 26610)

>3plus1_GFP11_Key_Cterm_10
RLIEEVVRLLRENLDVVRRILEALAKLIKELLEALEEVLRRNKELIRELLRVLDEALK (SEQ ID NO: 26611)

>3plus1_GFP11_Key_Cterm_11
DIVRAMEEVIRRLIEILRRDVELNLDVAKKLLELLKEDSKLNLDVARELLELLDR (SEQ ID NO: 26612)

>3plus1_GFP11_Key_Cterm_12
DIVRAMEEVIRRLIEILRRDVELNLDVAKKLLELLKEDSKLNLDVARELLELLDR (SEQ ID NO: 26613)

>3plus1_GFP11_Key_Cterm_13
RLIEEVVRLLRENLDVVRRILEALAKLIKELLEALEEVLRRNKELIRELLRVLDEALK (SEQ ID NO: 26614)

>3plus1_GFP11_Key_Cterm_14
RLIEEVVRLLRENLDVVRRILEALAKLIKELLEALEEVLRRNKELIRELLRVLDEALK (SEQ ID NO: 26615)

>3plus1_GFP11_Key_Cterm_15
DLLRKLEEELRRIKEKLRKALEELEREHRELEKELDKLHDESRKEHERIEEELRR (SEQ ID NO: 26616)

>3plus1_GFP11_Key_Cterm_16
DLLRKLEEELRRIKEKLRKALEELEREHRELEKELDKLHDESRKEHERIEEELRR (SEQ ID NO: 26617)

>3plus1_GFP11_Key_Cterm_17
ELAREVERVIKELLDKSKEILERIERAIDELLKVSEEILKLSEDASEELLKILREFAK (SEQ ID NO: 26618)

>3plus1_GFP11_Key_Cterm_18
DVKDIIRTILEVARDLLRLLEEDSRTNSEVVKRLLDLLREDSKANSEVVKRLLDVLRE (SEQ ID NO: 26619)

-continued

>3plus1_GFP11_Key_Cterm_19                                          (SEQ ID NO: 26620)
DLERLRRKVEELEDRLRRLLEKLARDSAELMRELERILDRYARESEELDRRLAE >3plus1_GFP11_Key_Cterm_20                                          (SEQ ID NO: 26621)
DLERLRRKVEELEDRLRRLLEKLARDSAELMRELERILDRYARESEELDRRLAE >3plus1_GFP11_Key_Cterm_21                                          (SEQ ID NO: 26622)
RLIEEVVRLLRENLDVVRRILEALAKLIKELLEALEEVLRRNKELIRELLRVLDEALK >3plus1_GFP11_Key_Cterm_22                                          (SEQ ID NO: 26623)
DLEDILRKNLDRLRKLLERLREILRENLEALKKTLKRLEDVVREILEDLKRERK >3plus1_GFP11_Key_Cterm_23                                          (SEQ ID NO: 26624)
DLLRKLEEELRRIKEKLRKALEELEREHRELEKELDKLHDESRKEHERIEEELRR >3plus1_GFP11_Key_Cterm_24                                          (SEQ ID NO: 26625)
DEDLLEKIKRVIREHIKALEKLARDLKEILRRHIEALKELARDLAEVIRKLLEDVKR >3plus1_GFP11_Key_Cterm_25                                          (SEQ ID NO: 26626)
ELVRIAIEVLKRLLEIIEELVRLNNEILERLLKIVRELHKDNIKILEDLLRIIEEVLR >3plus1_GFP11_Key_Cterm_26                                          (SEQ ID NO: 26627)
ELVRIAIEVLKRLLEIIEELVRLNNEILERLLKIVRELHKDNIKILEDLLRIIEEVLR >3plus1_GFP11_Key_Cterm_27                                          (SEQ ID NO: 26628)
RLARLLKALADKLIRVLEEILKINEELNRKIIKFARENLERNRRVNKKVIEVLREAAR >3plus1_GFP11_Key_Cterm_28                                          (SEQ ID NO: 26628)
DLERLRRKVEELEDRLRRLLEKLARDSAELMRELERILDRYARESEELDRRLAE >3plus1_GFP11_Key_Cterm_29                                          (SEQ ID NO: 26630)
ELVRIAIEVLKRLLEIIEELVRLNNEILERLLKIVRELHKDNIKILEDLLRIIEEVLR >3plus1_GFP11_Key_Cterm_30                                          (SEQ ID NO: 26631)
ELVRIAIEVLKRLLEIIEELVRLNNEILERLLKIVRELHKDNIKILEDLLRIIEEVLR >3plus1_GFP11_Key_Cterm_31                                          (SEQ ID NO: 26632)
DIVRAMEEVIRRLIEILRRDVELNLDVAKKLLELLKEDSKLNLDVARELLELLDR >3plus1_GFP11_Key_Cterm_32                                          (SEQ ID NO: 26633)
RKIAKIIEELKRLLEDLARDTRRVIEEAKRLLKEWRDRNKEVADTLKKLLEDLIRKIR >3plus1_GFP11_Key_Cterm_33                                          (SEQ ID NO: 26634)
DLLRKLEEELRRIKEKLRKALEELEREHRELEKELDKLHDESRKEHERIEEELRR >3plus1_GFP11_Key_Cterm_34                                          (SEQ ID NO: 26635)
DLLRKLEEELRRIKEKLRKALEELEREHRELEKELDKLHDESRKEHERIEEELRR >3plus1_GFP11_Key_Cterm_35                                          (SEQ ID NO: 26636)
RKIAKIIEELKRLLEDLARDTRRVIEEAKRLLKEWRDRNKEVADTLKKLLEDLIRKIR >3plus1_GFP11_Key_Cterm_36                                          (SEQ ID NO: 26637)
ELVRIAIEVLKRLLEIIEELVRLNNEILERLLKIVRELHKDNIKILEDLLRIIEEVLR >3plus1_GFP11_Key_Cterm_37                                          (SEQ ID NO: 26638)
TVRRLREALKKLEDDLRKIERDAEREYKKLKDELEELTERYRREIRKLKEELKADRK >3plus1_GFP11_Key_Cterm_38                                          (SEQ ID NO: 26639)
DEAERRRELKDKLDRLREEHEEVKRRLEEELTRLRETHKKIEKELREALKRVRDRST -continued >3plus1_GFP11_Key_Cterm_39                                          (SEQ ID NO: 26640)
DEAERRRRELKDKLDRLREEHEEVKRRLEEELTRLRETHKKIEKELREALKRVRDRST >3plus1_GFP11_Key_Cterm_40                                          (SEQ ID NO: 26641)
DLEDILRKNLDRLRKLLERLREILRENLEALKKTLKRLEDVVREILEDLKRERK >3plus1_GFP11_Key_Cterm_41                                          (SEQ ID NO: 26642)
DLERLRRKVEELEDRLRRLLEKLARDSAELMRELERILDRYARESEELDRRLAE >3plus1_GFP11_Key_Cterm_42                                          (SEQ ID NO: 26643)
DEAERRRRELKDKLDRLREEHEEVKRRLEEELTRLRETHKKIEKELREALKRVRDRST >3plus1_GFP11_Key_Cterm_43                                          (SEQ ID NO: 26644)
DEAERRRRELKDKLDRLREEHEEVKRRLEEELTRLRETHKKIEKELREALKRVRDRST >3plus1_GFP11_Key_Cterm_44                                          (SEQ ID NO: 26645)
DEAERRRRELKDKLDRLREEHEEVKRRLEEELTRLRETHKKIEKELREALKRVRDRST >3plus1_GFP11_Key_Cterm_45                                          (SEQ ID NO: 26646)
DKAVEELEKALEEIKRRLKEVIDRYEDELRKLRKEYKEKIDKYERKLEEIERRERT >3plus1_GFP11_Key_Cterm_46                                          (SEQ ID NO: 26647)
DVKRALEELVSRLRKLLEDVKKASEDIVREVERIVRELAKRSDEILKKLEDIVEKLRE >3plus1_GFP11_Key_Cterm_47                                          (SEQ ID NO: 26648)
DVKRALEELVSRLRKLLEDVKKASEDIVREVERIVRELAKRSDEILKKLEDIVEKLRE >3plus1_GFP11_Key_Cterm_48                                          (SEQ ID NO: 26649)
DEAERRRRELKDKLDRLREEHEEVKRRLEEELTRLRETHKKIEKELREALKRVRDRST >3plus1_GFP11_Key_Cterm_49                                          (SEQ ID NO: 26650)
DVKRALEELVSRLRKLLEDVKKASEDIVREVERIVRELAKRSDEILKKLEDIVEKLRE >3plus1_GFP11_Key_Cterm_50                                          (SEQ ID NO: 26651)
EVKRRLEEKERRIRTRYEELRRRLRKRVKDYEDKLREIEKKVRRDAERIEEELERAKK >3plus1_GFP11_Key_Cterm_51                                          (SEQ ID NO: 26652)
DEAERRRRELKDKLDRLREEHEEVKRRLEEELTRLRETHKKIEKELREALKRVRDRST >3plus1_GFP11_Key_Cterm_52                                          (SEQ ID NO: 26653)
KIAEEIERELEELRRMIKRLHEDLERKLKESEDELREIEARLEEKIRRLEEKLERKRR >3plus1_GFP11_Key_Cterm_53                                          (SEQ ID NO: 26654)
KIAEEIERELEELRRMIKRLHEDLERKLKESEDELREIEARLEEKIRRLEEKLERKRR >3plus1_GFP11_Key_Cterm_54                                          (SEQ ID NO: 26655)
DKAVEELEKALEEIKRRLKEVIDRYEDELRKLRKEYKEKIDKYERKLEEIERRERT >3plus1_GFP11_Key_Cterm_55                                          (SEQ ID NO: 26656)
KIAEEIERELEELRRMIKRLHEDLERKLKESEDELREIEARLEEKIRRLEEKLERKRR >3plus1_GFP11_Key_Cterm_56                                          (SEQ ID NO: 26657)
ELVRIAIEVLKRLLEIIEELVRLNNEILERLLKIVRELHKDNIKILEDLLRIIEEVLR >3plus1_GFP11_Key_Cterm_57                                          (SEQ ID NO: 26658)
DEVEREIRRVKEDLDRILEEYRRLLEEIKRKLEEILRRVEELHRRLRRKLEEIDR >3plus1_GFP11_Key_Cterm_58                                          (SEQ ID NO: 26659)
DVKRALEELVSRLRKLLEDVKKASEDIVREVERIVRELAKRSDEILKKLEDIVEKLRE -continued >3plus1_GFP11_Key_Cterm_59
(SEQ ID NO: 26660)
DEAERRRELKDKLDRLREEHEEVKRRLEEELTRLRETHKKIEKELREALKRVRDRST >3plus1_GFP11_Key_Cterm_60
(SEQ ID NO: 26661)
DEAERRRELKDKLDRLREEHEEVKRRLEEELTRLRETHKKIEKELREALKRVRDRST >3plus1_GFP11_Key_Cterm_61
(SEQ ID NO: 26662)
TLREVVRKVLEEAKRLLDELEEVHKRVKKELEDIIEENRRVVKRVRDELREIKRELDE >3plus1_GFP11_Key_Cterm_62
(SEQ ID NO: 26663)
DVKRALEELVSRLRKLLEDVKKASEDIVREVERIVRELAKRSDEILKKLEDIVEKLRE >3plus1_GFP11_Key_Cterm_63
(SEQ ID NO: 26664)
DVKRALEELVSRLRKLLEDVKKASEDIVREVERIVRELAKRSDEILKKLEDIVEKLRE >3plus1_GFP11_Key_Cterm_64
(SEQ ID NO: 26665)
DEAERRRELKDKLDRLREEHEEVKRRLEEELTRLRETHKKIEKELREALKRVRDRST >3plus1_GFP11_Key_Cterm_65
(SEQ ID NO: 26666)
DEAERRRELKDKLDRLREEHEEVKRRLEEELTRLRETHKKIEKELREALKRVRDRST >3plus1_GFP11_Key_Cterm_66
(SEQ ID NO: 26667)
KIAEEIERELEELRRMIKRLHEDLERKLKESEDELREIEARLEEKIRRLEEKLERKRR >3plus1_GFP11_Key_Cterm_67
(SEQ ID NO: 26668)
DVKRALEELVSRLRKLLEDVKKASEDIVREVERIVRELAKRSDEILKKLEDIVEKLRE >3plus1_GFP11_Key_Nterm_68
(SEQ ID NO: 26669)
SEAERLADEVRKAVKKSEEDNETLVREVEKAVRELKKNNKTWVDEVRKLMKRLVDLLR >3plus1_GFP11_Key_Nterm_69
(SEQ ID NO: 26670)
SEAERLADEVRKAVKKSEEDNETLVREVEKAVRELKKNNKTWVDEVRKLMKRLVDLLR >3plus1_GFP11_Key_Nterm_70
(SEQ ID NO: 26671)
DKDKRLEELLKRLKELNDKTFEELERILEELKRANEASLREAERILEELRARIEGGNL >3plus1_GFP11_Key_Nterm_71
(SEQ ID NO: 26672)
SEAEDLEELIKELAELLKDVIRKLEKINRRLVKILEDIIRRLKEISKEAEEELRKGTV >3plus1_GFP11_Key_Nterm_72
(SEQ ID NO: 26673)
SDKEEIKRRVEKTARDLETEHDKIKKRLEDTVRDIKRELDELLEKYERVLRKIEKTLR >3plus1_GFP11_Key_Nterm_73
(SEQ ID NO: 26674)
SEAEKIREALETNLRLLEELIKRLKEILDTHNELLRRVIETLERLLKELLELLEEGGL >3plus1_GFP11_Key_Nterm_74
(SEQ ID NO: 26675)
SEAEKIREALETNLRLLEELIKRLKEILDTHNELLRRVIETLERLLKELLELLEEGGL >3plus1_GFP11_Key_Nterm_75
(SEQ ID NO: 26676)
SKEERLREVAEKHKKDLEDIVKRVDEAAKETARRLEEILKRLEEVLKKILDDLEKGPD >3plus1_GFP11_Key_Nterm_76
(SEQ ID NO: 26677)
SLEEITKRLLELVEENLARHEEILRELLELAKRLAKEDRDILEEVLKLIEELLKLLED >3plus1_GFP11_Key_Nterm_77
(SEQ ID NO: 26678)
SKEETLKRLLDELEKRNRETVERLERLLKELEDRNASLEELEAVLEELERKIEESGL >3plus1_GFP11_Key_Nterm_78
(SEQ ID NO: 26679)
SKEETLKRLLDELEKRNRETVERLERLLKELEDRNASLEELEAVLEELERKIEESGL -continued >3plus1_GFP11_Key_Nterm_79 (SEQ ID NO: 26680)
SKEETLKRLLDELEKRNRETVERLERLLKELEDRNRASLEELEAVLEELERKIEESGL >3plus1_GFP11_Key_Nterm_80 (SEQ ID NO: 26681)
STREKAKKVLDTLRADNEDMKRVVEKILRALKRTNERAEKLAREITEEIKRILKEVGV >3plus1_GFP11_Key_Nterm_81 (SEQ ID NO: 26682)
DAEEVVKRLADVLRENDETIRKVVEDLVRIAEENDRLWKKLVEDIAEILRRIVELLRR >3plus1_GFP11_Key_Nterm_82 (SEQ ID NO: 26683)
SKEETLKRLLDELEKRNRETVERLERLLKELEDRNRASLEELEAVLEELERKIEESGL >3plus1_GFP11_Key_Nterm_83 (SEQ ID NO: 26684)
STREKAKKVLDTLRADNEDMKRVVEKILRALKRTNERAEKLAREITEEIKRILKEVGV >3plus1_GFP11_Key_Nterm_84 (SEQ ID NO: 26685)
SKEEEVEKVLRKWEEILRRLIEENKRANDKIRREYEELVKEIRRVLEEIKEVAERLGV >3plus1_GFP11_Key_Nterm_85 (SEQ ID NO: 26686)
DREKSVRDIEEDLKRVLDKLRRRVETSKEELKKVLKADKENADELEKTLRDVVRELDR >3plus1_GFP11_Key_Nterm_86 (SEQ ID NO: 26687)
SDKEEIKRRVEKTARDLETEHDKIKKRLEDTVRDIKRELDELLEKYERVLRKIEKTLR >3plus1_GFP11_Key_Nterm_87 (SEQ ID NO: 26688)
STREKAKKVLDTLRADNEDMKRVVEKILRALKRTNERAEKLAREITEEIKRILKEVGV >3plus1_GFP11_Key_Nterm_88 (SEQ ID NO: 26689)
SKDEELARLLEELVERWRKIVEDLERDHRRLVKEIRELVERIRKKLEELVDRIRKNGI >3plus1_GFP11_Key_Nterm_89 (SEQ ID NO: 26690)
SEAERLADEVRKAVKKSEEDNETLVREVEKAVRELKKNNKTWVDEVRKLMKRLVDLLR >3plus1_GFP11_Key_Nterm_90 (SEQ ID NO: 26691)
SKDEELARLLEELVERWRKIVEDLERDHRRLVKEIRELVERIRKKLEELVDRIRKNGI >3plus1_GFP11_Key_Nterm_91 (SEQ ID NO: 26692)
KEIEETLKELEDLNREMVETNRRVLEETRRLNKETVDRVKATLDELAKMLKKLVDDVR >3plus1_GFP11_Key_Nterm_92 (SEQ ID NO: 26693)
SEAERLADEVRKAVKKSEEDNETLVREVEKAVRELKKNNKTWVDEVRKLMKRLVDLLR >3plus1_GFP11_Key_Nterm_93 (SEQ ID NO: 26694)
SKEETLKRLLDELEKRNRETVERLERLLKELEDRNRASLEELEAVLEELERKIEESGL >3plus1_GFP11_Key_Nterm_94 (SEQ ID NO: 26695)
DKAEVLREALKLLKDLLEELIKIHEESLKRILDLIDTLVKVHEDALRALKELLERSGL >3plus1_GFP11_Key_Nterm_95 (SEQ ID NO: 26696)
SKEEEVEKVLRKWEEILRRLIEENKRANDKIRREYEELVKEIRRVLEEIKEVAERLGV >3plus1_GFP11_Key_Nterm_96 (SEQ ID NO: 26697)
SKEETLKRLLDELEKRNRETVERLERLLKELEDRNRASLEELEAVLEELERKIEESGL >3plus1_GFP11_Key_Cterm_97 (SEQ ID NO: 26698)
SERVKEILERILRVVEEAVRLNEESLRRILDVVRKAVKLDRESLKKILDVVEEAVR >3plus1_GFP11_Key_Cterm_98 (SEQ ID NO: 26699)
SERVKEILERILRVVEEAVRLNEESLRRILDVVRKAVKLDRESLKKILDVVEEAVR -continued

```
>3plus1_GFP11_Key_Cterm_99                                      (SEQ ID NO: 26700)
DERRIAERIRELLRESKKLVRDVVEEAKRLLKENRDSTRKIIEDIRRLLRKIEDSTR >3plus1_GFP11_Key_Cterm_100                                     (SEQ ID NO: 26701)
DALSRLLEELLRVVDDLIRVLKELIDKSRKVIEELLELLKRINEENLKVLAEIIK >3plus1_GFP11_Key_Cterm_101                                     (SEQ ID NO: 26702)
DERRIAERIRELLRESKKLVRDVVEEAKRLLKENRDSTRKIIEDIRRLLRKIEDSTR >3plus1_GFP11_Key_Cterm_102                                     (SEQ ID NO: 26703)
EALRKLVELLVEVLRRLIRVNRELVKLLREVLERLLRILRESVKKLKRLIEKVIKDAT >3plus1_GFP11_Key_Cterm_103                                     (SEQ ID NO: 26704)
EALRKLVELLVEVLRRLIRVNRELVKLLREVLERLLRILRESVKKLKRLIEKVIKDAT >3plus1_GFP11_Key_Cterm_104                                     (SEQ ID NO: 26705)
AAKRLVEELLKAVTDLSRKNKRILEELLKAIETLSDENKKILTEILDALRRLVEKIEK >3plus1_GFP11_Key_Cterm_105                                     (SEQ ID NO: 26706)
EALRKLVELLVEVLRRLIRVNRELVKLLREVLERLLRILRESVKKLKRLIEKVIKDAT >3plus1_GFP11_Key_Cterm_106                                     (SEQ ID NO: 26707)
EALRKLVELLVEVLRRLIRVNRELVKLLREVLERLLRILRESVKKLKRLIEKVIKDAT >3plus1_GFP11_Key_Cterm_107                                     (SEQ ID NO: 26708)
DALSRLLEELLRVVDDLIRVLKELIDKSRKVIEELLELLKRINEENLKVLAEIIK >3plus1_GFP11_Key_Cterm_108                                     (SEQ ID NO: 26709)
DALSRLLEELLRVVDDLIRVLKELIDKSRKVIEELLELLKRINEENLKVLAEIIK >3plus1_GFP11_Key_Cterm_109                                     (SEQ ID NO: 26710)
RAVKKLDEIVKEVAKKLEDVVRANEELWRALVELNKESVRRLREIVERVARDLEETAR >3plus1_GFP11_Key_Cterm_110                                     (SEQ ID NO: 26711)
DRLDKVEELVKKLLEDTKRTVDRVRELVRKILKKSRETLEELERLIEKILRELEKDAR >3plus1_GFP11_Key_Cterm_111                                     (SEQ ID NO: 26712)
DALSRLLEELLRVVDDLIRVLKELIDKSRKVIEELLELLKRINEENLKVLAEIIK >3plus1_GFP11_Key_Cterm_112                                     (SEQ ID NO: 26713)
RAVKKLDEIVKEVAKKLEDVVRANEELWRALVELNKESVRRLREIVERVARDLEETAR >3plus1_GFP11_Key_Cterm_113                                     (SEQ ID NO: 26714)
RAVKKLDEIVKEVAKKLEDVVRANEELWRALVELNKESVRRLREIVERVARDLEETAR >3plus1_GFP11_Key_Cterm_114                                     (SEQ ID NO: 26715)
SEDDLKRVVDEVEKKLRELKRRYAEALERIKEKIKELKDRYERAVREVVAELRKTTK >3plus1_GFP11_Key_Cterm_115                                     (SEQ ID NO: 26716)
RAVKKLDEIVKEVAKKLEDVVRANEELWRALVELNKESVRRLREIVERVARDLEETAR >3plus1_GFP11_Key_Cterm_116                                     (SEQ ID NO: 26717)
DEVEREIRRVKEDLDRILEEYRRLLEEIKRKLEEILRRVEELHRRLRRKLEEIDR >3plus1_GFP11_Key_Cterm_117                                     (SEQ ID NO: 26718)
SEDDLKRVVDEVEKKLRELKRRYAEALERIKEKIKELKDRYERAVREVVAELRKTTK >3plus1_GFP11_Key_Nterm_118                                     (SEQ ID NO: 26719)
DEAKELLDEIRKAVKESEDRLEKLLRDYEKELRRLEKELRDLKRRIEEKLEELRRGSL
```

```
>3plus1_GFP11_Key_Nterm_119                                    (SEQ ID NO: 26720)
SEKEDAARKLRKLVEELTREYEELVKKLERLIEEIEKVSEESVRKLEKLLAEISEEVR >3plus1_GFP11_Key_Nterm_120                                    (SEQ ID NO: 26721)
SEDEIIKKIIEDLRRVLKEVEEIHKEVEERLDKVLKEAEEMHKEVLKELDRVLDEVKR >3plus1_GFP11_Key_Nterm_121                                    (SEQ ID NO: 26722)
SKAEEIAEKLDRLLEENRRALEEITTRLDDLLRRNKDALRKVMEKLKRLLDDLRRGGI >3plus1_GFP11_Key_Nterm_122                                    (SEQ ID NO: 26723)
SEKEKLLKESEEEVRRLRRTLEELLRKYREVLERLRKELREIEERVRDVVRRLKEVLD >3plus1_GFP11_Key_Nterm_123                                    (SEQ ID NO: 26724)
SEKEDAARKLRKLVEELTREYEELVKKLERLIEEIEKVSEESVRKLEKLLAEISEEVR >3plus1_GFP11_Key_Nterm_124                                    (SEQ ID NO: 26725)
SKEETLRKEAEDLLRRLEELTRRLEKKARELLERAKKLSRDLAEELKRLLKELREKGV >3plus1_GFP11_Key_Nterm_125                                    (SEQ ID NO: 26726)
SEKEDAARKLRKLVEELTREYEELVKKLERLIEEIEKVSEESVRKLEKLLAEISEEVR >3plus1_GFP11_Key_Nterm_126                                    (SEQ ID NO: 26727)
SKAEEIAEKLDRLLEENRRALEEITTRLDDLLRRNKDALRKVMEKLKRLLDDLRRGGI >3plus1_GFP11_Key_Nterm_127                                    (SEQ ID NO: 26728)
SEKEDAARKLRKLVEELTREYEELVKKLERLIEEIEKVSEESVRKLEKLLAEISEEVR >3plus1_GFP11_Key_Nterm_128                                    (SEQ ID NO: 26729)
SKAEEIAEKLDRLLEENRRALEEITTRLDDLLRRNKDALRKVMEKLKRLLDDLRRGGI >3plus1_GFP11_Key_Nterm_129                                    (SEQ ID NO: 26730)
SKEETLRKEAEDLLRRLEELTRRLEKKARELLERAKKLSRDLAEELKRLLKELREKGV >3plus1_GFP11_Key_Nterm_130                                    (SEQ ID NO: 26731)
SRVEELKKLIEDILRISREVVERIKRVAEDIHRINRRVLDDLRKLIEDILRTVEEILA >3plus1_GFP11_Key_Nterm_131                                    (SEQ ID NO: 26732)
SKEETLRKEAEDLLRRLEELTRRLEKKARELLERAKKLSRDLAEELKRLLKELREKGV >3plus1_GFP11_Key_Nterm_132                                    (SEQ ID NO: 26733)
SKAEEIAEKLDRLLEENRRALEEITTRLDDLLRRNKDALRKVMEKLKRLLDDLRRGGI >3plus1_GFP11_Key_Nterm_133                                    (SEQ ID NO: 26734)
SKEETLRKEAEDLLRRLEELTRRLEKKARELLERAKKLSRDLAEELKRLLKELREKGV >3plus1_GFP11_Key_Nterm_134                                    (SEQ ID NO: 26735)
SEKEDAARKLRKLVEELTREYEELVKKLERLIEEIEKVSEESVRKLEKLLAEISEEVR >3plus1_GFP11_Key_Nterm_135                                    (SEQ ID NO: 26736)
SKEETLRKEAEDLLRRLEELTRRLEKKARELLERAKKLSRDLAEELKRLLKELREKGV >3plus1_GFP11_Key_Nterm_136                                    (SEQ ID NO: 26737)
SERETVKRRLEELLKEVKRTLDKLKEEHDRLLEDVRRVVEELKREHDKLLKEVKDSGV >3plus1_GFP11_Key_Nterm_137                                    (SEQ ID NO: 26738)
SEKEDAARKLRKLVEELTREYEELVKKLERLIEEIEKVSEESVRKLEKLLAEISEEVR >3plus1_GFP11_Key_Nterm_138                                    (SEQ ID NO: 26739)
SKEETLRKEAEDLLRRLEELTRRLEKKARELLERAKKLSRDLAEELKRLLKELREKGV
```

-continued

>3plus1_GFP11_Key_Nterm_139                                          (SEQ ID NO: 26740)
KEREEVKEKLDRLLEEVEKTVRELKREHDELLKEVEKLVRDLKKEHDELLKKVKDDGV >3plus1_GFP11_Key_Nterm_140                                          (SEQ ID NO: 26741)
SREEVLRELEEVIEDNRRLLEELIEKSKKVLDESLKLIDELLRRLEEVLERVLRLLEE >2plus1_GFP11_Key_Cterm_1                                            (SEQ ID NO: 26742)
DEVVKRVRDLLDTVRRRNEKVNEDVKRMNDKLRRDNEDVIRRVEKLLRELEEKRRT >2plus1_GFP11_Key_Cterm_2                                            (SEQ ID NO: 26743)
SEDSVERIARELERNLDDLARVLKESEDDLAEILRRLKEVLEESERDLERVEREVRK >2plus1_GFP11_Key_Cterm_3                                            (SEQ ID NO: 26744)
SKELLEKAKAVVDEIKRLAEESLKRLEDLSRDHKRRAKELNDEIAKVVDELAKRAT >2plus1_GFP11_Key_Cterm_4                                            (SEQ ID NO: 26745)
SKEKIDRIIRELERILEEAKKKHEDVLRRLEDSLRRVAELLKAALDRLREIVDRLRR >2plus1_GFP11_Key_Cterm_5                                            (SEQ ID NO: 26746)
DEVVKRVRDLLDTVRRRNEKVNEDVKRMNDKLRRDNEDVIRRVEKLLRELEEKRRT >2plus1_GFP11_Key_Cterm_6                                            (SEQ ID NO: 26747)
DIKTLLDRVRKLAEEDAERLDRLRRESEELNERVRRVDKKLLEEIRRKAKKVEDDTR >2plus1_GFP11_Key_Cterm_7                                            (SEQ ID NO: 26748)
DAETLLRELEKLSRDNKELLKKIEKEIRDLIKEDKERNIELSERLRKLVEELKKKAT >2plus1_GFP11_Key_Cterm_8                                            (SEQ ID NO: 26749)
DEVVKRVRDLLDTVRRRNEKVNEDVKRMNDKLRRDNEDVIRRVEKLLRELEEKRRT >2plus1_GFP11_Key_Cterm_9                                            (SEQ ID NO: 26750)
DIKTLLDRVRKLAEEDAERLDRLRRESEELNERVRRVDKKLLEEIRRKAKKVEDDTR >2plus1_GFP11_Key_Cterm_10                                           (SEQ ID NO: 26751)
SEELSAEVKKLLDEVRKALARHKDENDKLLKEIEDSLRRHKEENDRLLEKLKESTR >2plus1_GFP11_Key_Cterm_11                                           (SEQ ID NO: 26752)
DADDVLARVEELAKRAHDENERLIREVEELVRAHNKRNKELVDEVKRLVEKVIEEER >2plus1_GFP11_Key_Cterm_12                                           (SEQ ID NO: 26753)
SKEKIDRIIRELERILEEAKKKHEDVLRRLEDSLRRVAELLKAALDRLREIVDRLRR >2plus1_GFP11_Key_Cterm_13                                           (SEQ ID NO: 26754)
DEVVKRVRDLLDTVRRRNEKVNEDVKRMNDKLRRDNEDVIRRVEKLLRELEEKRRT >2plus1_GFP11_Key_Cterm_14                                           (SEQ ID NO: 26755)
SEELSAEVKKLLDEVRKALARHKDENDKLLKEIEDSLRRHKEENDRLLEKLKESTR >2plus1_GFP11_Key_Cterm_15                                           (SEQ ID NO: 26756)
DAETVLRSAEDIVAKNRKLAEEVLRRVKKIVEENRKIASEVLDDVRKLVEDVLARAS >2plus1_GFP11_Key_Cterm_16                                           (SEQ ID NO: 26757)
DADDVLARVEELAKRAHDENERLIREVEELVRAHNKRNKELVDEVKRLVEKVIEEER >2plus1_GFP11_Key_Cterm_17                                           (SEQ ID NO: 26758)
SKEKIDRIIRELERILEEAKKKHEDVLRRLEDSLRRVAELLKAALDRLREIVDRLRR >2plus1_GFP11_Key_Cterm_18                                           (SEQ ID NO: 26759)
DEEKLKDLIRKLRDILRRAAEAHKKLIDDARESLERAKREHEKLIDRLKKILEELER

```
>2plus1_GFP11_Key_Cterm_19                                                  (SEQ ID NO: 26760)
DIKTLLDRVRKLAEEDAERLDRLRRESEELNERVRRVDKKLLEEIRRKAKKVEDDTR >2plus1_GFP11_Key_Cterm_20                                                  (SEQ ID NO: 26761)
DATRVIEEAKRILDEARKLNEETIRRSEELVRRIERVIEEIIKRSEKLLEDVARESK >2plus1_GFP11_Key_Cterm_21                                                  (SEQ ID NO: 26762)
SEELSAEVKKLLDEVRKALARHKDENDKLLKEIEDSLRRHKEENDRLLEKLKESTR >2plus1_GFP11_Key_Cterm_22                                                  (SEQ ID NO: 26763)
DAETVLRSAEDIVAKNRKLAEEVLRRVKKIVEENRKIASEVLDDVRKLVEDVLARAS >2plus1_GFP11_Key_Cterm_23                                                  (SEQ ID NO: 26764)
DADDVLARVEELAKRAHDENERLIREVEELVRAHNKRNKELVDEVKRLVEKVIEEER >2plus1_GFP11_Key_Cterm_24                                                  (SEQ ID NO: 26765)
SKELLEKAKAVVDEIKRLAEESLKRLEDLSRDHKRRAKELNDEIAKVVDELAKRAT >2plus1_GFP11_Key_Cterm_25                                                  (SEQ ID NO: 26766)
DEEVLKKLAEIVRRVKEENRKVNEEVEKRLRELEEENKKVIEDLKSTVEELVERLR >2plus1_GFP11_Key_Cterm_26                                                  (SEQ ID NO: 26767)
DEEVLKKLAEIVRRVKEENRKVNEEVEKRLRELEEENKKVIEDLKSTVEELVERLR >2plus1_GFP11_Key_Cterm_27                                                  (SEQ ID NO: 26768)
DKLLKEARDLIREIEKRLEELLKRVEKLTEDAKRDLERSNREHKELADRIKETAR >2plus1_GFP11_Key_Cterm_28                                                  (SEQ ID NO: 26769)
DKDSARELERIVKENAELAERVFREVEKIVRENTKLAEDSVRELKRLVEELKKRAK >2plus1_GFP11_Key_Cterm_29                                                  (SEQ ID NO: 26770)
SKEKIDRIIRELERILEEAKKKHEDVLRRLEDSLRRVAELLKAALDRLREIVDRLRR >2plus1_GFP11_Key_Cterm_30                                                  (SEQ ID NO: 26771)
DEEKLKDLIRKLRDILRRAAEAHKKLIDDARESLERAKREHEKLIDRLKKILEELER >2plus1_GFP11_Key_Cterm_31                                                  (SEQ ID NO: 26772)
DEVVKRVRDLLDTVRRRNEKVNEDVKRMNDKLRRDNEDVIRRVEKLLRELEEKRRT >2plus1_GFP11_Key_Cterm_32                                                  (SEQ ID NO: 26773)
DEEVLRTLEEIIRRLTKELEDVLREYERELRRLEEENKRVIDKTEEEIRRLADRLRR >2plus1_GFP11_Key_Cterm_33                                                  (SEQ ID NO: 26774)
DERILRELEERVKELEKEAREILKRSEDETDKLREKAERILEDLERANRRTMDEARR >2plus1_GFP11_Key_Cterm_34                                                  (SEQ ID NO: 26775)
SEELSAEVKKLLDEVRKALARHKDENDKLLKEIEDSLRRHKEENDRLLEKLKESTR >2plus1_GFP11_Key_Cterm_35                                                  (SEQ ID NO: 26776)
LPEEVLRELEELLKESEERIKRIEEEIKKIIDKSREDIKRVLEEIERLNAKAADDLRK >2plus1_GFP11_Key_Cterm_36                                                  (SEQ ID NO: 26777)
DADDVLARVEELAKRAHDENERLIREVEELVRAHNKRNKELVDEVKRLVEKVIEEER >2plus1_GFP11_Key_Cterm_37                                                  (SEQ ID NO: 26778)
DEEVLKKLAEIVRRVKEENRKVNEEVEKRLRELEEENKKVIEDLKSTVEELVERLR >2plus1_GFP11_Key_Cterm_38                                                  (SEQ ID NO: 26779)
DKLLKEARDLIREIEKRLEELLKRVEKLTEDAKRDLERSNREHKELADRIKETAR
```

-continued

>2p1us1_GFP11_Key_Cterm_39 (SEQ ID NO: 26780)
DEEVLRTLEEIIRRLTKELEDVLREYERELRRLEEENKRVIDKTEEEIRRLADRLRR >2p1us1_GFP11_Key_Cterm_40 (SEQ ID NO: 26781)
DRRIEKVLKEIEEKIREVIKEWERVHREVEELLKRLIDENRKVLDEIRKLLEEKSK >2p1us1_GFP11_Key_Cterm_41 (SEQ ID NO: 26782)
DERILRELEERVKELEKEAREILKRSEDETDKLREKAERILEDLERANRRTMDEARR >2p1us1_GFP11_Key_Cterm_42 (SEQ ID NO: 26783)
SEELSAEVKKLLDEVRKALARHKDENDKLLKEIEDSLRRHKEENDRLLEKLKESTR >2p1us1_GFP11_Key_Cterm_43 (SEQ ID NO: 26784)
DEEVLKKLAEIVRRVKEENRKVNEEVEKRLRELEEENKKVIEDLKSTVEELVERLR >2p1us1_GFP11_Key_Cterm_44 (SEQ ID NO: 26785)
SKEKIDRIIRELERILEEAKKKHEDVLRRLEDSLRRVAELLKAALDRLREIVDRLRR >2p1us1_GFP11_Key_Cterm_45 (SEQ ID NO: 26786)
DRRIEKVLKEIEEKIREVIKEWERVHREVEELLKRLIDENRKVLDEIRKLLEEKSK >2p1us1_GFP11_Key_Cterm_46 (SEQ ID NO: 26787)
TLRELARSIRKLSAENKERLKELLRELKKLSDENKERIKKLLSDAEKIIEDVARRAK >2p1us1_GFP11_Key_Cterm_47 (SEQ ID NO: 26788)
DERILRELEERVKELEKEAREILKRSEDETDKLREKAERILEDLERANRRTMDEARR >2p1us1_GFP11_Key_Cterm_48 (SEQ ID NO: 26789)
EKLKELRDVIAEVAKRIDELDEYTRESIRRAKKEIERLNRETKKVIEEVVKRIEEERK >2p1us1_GFP11_Key_Cterm_49 (SEQ ID NO: 26790)
DERVREELKKLLTRVEEEHRKVLETDKKILKEAHKESKEVNDRDRELLERLEESVR >2p1us1_GFP11_Key_Cterm_50 (SEQ ID NO: 26791)
DADDVLARVEELAKRAHDENERLIREVEELVRAHNKRNKELVDEVKRLVEKVIEEER >2p1us1_GFP11_Key_Cterm_51 (SEQ ID NO: 26792)
TVKRLLDELRELLERLKRTIEELLKRNRDLLADAEEKARRLLEENRKLLKAARDTAT >2p1us1_GFP11_Key_Cterm_52 (SEQ ID NO: 26793)
DEEVLKKLAEIVRRVKEENRKVNEEVEKRLRELEEENKKVIEDLKSTVEELVERLR >2p1us1_GFP11_Key_Cterm_53 (SEQ ID NO: 26794)
SKEKIDRIIRELERILEEAKKKHEDVLRRLEDSLRRVAELLKAALDRLREIVDRLRR >2p1us1_GFP11_Key_Cterm_54 (SEQ ID NO: 26795)
DERILRELEERVKELEKEAREILKRSEDETDKLREKAERILEDLERANRRTMDEARR >2p1us1_GFP11_Key_Cterm_55 (SEQ ID NO: 26796)
DATRVIEEAKRILDEARKLNEETIRRSEELVRRIERVIEEIIKRSEKLLEDVARESK >2p1us1_GFP11_Key_Cterm_56 (SEQ ID NO: 26797)
EAAREIIKRLREVNKRTKEKLDELIKHSEEVLERVKRLIDELRKHSEEVLEDLRRRAK >2p1us1_GFP11_Key_Cterm_57 (SEQ ID NO: 26798)
EKLKELRDVIAEVAKRIDELDEYTRESIRRAKKEIERLNRETKKVIEEVVKRIEEERK >2p1us1_GFP11_Key_Cterm_58 (SEQ ID NO: 26799)
ELLRRIKKLLDEIKKAIEDSSREIKRLLEESERVMKRSSEDIKRTLDDTRRVVEEVRR -continued >2p1us1_GFP11_Key_Cterm_59       (SEQ ID NO: 26800)
SKAIKDVRDIVKKVKDELKEWRDRNKELVDRLSEELKEWLKDVERVLKELTDKDR >2p1us1_GFP11_Key_Cterm_60       (SEQ ID NO: 26801)
DERVREELKKLLTRVEEEHRKVLETDKKILKEAHKESKEVNDRDRELLERLEESVR >2p1us1_GFP11_Key_Cterm_61       (SEQ ID NO: 26802)
DIDKLLKELRDLVEKIKKDLKELLERYEEIVRRIKELLKDLNREAEEVVRRLKEELR >2p1us1_GFP11_Key_Cterm_62       (SEQ ID NO: 26803)
DADDVLARVEELAKRAHDENERLIREVEELVRAHNKRNKELVDEVKRLVEKVIEEER >2p1us1_GFP11_Key_Cterm_63       (SEQ ID NO: 26804)
DEEVLKKLAEIVRRVKEENRKVNEEVEKRLRELEEENKKVIEDLKSTVEELVERLR >2p1us1_GFP11_Key_Cterm_64       (SEQ ID NO: 26805)
EREEELKEVADRVKEKLDRLNRENEKSSEELKRELDKINDENRETSERLKREIDETTR >2p1us1_GFP11_Key_Cterm_65       (SEQ ID NO: 26806)
SKEKIDRIIRELERILEEAKKKHEDVLRRLEDSLRRVAELLKAALDRLREIVDRLRR >2p1us1_GFP11_Key_Cterm_66       (SEQ ID NO: 26807)
SKEKIDRIIRELERILEEAKKKHEDVLRRLEDSLRRVAELLKAALDRLREIVDRLRR >2p1us1_GFP11_Key_Cterm_67       (SEQ ID NO: 26808)
TKDLLDENSKRSNEISREVKKDLERTVRENKKIVDEVAKALEDTVDKNRRIVEEVTT >2p1us1_GFP11_Key_Cterm_68       (SEQ ID NO: 26809)
DEVVKRVRDLLDTVRRRNEKVNEDVKRMNDKLRRDNEDVIRRVEKLLRELEEKRRT >2p1us1_GFP11_Key_Cterm_69       (SEQ ID NO: 26810)
DRRIEKVLKEIEEKIREVIKEWERVHREVEELLKRLIDENRKVLDEIRKLLEEKSK >2p1us1_GFP11_Key_Cterm_70       (SEQ ID NO: 26811)
ELLRRIKKLLDEIKKAIEDSSREIKRLLEESERVMKRSSEDIKRTLDDTRRVVEEVRR >2p1us1_GFP11_Key_Cterm_71       (SEQ ID NO: 26812)
SEELSAEVKKLLDEVRKALARHKDENDKLLKEIEDSLRRHKEENDRLLEKLKESTR >2p1us1_GFP11_Key_Cterm_72       (SEQ ID NO: 26813)
DIDKLLKELRDLVEKIKKDLKELLERYEEIVRRIKELLKDLNREAEEVVRRLKEELR >2p1us1_GFP11_Key_Cterm_73       (SEQ ID NO: 26814)
DADDVLARVEELAKRAHDENERLIREVEELVRAHNKRNKELVDEVKRLVEKVIEEER >2p1us1_GFP11_Key_Cterm_74       (SEQ ID NO: 26815)
DEEVLKKLAEIVRRVKEENRKVNEEVEKRLRELEEENKKVIEDLKSTVEELVERLR >2p1us1_GFP11_Key_Cterm_75       (SEQ ID NO: 26816)
DEEVLKKLAEIVRRVKEENRKVNEEVEKRLRELEEENKKVIEDLKSTVEELVERLR >2p1us1_GFP11_Key_Cterm_76       (SEQ ID NO: 26817)
SKEKIDRIIRELERILEEAKKKHEDVLRRLEDSLRRVAELLKAALDRLREIVDRLRR >2p1us1_GFP11_Key_Cterm_77       (SEQ ID NO: 26818)
SEELREELKKLERKIEKVAKEIHDHDKEVTERLEDLLRRITEHARKSDREIEETAR >2p1us1_GFP11_Key_Cterm_78       (SEQ ID NO: 26819)
DRRIEKVLKEIEEKIREVIKEWERVHREVEELLKRLIDENRKVLDEIRKLLEEKSK -continued >2plus1_GFP11_Key_Cterm_79                                    (SEQ ID NO: 26820)
DATRVIEEAKRILDEARKLNEETIRRSEELVRRIERVIEEIIKRSEKLLEDVARESK >2plus1_GFP11_Key_Cterm_80                                    (SEQ ID NO: 26821)
EKLKELRDVIAEVAKRIDELDEYTRESIRRAKKEIERLNRETKKVIEEVVKRIEEERK >2plus1_GFP11_Key_Cterm_81                                    (SEQ ID NO: 26822)
ELLRRIKKLLDEIKKAIEDSSREIKRLLEESERVMKRSSEDIKRTLDDTRRVVEEVRR >2plus1_GFP11_Key_Cterm_82                                    (SEQ ID NO: 26823)
DIDKLLKELRDLVEKIKKDLKELLERYEEIVRRIKELLKDLNREAEEVVRRLKEELR >2plus1_GFP11_Key_Cterm_83                                    (SEQ ID NO: 26824)
EAKKKLDEVLERAKRTIDRLLETSDRSLEKVEADLRRLNEELDRSLERAERTIRELAK >2plus1_GFP11_Key_Cterm_84                                    (SEQ ID NO: 26825)
DEEVLKKLAEIVRRVKEENRKVNEEVEKRLRELEEENKKVIEDLKSTVEELVERLR >2plus1_GFP11_Key_Cterm_85                                    (SEQ ID NO: 26826)
DEEVLKKLAEIVRRVKEENRKVNEEVEKRLRELEEENKKVIEDLKSTVEELVERLR >2plus1_GFP11_Key_Cterm_86                                    (SEQ ID NO: 26827)
DRRIEKVLKEIEEKIREVIKEWERVHREVEELLKRLIDENRKVLDEIRKLLEEKSK >2plus1_GFP11_Key_Cterm_87                                    (SEQ ID NO: 26828)
DERILRELEERVKELEKEAREILKRSEDETDKLREKAERILEDLERANRRTMDEARR >2plus1_GFP11_Key_Cterm_88                                    (SEQ ID NO: 26829)
DLKRVEERAREVSRRNEESMRRVKEDADRVSEANKEVLDRVREEVKRLIEEVRETLR >2plus1_GFP11_Key_Cterm_89                                    (SEQ ID NO: 26830)
EKLKELRDVIAEVAKRIDELDEYTRESIRRAKKEIERLNRETKKVIEEVVKRIEEERK >2plus1_GFP11_Key_Cterm_90                                    (SEQ ID NO: 26831)
ELLRRIKKLLDEIKKAIEDSSREIKRLLEESERVMKRSSEDIKRTLDDTRRVVEEVRR >2plus1_GFP11_Key_Cterm_91                                    (SEQ ID NO: 26832)
ELLRRIKKLLDEIKKAIEDSSREIKRLLEESERVMKRSSEDIKRTLDDTRRVVEEVRR >2plus1_GFP11_Key_Cterm_92                                    (SEQ ID NO: 26833)
LPEEVLRELEELLKESEERIKRIEEEIKKIIDKSREDIKRVLEEIERLNAKAADDLRK >2plus1_GFP11_Key_Cterm_93                                    (SEQ ID NO: 26834)
EAKKKLDEVLERAKRTIDRLLETSDRSLEKVEADLRRLNEELDRSLERAERTIRELAK >2plus1_GFP11_Key_Cterm_94                                    (SEQ ID NO: 26835)
DEEVLKKLAEIVRRVKEENRKVNEEVEKRLRELEEENKKVIEDLKSTVEELVERLR >2plus1_GFP11_Key_Cterm_95                                    (SEQ ID NO: 26836)
DKLLKEARDLIREIEKRLEELLKRVEKLTEDAKRDLERSNREHKELADRIKETAR >2plus1_GFP11_Key_Cterm_96                                    (SEQ ID NO: 26837)
DKLLKEARDLIREIEKRLEELLKRVEKLTEDAKRDLERSNREHKELADRIKETAR >2plus1_GFP11_Key_Cterm_97                                    (SEQ ID NO: 26838)
DIVRKIERIVETIEREVRESVKKVEEIARDIRRKVDESVKNVEKLLRDVDKKARDRKK >2plus1_GFP11_Key_Cterm_98                                    (SEQ ID NO: 26839)
DEIKRIVDEVRERLKRIVDENAKIVEDARRALEKIVKENEEILRRLKKELRELRK -continued >2plus1_GFP11_Key_Cterm_99 (SEQ ID NO: 26840)
DRRIEKVLKEIEEKIREVIKEWERVHREVEELLKRLIDENRKVLDEIRKLLEEKSK >2plus1_GFP11_Key_Cterm_100 (SEQ ID NO: 26841)
DLKRVEERAREVSRRNEESMRRVKEDADRVSEANKEVLDRVREEVKRLIEEVRETLR >2plus1_GFP11_Key_Cterm_101 (SEQ ID NO: 26842)
DATRVIEEAKRILDEARKLNEETIRRSEELVRRIERVIEEIIKRSEKLLEDVARESK >2plus1_GFP11_Key_Cterm_102 (SEQ ID NO: 26843)
DAETIERVVRELLEENKEVLRKTEEAVKRSTETNKRLLEASKEVADRLRERIKEAAK >2plus1_GFP11_Key_Cterm_103 (SEQ ID NO: 26844)
EKLKELRDVIAEVAKRIDELDEYTRESIRRAKKEIERLNRETKKVIEEVVKRIEEERK >2plus1_GFP11_Key_Cterm_104 (SEQ ID NO: 26845)
ELLRRIKKLLDEIKKAIEDSSREIKRLLEESERVMKRSSEDIKRTLDDTRRVVEEVRR >2plus1_GFP11_Key_Cterm_105 (SEQ ID NO: 26846)
DEVVERAERISEENKRRVEDVARKSKELVEDVRRHSEEVVRRVEELVKEVEERVR >2plus1_GFP11_Key_Cterm_106 (SEQ ID NO: 26847)
EAKKKLDEVLERAKRTIDRLLETSDRSLEKVEADLRRLNEELDRSLERAERTIRELAK >2plus1_GFP11_Key_Cterm_107 (SEQ ID NO: 26848)
TAERARETLKRLLDENRDRSKKVKEEIRRILEDLTRTTERVKREIAKLLKELEDTAR >2plus1_GFP11_Key_Cterm_108 (SEQ ID NO: 26849)
EAVRRLKEILERLKEEVRRSLEELRKEVERLKKEVEDSLRELKKSLEEWVKSLEEATR >2plus1_GFP11_Key_Cterm_109 (SEQ ID NO: 26850)
DERILRELEERVKELEKEAREILKRSEDETDKLREKAERILEDLERANRRTMDEARR >2plus1_GFP11_Key_Cterm_110 (SEQ ID NO: 26851)
DATRVIEEAKRILDEARKLNEETIRRSEELVRRIERVIEEIIKRSEKLLEDVARESK >2plus1_GFP11_Key_Cterm_111 (SEQ ID NO: 26852)
DKARKVAEVAEKVLRDIDKLDRESKEAFRATNEEIAKLDEDTARVAERVKKAIEDLAK >2plus1_GFP11_Key_Cterm_112 (SEQ ID NO: 26853)
EKLKELRDVIAEVAKRIDELDEYTRESIRRAKKEIERLNRETKKVIEEVVKRIEEERK >2plus1_GFP11_Key_Cterm_113 (SEQ ID NO: 26854)
ELLRRIKKLLDEIKKAIEDSSREIKRLLEESERVMKRSSEDIKRTLDDTRRVVEEVRR >2plus1_GFP11_Key_Cterm_114 (SEQ ID NO: 26855)
DKVERVVREVEKLHEEDRKRLEESTRSVRKLLEELKRELEKSTRSVKALVDELRERVR >2plus1_GFP11_Key_Cterm_115 (SEQ ID NO: 26856)
DEVVERAERISEENKRRVEDVARKSKELVEDVRRHSEEVVRRVEELVKEVEERVR >2plus1_GFP11_Key_Cterm_116 (SEQ ID NO: 26857)
EAKKKLDEVLERAKRTIDRLLETSDRSLEKVEADLRRLNEELDRSLERAERTIRELAK >2plus1_GFP11_Key_Cterm_117 (SEQ ID NO: 26858)
TAERARETLKRLLDENRDRSKKVKEEIRRILEDLTRTTERVKREIAKLLKELEDTAR >2plus1_GFP11_Key_Cterm_118 (SEQ ID NO: 26859)
DERILRELEERVKELEKEAREILKRSEDETDKLREKAERILEDLERANRRTMDEARR -continued

```
>2plus1_GFP11_Key_Cterm_119                              (SEQ ID NO: 26860)
DERILRELEERVKELEKEAREILKRSEDETDKLREKAERILEDLERANRRTMDEARR >2plus1_GFP11_Key_Cterm_120                              (SEQ ID NO: 26861)
DLKRVEERAREVSRRNEESMRRVKEDADRVSEANKEVLDRVREEVKRLIEEVRETLR >2plus1_GFP11_Key_Cterm_121                              (SEQ ID NO: 26862)
DKARKVAEVAEKVLRDIDKLDRESKEAFRATNEEIAKLDEDTARVAERVKKAIEDLAK >2plus1_GFP11_Key_Cterm_122                              (SEQ ID NO: 26863)
ELLRRIKKLLDEIKKAIEDSSREIKRLLEESERVMKRSSEDIKRTLDDTRRVVEEVRR >2plus1_GFP11_Key_Cterm_123                              (SEQ ID NO: 26864)
SKAIKDVRDIVKKVKDELKEWRDRNKELVDRLSEELKEWLKDVERVLKELTDKDR >2plus1_GFP11_Key_Cterm_124                              (SEQ ID NO: 26865)
DKVERVVREVEKLHEEDRKRLEESTRSVRKLLEELKRELEKSTRSVKALVDELRERVR >2plus1_GFP11_Key_Cterm_125                              (SEQ ID NO: 26866)
DIDKLLKELRDLVEKIKKDLKELLERYEEIVRRIKELLKDLNREAEEVVRRLKEELR >2plus1_GFP11_Key_Cterm_126                              (SEQ ID NO: 26867)
EAKKKLDEVLERAKRTIDRLLETSDRSLEKVEADLRRLNEELDRSLERAERTIRELAK >2plus1_GFP11_Key_Cterm_127                              (SEQ ID NO: 26868)
DKLLKEARDLIREIEKRLEELLKRVEKLTEDAKRDLERSNREHKELADRIKETAR >2plus1_GFP11_Key_Cterm_128                              (SEQ ID NO: 26869)
TAERARETLKRLLDENRDRSKKVKEEIRRILEDLTRTTERVKREIAKLLKELEDTAR >2plus1_GFP11_Key_Cterm_129                              (SEQ ID NO: 26870)
DEIKRIVDEVRERLKRIVDENAKIVEDARRALEKIVKENEEILRRLKKELRELRK >2plus1_GFP11_Key_Cterm_130                              (SEQ ID NO: 26871)
DRIEEELKRLIDTLREKNREVEKRARDSNRDLKRTNDEIAKEVRELIKKLREDLK >2plus1_GFP11_Key_Cterm_131                              (SEQ ID NO: 26872)
DERILRELEERVKELEKEAREILKRSEDETDKLREKAERILEDLERANRRTMDEARR >2plus1_GFP11_Key_Cterm_132                              (SEQ ID NO: 26873)
DAETIERVVRELLEENKEVLRKTEEAVKRSTETNKRLLEASKEVADRLRERIKEAAK >2plus1_GFP11_Key_Cterm_133                              (SEQ ID NO: 26874)
DKARKVAEVAEKVLRDIDKLDRESKEAFRATNEEIAKLDEDTARVAERVKKAIEDLAK >2plus1_GFP11_Key_Cterm_134                              (SEQ ID NO: 26875)
DKVERVVREVEKLHEEDRKRLEESTRSVRKLLEELKRELEKSTRSVKALVDELRERVR >2plus1_GFP11_Key_Cterm_135                              (SEQ ID NO: 26876)
DIERILRELEAVLKKLTDESERLNREVERVSRDTKKKSKELNEELKAVLDEVKRKAD >2plus1_GFP11_Key_Cterm_136                              (SEQ ID NO: 26877)
DEVVERAERISEENKRRVEDVARKSKELVEDVRRHSEEVVRRVEELVKEVEERVR >2plus1_GFP11_Key_Cterm_137                              (SEQ ID NO: 26878)
EAKKKLDEVLERAKRTIDRLLETSDRSLEKVEADLRRLNEELDRSLERAERTIRELAK >2plus1_GFP11_Key_Cterm_138                              (SEQ ID NO: 26879)
TAERARETLKRLLDENRDRSKKVKEEIRRILEDLTRTTERVKREIAKLLKELEDTAR
```

-continued

>2plus1_GFP11_Key_Cterm_139 (SEQ ID NO: 26880)
DEIKRIVDEVRERLKRIVDENAKIVEDARRALEKIVKENEEILRRLKKELRELRK >2plus1_GFP11_Key_Cterm_140 (SEQ ID NO: 26881)
DRRIEKVLKEIEEKIREVIKEWERVHREVEELLKRLIDENRKVLDEIRKLLEEKSK >2plus1_GFP11_Key_Cterm_141 (SEQ ID NO: 26882)
DLKRVEERAREVSRRNEESMRRVKEDADRVSEANKEVLDRVREEVKRLIEEVRETLR >2plus1_GFP11_Key_Cterm_142 (SEQ ID NO: 26883)
DAETIERVVRELLEENKEVLRKTEEAVKRSTETNKRLLEASKEVADRLRERIKEAAK >2plus1_GFP11_Key_Cterm_143 (SEQ ID NO: 26884)
DKARKVAEVAEKVLRDIDKLDRESKEAFRATNEEIAKLDEDTARVAERVKKAIEDLAK >2plus1_GFP11_Key_Cterm_144 (SEQ ID NO: 26885)
ELLRRIKKLLDEIKKAIEDSSREIKRLLEESERVMKRSSEDIKRTLDDTRRVVEEVRR >2plus1_GFP11_Key_Cterm_145 (SEQ ID NO: 26886)
DKVERVVREVEKLHEEDRKRLEESTRSVRKLLEELKRELEKSTRSVKALVDELRERVR >2plus1_GFP11_Key_Cterm_146 (SEQ ID NO: 26887)
EAKKKLDEVLERAKRTIDRLLETSDRSLEKVEADLRRLNEELDRSLERAERTIRELAK >2plus1_GFP11_Key_Cterm_147 (SEQ ID NO: 26888)
TAERARETLKRLLDENRDRSKKVKEEIRRILEDLTRTTERVKREIAKLLKELEDTAR >2plus1_GFP11_Key_Cterm_148 (SEQ ID NO: 26889)
DEIKRIVDEVRERLKRIVDENAKIVEDARRALEKIVKENEEILRRLKKELRELRK >2plus1_GFP11_Key_Cterm_149 (SEQ ID NO: 26890)
DKARKVAEVAEKVLRDIDKLDRESKEAFRATNEEIAKLDEDTARVAERVKKAIEDLAK >2plus1_GFP11_Key_Cterm_150 (SEQ ID NO: 26891)
DEVTKVKKVADDVLAEIKKLDDETRRVIEDTNKKIADLDKATRDVVRKVLEEVKKLEK >2plus1_GFP11_Key_Cterm_151 (SEQ ID NO: 26892)
DIDKLLKELRDLVEKIKKDLKELLERYEEIVRRIKELLKDLNREAEEVVRRLKEELR >2plus1_GFP11_Key_Cterm_152 (SEQ ID NO: 26893)
TAERARETLKRLLDENRDRSKKVKEEIRRILEDLTRTTERVKREIAKLLKELEDTAR >2plus1_GFP11_Key_Cterm_153 (SEQ ID NO: 26894)
DEIKRIVDEVRERLKRIVDENAKIVEDARRALEKIVKENEEILRRLKKELRELRK >2plus1_GFP11_Key_Cterm_154 (SEQ ID NO: 26895)
RLVREVEDLVRRLVRRSEKSNEEVKRTVEELVRRMEESNDRVRDLVRRLVEELKRAVD >2plus1_GFP11_Key_Cterm_155 (SEQ ID NO: 26896)
DKARKVAEVAEKVLRDIDKLDRESKEAFRATNEEIAKLDEDTARVAERVKKAIEDLAK >2plus1_GFP11_Key_Cterm_156 (SEQ ID NO: 26897)
EAKKKLDEVLERAKRTIDRLLETSDRSLEKVEADLRRLNEELDRSLERAERTIRELAK >2plus1_GFP11_Key_Cterm_157 (SEQ ID NO: 26898)
RLVREVEDLVRRLVRRSEKSNEEVKRTVEELVRRMEESNDRVRDLVRRLVEELKRAVD >2plus1_GFP11_Key_Cterm_158 (SEQ ID NO: 26899)
DKARKVAEVAEKVLRDIDKLDRESKEAFRATNEEIAKLDEDTARVAERVKKAIEDLAK -continued

```
>2plus1_GFP11_Key_Cterm_159                                (SEQ ID NO: 26900)
DEVTKVKKVADDVLAEIKKLDDETRRVIEDTNKKIADLDKATRDVVRKVLEEVKKLEK >2plus1_GFP11_Key_Cterm_160                                (SEQ ID NO: 26901)
TAERARETLKRLLDENRDRSKKVKEEIRRILEDLTRTTERVKREIAKLLKELEDTAR >2plus1_GFP11_Key_Cterm_161                                (SEQ ID NO: 26902)
DLKRVEERAREVSRRNEESMRRVKEDADRVSEANKEVLDRVREEVKRLIEEVRETLR >2plus1_GFP11_Key_Cterm_162                                (SEQ ID NO: 26903)
DKARKVAEVAEKVLRDIDKLDRESKEAFRATNEEIAKLDEDTARVAERVKKAIEDLAK >2plus1_GFP11_Key_Cterm_163                                (SEQ ID NO: 26904)
DEVTKVKKVADDVLAEIKKLDDETRRVIEDTNKKIADLDKATRDVVRKVLEEVKKLEK >2plus1_GFP11_Key_Cterm_164                                (SEQ ID NO: 26905)
DKVERVVREVEKLHEEDRKRLEESTRSVRKLLEELKRELEKSTRSVKALVDELRERVR >2plus1_GFP11_Key_Cterm_165                                (SEQ ID NO: 26906)
EAKKKLDEVLERAKRTIDRLLETSDRSLEKVEADLRRLNEELDRSLERAERTIRELAK >2plus1_GFP11_Key_Cterm_166                                (SEQ ID NO: 26907)
TAERARETLKRLLDENRDRSKKVKEEIRRILEDLTRTTERVKREIAKLLKELEDTAR >2plus1_GFP11_Key_Cterm_167                                (SEQ ID NO: 26908)
TAERARETLKRLLDENRDRSKKVKEEIRRILEDLTRTTERVKREIAKLLKELEDTAR >2plus1_GFP11_Key_Cterm_168                                (SEQ ID NO: 26909)
DKARKVAEVAEKVLRDIDKLDRESKEAFRATNEEIAKLDEDTARVAERVKKAIEDLAK >2plus1_GFP11_Key_Cterm_169                                (SEQ ID NO: 26910)
DEVTKVKKVADDVLAEIKKLDDETRRVIEDTNKKIADLDKATRDVVRKVLEEVKKLEK >2plus1_GFP11_Key_Cterm_170                                (SEQ ID NO: 26911)
DKVERVVREVEKLHEEDRKRLEESTRSVRKLLEELKRELEKSTRSVKALVDELRERVR >2plus1_GFP11_Key_Cterm_171                                (SEQ ID NO: 26912)
TAERARETLKRLLDENRDRSKKVKEEIRRILEDLTRTTERVKREIAKLLKELEDTAR >2plus1_GFP11_Key_Cterm_172                                (SEQ ID NO: 26913)
DKARKVAEVAEKVLRDIDKLDRESKEAFRATNEEIAKLDEDTARVAERVKKAIEDLAK >2plus1_GFP11_Key_Cterm_173                                (SEQ ID NO: 26914)
RLVREVEDLVRRLVRRSEKSNEEVKRTVEELVRRMEESNDRVRDLVRRLVEELKRAVD >2plus1_GFP11_Key_Nterm_174                                (SEQ ID NO: 26915)
SESDEVIRDLARLLDELARHVDDSVRRMDEVVKRSTREADELAKRLDELVKEVEKKPG >2plus1_GFP11_Key_Nterm_175                                (SEQ ID NO: 26916)
SRAETVLKEVTDKIKKLADSSDELLRRNKENIDELKKSSEELLRRLTKAIEEIEKGSV >2plus1_GFP11_Key_Nterm_176                                (SEQ ID NO: 26917)
SVDEVLKEIEDALRRLKEEVERVLKENEDELRRLEEEVRRVLKEDEELLESLKRGVGE >2plus1_GFP11_Key_Nterm_177                                (SEQ ID NO: 26918)
SEVDEIIKELERLLAEIARENERIIRESRKLADEVRKRNEDAIRKLEELVARLADAVR >2plus1_GFP11_Key_Nterm_178                                (SEQ ID NO: 26919)
SEVDDVLRRLEELIKTLEDINAKSLEDIKKLIDDLAKILEDALRKHEKLIRELREAKK
```

-continued

>2plus1_GFP11_Key_Nterm_179
(SEQ ID NO: 26920)
SEVDDVLRRLEELIKTLEDINAKSLEDIKKLIDDLAKILEDALRKHEKLIRELREAKK >2plus1_GFP11_Key_Nterm_180
(SEQ ID NO: 26921)
SRAETVLKEVTDKIKKLADSSDELLRRNKENIDELKKSSEELLRRLTKAIEEIEKGSV >2plus1_GFP11_Key_Nterm_181
(SEQ ID NO: 26922)
KEVEDAVKELEDLLRANEDKTRSIVEDMRASNKDLEDHSRASEEEVRKLLDDLRRAGV >2plus1_GFP11_Key_Nterm_182
(SEQ ID NO: 26923)
SEVDDVLRRLEELIKTLEDINAKSLEDIKKLIDDLAKILEDALRKHEKLIRELREAKK >2plus1_GFP11_Key_Nterm_183
(SEQ ID NO: 26924)
SESDEVIRDLARLLDELARHVDDSVRRMDEVVKRSTREADELAKRLDELVKEVEKKPG >2plus1_GFP11_Key_Nterm_184
(SEQ ID NO: 26925)
SESDDVIRKLRELLEELRTHVEKSIRDLRKILEDSTRHAKRSIEELERLLEEVRKKPG >2plus1_GFP11_Key_Nterm_185
(SEQ ID NO: 26926)
SRAETVLKEVTDKIKKLADSSDELLRRNKENIDELKKSSEELLRRLTKAIEEIEKGSV >2plus1_GFP11_Key_Nterm_186
(SEQ ID NO: 26927)
SEAEKAKETIDRLADRVRKLLEEIKRSLDDSRRKSKETVEENEKTLDRMRKEVDAAKR >2plus1_GFP11_Key_Nterm_187
(SEQ ID NO: 26928)
SEAEKAKETIDRLADRVRKLLEEIKRSLDDSRRKSKETVEENEKTLDRMRKEVDAAKR >2plus1_GFP11_Key_Nterm_188
(SEQ ID NO: 26929)
SEVEELIKRLAKVLKELVDKVRKVIEDTKELLERLKRRSEDHIRKLREVLKEAKDQPI >2plus1_GFP11_Key_Nterm_189
(SEQ ID NO: 26930)
SELEEIEKKVRELTKRHRELVERVRKTVKELIETNRRLLETLTERIKRVLEEVRDLER >2plus1_GFP11_Key_Nterm_190
(SEQ ID NO: 26931)
SSEERLRAVIEDLKRLAEESRKRHKELIDELAKAVERIERRHKKLLDEIKAVVDDIRR >2plus1_GFP11_Key_Nterm_191
(SEQ ID NO: 26932)
DEIRKVVKEITDLLKASNDKNRKVVEEIRDLLRKSKKLADELVERLRALVEDLRRRID >2plus1_GFP11_Key_Nterm_192
(SEQ ID NO: 26933)
STAETVAEEVERVLKHSDDLIKEVEDVNRRVEEEIKRVIRELEEENERLVAEVRKGVK >2plus1_GFP11_Key_Nterm_193
(SEQ ID NO: 26934)
SEVDEIIKELERLLAEIARENERIIRESRKLADEVRKRNEDAIRKLEELVARLADAVR >2plus1_GFP11_Key_Nterm_194
(SEQ ID NO: 26935)
SEIDEVLTRLRKISKDLNETSDRVNERARKIIDDIKKESKRVNDEAREIVERLKREID >2plus1_GFP11_Key_Nterm_195
(SEQ ID NO: 26936)
SEDEDLDRVAEKLAREHKKSVEEIKRVLKSADEESKKLVRDTERVIEEIKREVEEARR >2plus1_GFP11_Key_Nterm_196
(SEQ ID NO: 26937)
SSVEELLERLRRISEENKRRIEKLLREVEKVLRELKDRHRKLLKRVEEIIRKVKEEIK >2plus1_GFP11_Key_Nterm_197
(SEQ ID NO: 26938)
SAADEVVERMKELVATVKRENDEVVKELKKLVKELEDDNRRVVEESKKSVEDLARRVG >2plus1_GFP11_Key_Nterm_198
(SEQ ID NO: 26939)
SESDEVIRDLARLLDELARHVDDSVRRMDEVVKRSTREADELAKRLDELVKEVEKKPG -continued

```
>2plus1_GFP11_Key_Nterm_199                                    (SEQ ID NO: 26940)
KEVEDAVKELEDLLRANEDKTRSIVEDMRASNKDLEDHSRASEEEVRKLLDDLRRAGV >2plus1_GFP11_Key_Nterm_200                                    (SEQ ID NO: 26941)
DEIRKVVKEITDLLKASNDKNRKVVEEIRDLLRKSKKLADELVERLRALVEDLRRRID >2plus1_GFP11_Key_Nterm_201                                    (SEQ ID NO: 26942)
SRVEEIIEDLRRLLEEIRKENEDSIRRSKELLDRVKEINDTIIAELERLLKDIEKEVR >2plus1_GFP11_Key_Nterm_202                                    (SEQ ID NO: 26943)
SRVEEIIEDLRRLLEEIRKENEDSIRRSKELLDRVKEINDTIIAELERLLKDIEKEVR >2plus1_GFP11_Key_Nterm_203                                    (SEQ ID NO: 26944)
SEVDDVLRRLEELIKTLEDINAKSLEDIKKLIDDLAKILEDALRKHEKLIRELREAKK >2plus1_GFP11_Key_Nterm_204                                    (SEQ ID NO: 26945)
SKLEEVEKAVRKVIEDSRRVNEEVNRRSEEVVRELEKVHREVNDASRRVVEKARRVLK >2plus1_GFP11_Key_Nterm_205                                    (SEQ ID NO: 26946)
SESDEVIRDLARLLDELARHVDDSVRRMDEVVKRSTREADELAKRLDELVKEVEKKPG >2plus1_GFP11_Key_Nterm_206                                    (SEQ ID NO: 26947)
SESDEVIRDLARLLDELARHVDDSVRRMDEVVKRSTREADELAKRLDELVKEVEKKPG >2plus1_GFP11_Key_Nterm_207                                    (SEQ ID NO: 26948)
SESDDVIRKLRELLEELRTHVEKSIRDLRKILEDSTRHAKRSIEELERLLEEVRKKPG >2plus1_GFP11_Key_Nterm_208                                    (SEQ ID NO: 26949)
DEVRELLERNRRLLEEIKKTVKDLIRANEELLKRIEDDAKRLIDRNEELLDELEKGLS >2plus1_GFP11_Key_Nterm_209                                    (SEQ ID NO: 26950)
DEIRKVVKEITDLLKASNDKNRKVVEEIRDLLRKSKKLADELVERLRALVEDLRRRID >2plus1_GFP11_Key_Nterm_210                                    (SEQ ID NO: 26951)
SRAETVLKEVTDKIKKLADSSDELLRRNKENIDELKKSSEELLRRLTKAIEEIEKGSV >2plus1_GFP11_Key_Nterm_211                                    (SEQ ID NO: 26952)
DEEEDLERAIKKLLDENRELLKRIAEELRRLLEELRRLTEESADRLRRLLKELKDRGV >2plus1_GFP11_Key_Nterm_212                                    (SEQ ID NO: 26953)
DEIRKVVKEITDLLKASNDKNRKVVEEIRDLLRKSKKLADELVERLRALVEDLRRRID >2plus1_GFP11_Key_Nterm_213                                    (SEQ ID NO: 26954)
SKEDRLREELKKLLARLAEEIERLKRALEESNKDLKRTIDASEKHLRDVNEDVKRGGV >2plus1_GFP11_Key_Nterm_214                                    (SEQ ID NO: 26955)
SESDEVIRDLARLLDELARHVDDSVRRMDEVVKRSTREADELAKRLDELVKEVEKKPG >2plus1_GFP11_Key_Nterm_215                                    (SEQ ID NO: 26956)
SESDEVIRDLARLLDELARHVDDSVRRMDEVVKRSTREADELAKRLDELVKEVEKKPG >2plus1_GFP11_Key_Nterm_216                                    (SEQ ID NO: 26957)
SESDDVIRKLRELLEELRTHVEKSIRDLRKILEDSTRHAKRSIEELERLLEEVRKKPG >2plus1_GFP11_Key_Nterm_217                                    (SEQ ID NO: 26958)
SRVEEIIEDLRRLLEEIRKENEDSIRRSKELLDRVKEINDTIIAELERLLKDIEKEVR >2plus1_GFP11_Key_Nterm_218                                    (SEQ ID NO: 26959)
SEVDEIIKELERLLAEIARENERIIRESRKLADEVRKRNEDAIRKLEELVARLADAVR
```

-continued

>2plus1_GFP11_Key_Nterm_219 (SEQ ID NO: 26960)
SSVEELLERLRRISEENKRRIEKLLREVEKVLRELKDRHRKLLKRVEEIIRKVKEEIK >2plus1_GFP11_Key_Nterm_220 (SEQ ID NO: 26961)
SELEEVLRRIEALVRKAHKENEDVLREIERLVRTAHRLNKKVDDDSAKIAEDLKRGGR >2plus1_GFP11_Key_Nterm_221 (SEQ ID NO: 26962)
SESDEVIRDLARLLDELARHVDDSVRRMDEVVKRSTREADELAKRLDELVKEVEKKPG >2plus1_GFP11_Key_Nterm_222 (SEQ ID NO: 26963)
SESDDVIRKLRELLEELRTHVEKSIRDLRKILEDSTRHAKRSIEELERLLEEVRKKPG >2plus1_GFP11_Key_Nterm_223 (SEQ ID NO: 26964)
SRAETVLKEVTDKIKKLADSSDELLRRNKENIDELKKSSEELLRRLTKAIEEIEKGSV >2plus1_GFP11_Key_Nterm_224 (SEQ ID NO: 26965)
DEVRELLERNRRLLEEIKKTVKDLIRANEELLKRIEDDAKRLIDRNEELLDELEKGLS >2plus1_GFP11_Key_Nterm_225 (SEQ ID NO: 26966)
STEEVLDEIRKLHKTLTEDIKRVLREIEELHRRTIEENKEVLDKIAEDYKRVIDDVRT >2plus1_GFP11_Key_Nterm_226 (SEQ ID NO: 26967)
SEIEKILKEIEDLARRDEEVSKKIVEDIRRLAKEVEDTSRDIVRKIEELAKRVLDRLR >2plus1_GFP11_Key_Nterm_227 (SEQ ID NO: 26968)
SEAERLEARARELLRANEELMDDLRAKAEELLKRNDRLVKEIEKKVREVLAAIEELKR >2plus1_GFP11_Key_Nterm_228 (SEQ ID NO: 26969)
DDLERAREEVADLIRKHEEKTRRILEESRRLNERHRELSARILDEIRKLAERIEELIK >2plus1_GFP11_Key_Nterm_229 (SEQ ID NO: 26970)
DEEEDLERAIKKLLDENRELLKRIAEELRRLLEELRRLTEESADRLRRLLKELKDRGV >2plus1_GFP11_Key_Nterm_230 (SEQ ID NO: 26971)
DEIRKVVKEITDLLKASNDKNRKVVEEIRDLLRKSKKLADELVERLRALVEDLRRRID >2plus1_GFP11_Key_Nterm_231 (SEQ ID NO: 26972)
DEIRKVVKEITDLLKASNDKNRKVVEEIRDLLRKSKKLADELVERLRALVEDLRRRID >2plus1_GFP11_Key_Nterm_232 (SEQ ID NO: 26973)
STAETVEKKVEEVIRENEKSMRESEEKVDRSTKRIEDVLRRLEETIRKTSDDIAKGVK >2plus1_GFP11_Key_Nterm_233 (SEQ ID NO: 26974)
SRVEEIIEDLRRLLEEIRKENEDSIRRSKELLDRVKEINDTIIAELERLLKDIEKEVR >2plus1_GFP11_Key_Nterm_234 (SEQ ID NO: 26975)
SRVEEIIEDLRRLLEEIRKENEDSIRRSKELLDRVKEINDTIIAELERLLKDIEKEVR >2plus1_GFP11_Key_Nterm_235 (SEQ ID NO: 26976)
REVEEMIKELEELLKDLKEKNERASKRNRELVRRLEEENKRVIEELKKLVKELEDLVR >2plus1_GFP11_Key_Nterm_236 (SEQ ID NO: 26977)
SEVDDVLRRLEELIKTLEDINAKSLEDIKKLIDDLAKILEDALRKHEKLIRELREAKK >2plus1_GFP11_Key_Nterm_237 (SEQ ID NO: 26978)
SKLEEVEKAVRKVIEDSRRVNEEVNRRSEEVVRELEKVHREVNDASRRVVEKARRVLK >2plus1_GFP11_Key_Nterm_238 (SEQ ID NO: 26979)
DEVEDVLRKIEKILDDHRKRIEKNSRDMARIIDEHRRKVEENSREMKKLVDDLKKAVD

```
>2plus1_GFP11_Key_Nterm_239                                    (SEQ ID NO: 26980)
SSVEELLERLRRISEENKRRIEKLLREVEKVLRELKDRHRKLLKRVEEIIRKVKEEIK >2plus1_GFP11_Key_Nterm_240                                    (SEQ ID NO: 26981)
DEVEKVLEEIKRALDDLRKKVEESKREIKEALKAVEKHTRDSDTANKRTLAEIERGVK >2plus1_GFP11_Key_Nterm_241                                    (SEQ ID NO: 26982)
SESDEVIRDLARLLDELARHVDDSVRRMDEVVKRSTREADELAKRLDELVKEVEKKPG >2plus1_GFP11_Key_Nterm_242                                    (SEQ ID NO: 26983)
KEVEDAVKELEDLLRANEDKTRSIVEDMRASNKDLEDHSRASEEEVRKLLDDLRRAGV >2plus1_GFP11_Key_Nterm_243                                    (SEQ ID NO: 26984)
DEIRKVVKEITDLLKASNDKNRKVVEEIRDLLRKSKKLADELVERLRALVEDLRRRID >2plus1_GFP11_Key_Nterm_244                                    (SEQ ID NO: 26985)
STAETVAEEVERVLKHSDDLIKEVEDVNRRVEEEIKRVIRELEEENERLVAEVRKGVK >2plus1_GFP11_Key_Nterm_245                                    (SEQ ID NO: 26986)
SRVEEIIEDLRRLLEEIRKENEDSIRRSKELLDRVKEINDTIIAELERLLKDIEKEVR >2plus1_GFP11_Key_Nterm_246                                    (SEQ ID NO: 26987)
SEVDEIIKELERLLAEIARENERIIRESRKLADEVRKRNEDAIRKLEELVARLADAVR >2plus1_GFP11_Key_Nterm_247                                    (SEQ ID NO: 26988)
SEVDDVLRRLEELIKTLEDINAKSLEDIKKLIDDLAKILEDALRKHEKLIRELREAKK >2plus1_GFP11_Key_Nterm_248                                    (SEQ ID NO: 26989)
SKLEEVEKAVRKVIEDSRRVNEEVNRRSEEVVRELEKVHREVNDASRRVVEKARRVLK >2plus1_GFP11_Key_Nterm_249                                    (SEQ ID NO: 26990)
SAEEVKEELKRIATKLKEEIKENIRRLEESVEKIAKELAENIKRLEDILRDVKRGLRD >2plus1_GFP11_Key_Nterm_250                                    (SEQ ID NO: 26991)
SDVDRVLEEIRKLLEDLKRHSEKVSEENEDLLRANTELNKRVSEDNERLLEELKRLRE >2plus1_GFP11_Key_Nterm_251                                    (SEQ ID NO: 26992)
DEVEDVLRKIEKILDDHRKRIEKNSRDMARIIDEHRRKVEENSREMKKLVDDLKKAVD >2plus1_GFP11_Key_Nterm_252                                    (SEQ ID NO: 26993)
SSVEELLERLRRISEENKRRIEKLLREVEKVLRELKDRHRKLLKRVEEIIRKVKEEIK >2plus1_GFP11_Key_Nterm_253                                    (SEQ ID NO: 26994)
DREREVKKRLDEVRERIERLLRRVEEESRRVAEEIRRLIEEVRRRNKKVTEEIRELLK >2plus1_GFP11_Key_Nterm_254                                    (SEQ ID NO: 26995)
SRAETVLKEVTDKIKKLADSSDELLRRNKENIDELKKSSEELLRRLTKAIEEIEKGSV >2plus1_GFP11_Key_Nterm_255                                    (SEQ ID NO: 26996)
SEIEKILKEIEDLARRDEEVSKKIVEDIRRLAKEVEDTSRDIVRKIEELAKRVLDRLR >2plus1_GFP11_Key_Nterm_256                                    (SEQ ID NO: 26997)
SEAEKAKETIDRLADRVRKLLEEIKRSLDDSRRKSKETVEENEKTLDRMRKEVDAAKR >2plus1_GFP11_Key_Nterm_257                                    (SEQ ID NO: 26998)
SEVEELIKRLAKVLKELVDKVRKVIEDTKELLERLKRRSEDHIRKLREVLKEAKDQPI >2plus1_GFP11_Key_Nterm_258                                    (SEQ ID NO: 26999)
DEIRKVVKEITDLLKASNDKNRKVVEEIRDLLRKSKKLADELVERLRALVEDLRRRID
```

-continued

>2plus1_GFP11_Key_Nterm_259                                        (SEQ ID NO: 27000)
DEIRKVVKEITDLLKASNDKNRKVVEEIRDLLRKSKKLADELVERLRALVEDLRRRID >2plus1_GFP11_Key_Nterm_260                                        (SEQ ID NO: 27001)
STAETVEKKVEEVIRENEKSMRESEEKVDRSTKRIEDVLRRLEETIRKTSDDIAKGVK >2plus1_GFP11_Key_Nterm_261                                        (SEQ ID NO: 27002)
SRVEEIIEDLRRLLEEIRKENEDSIRRSKELLDRVKEINDTIIAELERLLKDIEKEVR >2plus1_GFP11_Key_Nterm_262                                        (SEQ ID NO: 27003)
REVEEMIKELEELLKDLKEKNERASKRNRELVRRLEEENKRVIEELKKLVKELEDLVR >2plus1_GFP11_Key_Nterm_263                                        (SEQ ID NO: 27004)
DAVEEAEKLIRKVIADSEKLLRDLADLNAKSIRRSEKLVEDDRRANEDVIRKLEELRR >2plus1_GFP11_Key_Nterm_264                                        (SEQ ID NO: 27004)
SEVDDVLRRLEELIKTLEDINAKSLEDIKKLIDDLAKILEDALRKHEKLIRELREAKK >2plus1_GFP11_Key_Nterm_265                                        (SEQ ID NO: 27006)
SEIERVKKRLEELLAEVEESTRRLEERLKRLLEEAKRSSEEVEKELRRLLEAVRRGLS >2plus1_GFP11_Key_Nterm_266                                        (SEQ ID NO: 27007)
SDVDRVLEEIRKLLEDLKRHSEKVSEENEDLLRANTELNKRVSEDNERLLEELKRLRE >2plus1_GFP11_Key_Nterm_267                                        (SEQ ID NO: 27008)
DEVEDVLRKIEKILDDHRKRIEKNSRDMARIIDEHRRKVEENSREMKKLVDDLKKAVD >2plus1_GFP11_Key_Nterm_268                                        (SEQ ID NO: 27009)
SESDEVIRDLARLLDELARHVDDSVRRMDEVVKRSTREADELAKRLDELVKEVEKKPG >2plus1_GFP11_Key_Nterm_269                                        (SEQ ID NO: 27010)
SRAETVLKEVTDKIKKLADSSDELLRRNKENIDELKKSSEELLRRLTKAIEEIEKGSV >2plus1_GFP11_Key_Nterm_270                                        (SEQ ID NO: 27011)
DEEEDLERAIKKLLDENRELLKRIAEELRRLLEELRRLTEESADRLRRLLKELKDRGV >2plus1_GFP11_Key_Nterm_271                                        (SEQ ID NO: 27012)
DEIRKVVKEITDLLKASNDKNRKVVEEIRDLLRKSKKLADELVERLRALVEDLRRRID >2plus1_GFP11_Key_Nterm_272                                        (SEQ ID NO: 27013)
DAVEEAEKLIRKVIADSEKLLRDLADLNAKSIRRSEKLVEDDRRANEDVIRKLEELRR >2plus1_GFP11_Key_Nterm_273                                        (SEQ ID NO: 27014)
SEDEDLDRVAEKLAREHKKSVEEIKRVLKSADEESKKLVRDTERVIEEIKREVEEARR >2plus1_GFP11_Key_Nterm_274                                        (SEQ ID NO: 27015)
SKEDRLREELKKLLARLAEEIERLKRALEESNKDLKRTIDASEKHLRDVNEDVKRGGV >3plus1_Key_668_Nterm                                              (SEQ ID NO: 27,322)
DEAKELLDEIRKAVKESEDRLEKLLRDYEKELRRLEKELRDLKRRIEEKLEELRRGSL >3plus1_Key_668_Cterm                                              (SEQ ID NO: 27,323)
RGADALSRLLEELLRVVDDLIRVLKELIDKSRKVIEELLELLKRINEENLKVLAEIIK >3plus1_Key_668_Cterm                                              (SEQ ID NO: 27,324)
SEKEKLLKESEEEVRRLRRTLEELLRKYREVLERLRKELREIEERVRDVVRRLKEVLD >3plus1_Key_668_Cterm                                              (SEQ ID NO: 27,325)
SEKEDAARKLRKLVEELTREYEELVKKLERLIEEIEKVSEESVRKLEKLLAEISEEVR -continued

```
>3plus1_Key_668_Cterm
                                                           (SEQ ID NO: 27,326)
EALRKLVELLVEVLRRLIRVNRELVKLLREVLERLLRILRESVKKLKRLIEKVIKDAT >3plus1_Key_669_Nterm
                                                           (SEQ ID NO: 27,327)
RAVKKLDEIVKEVAKKLEDVVRANEELWRALVELNKESVRRLREIVERVARDLEETAR >3plus1_Key_670_Nterm
                                                           (SEQ ID NO: 27,328)
SDERRIAERIRELLRESKKLVRDVVEEAKRLLKENRDSTRKIIEDIRRLLRKIEDSTR >3plus1_Key_670_Cterm
                                                           (SEQ ID NO: 27,329)
SKEETLRKEAEDLLRRLEELTRRLEKKARELLERAKKLSRDLAEELKRLLKELREKGV >3plus1_Key_670_Cterm
                                                           (SEQ ID NO: 27,330)
AAKRLVEELLKAVTDLSRKNKRILEELLKAIETLSDENKKILTEILDALRRLVEKIEK >3plus1_Key_670_Cterm
                                                           (SEQ ID NO: 27,331)
KEREEVKEKLDRLLEEVEKTVRELKREHDELLKEVEKLVRDLKKEHDELLKKVKDDGV >3plus1_Key_670_Nterm
                                                           (SEQ ID NO: 27,332)
DRLDKVEELVKKLLEDTKRTVDRVRELVRKILKKSRETLEELERLIEKILRELEKDAR >3plus1_Key_670_Cterm
                                                           (SEQ ID NO: 27,333)
SERETVKRRLEELLKEVKRTLDKLKEEHDRLLEDVRRVVEELKREHDKLLKEVKDSGV >3plus1_Key_670_Nterm
                                                           (SEQ ID NO: 27,334)
SEDEIIKKIIEDLRRVLKEVEEIHKEVEERLDKVLKEAEEMHKEVLKELDRVLDEVKR >3plus1_Key_670_Nterm
                                                           (SEQ ID NO: 27,335)
SREEVLRELEEVIEDNRRLLEELIEKSKKVLDESLKLIDELLRRLEEVLERVLRLLEE >3plus1_Key_670_Nterm
                                                           (SEQ ID NO: 27,336)
ISEDDLKRVVDEVEKKLRELKRRYAEALERIKEKIKELKDRYERAVREVVAELRKTTK >3plus1_Key_670_Nterm
                                                           (SEQ ID NO: 27,337)
SKAEEIAEKLDRLLEENRRALEEITTRLDDLLRRNKDALRKVMEKLKRLLDDLRRGGI >3plus1_Key_671_Cterm
                                                           (SEQ ID NO: 27,338)
VDSERVKEILERILRVVEEAVRLNEESLRRILDVVRKAVKLDRESLKKILDVVEEAVR >3plus1_Key_671_Cterm
                                                           (SEQ ID NO: 27,339)
VKDDEVEREIRRVKEDLDRILEEYRRLLEEIKRKLEEILRRVEELHRRLRRKLEEIDR >3plus1_Key_671_Cterm
                                                           (SEQ ID NO: 27,340)
SRVEELKKLIEDILRISREVVERIKRVAEDIHRINRRVLDDLRKLIEDILRTVEEILA >3plus1_Key_671_Cterm
                                                           (SEQ ID NO: 27,341)
RGADALSRLLEELLRVVDDLIRVLKELIDKSRKVIEELLELLKRINEENLKVLAEIIK >3plus1_Key_672_Cterm
                                                           (SEQ ID NO: 27,342)
RGADALSRLLEELLRVVDDLIRVLKELIDKSRKVIEELLELLKRINEENLKVLAEIIK >3plus1_Key_67>3_Nterm
                                                           (SEQ ID NO: 27,343)
EALRKLVELLVEVLRRLIRVNRELVKLLREVLERLLRILRESVKKLKRLIEKVIKDAT >3plus1_Key_67>3_Cterm
                                                           (SEQ ID NO: 27,344)
SEKEDAARKLRKLVEELTREYEELVKKLERLIEEIEKVSEESVRKLEKLLAEISEEVR >3plus1_Key_67>3_Nterm
                                                           (SEQ ID NO: 27,345)
SEKEDAARKLRKLVEELTREYEELVKKLERLIEEIEKVSEESVRKLEKLLAEISEEVR
```

-continued

```
>3plus1_Key_674_Nterm                                                        (SEQ ID NO: 27,346)
SEKEDAARKLRKLVEELTREYEELVKKLERLIEEIEKVSEESVRKLEKLLAEISEEVR >3plus1_Key_674_Cterm                                                        (SEQ ID NO: 27,347)
RAVKKLDEIVKEVAKKLEDVVRANEELWRALVELNKESVRRLREIVERVARDLEETAR >3plus1_Key_675_Nterm                                                        (SEQ ID NO: 27,348)
RAVKKLDEIVKEVAKKLEDVVRANEELWRALVELNKESVRRLREIVERVARDLEETAR >3plus1_Key_676_Nterm                                                        (SEQ ID NO: 27,349)
RAVKKLDEIVKEVAKKLEDVVRANEELWRALVELNKESVRRLREIVERVARDLEETAR >3plus1_Key_677_Nterm                                                        (SEQ ID NO: 27,350)
SDERRIAERIRELLRESKKLVRDVVEEAKRLLKENRDSTRKIIEDIRRLLRKIEDSTR >3plus1_Key_677_Cterm                                                        (SEQ ID NO: 27,351)
SKEETLRKEAEDLLRRLEELTRRLEKKARELLERAKKLSRDLAEELKRLLKELREKGV >3plus1_Key_678_Nterm                                                        (SEQ ID NO: 27,352)
SKEETLRKEAEDLLRRLEELTRRLEKKARELLERAKKLSRDLAEELKRLLKELREKGV >3plus1_Key_678_Cterm                                                        (SEQ ID NO: 27,353)
SKEETLRKEAEDLLRRLEELTRRLEKKARELLERAKKLSRDLAEELKRLLKELREKGV >3plus1_Key_678_Cterm                                                        (SEQ ID NO: 27,354)
ISEDDLKRVVDEVEKKLRELKRRYAEALERIKEKIKELKDRYERAVREVVAELRKTTK >3plus1_Key_678_Nterm                                                        (SEQ ID NO: 27,355)
SKAEEIAEKLDRLLEENRRALEEITTRLDDLLRRNKDALRKVMEKLKRLLDDLRRGGI >3plus1_Key_678_Nterm                                                        (SEQ ID NO: 27,356)
VDSERVKEILERILRVVEEAVRLNEESLRRILDVVRKAVKLDRESLKKILDVVEEAVR >3plus1_Key_679_Cterm                                                        (SEQ ID NO: 27,357)
SKAEEIAEKLDRLLEENRRALEEITTRLDDLLRRNKDALRKVMEKLKRLLDDLRRGGI >3plus1_Key_679_Nterm                                                        (SEQ ID NO: 27,358)
SKAEEIAEKLDRLLEENRRALEEITTRLDDLLRRNKDALRKVMEKLKRLLDDLRRGGI
```

In a specific embodiment, the key polypeptides share 40%, 45%, 50%, 55%, 60%, 65%, 70%, 75%, 80%, 85%, 90%, 91%, 92%, 93%, 94%, 95%, 96%, 97%, 98%, 99%, or 100% sequence identity along their length to the amino acid sequence of a key polypeptide in Table 2 (polypeptides with an odd-numbered SEQ ID NO between SEQ ID NOS: 27127 and 27277), Table 3, and/or Table 4. In another specific embodiment, the key polypeptides share 40%, 45%, 50%, 55%, 60%, 65%, 70%, 75%, 80%, 85%, 90%, 91%, 92%, 93%, 94%, 95%, 96%, 97%, 98%, 99%, or 100% sequence identity along their length to the amino acid sequence of a key polypeptide in Table 3. In another specific embodiment, the key polypeptides share 40%, 45%, 50%, 55%, 60%, 65%, 70%, 75%, 80%, 85%, 90%, 91%, 92%, 93%, 94%, 95%, 96%, 97%, 98%, 99%, or 100% sequence identity along their length to the amino acid sequence of a key polypeptide in Table 4. In one embodiment of each of the above, the percent identify may be determined without the optional N- and C-terminal 60 amino acids; in another embodiment, the percent identify may be determined with the optional N- and C-terminal 60 amino acids.

The polypeptides of the disclosure (i.e.: cage polypeptides and key polypeptides) may include additional residues at the N-terminus, C-terminus, internal to the polypeptide, or a combination thereof; these additional residues are not included in determining the percent identity of the polypeptides of the invention relative to the reference polypeptide. Such residues may be any residues suitable for an intended use, including but not limited to tags. As used herein, "tags" include general detectable moieties (i.e.: fluorescent proteins, antibody epitope tags, etc.), therapeutic agents, purification tags (His tags, etc.), linkers, ligands suitable for purposes of purification, ligands to drive localization of the polypeptide, peptide domains that add functionality to the polypeptides, etc. Examples are provided herein.

Figure 3A:
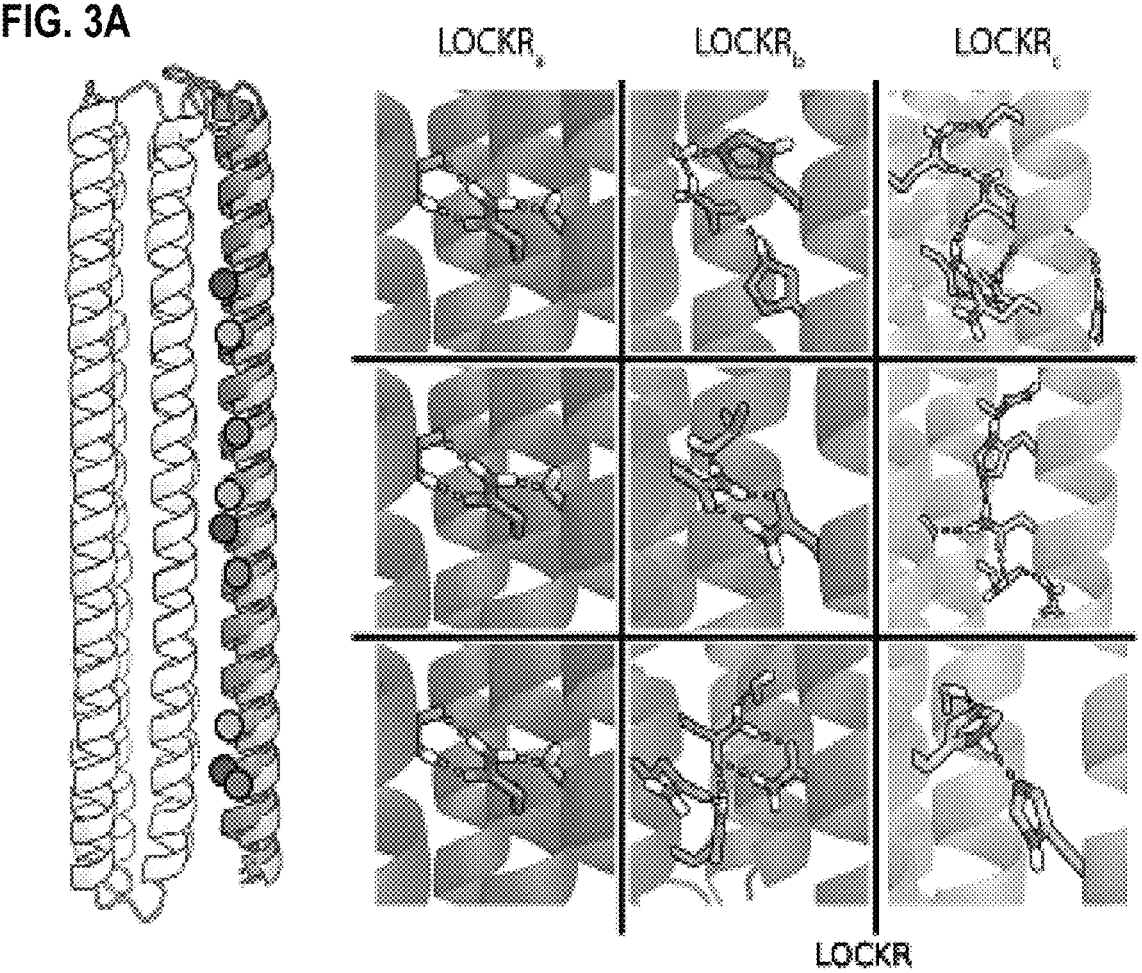
FIG. 3A-3C: Design and validation of orthogonal Bim-LOCKR.
Figure 3B:
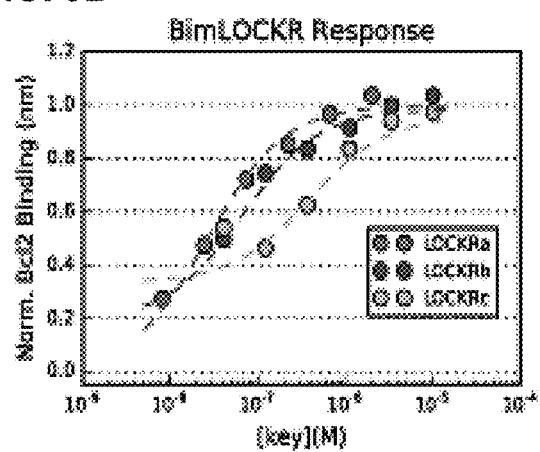
Figure 3C:
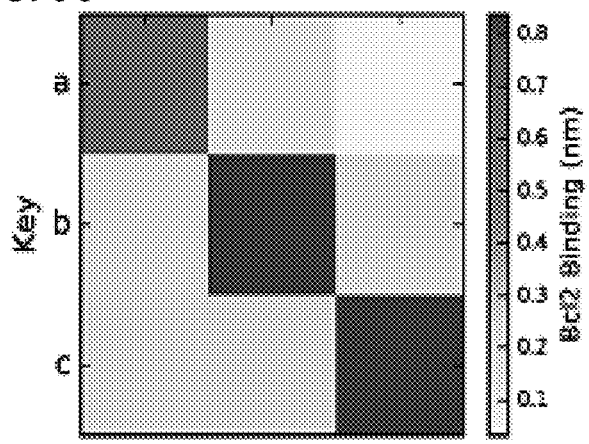

In one embodiment, the polypeptides are fusion proteins that comprise a cage polypeptide disclosed herein fused to a key polypeptide disclosed herein. In one embodiment, the fusion protein comprises a cage polypeptide fused to a key polypeptide, wherein the cage polypeptide is not activated by the key polypeptide. As noted herein, orthogonal LOCKR designs (see FIG. 3) are denoted by lowercase letter subscripts: LOCKR$_a$ consists of Cage$_a$ and Key$_a$, and LOCKR$_b$ consists of Cage$_b$ and Key$_b$, etc. such that Cage$_a$ is only activated by Key$_a$, and Cage$_b$ is only activated by Key$_b$, etc. Thus, for example, the fusion protein may comprise a cage, polypeptide fused to a key_b polypeptide. Such embodiments may be used, for example, in combinations to improve control of orthogonal LOCKR designs (ex: LOCKR 1 comprises a cage_a-key_b fusion polypeptide, and LOCKR 2 comprises a cage_b-key_a fusion polypeptide, which can then be expressed in the same cell)

In one embodiment of the fusion proteins disclosed herein, the cage polypeptide and the key polypeptide components of the fusion protein comprise at least one cage polypeptide and at least one key polypeptide having an amino acid sequence having at least 45%, 50%, 55%, 60%, 65%, 70%, 75%, 80%, 85%, 90%, 91%, 92%, 93%, 94%, 95%, 96%, 97%, 98%, 99%, or 100% sequence identity along its length to a cage polypeptide and a key polypeptide, respectively, in different rows of Table 1, Table 2, Table 3, and/or Table 4 (i.e.: each cage polypeptide in row 1 column 1 of the table can be fused with any key polypeptide in row 1 column 2, and so on).

TABLE 1

| Row number | Cage (column 1) | Key (column 2) |
|---|---|---|
| 1 | SB76L (SEQ ID NO: 1), SB76L_17 (SEQ ID NO: 2), SB76L_18 (SEQ ID NO: 3), LOCKR_extend5 (SEQ ID NO: 4), LOCKR_extend9 (SEQ ID NO: 5), LOCKR_extend18 (SEQ ID NO: 6), miniLOCKRa_1 (SEQ ID NO: 12), miniLOCKRa_2 (SEQ ID NO: 13), aBcl2LOCKR (SEQ ID NO: 18), pBimLOCKR (SEQ ID NO: 19), BimLOCKR_extend5 (SEQ ID NO: 20), BimLOCKR_extend9 (SEQ ID NO: 21), BimLOCKR_extend18 (SEQ ID NO: 22), strepLOCKRa (all variants; SEQ ID NOs: 26-34), SB13_LOCKR (SEQ ID NO: 35), SB13_LOCKR_extend18 (SEQ ID NO: 37), ZCX12_LOCKR (SEQ ID NO: 36), ZCX12_LOCKR_extend18 (SEQ ID NO: 38), fretLOCKRa (SEQ ID NO: 39), 1fix-latch_Mad1SID_t0_1 (SEQ ID NO: 61), 1fix-latch_Mad1SID_T0_2 (SEQ ID NO: 65), 1fix-long-Bim-t0 (SEQ ID NO: 54), 1fix-long-GFP-t0 (SEQ ID NO: 55), 1fix-short-BIM-t0 (SEQ ID NO: 56), 1fix-short-GFP-t0 (SEQ ID NO: 57), 1fix-short-noBim-t0 (SEQ ID NO: 16), 1fix-short-noBim(AYYA)-t0 (SEQ ID NO: 17), 1fix-short-Bim-t0-relooped (SEQ ID NO: 67), 1fix-short-spytag-t0_2 (SEQ ID NO: 68), 1fix-short-spytag-t0_8 (SEQ ID NO: 69), 1fix-short-TEV-t0_1 (SEQ ID NO: 70), 1fix-short-TEV-t0_6 (SEQ ID NO: 71), 1fix-short-nanoBit-t0_1 (SEQ ID NO: 72), 1fix-short-nanoBit-t0_3 (SEQ ID NO: 73), 1fix-short-RHIM-t0_8 (SEQ ID NO: 74), 1fix-short-RHIM-t0_19 (SEQ ID NO: 75), 1fix-short-RHIM-t0_22 (SEQ ID NO: 76), 1fix-short-gcn4-t0_4 (SEQ ID NO: 77), 1fix-short-ccDi-t0_6 (SEQ ID NO: 78), 1fix-short-cc-a-t0_6 (SEQ ID NO: 79), 1fix-short-cc-b-t0_6 (SEQ ID NO: 80) | sB76_C-helix (SEQ ID NO: 27016), sB76_C-helix-biotin (SEQ ID NO: 27017), p5_MBP (SEQ ID NO: 27018), p9_MBP (SEQ ID NO: 27019), p18_MBP (SEQ ID NO: 27020), p76-long (SEQ ID NO: 27027), p76-short (SEQ ID NO: 27028), k76-long (SEQ ID NO: 27029), k76-short (SEQ ID NO: 27030), p76_GLISE (SEQ ID NO: 27031), p76_GSSEKIS (SEQ ID NO: 27032), p76_R26G (SEQ ID NO: 27033), p76-short_E19G (SEQ ID NO: 27034), p76-short_GLISE_E01_EGFR (SEQ ID NO: 27035), p76-short_AE_EGFR (SEQ ID NO: 27036), p76-short_AAE_EGFR (SEQ ID NO: 27037), p76-short_EE_EGFR (SEQ ID NO: 27038) |
| 2 | LOCKRb (SEQ ID NO: 7), BimLOCKRb (SEQ ID NO: 23), fretLOCKRb (SEQ ID NO: 40) | key_b (SEQ ID NO: 27022) |
| 3 | LOCKRc (SEQ ID NO: 8), miniLOCKRc_1 (SEQ ID NO: 14), miniLOCKRc_2 (SEQ ID NO: 15), BimLOCKRc (SEQ ID NO: 24), fretLOCKRc (SEQ ID NO: 41) | key_c (SEQ ID NO: 27023) |
| 4 | LOCKRd (SEQ ID NO: 9), BimLOCKRd (SEQ ID NO: 25), fretLOCKRd (SEQ ID NO: 42) | key_d (SEQ ID NO: 27024) |
| 5 | LOCKRe (SEQ ID NO: 10) | key_e (SEQ ID NO: 27025) |
| 6 | LOCKRf (SEQ ID NO: 11) | key_f (SEQ ID NO: 27026) |
| 7 | 1fix_VMAc_C_BIMlatcht9 (SEQ ID NO: 51) sfGFP_VMAn_1fix_BIM_t0_latch (SEQ ID NO: 52) sfGFP_VMAn_1fix_BIM_t0_latch (SEQ ID NO: 53) | sfGFP_VMAn_p18 (SEQ ID NO: 27041) p18_VMAc_mCherry (SEQ ID NO: 27042) |
| 8 | Spycatcher-1fix-long-GFP-t0 (SEQ ID NO: 58), Spycatcher-1fix-short-GFP-t0 (SEQ ID NO: 59) | p76-spytag (SEQ ID NO: 27039), p76-short-spytag (SEQ ID NO: 27040) |
| 9 | STREPII-2plus1_LOCK_1 (SEQ ID NO: 81) | 2plus1_Key_1 (SEQ ID NO: 27043) |

TABLE 1-continued

| Row number | Cage (column 1) | Key (column 2) |
|---|---|---|
| 10 | STREPII-2plus1_LOCK_2 (SEQ ID NO: 82) | 2plus1_Key_2 (SEQ ID NO: 27044) |
| 11 | STREPII-2plus1_LOCK_3, (SEQ ID NO: 83) STREPII-2plus1_LOCK_3-relooped (SEQ ID NO: 91) | 2plus1_Key_3 (SEQ ID NO: 27045) |
| 12 | STREPII-2plus1_LOCK_4C (SEQ ID NO: 84) | 2plus1_Key_4C (SEQ ID NO: 27046) |
| 13 | STREPII-3plus1_LOCK_1 (SEQ ID NO: 86) | 3plus1_Key_1 (SEQ ID NO: 27047) |
| 14 | STREPII-3plus1_LOCK_2 (SEQ ID NO: 87) | 3plus1_Key_2 (SEQ ID NO: 27048) |
| 15 | STREPII-3plus1_LOCK_3 (SEQ ID NO: 88), STREPII-3plus1_LOCK_3-relooped (SEQ ID NO: 90) | 3plus1_Key_3 SEQ ID NO: 27049) |
| 16 | STREPII-3plus1_LOCK_4 (SEQ ID NO: 89) | 3plus1_Key_4 (SEQ ID NO: 27050) |

TABLE 2

| Cage Name | Cage Sequence | Key Name | Key Sequence |
|---|---|---|---|
| 2plus1_Cage_Cterm_2406 | SEVDEVVKEVEDLVRRNEELVEEVVR RVEKVVTDDRRLVEEVVREIRKIVKD VEDLARKLDKEELKRVLDEMRERIER LLEKLRRHSKKLDDELKRLLEELREH SRRVEKRLEDLLKELRERGVDEKVLR KLEKVIREVRERSTRALRKVEEVIRR VREESERALRDLERVVKEVEKRMREA AR(SEQ ID NO: 27126) | 2plus1_Key_Cterm_2406 | EKVLRKLEKV IREVRERSTR ALRKVEEVIR RVREESERAL RDLERVVKEV EKRMREAAR (SEQ ID NO: 27127) |
| 2plus1_Cage_Cterm_5398 | SVEELLRKLEEVLRKIREENERSLKE LRDRAREIVKRNRETNRELEEVIKEL EKRLSGADKEKVEELVRRIRRIVERV VEEDRRTVEEIEKIAREVVKRDRDSA DRVRRTVEDVLRKATGSEDIVRKIER IVETIEREVVRESVKKVEEIARDIRRK VDESVKNVEKLLRDVDKKARDRKK (SEQ ID NO: 27128) | 2plus1_Key_Cterm_5398 | EDIVRKIERI VETIEREVRE SVKKVEEIAR DIRRKVDESV KNVEKLLRDV DKKARDRKK (SEQ ID NO: 27129) |
| 2plus1_Cage_Cterm_5405 | SESDDVIRKLRELLEELRTHVEKSIR DLRKILEDSTRHAKRSIEEELERLLEE VRKKPGDEEVRKTVEEISRRVAENVK RLEDLYRRMEEEVKKNLDRLRKRVED IIREVEEARKKGVDEEKLKDLIRKLR DILRRAAEAHKKLIDDARESLERAKR EHEKLIDRLKKILEELER (SEQ ID NO: 27130) | 2plus1_Key_Cterm_5405 | EEKLKDLIRK LRDILRRAAE AHKKLIDDAR ESLERAKREH EKLIDRLKKI LEELER (SEQ ID NO: 27131) |
| 2plus1_Cage_Cterm_5406 | DREREVKKRLDEVRERIERLLRRVEE ESRRVAEEIRRLIEEVRRRNKKVTEE IRELLKGLKDKEEVRRVLERLRKLNA ESDELLERILERLRRLVEATNRLVKA IIEELRRLVEKIVREVPDSEELREEL KKLERKIEKVAKEIHDHDKEVTERLE DLLRRITEHARKSDREIEETAR (SEQ ID NO: 27132) | 2plus1_Key_Cterm_5406 | EELREELKKL ERKIEKVAKE IHDHDKEVTE RLEDLLRRIT EHARKSDREI EETAR (SEQ ID NO: 27133) |
| 2plus1_Cage_Cterm_5409 | SEAEELLKRLEDRAEEILRRLEEILR TSRKLAEDVLRELEKLLRESERRIRE VLEELRGIKDKKELEDVIREVEKELD ESLERSRELLKDVLKKLDDNLKESER LVEDIDRELAKILEDLKKAGVPKEVV DEIKRIVDEVRERLKRIVDENAKIVE DARRALEKIVKENEEILRRLKKELRE LRK(SEQ ID NO: 27134) | 2plus1_Key_Cterm_5409 | KEVVDEIKRI VDEVRERLKR IVDENAKIVE DARRALEKIV KENEEILRRL KKELRELRK (SEQ ID NO: 27135) |
| 2plus1_Cage_Cterm_5410 | SRAETVLKEVTDKIKKLADSSDELLR RNKENIDELKKSSEELLRRLTKAIEE IEKGSVDEETLEELIRRVEAELEAHH | 2plus1_Key_Cterm_5410 | DEVVKRVRDL LDTVRRRNEK VNEDVKRMND |

TABLE 2-continued

| Cage Name | Cage Sequence | Key Name | Key Sequence |
|---|---|---|---|
| | RELEKNSREDEKRNRDHHAKLEEEMR RVEERLEREGIDDEVVKRVRDLLDTV RRRNEKVNEDVKRMNDKLRRDNEDVI RRVEKLLRELEEKRRT (SEQ ID NO: 27136) | | KLRRDNEDVI RRVEKLLREL EEKRRT (SEQ ID NO: 27137) |
| 2plus1_Cage_Cterm_5413 | STEEVLDEIRKLHKTLTEDIKRVLRE IEELHRRTIEENKEVLDKIAEDYKRV IDDVRTKDTPNVEKLLKDLEKSAKEN IEHNERTLREDDRVLKEIRRRATELL KANEEMLRRIEEVARKGGVDAEELLR ESKEAIKEVKRVLEELRKESKRVVDE TRKLSEENLEHSERVLRKVEEDLR (SEQ ID NO: 27138) | 2plus1_Key_Cterm_5413 | AEELLRESKE AIKEVKRVLE ELRKESKRVV DETRKLSEEN LEHSERVLRK VEEDLR (SEQ ID NO: 27139) |
| 2plus1_Cage_5414_GFP11_Cterm | SEIEKILKEIEDLARRDEEVSKKIVE DIRRLAKEVEDTSRDIVRKIEELAKR VLDRLRKDGSKEELEKEVREVVKTLE ELVKDNHRLIRRAVEEMKRLVEENHR HSREVVKELEDLVRELRKGSGSEDSE RDHMVLHEYVNAAGITSEKSNEEVKR TVEELVRRMEESNDRVRDLVRRLVEE LKRAVD(SEQ ID NO: 27140) | 2plus1_Key_Cterm_5414 | EDSERLVREV EDLVRRLVRR SEKSNEEVKR TVEELVRRME ESNDRVRDLV RRLVEELKRA VD(SEQ ID NO: 27141) |
| 2plus1_Cage_5414_GFP11_Cterm | SEIEKILKEIEDLARRDEEVSKKIVE DIRRLAKEVEDTSRDIVRKIEELAKR VLDRLRKDGSKEELEKEVREVVKTLE ELVKDNHRLIRRAVEEMKRLVEENHR HSREVVKELEDLVRELRKGSGSEDSE RRDHMVLHEYVNAAGITEKSNEEVKR TVEELVRRMEESNDRVRDLVRRLVEE LKRAVD(SEQ ID NO: 27142) | 2plus1_Key_Cterm_5414 | EDSERLVREV EDLVRRLVRR SEKSNEEVKR TVEELVRRME ESNDRVRDLV RRLVEELKRA VD(SEQ ID NO: 27143) |
| 2plus1_Cage_5414_GFP11_Cterm | SEIEKILKEIEDLARRDEEVSKKIVE DIRRLAKEVEDTSRDIVRKIEELAKR VLDRLRKDGSKEELEKEVREVVKTLE ELVKDNHRLIRRAVEEMKRLVEENHR HSREVVKELEDLVRELRKGSGSEDSE RLVREVRDHMVLHEYVNAAGITEVKR TVEELVRRMEESNDRVRDLVRRLVEE LKRAVD(SEQ ID NO: 27144) | 2plus1_Key_Cterm_5414 | EDSERLVREV EDLVRRLVRR SEKSNEEVKR TVEELVRRME ESNDRVRDLV RRLVEELKRA VD(SEQ ID NO: 27145) |
| 2plus1_Cage_Cterm_5421 | SVDEVLKEIEDALRRLKEEVERVLKE NEDELRRLEEEVRRVLKEDEELLESL KRGVGESDEVDRVVDEIAKLSAEILE KVKKVVKEIRDSLETVKRRVDDVVRR LKELLDEIKRGSDEKAIRDVAKEIRD RLKELEEEIEEVTRRNLKLLADVEEE IRRVHEKTRRLLETVLRRAT (SEQ ID NO: 27146) | 2plus1_Key_Cterm_5421 | EKAIRDVAKE IRDRLKELEE EIEEVTRRNL KLLADVEEEI RRVHEKTRRL LETVLRRAT (SEQ ID NO: 27147) |
| 2plus1_Cage_Cterm_5432 | DEIRKVVKEITDLLKASNDKNRKVVE EIRDLLRKSKKLADELVERLRALVED LRRRIDKSGDKETAEDIVRRIIEELK RILKEIEDLARRINREIERLVEEVER DNRDVNRAIEELLKDIARRGGSEDLK RVEERAREVSRRNEESMRRVKEDADR VSEANKEVLDRVREEVKRLIEEVRET LR(SEQ ID NO: 27148) | 2plus1_Key_Cterm_5432 | SEDLKRVEER AREVSRRNEE SMRRVKEDAD RVSEANKEVL DRVREEVKRL IEEVRETLR (SEQ ID NO: 27149) |
| 2plus1_Cage_Cterm_5435 | STAETVAEEVERVLKHSDDLIKEVED VNRRVEEEIKRVIRELEEENERLVAE VRKGVKGEILAEIEKRLADNSEKVRE VAERAKKLLEENTARVKDILRESRKL VKDLLDEVRGTGSEEAAREIIKRLRE VNKRTKEKLDELIKHSEEVLERVKRL IDELRKHSEEVLEDLRRRAK (SEQ ID NO:27150) | 2plus1_Key_Cterm_5435 | EEAAREIIKR LREVNKRTKE KLDELIKHSE EVLERVKRLI DELRKHSEEV LEDLRRRAK (SEQ ID NO: 27151) |
| 2plus1_Cage_Cterm_5437 | DEVREVAERLRRLVDESRKRNEEVIK ESEALVDRVRKTNEEVMKRLRELIDK LEKDIRRSGDKETVEKIIREVLSAID ELLKRVERTNAEISKENARLLDEVRK TNEEISRRLAKLLEDIRRGSDAETI ERVVRELLEENKEVLRKTEEAVKRST ETNKRLLEASKEVADRLRERIKKAAK (SEQ ID NO: 27152) | 2plus1_Key_Cterm_5437 | AETIERVVRE LLEENKEVLR KTEEAVKRST ETNKRLLEAS KEVADRLRER IKEAAK (SEQ ID NO: 27153) |

TABLE 2-continued

| Cage Name | Cage Sequence | Key Name | Key Sequence |
|---|---|---|---|
| 2plus1_Cage_Cterm_5439 | SRVEEIIEDLRRLLEEIRKENEDSIR RSKELLDRVKEINDTIIAELERLLKD IEKEVREKGSESEEVKKALRAVLEEL EKLLRRVAEINEEVLRRNSKLVEEDE RRNREVLKELARLVEELIREIGDEDK ARKVAEVAEKVLRDIDKLDRESKEAF RATNEEIAKLDEDTARVAERVKKAIE DLAK(SEQ ID NO: 27154) | 2plus1_Key_Cterm_5439 | EDKARKVAEV AEKVLRDIDK LDRESKEAFR ATNEEIAKLD EDTARVAERV KKAIEDLAK (SEQ ID NO: 27155) |
| 2plus1_Cage_Cterm_5447 | SEADDVLKKLAETVKRIIERLKKLTD DSRRLVEEVHRRNDKLSKESAEAVRK AEERGIDEKDVRKLLEDLKKKSEEVA ERNKRILDTLREISKRAEDEVRKVLK ELEKTLKELEDRRPDSEELSAEVKKL LDEVRKALARHKDENDKLLKEIEDSL RRHKEENDRLLEKLKESTR (SEQ ID NO: 27156) | 2plus1_Key_Cterm_5447 | EELSAEVKKL LDEVRKALAR HKDENDKLLK EIEDSLRRHK EENDRLLEKL KESTR (SEQ ID NO: 27157) |
| 2plus1_Cage_Cterm_5456 | SAEELLREVAELVKRVDEDLRRLLEE VRASNEEVIRRLEEILKRIEEENRKV VEELRRGGVSEDLVRESKRLVDESRR VIEKLVKESADSVERTRETVDRLREE LKRLVEEIAKMVKGGSSEETVKRLLD ELRELLERLKRTIEELLKRNRDLLAD AEEKARRLLEENRKLLKAARDTAT (SEQ ID NO: 27158) | 2plus1_Key_Cterm_5465 | EETVKRLLDE LRELLERLKR TIEELLKRNR DLLADAEEKA RRLLEENRKL LKAARDTAT (SEQ ID NO: 27159) |
| 2plus1_Cage_Cterm_5470 | SKEDRLREELKKLLARLAEEIERLKR ALEESNKDLKRTIDASEKHLRDVNED VKRGGVSEELLRELERSTAENKERAK ELLKRHEDLVRKVEKELADLLRRLEE IVARVDEALKRGISEEELDKLLKEAR DLIREIEKRLEELLKRVEKLTEDAKR DLERSNREHKELADRIKETAR (SEQ ID NO: 27160) | 2plus1_Key_Cterm_5470 | EEELDKLLKE ARDLIREIEK RLEELLKRVE KLTEDAKRDL ERSNREHKEL ADRIKETAR (SEQ ID NO: 27161) |
| 2plus1_Cage_Nterm_2406 | SEVDEVVKEVEDLVRRNEELVEEVVR RVEKVVTDDRRLVEEVVREIRKIVKD VEDLARKLDKEELKRVLDEMRERIER LLEKLRRHSKKLDDELKRLLEELREH SRRVEKRLEDLLKELRERGVDEKVLR KLEKVIREVRERSTRALRKVEEVIRR VREESERALRDLERVVKEVEKRMREA AR(SEQ ID NO: 27162) | 2plus1_Key_Nterm_2406 | SEVDEVVKEV EDLVRRNEEL VEEVVRRVEK VVTDDRRLVE EVVREIRKIV KDVEDLARK (SEQ ID NO: 27163) |
| 2plus1_Cage_Nterm_5406 | DREREVKKRLDEVRERIERLLRRVEE ESRRVAEEIRRLIEEVRRRNKKVTEE IRELLKGLKDKEEVRRVLERLRKLNA ESDELLERILERLRRLVEATNRLVKA IIEELRRLVEKIVREVPDSEELREEL KKLERKIEKVAKEIHDHDKEVTERLE DLLRRITEHARKSDREIEETAR (SEQ ID NO: 27164) | 2plus1_Key_Nterm_5406 | DREREVKKRL DEVRERIERL LRRVEEESRR VAEEIRRLIE EVRRRNKKVT EEIRELLKGL (SEQ ID NO: 27165) |
| 2plus1_Cage_Nterm_5409 | SEAEELLKRLEDRAEEILRRLEEILR TSRKLAEDVLRELEKLLRESERRIRE VLEELRGIKDKKELEDVIREVEKELD ESLERSRELLKDVLKKLDDNLKESER LVEDIDRELAKILEDLKKAGVPKEVV DEIKRIVDEVRERLKRIVDENAKIVE DARRALEKIVKENEEILRRLKKELRE LRK(SEQ ID NO: 27166) | 2plus1_Key_Nterm_5409 | SEAEELLKRL EDRAEEILRR LEEILRTSRK LAEDVLRELE KLLRESERRI REVLEELRGI (SEQ ID NO: 27167) |
| 2plus1_Cage_Nterm_5410 | SRAETVLKEVTDKIKKLADSSDELLR RNKENIDELKKSSEELLRRLTKAIEE IEKGSVDEETLEELIRRVEAELEAHH RELEKNSREDEKRNRDHHAKLEEEMR RVEERLEREGIDDEVVKRVRDLLDTV RRRNEKVNEDVKRMNDKLRRDNEDVI RRVEKLLRELEEKRRT (SEQ ID NO: 27168) | 2plus1_Key_Nterm_5410 | SRAETVLKEV TDKIKKLADS SDELLRRNKE NIDELKKSSE ELLRRLTKAI EEIEKGS (SEQ ID NO: 27169) |
| 2plus1_Cage_Nterm_5413 | STEEVLDEIRKLHKTLTEDIKRVLRE IEELHRRTIEENKEVLDKIAEDYKRV IDDVRTKDTPNVEKLLKDLEKSAKEN IEHNERTLREDDRVLKEIRRRATELL | 2plus_1Key_Nterm_5413 | STEEVLDEIR KLHKTLTEDI KRVLREIEEL HRRTIEENKE |

TABLE 2-continued

| Cage Name | Cage Sequence | Key Name | Key Sequence |
|---|---|---|---|
| | KANEEMLRRIEEVARKGGVDAEELLR ESKEAIKEVKRVLEELRKESKRVVDE TRKLSEENLEHSERVLRKVEEDLR (SEQ ID NO: 27170) | | VLDKIAEDYK RVIDDVRTKD (SEQ ID NO: 27171) |
| 2plus1_Cage_5414_GFP11_Nterm | SEIEKILKEIEDLARRDEEVSKKIVE IRRLAKEVEDTSRRDHMVLHEYVNAA GITLRKDGSKEELEKEVREVVKTLEE LVKDNHRLIRRAVEEMKRLVEENHRH SREVVKELEDLVRELRKGSGSEDSER LVREVEDLVRRLVRRSEKSNEEVKRT VEELVRRMEESNDRVRDLVRRLVEEL KRAVD(SEQ ID NO: 27172) | 2plus1_Key_Nterm_5414 | SEIEKILKEI EDLARRDEEV SKKIVEDIRR LAKEVEDTSR DIVRKIEELA KRVLDRLRKD (SEQ ID NO: 27173) |
| 2plus1_Cage_541_GFP11_Nterm | SEIEKILKEIEDLARRDEEVSKKIVE DIRRLAKEVEDTSRDIRDHMVLHEYV NAAGITKDGSKEELEKEVREVVKTLE ELVKDNHRLIRRAVEEMKRLVEENHR HSREVVKELEDLVRELRKGSGSEDSE RLVREVEDLVRRLVRRSEKSNEEVKR TVEELVRRMEESNDRVRDLVRRLVEE LKRAVD(SEQ ID NO: 27174) | 2plus1_Key_Nterm_5414 | SEIEKILKEI EDLARRDEEV SKKIVEDIRR LAKEVEDTSR DIVRKIEELA KRVLDRLRKD (SEQ ID NO: 27175) |
| 2plus1_Cage_Nterm_5439 | SRVEEIIEDLRRLLEEIRKENEDSIR RSKELLDRVKEINDTIIAELERLLKD IEKEVREKGSESEEVKKALRAVLEEL EKLLRRVAEINEEVLRRNSKLVEEDE RRNREVLKELARLVEELIREIGDEDK ARKVAEVAEKVLRDIDKLDRESKEAF RATNEEIAKLDEDTARVAERVKKAIE DLAK(SEQ ID NO: 27176) | 2plus1_Key_Nterm_5439 | SRVEEIIEDL RRLLEEIRKE NEDSIRRSKE LLDRVKEIND TIIAELERLL KDIEKEVREK G(SEQ ID NO: 27177) |
| 3plus_Cage_529_GFP11_Cterm | SEAEDLEELIKELAELLKDVIRKLEK INRRLVKILEDIIRRLKEISKEAEEE LRKGTVEDKDILRDLERRLREILEES DRLLEELKRRLEEILRKSKELLRRLE EVLREILKRAEEVKRSNLPKEELIKE IVKLLEELLRVIEKILEDNIRLLEEL VEVIKEILEKHLRLLEELVRVIERIL REVGKDKDEAERRDHMVLHEYVNAAG ITEEVKRRLEEELTRLRETHKKIEKE LREALKRVRDRST (SEQ ID NO: 27178) | 3plus_Key_Cterm_529 | KDEAERRRRE LKDKLDRLRE EHEEVKRRLE EELTRLRETH KKIEKELREA LKRVRDRST (SEQ ID NO: 27179) |
| 3plus1_Cage_Cterm_263 | SLVDELRKSLERNVRVSEEVARRLKE ALKRWVDVVRKVVEDLIRLNEDVVRV VEKVTVDESAIERVRRIIEELNRKLD AVLKKNEDLVRRLTELLDKLLEENRR LVEEELDEDLKRRGGTEEVIDTILELI ERSIERLKRLLDDELLRIVREALKDNK RVADENLKKLKEILDELRKDGVEDEE LKRVLEKAADLHRRLKDRHRKLLEDL ERIIRELKKKLDEVVEENKRSVDELK R(SEQ ID NO: 27180) | 3plus1_Key_Cterm_263 | DEELKRVLEK AADLHRRLKD RHRKLLEDLE RIIRELKKKL DEVVEENKRS VDELKR (SEQ ID NO: 27181) |
| 3plus1_Cage_Cterm_494 | SKEDKARELEKRLRDNLKKLEEVVRE LAEVLKRNLEKLRRLAEELLRALKRL LDKLRAGGLPKDELEDLRREVEDVLR RLEDLLRKLKKANDESLTRLEELLRR AEEENRRVLTTLRELLRGNGDDRDLA RLVARLVEANNRALEELLRLVAKNVE DNNRVLEELLRLVKELAKRLLGRIRD EDLVRDIRRELKELEERARKILRDDE RDLRALEKRIRDIIREDREELERLKE RARK(SEQ ID NO: 27182) | 3plus1_Key_Cterm_494 | EDLVRDIRRE LKELEERARK ILRDDERDLR ALEKRIRDII REDREELERL KERARK (SEQ ID NO: 27183) |
| 3plus1_Cage_Cterm_500 | SEKEELKRLLDKLLKELKRLSDELKA TIDKILKILKEVSEEVKRTADELLDA IRRGGVDEEVLREIKREIEEIEKKLR KVNKEIEDEIREIKKKLDEVDDKITK EVEKIKEALDKGGVDAKEVIKALKEI LKEHADVFEDVLRRLKEIIKRHRDVV KEVLEELRKILEKVAEVLKRQGRSED ELRKVEEDLKRLEDKLKKLLEDYEKK VRELEETLDDLLRKYEETLRRLEKEL EEAER(SEQ ID NO: 27184) | 3plus1_KeyCterm_500 | EDELRKVEED LKRLEDKLKK LLEDYEKKVR ELEETLDDLL RKYEETLRRL EKELEEAER (SEQ ID NO: 27185) |

TABLE 2-continued

| Cage Name | Cage Sequence | Key Name | Key Sequence |
|---|---|---|---|
| 3plus1_Cage_506_GFP11_Cterm | SAEETLRRITEESKRVLEEITKKYED LERESREVLRKLREDLDRIKRELEDV LTKGGDDKDEVLTVLEKVLDELLKLH RENLRVIKELLRKVLEVDRENLEVLK RLLEKARDLLRRSGRDEKDLKKLEDE LRKVKEELEKKHEASKRDIEDLEREL DKVTEEVERLLRKLKEELRRAAEGSD ERDHMVLHEYVNAAGITIRVLEEILK INEELNRKIIKFARENLERNRRVNKK VIEVLREAAR (SEQ ID NO: 27186) | 3plus1_Key_Cterm_506 | RERLARLLKA LADKLIRVLE EILKINEELN RKIIKFAREN LERNRRVNKK VIEVLREAAR (SEQ ID NO: 27187) |
| 3plus1_Cage_508_GFP11_Cterm | STEEILKRVKEILDELAKELRDIIRE SLRTIEELLDELRRILEESERTLEEL VKTIKDGVKDSEELLRRLKRLLEDLR RAHEELLKRLKEAVDEHRDRLRKILE ELERVLKELRKRIEELRRSGDRISEK DVLRKLEEVLRKALEILERLLKKIRE SARELLKIIEEVLDANIKVMEEALKT IKELLKDGRDHMVLHEYVNAAGITTR YEELRRRLRKRVKDYEDKLREIEKKV RRDAERIEEELERAKK (SEQ ID NO: 27188) | 3plus1_Key_Cterm_508 | DEVKRRLEEK ERRIRTRYEE LRRRLRKRVK DYEDKLREIE KKVRRDAERI EEELERAKK (SEQ ID NO: 27189) |
| 3plus1_Cage_Cterm_510 | SEKEELLKLIKRVIELLKRVLEEHLR LVEDVIRRLKELLDSNEKIVREVIED LKRLLDEVRGDKEELDRIKEKLEEVL ERYKRRLEEIKRDLERMLEDYKRELK RIEEDLRRVLEEVERIATRGEGPAEA LIDKLRKILERALRELDKLSKKLDEL LKKVLEELEKSNREIDKLLKDVLRRV EEGGASEDLLRKAKKVITEVREKLKR NLEDVRRVIEDVKRKSARILEEARRL IEEVERELEKIRK (SEQ ID NO: 27190) | 3plus1_Key_Cterm_510 | EDLLRKAKKV ITEVREKLKR NLEDVRRVIE DVKRKSARIL EEARRLIEEV ERELEKIRK (SEQ ID NO: 27191) |
| 3plus1_Cage_528_GFP11_Cterm | SEAEDLEELIKELAELLKDVIRKLEK INRRLVKILEDIIRRLKEISKEAEEE LRKGTVEDKDILRDLERRLREILEES DRLLEELKRRLEEILRKSKELLRRLE EVLREILKRAEEVKRSNLPKEELIKE IVKLLEELLRVIEKILEDNIRLLEEL VEVIKEILEKHLRLLEELVRVIERIL REVGRDHMVLHEYVNAAGITLDRLRE EHEEVKRRLEEELTRLRETHKKIEKE LREALKRVRDST (SEQ ID NO: 27192) | 3plus1_Key_Cterm_528 | KDEAERRRRE LKDKLDRLRE EHEEVKRRLE EELTRLRETH KKIEKELREA LKRVRDRST (SEQ ID NO: 27193) |
| 3plus1_Cage_528_GFP11_Cterm | SEAEDLEELIKELAELLKDVIRKLEK INRRLVKILEDIIRRLKEISKEAEEE LRKGTVEDKDILRDLERRLREILEES DRLLEELKRRLEEILRKSKELLRRLE EVLREILKRAEEVKRSNLPKEELIKE IVKLLEELLRVIEKILEDNIRLLEEL VEVIKEILEKHLRLLEELVRVIERIL REVGKDKRDHMVLHEYVNAAGITLRE EHEEVKRRLEEELTRLRETHKKIEKE LREALKRVRDST (SEQ ID NO: 27194) | 3plus1_Key_Cterm_528 | KDEAERRRRE LKDKLDRLRE EHEEVKRRLE EELTRLRETH KKIEKELREA LKRVRDRST (SEQ ID NO: 27195) |
| 3plus1_Cage_528_GFP11_Cterm | SEAEDLEELIKELAELLKDVIRKLEK INRRLVKILEDIIRRLKEISKEAEEE LRKGTVEDKDILRDLERRLREILEES DRLLEELKRRLEEILRKSKELLRRLE EVLREILKRAEEVKRSNLPKEELIKE IVKLLEELLRVIEKILEDNIRLLEEL VEVIKEILEKHLRLLEELVRVIERIL REVGKDKDEAERDHMVLHEYVNAAGI THEEVKRRLEEELTRLRETHKKIEKE LREALKRVRDST (SEQ ID NO: 27196) | 3plus1_Key_Cterm_528 | KDEAERRRRE LKDKLDRLRE EHEEVKRRLE EELTRLRETH KKIEKELREA LKRVRDRST (SEQ ID NO: 27197) |
| 3plus1_Cage_529_GFP11_Cterm | SEAEDLEELIKELAELLKDVIRKLEK INRRLVKILEDIIRRLKEISKEAEEE LRKGTVEDKDILRDLERRLREILEES DRLLEELKRRLEEILRKSKELLRRLE | 3plus1_Key_Cterm_529 | KDEAERRRRE LKDKLDRLRE EHEEVKRRLE EELTRLRETH |

TABLE 2-continued

| Cage Name | Cage Sequence | Key Name | Key Sequence |
|---|---|---|---|
| | EVLREILKRAEEVKRSNLPKEELIKE<br>IVKLLEELLRVIEKILEDNIRLLEEL<br>VEVIKEILEKHLRLLEELVRVIERIL<br>REVGKRDHMVLHEYVNAAGITDRLRE<br>EHEEVKRRLEEELTRLRETHKKIEKE<br>LREALKRVRDRST<br>(SEQ ID NO: 27198) | | KKIEKELREA<br>LKRVRDRST<br>(SEQ ID<br>NO: 27199) |
| 3plus1_Cage_529_GFP11_Cterm | SEAEDLEELIKELAELLKDVIRKLEK<br>INRRLVKILEDIIRRLKEISKEAEEE<br>LRKGTVEDKDILRDLERRLREILEES<br>DRLLEELKRRLEEILRKSKELLRRLE<br>EVLREILKRAEEVKRSNLPKEELIKE<br>IVKLLEELLRVIEKILEDNIRLLEEL<br>VEVIKEILEKHLRLLEELVRVIERIL<br>REVGKRDHMVLHEYVNAAGITRLRE<br>EHEEVKRRLEEELTRLRETHKKIEKE<br>LREALKRVRDRST<br>(SEQ ID NO: 27200) | 3plus1_Key_Cterm_529 | KDEAERRRRE<br>LKDKLDRLRE<br>EHEEVKRRLE<br>EELTRLRETH<br>KKIEKELREA<br>LKRVRDRST<br>(SEQ ID<br>NO: 27201) |
| 3plus1_Cage_529_GFP11_Cterm | SEAEDLEELIKELAELLKDVIRKLEK<br>INRRLVKILEDIIRRLKEISKEAEEE<br>LRKGTVEDKDILRDLERRLREILEES<br>DRLLEELKRRLEEILRKSKELLRRLE<br>EVLREILKRAEEVKRSNLPKEELIKE<br>IVKLLEELLRVIEKILEDNIRLLEEL<br>VEVIKEILEKHLRLLEELVRVIERIL<br>REVGKDKDRDHMVLHEYVNAAGITRE<br>EHEEVKRRLEEELTRLRETHKKIEKE<br>LREALKRVRDRST<br>(SEQ ID NO: 27202) | 3plus1_Key_Cterm_529 | KDEAERRRRE<br>LKDKLDRLRE<br>EHEEVKRRLE<br>EELTRLRETH<br>KKIEKELREA<br>LKRVRDRST<br>(SEQ ID<br>NO: 27203) |
| 3plus1_Cage_Cterm_530 | SDKEEIKRRVEKTARDLETEHDKIKK<br>RLEDTVRDIKRELDELLEKYERVLRK<br>IEKTLREGDGDATDLVDKLLETVKRL<br>NEEVLRTVKKIADELRRLVEEVLRVL<br>RESNETLARLLEEGNVGDEVRERLEE<br>VLRRTEEIIKTLEEIVKRLLDELRRL<br>VEELRRISKKLKDELDKIKEKGKDEK<br>RLIEEVVRLLRENLDVVRRILEALAK<br>LIKELLEALEEVLRRNKELIRELLRV<br>LDEALK(SEQ ID NO: 27204) | 3plus1_Key_Cterm_530 | EKRLIEEVVR<br>LLRENLDVVR<br>RILEALAKLI<br>KELLEALEEV<br>LRRNKELIRE<br>LLRVLDEALK<br>(SEQ ID<br>NO: 27205) |
| 3plus1_Cage_534_GFP11_Cterm | DEDRIIEEIARLLEELLRELLELIKK<br>LIETNRRLNEEHERAVRELARLLEEL<br>LDRLVKKGISDEKLKRIRERLKRALD<br>DLERLHREINKRLEDLVRELEKLVRE<br>ILKELKDALEELRRASARAGGEEVLR<br>RLEEIVKKLLDLVRRILERLKEIHKD<br>NVRLLRELNERLTRIVEDLVRLIREI<br>LREAGVDERDHMVLHEYVNAAGITIK<br>RLHEDLERKLKESEDELREIEARLEE<br>KIRRLEEKLERKRR<br>(SEQ ID NO: 27206) | 3plus1_Key_Cterm_534 | EKIAEEIERE<br>LEELRRMIKR<br>LHEDLERKLK<br>ESEDELREIE<br>ARLEEKIRRL<br>EEKLERKRR<br>(SEQ ID<br>NO: 27207) |
| 3plus1_Cage_534_GFP11_Cterm | DEDRIIEEIARLLEELLRELLELIKK<br>LIETNRRLNEEHERAVRELARLLEEL<br>LDRLVKKGISDEKLKRIRERLKRALD<br>DLERLHREINKRLEDLVRELEKLVRE<br>ILKELKDALEELRRASARAGGEEVLR<br>RLEEIVKKLLDLVRRILERLKEIHKD<br>NVRLLRELNERLTRIVEDLVRLIREI<br>LREAGVDEKIRDHMVLHEYVNAAGIT<br>RLHEDLERKLKESEDELREIEARLEE<br>KIRRLEEKLERKRR<br>(SEQ ID NO: 27208) | 3plus1_Key_Cterm_534 | EKIAEEIERE<br>LEELRRMIKR<br>LHEDLERKLK<br>ESEDELREIE<br>ARLEEKIRRL<br>EEKLERKRR<br>(SEQ ID<br>NO: 27209) |
| 3plus1_Cage_534_GFP11_Cterm | DEDRIIEEIARLLEELLRELLELIKK<br>LIETNRRLNEEHERAVRELARLLEEL<br>LDRLVKKGISDEKLKRIRERLKRALD<br>DLERLHREINKRLEDLVRELEKLVRE | 3plus1_Key_Cterm_534 | EKIAEEIERE<br>LEELRRMIKR<br>LHEDLERKLK<br>ESEDELREIE |

TABLE 2-continued

| Cage Name | Cage Sequence | Key Name | Key Sequence |
|---|---|---|---|
| | ILKELKDALEELRRASARAGGEEVLR RLEEIVKKLLDLVRRILERLKEIHKD NVRLLRELNERLTRIVEDLVRLIREI LREAGVDEKIAEEIERDHMVLHEYVN AAGITLERKLKESEDELREIEARLEE KIRRLEEKLERKRR (SEQ ID NO: 27210) | | ARLEEKIRRL EEKLERKRR (SEQ ID NO: 27211) |
| 3plus1_Cage_Cterm_539 | SEKEKLLKESEEEVRRLRRTLEELLR KYREVLERLRKELREIEERVRDVVRR LKEVLDRKGLDIDTIIKEVEDLLKTV LDRLRELLDKIRRLTKEAIEVVREII ERIVRHAERVKDELRKEGGDKEKLDR VDRLIKENTRHLKEILDRIEDLVRRS EKKLRDIIREVRRLIEELRKKAEEIK KGPDERLVKTLIEDVEAVIKRILELI TRVAEDNERVLERIIRELTDNLERHL KIVREIVK (SEQ ID NO: 27212) | 3plus1_Key_Cterm_539 | ERLVKTLIED VEAVIKRILE LITRVAEDNE RVLERIIREL TDNLERHLKI VREIVK (SEQ ID NO: 27213) |
| 3plus1_Cage_Cterm_548 | DKAEVLREALKLLKDLLEELIKIHEE SLKRILDLIDTLVKVHEDALRALKEL LERSGLDERELRKVERMATESLRTIA KLKEELRDLARRSLEKLREDLKRVDD TLRKVEEKVRRTGPSEELIEELIRTI EKLLKEIVRINEEVLKAVRELLKTLL KLSEDVVRRIEEILRKGGVPEEIDRE LKRVVEELRRLHEEIKERLDDVARRS EEELRRIIKKLKEVVKEIRKKLK (SEQ ID NO: 27214) | 3plus1_Key_Cterm_548 | EEIDRELKRV VEELRRLHEE IKERLDDVAR RSEEELRRII KKLKEVVKEI RKKLK (SEQ ID NO: 27215) |
| 3plus1_Cage_Cterm_556 | SERELIERWLELHKEILRLIRELVER LLKLHREILDTIKKLIRELLELLEDI ARKLGLDKEAKDELREIAKRVEDKLE KLERESRKVEEDLKRKLKELTDESDT VEKRVRDVVRRGTQSREEIAEELLRL DRKLLKAVEELLKEILDLNKKLLDDV RAILEETRRVLEKLLDRVRRGERTDD ERRTLTELLKRMEDILEKVERTLKKL LDDSARMAEEVKKTLKELLERSEKVA EDVRK (SEQ ID NO: 27216) | 3plus1_Key_Cterm_556 | DDERRTLTEL LKRMEDILEK VERTLKKLLD DSARMAEEVK KTLKELLERS EKVAEDVRK (SEQ ID NO: 27217) |
| 3plus1_Cage_Cterm_560 | SKKELLEEVVRRAIELLKRHLEKLKR ILEEIVRLLEEHLEKVERVLEAILSL LDDLLRRGGDERAIRTLEDVKRRLRE ILERLADENAKAIKRLADLLDKLEKR NKEAIERLEEILEELKRVRRDEELLR VLETLLKIIEDILRENTKVLEDLLRL VEEILEANLRVVEELLRLAREILTEI VGDEDKLKEIEDELRRLLEELRRLDK AIKDRLRELKKDLDEANRRIKETLKK LLREVEK (SEQ ID NO: 27218) | 3plus1_Key_Cterm_560 | EDKLKEIEDE LRRLLEELRR LDKAIKDRLR ELKKDLDEAN RRIKETLKKL LREVEK (SEQ ID NO: 27219) |
| 3plus1_Cage_568_GFP11_Cterm | KEIEETLKELEDLNREMVETNRRVLE ETRRLNKETVDRVKATLDELAKMLKK LVDDVRKGPTSEELKRLLAELEELLA RVVRRVEELLKKSTDLLERAVKDSAD ALRRSHEVLKEVASRVKRAKDEGLPR EEVLRLLRELLERHAKVLKDIVRVSE KLLREHLKVLREIVEVLEELLERILK VILDTTRDHMVLHEYVNAAGITKRRL KEVIDRYEDELRKLRKEYKEKIDKYE RKLEEIERRERT (SEQ ID NO: 27220) | 3plus1_Key_Cterm_568 | KAVEELEKAL EEIKRRLKEV IDRYEDELRK LRKEYKEKID KYERKLEEIE RRERT (SEQ ID NO: 27221) |
| 3plus1_Cage_568_GFP11_Cterm | KEIEETLKELEDLNREMVETNRRVLE ETRRLNKETVDRVKATLDELAKMLKK LVDDVRKGPTSEELKRLLAELEELLA RVVRRVEELLKKSTDLLERAVKDSAD ALRRSHEVLKEVASRVKRAKDEGLPR EEVLRLLRELLERHAKVLKDIVRVSE KLLREHLKVLREIVEVLEELLERILK VILDTTGGDRDHMVLHEYVNAAGITL KEVIDRYEDELRKLRKEYKEKIDKYE RKLEEIERRERT (SEQID NO: 27222) | 3plus1_Key_Cterm_568 | KAVEELEKAL EEIKRRLKEV IDRYEDELRK LRKEYKEKID KYERKLEEIE RRERT (SEQ ID NO: 27223) |

TABLE 2-continued

| Cage Name | Cage Sequence | Key Name | Key Sequence |
|---|---|---|---|
| 3plus1_Cage_Cterm_572 | DEDELIRKLLEDLKDIVRKILELIER DLRDIERVVRRIVKVIRDDLKKIKEV VDDIARGVPRTEELERVIKRIEELLR TSEEELDRILKEIEELLRESRRRLEE VVSAVEELLRRVEEIVDKGRESKEDV IKLLREVVDDILRLVEEVVRTNLEII KRILELIERVIRLNLSIIRDILRLLE GTVDSELADRIRKLIEDLERHTAKVL EDVKRAITELRKNSKDILEEVRKLID ELRKRIKEVED (SEQ ID NO: 27224) | 3plus1_Key_Cterm_572 | SELADRIRKL IEDLERHTAK VLEDVKRAIT ELRKNSKDIL EEVRKLIDEL RKRIKEVED (SEQ ID NO: 27225) |
| 3plus1_Cage_Cterm_581 | SALETVKKLLEDSSEKIERIVEEDER VAKESSDRIRRLVEEDKRVADEILDL IEKIGDTDTLLKLVEEWSRTSKKLLD DVLKLHKDWSDDSRRLLEEILRVHEE LIRRVKEILDREGKPEEVVRELEKVL KESLDTLEEIIRRLDEANAATVKRVA DVIRELEDINRKVLEEIKRGSDDAEA VIKVIEKLIRANKRVWDALLKINEDL VRVNKTVWKELLRVNEKLARDLERVV K(SEQ ID NO: 27226) | 3plus1_Key_Cterm_581 | AEAVIKVIEK LIRANKRVWD ALLKINEDLV RVNKTVWKEL LRVNEKLARD LERVVK (SEQ ID NO: 27227) |
| 3plus1_Cage_Cterm_585 | SKEEKLKDDVRAVLEDLDRVLKELEK LSEDNLRELKRVLDRITDLHRRILDE LRKGIGSEELLRRVEKVLKDNLDLLR KLVEEHKESSERDLKRVEDLVREIKE VLRKLLELEDRGTDIRKIEEEIERLL RKIRKAVEESKDLNRRNSERIEEVAR RSEELARRLLKEIRERGDSKAAEDIL RVLEKLVKVSREAIKLILELSEHHVR VSTRIARLLLDVARKLAEVIKEAER (SEQ ID NO: 27228) | 3plus1_Key_Cterm_585 | SKAAEDILRV LEKLVKVSRE AIKLILELSE HHVRVSTRIA RLLLDVARKL AEVIKEAER (SEQ ID NO: 27229) |
| 3plus1_Cage_Cterm_587 | SEIEDVIRRLRKILEDLERVSEKLLR EIKKILDEARRLNEEVIKEIKRVLED AVRVFRDGSGSKEELAKLVEELIREL AKLAKEVDEIHKRIVERLKALVEDAE RIHRKIVETLEEIVRGVPSEELKRVV EAIVEVIKEHLKVLADVIRRIIKAIE ENAETIKRVLEDIVRVLELVLRGEGS IEDLVREVERLIKRIEDSLRELEKTV RELLKRIKEASDKVREDVDRLIKELK EAAD(SEQ ID NO: 27230) | 3plus1_Key_Cterm_587 | IEDLVREVER LIKRIEDSLR ELEKTVRELL KRIKEASDKV REDVDRLIKE LKEAAD (SEQ ID NO: 27231) |
| 3plus1_Cage_Cterm_605 | SREELLDRILEAIAKILEDLKRLIDE NLARLEEVVRELERIIDRNLKLIREI LDELKKGSGSEEILEKIKKVDKELED LIRRLLKKLEDLIRETERRLREILKR IRDLLKEVKDRDKDLERLLEVLEEVL RVIAELAKELLDSLRKVLKVVEEVLR LLNEVNKEVLDVIRELAKDGGSDEII RKLDELLKEVEKVHKEVKDRIRKLLE DHKRSLDEVKKKLERLLERAKEVVER EKK(SEQ ID NO: 27232) | 3plus1_Key_Cterm_605 | DEIIRKLDEL LKEVEKVHKE VKDRIRKLLE DHKRSLDEVK KKLERLLERA KEVVEREKK (SEQ ID NO: 27233) |
| 3plus1_Cage_Cterm_607 | SEREELLERIKEILKRVKDKLDEDLK RLKEILEKLKEKADRDLEELRRRIEE VREKLERTGRTDELVKEVLDTVRRNL ENLKRLVEDILRKLEENVKNLTDLVR EILKLITELIKRLEDGGLPKEVLDAL RRVLEKLEELLREILERLKRSLEAVK RKIEELLKELERSLDELRRALERIRK EIGDSETAVRAIIRVLEKHLEAVRRV LEELLKVLAEHLETVRELIERLKRVL EEAIEVVERVAR (SEQ ID NO: 27234) | 3plus1_Key_Cterm_607 | SETAVRAIIR VLEKHLEAVR RVLEELLKVL AEHLETVREL IERLKRVLEE AIEVVERVAR (SEQ ID NO: 27235) |
| 3plus1_Cage_Cterm_610 | SLEEITKRLLELVEENLARHEEILRE LLELAKRLAKEDRDILEEVLKLIEEL LKLLEDNGSSEEDLKRLLKEVIEELR AVVKRVKDKWDEVVKRIEDLVKKLKE | 3plus1_Key_Cterm_610 | ERTLREVVRK VLEEAKRLLD ELEEVHKRVK KELEDIIEEN |

TABLE 2-continued

| Cage Name | Cage Sequence | Key Name | Key Sequence |
|---|---|---|---|
| | LHDDTLRKLRELVRKIVTDISESGGE<br>AEKVKRVVEKILELVERLAKVVKESV<br>EKLLEILRELAEVSKRVAEALLRLLE<br>ELVRVIRIKDERTLREVVRKVLEEAK<br>RLLDELEEVHKRVKKELEDIIEENRR<br>VVKRVRDELREIKRELDE<br>(SEQ ID NO: 27236) | | RRVVKRVRDE<br>LREIKRELDE<br>(SEQ ID<br>NO: 27237) |
| 3plus1_Cage_611_GFP11_Cterm | SLEEITKRLLELVEENLARHEEILRE<br>LLELAKRLAKEDRDILEEVLKLIEEL<br>LKLLEDNGSSEEDLKRLLKEVIEELR<br>AVVKRVKDKWDEVVKRIEDLVKKLKE<br>LHDDTLRKLRELVRKIVTDISESGGE<br>AEKVKRVVEKILELVERLAKVVKESV<br>EKLLEILRELAEVSKRVAEALLRLLE<br>ELVRVIRIKDERDHMVLHEYVNAAGI<br>TLLDELEEVHKRVKKELEDIIEENRR<br>VVKRVRDELREIKRELDE<br>(SEQ ID NO: 27238) | 3plus1_Key_Cterm_611 | ERTLREVVRK<br>VLEEAKRLLD<br>ELEEVHKRVK<br>KELEDIIEEN<br>RRVVKRVRDE<br>LREIKRELDE<br>(SEQ ID<br>NO: 27239) |
| 3plus1_Cage_Cterm_632 | SEKELVDDIRRILEEILRLLRSLLEE<br>VIRLLEENEKLVRRHLKTVIDILRRV<br>AKLLDENGIRTDEADRVLERLEKAHR<br>ELLEDYKRALEKIKETLERVLREAEE<br>VVKKIDDALRKLGGSKEVLKRLLEEL<br>LRLVEKIAEEIKRLLSELVRVTEELV<br>RTNKELLEEAVRVIRKEVGDDSLVRE<br>VEELIKRLEKHIDDLLKTSRDLVKRV<br>LDLVDEVVKRVEDLVERVKEKIDT<br>(SEQ ID NO: 27240) | 3plus1_Key_Cterm_632 | DSLVREVEEL<br>IKRLEKHIDD<br>LLKTSRDLVK<br>RVLDLVDEVV<br>KRVEDLVERV<br>KEKIDT<br>(SEQ ID<br>NO: 27241) |
| 3plus1_Cage_Cterm_641 | DEVEELLKRVRELLKASEELVRKILE<br>DVKRLLERSIEEVEDLLRKVEELLKR<br>LLDLVERGGSLDEILRELVRLLKEIV<br>RKVLELNRKLVEDVIRIAKRLLELNA<br>ESVKEWDRILKLLRDGTGDKEELLKD<br>AEEALEKYERAVREILKELEEIIKEY<br>VRRVEELLKELKDAVDKAKDEVRKGS<br>GDEDLIRDVDRVLKEIMDLLRDLVRR<br>TKELLEELLRLLEELVRAHKELVRSI<br>LDEIRK(SEQ ID NO: 27242) | 3plus1_Key_Cterm_641 | EDLIRDVDRV<br>LKEIMDLLRD<br>LVRRTKELLE<br>ELLRLLEELV<br>RAHKELVRSI<br>LDEIRK<br>(SEQ ID<br>NO: 27243) |
| 3plus1_Cage_646_GFP11_Cterm | DAEEVVKRLADVLRENDETIRKVVED<br>LVRIAEENDRLWKKLVEDIAEILRRI<br>VELLRRGGVPEELLDRLAKVVKSIVE<br>KAEKILERLNRVSKAIAEKLKTIVDE<br>LNEVSKEIVKRAEDILRKGKDKETVL<br>RALRTLVKEYADLSKEVLERVERIVR<br>EYVKLSDEVVKSLAEIVEELIRIIED<br>LLRKGNRDHMVLHEYVNAAGITRKLL<br>EDVKKASEDIVREVERIVRELAKRSD<br>EILKKLEDIVEKLRE<br>(SEQ ID NO: 27244) | 3plus1_Key_Cterm_646 | EDVKRALEEL<br>VSRLRKLLED<br>VKKASEDIVR<br>EVERIVRELA<br>KRSDEILKKL<br>EDIVEKLRE<br>(SEQ ID<br>NO: 27245) |
| 3plus1_Cage_646_GFP11_Cterm | DAEEVVKRLADVLRENDETIRKVVED<br>LVRIAEENDRLWKKLVEDIAEILRRI<br>VELLRRGGVPEELLDRLAKVVKSIVE<br>KAEKILERLNRVSKAIAEKLKTIVDE<br>LNEVSKEIVKRAEDILRKGKDKETVL<br>RALRTLVKEYADLSKEVLERVERIVR<br>EYVKLSDEVVKSLAEIVEELIRIIED<br>LLRKGNLDEDRDHMVLHEYVNAAGIT<br>EDVKKASEDIVREVERIVRELAKRSD<br>EILKKLEDIVEKLRE<br>(SEQ ID NO: 27246) | 3plus1_Key_Cterm_646 | EDVKRALEEL<br>VSRLRKLLED<br>VKKASEDIVR<br>EVERIVRELA<br>KRSDEILKKL<br>EDIVEKLRE<br>(SEQ ID<br>NO: 27247) |
| 3plus1_Cage_646_GFP11_Cterm | DAEEVVKRLADVLRENDETIRKVVED<br>LVRIAEENDRLWKKLVEDIAEILRRI<br>VELLRRGGVPEELLDRLAKVVKSIVE<br>KAEKILERLNRVSKAIAEKLKTIVDE<br>LNEVSKEIVKRAEDILRKGKDKETVL<br>RALRTLVKEYADLSKEVLERVERIVR<br>EYVKLSDEVVKSLAEIVEELIRIIED<br>LLRKGNLDEDVRDHMVLHEYVNAAGI<br>TDVKKASEDIVREVERIVRELAKRSD<br>EILKKLEDIVEKLRE<br>(SEQ ID NO: 27248) | 3plus1_Key_Cterm_646 | EDVKRALEEL<br>VSRLRKLLED<br>VKKASEDIVR<br>EVERIVRELA<br>KRSDEILKKL<br>EDIVEKLRE<br>(SEQ ID<br>NO: 27249) |

TABLE 2-continued

| Cage Name | Cage Sequence | Key Name | Key Sequence |
|---|---|---|---|
| 3plus1_Cage_647_GFP11_Cterm | DAEEVVKRLADVLRENDETIRKVVED LVRIAEENDRLWKKLVEDIAEILRRI VELLRRGGVPEELLDRLAKVVKSIVE KAEKILERLNRVSKAIAEKLKTIVDE LNEVSKEIVKRAEDILRKGKDKETVL RALRTLVKEYADLSKEVLERVERIVR EYVKLSDEVVKSLAEIVEELIRIIED LLRKGNLRDHMVLHEYVNAAGITKLL EDVKKASEDIVREVERIVRELAKRSD EILKKLEDIVEKLRE (SEQ ID NO: 27250) | 3plus1_Key_Cterm_647 | EDVKRALEEL VSRLRKLLED VKKASEDIVR EVERIVRELA KRSDEILKKL EDIVEKLRE (SEQ ID NO: 27251) |
| 3plus1_Cage_647_GFP11_Cterm | DAEEVVKRLADVLRENDETIRKVVED LVRIAEENDRLWKKLVEDIAEILRRI VELLRRGGVPEELLDRLAKVVKSIVE KAEKILERLNRVSKAIAEKLKTIVDE LNEVSKEIVKRAEDILRKGKDKETVL RALRTLVKEYADLSKEVLERVERIVR EYVKLSDEVVKSLAEIVEELIRIIED LLRKGNLDEDVKRALERDHMVLHEYV NAAGITSEDIVREVERIVRELAKRSD EILKKLEDIVEKLRE (SEQ ID NO: 27252) | 3plus1_Key_Cterm_647 | EDVKRALEEL VSRLRKLLED VKKASEDIVR EVERIVRELA KRSDEILKKL EDIVEKLRE (SEQ ID NO: 27253) |
| 3plus1_Cage_Cterm_647 | DAEEVVKRLADVLRENDETIRKVVED LVRIAEENDRLWKKLVEDIAEILRRI VELLRRGGVPEELLDRLAKVVKSIVE KAEKILERLNRVSKAIAEKLKTIVDE LNEVSKEIVKRAEDILRKGKDKETVL RALRTLVKEYADLSKEVLERVERIVR EYVKLSDEVVKSLAEIVEELIRIIED LLRKGNLDEDVKRALEELVSRLRKLL EDVKKASEDIVREVERIVRELAKRSD EILKKLEDIVEKLRE (SEQ ID NO: 27254) | 3plus1_Key_Cterm_647 | EDVKRALEEL VSRLRKLLED VKKASEDIVR EVERIVRELA KRSDEILKKL EDIVEKLRE (SEQ ID NO: 27255) |
| 3plus1_Cage_Cterm_653 | DEEETLRRLLERKVELAKEYLDVSKE VIDRTTKLLDEYLKTSKRIVDATVEL LERGDLGPDELIKRLAEELERSLREL EEEIKRLKRELEESLKKLKEIIDRLA EEAEKLLAVLKRGEGSEEEALRALAS LVRELIEVLRENDERLRDVLRRLIEA LRKNNEILERVLRKLVRAAEERGRDE SSREALEEARRLEELLRELNEITKD LEAKLEKLLRDLNELTKALEEELKRL LDELKKRTD (SEQ ID NO: 27256) | 3plus1_Key_Cterm_653 | SREALEEARR RLEEELLRELN EITKDLEAKL EKLLRDLNEL TKALEEELKR LLDELKKRTD (SEQ ID NO: 27257) |
| 3plus1_Cage_Cterm_658 | DEERIIKTLEDINAKLVEDIKRILDK VAELNERLADAIRKILEETKRILEAT TRKVRKDGEISEELLRRLEEKLRKLL EDLERVLAEHEDESRRILEEVERLLK RHADASKELLDRARSVARGVKSDKEL VDRLKKLIDDSLESVRELIERLKELL DRLVKSVEDLIRTIKELLDRLVEVLR EGVSDKDTLRTVEKLVEDVKRRLDKL LEDYKRLIEEVKKELDKLLKEYEDAL REIKKRIDE (SEQ ID NO: 27258) | 3plus1_Key_Cterm_658 | KDTLRTVEKL VEDVKRRLDK LLEDYKRLIE EVKKELDKLL KEYEDALREI KKRIDE (SEQ ID NO: 27259) |
| 3plus1_Cage_Cterm_660 | TEEEVVEDVKRVLDESHDDLRRLIET LTRVLRESLKRIKEALEELERVLKKL LDLLEGGRDAREVLDEIRKVLERLRE VIEELLRINKEVLRELERVIRELLKK NEDLARRVRSGVKSRLLEVLERLARE SLELNRAILEELRKLVEKSLRAVEKI LKRLEEIVRKLLKLVEDGGPREEVKR VLEEARDELRRLLEEYKAIIEELERE LERLLREHREVIRRIKEEIDKSSK (SEQ ID NO: 27260) | 3plus1_Key_Cterm_660 | REEVKRVLEE ARDELRRLLE EYKAIIEELE RELERLLREH REVIRRIKEE IDKSSK (SEQ ID NO: 27261) |
| 3plus1_Cage_Nterm_263 | SLVDELRKSLERNVRVSEEVARRLKE ALKRWVDVVRKVVEDLIRLNEDVVRV VEKVTVDESAIERVRRIIEELNRKLD AVLKKNEDLVRRLTELLDKLLEENRR | 3plus1_Key_Nterm_263 | SLVDELRKSL ERNVRVSEEV ARRLKEALKR WVDVVRKVVE |

TABLE 2-continued

| Cage Name | Cage Sequence | Key Name | Key Sequence |
|---|---|---|---|
| | LVEELDEDLKRRGGTEEVIDTILELI ERSIERLKRLLDELLRIVREALKDNK RVADENLKKLKEILDELRKDGVEDEE LKRVLEKAADLHRRLKDRHRKLLEDL ERIIRELKKKLDEVVEENKRSVDELK R(SEQ ID NO: 27262) | | DLIRLNEDVV RVVEKV (SEQ ID NO: 27263) |
| 3plus1_Cage_Nterm_500 | SEKEELKRLLDKLLKELKRLSDELKA TIDKILKILKEVSEEVKRTADELLDA IRRGGVDEEVLREIKREIEEIEKKLR KVNKEIEDEIREIKKKLDEVDDKITK EVEKIKEALDKGGVDAKEVIKALKEI LKEHADVFEDVLRRLKEIIKRHRDVV KEVLEELRKILEKVAEVLKRQGRSED ELRKVEEDLKRLEDKLKKLLEDYEKK VRELEETLDDLLRKYEETLRRLEKEL EEAER(SEQ ID NO: 27264) | 3plus1_Key_Nterm_500 | SEKEELKRLL DKLLKELKRL SDELKATIDK ILKILKEVSE EVKRTADELL DAIRRG (SEQ ID NO: 27265) |
| 3plus1_Cage_Nterm_510 | SEKEELLKLIKRVIELLKRVLEEHLR LVEDVIRRLKELLDSNEKIVREVIED LKRLLDEVRGDKEELDRIKEKLEEVL ERYKRRLEEIKRDLERMLEDYKRELK RIEEDLRRVLEEVERIATRGEGPAEA LIDKLRKILERALRELDKLSKKLDEL LKKVLEELEKSNREIDKLLKDVLRRV EEGGASEDLLRKAKKVITEVREKLKR NLEDVRRVIEDVKRKSARILEEARRL IEEVERELEKIRK (SEQ ID NO: 27266) | 3plus1_Key_Nterm_510 | SEKEELLKLI KRVIELLKRV LEEHLRLVED VIRRLKELLD SNEKIVREVI EDLKRLLDEV (SEQ ID NO: 27267) |
| 3plus1_Cage_529_GFP11_Nterm | SEAEDLEELIKELAELLKDVIRKLEK INRRLVKILRDHMVLHEYVNAAGITE LRKGTVEDKDILRDLERRLREILEES DRLLEELKRRLEEILRKSKELLRRLE EVLREILKRAEEVKRSNLPKEELIKE IVKLLEELLRVIEKILEDNIRLLEEL VEVIKEILEKHLRLLEELVRVIERIL REVGKDKDEAERRRRELKDKLDRLRE EHEEVKRRLEEELTRLRETHKKIEKE LREALKRVDRST (SEQ ID NO: 27268) | 3plus1_Key_Nterm_529 | SEAEDLEELI KELAELLKDV IRKLEKINRR LVKILEDIIR RLKEISKRAE EELRKG (SEQ ID NO: 27269) |
| 3plus1_Cage_568_GFP11_Nterm | KEIEETLKELEDLNREMVETNRRVLE ETRRLNKETVDRVKATRDHMVLHEYV NAAGITKGPTSEELKRLLAELEELLA RVVRRVEELLKKSTDLLERAVKDSAD ALRRSHEVLKEVASRVKRAKDEGLPR EEVLRLLRELLERHAKVLKDIVRVSE KLLREHLKVLREIVEVLEELLERILK VILDTTGGDKAVEELEKALEEIKRRL KEVIDRYEDELRKLRKEYKEKIDKYE RKLEEIERRERT (SEQ ID NO: 27270) | 3plus1_Key_Nterm_568 | KEIEETLKEL EDLNREMVET NRRVLEETRR LNKETVDRVK ATLDELAKML KKLVDDVRKG (SEQ ID NO: 27271) |
| 3plus1_Cage_Nterm_581 | SALETVKKLLEDSSEKIERIVEEDER VAKESSDRIRRLVEEDKRVADEILDL IEKIGDTDTLLKLVEEWSRTSKKLLD DVLKLHKDWSDDSRRLLEEILRVHEE LIRRVKEILDREGKPEEVVRELEKVL KESLDTLEEIIRRLDEANAATVKRVA DVIRELEDINRKVLEEIKRGSDDAEA VIKVIEKLIRANKRVWDALLKINEDL VRVNKTVWKELLRVNEKLARDLERVV K(SEQ ID NO: 27272) | 3plus1_Key_Nterm_581 | SALETVKKLL EDSSEKIERI VEEDERVAKE SSDRIRRLVE EDKRVADEIL DLIEKI (SEQ ID NO: 27273) |
| 3plus1_Cage_610_GFP11_Nterm | SLEEITKRLLELVEENLARHEEILRE LLELAKRLAKRDHMVLHEYVNAAGIT LKLLEDNGSSEEDLKRLLKEVIEELR AVVKRVKDKWDEVVKRIEDLVKKLKE LHDDTLRKLRELVRKIVTDISESGGE AEKVKRVVEKILELVERLAKVVKESV EKLLEILRELAEVSKRVAEALLRLLE ELVRVIRIKDERTLREVVRKVLEEAK RLLDELEEVHKRVKKELEDIIEENRR VVKRVRDELREIKRELDE (SEQ ID NO: 27274) | 3plus1_Key_Nterm_610 | SLEEITKRLL ELVEENLARH EEILRELLEL AKRLAKEDRD ILEEVLKLIE ELLKLLEDN (SEQ ID NO: 27275) |

TABLE 2-continued

| Cage Name | Cage Sequence | Key Name | Key Sequence |
|---|---|---|---|
| 3plus1_Cage_647_GFP11_Nterm | DAEEVVKRLADVLRENDETIRKVVED LVRIAEENDRLWRDHMVLHEYVNAAG ITLLRRGGVPEELLDRLAKVVKSIVE KAEKILERLNRVSKAIAEKLKTIVDE LNEVSKEIVKRAEDILRKGKDKETVL RALRTLVKEYADLSKEVLERVERIVR EYVKLSDEVVKSLAEIVEELIRIIED LLRKGNLDEDVKRALEELVSRLRKLL EDVKKASEDIVREVERIVRELAKRSD EILKKLEDIVEKLRE (SEQ ID NO: 27276) | 3plus1_Key_Nterm_647 | DAEEVVKRLA DVLRENDETI RKVVEDLVRI AEENDRLWKK LVEDIAEILR RIVELLRRG (SEQ ID NO: 27277) |

TABLE 3

| Row number | Cage (column 1) | Key (column 2) |
|---|---|---|
| 1 | LOCKR_extend18 (SEQ ID NO: 6), BimLOCKR_extend18 (SEQ ID NO: 22), , 1fix-long-Bim-t0 (SEQ ID NO: 54), 1fix-long-GFP-t0 (SEQ ID NO: 55), | p18_MBP (SEQ ID NO: 27020), p76-long (SEQ ID NO: 27027), p76-short (SEQ ID NO: 27028), |

TABLE 3-continued

| Row number | Cage (column 1) | Key (column 2) |
|---|---|---|
|  | 1fix-short-BIM-t0 (SEQ ID NO: 56), 1fix-short-GFP-t0 (SEQ ID NO: 57), |  |
| 2 | LOCKRb (SEQ ID NO: 7), | key_b (SEQ ID NO: 27022) |
| 3 | LOCKRc (SEQ ID NO: 8), | key_c (SEQ ID NO: 27023) |

TABLE 4

| Cage Name | Cage Sequence | Key Name | Key Sequence |
|---|---|---|---|
| 2plus1_CageCterm_2406 | SEVDEVVKEVEDLVRRNEELVEEV VRRVEKVVTDDRRLVEEVVREIRK IVKDVEDLARKLDKEELKRVLDEM RERIERLLEKLRRHSKKLDDELKR LLEELREHSRRVEKRLEDLLKELR ERGVDEKVLRKLEKVIREVRERST RALRKVEEVIRRVREESERALRDL ERVVKEVEKRMREAAR (SEQ ID NO: 27126) | 2plus1_Key_Cterm_2406 | EKVLRKLE KVIREVRE RSTRALRK VEEVIRRV REESERAL RDLERVVK EVEKRMRE AAR (SEQ ID NO: 27127) |
| 2plus1_Cage_Cterm_5398 | SVEELLRKLEEVLRKIREENERSL KELRDRAREIVKRNRETNRELEEV IKELEKRLSGADKEKVEELVRRIR RIVERVVEEDRRTVEEIEKIAREV VKRDRDSADRVRRTVEDVLRKATG SEDIVRKIERIVETIEREVRESVK KVEEIARDIRRKVDESVKNVEKLL RDVDKKARDRKK (SEQ ID NO: 27128) | 2plus1_Key_Cterm_5398 | EDIVRKIE RIVETIER EVRESVKK VEEIARDI RRKVDESV KNVEKLLR DVDKKARD RKK (SEQ ID NO: 27129) |
| 2plus1_Cage_Cterm_5405 | SESDDVIRKLRELLEELRTHVEKS IRDLRKILEDSTRHAKRSIEELER LLEEVRKKPGDEEVRKTVEEISRR VAENVKRLEDLYRRMEEEVKKNLD RLRKRVEDIIREVEEARKKGVDEE KLKDLIRKLRDILRRAAEAHKKLI DDARESLERAKREHEKLIDRLKKI LEELER (SEQ ID NO: 27130) | 2plus1_Key_Cterm_5405 | EEKLKDLI RKLRDILR RAAEAHKK LIDDARES LERAKREH EKLIDRLK KILEELER (SEQ ID NO: 27131) |
| 2plus1_Cage_Cterm_5406 | DREREVKKRLDEVRERIERLLRRV EEESRRVAEEIRRLIEEVRRRNKK VTEEIRELLKGLKDKEEVRRVLER LRKLNAESDELLERILERLRRLVE ATNRLVKAIIEELRRLVEKIVREV PDSEELREELKKLERKIEKVAKEI HDHDKEVTERLEDLLRRITEHARK SDREIEETAR (SEQ ID NO: 27132) | 2plus1_Key_Cterm_5406 | EELREELK KLERKIEK VAKEIHDH DKEVTERL EDLLRRIT EHARKSDR EIEETAR (SEQ ID NO: 27133) |

TABLE 4-continued

| Cage Name | Cage Sequence | Key Name | Key Sequence |
|---|---|---|---|
| 2plus1_Cage_Cterm_5409 | SEAEELLKRLEDRAEEILRRLEEI LRTSRKLAEDVLRELEKLLRESER RIREVLEELRGIKDKKELEDVIRE VEKELDESLERSRELLKDVLKKLD DNLKESERLVEDIDRELAKILEDL KKAGVPKEVVDEIKRIVDEVRERL KRIVDENAKIVEDARRALEKIVKE NEEILRRLKKELRELRK (SEQ ID NO: 27134) | 2plus1_Key_Cterm_5409 | KEVVDEIK RIVDEVRE RLKRIVDE NAKIVEDA RRALEKIV KENEEILR RLKKELRE LRK (SEQ ID NO: 27135) |
| 2plus1_Cage_5414_GFP11_Cterm | SEIEKILKEIEDLARRDEEVSKKI VEDIRRLAKEVEDTSRDIVRKIEE LAKRVLDRLRKDGSKEELEKEVRE VVKTLEELVKDNHRLIRRAVEEMK RLVEENHRHSREVVKELEDLVREL RKGSGSEDSERDHMVLHEYVNAAG ITSEKSNEEVKRTVEELVRRMEES NDRVRDLVRRLVEELKRAVD (SEQ ID NO: 27140) | 2plus1_Key_Cterm_5414 | EDSERLVR EVEDLVRR LVRRSEKS NEEVKRTV EELVRRME ESNDRVRD LVRRLVEE LKRAVD (SEQ ID NO: 27141) |
| 2plus1_Cage_Cterm_5421 | SVDEVLKEIEDALRRLKEEVERVL KENEDELRRLEEEVRRVLKEDEEL LESLKRGVGESDEVDRVVDEIAKL SAEILEKVKKVVKEIRDSLETVKR RVDDVVRRLKELLDEIKRGSDEKA IRDVAKEIRDRLKELEEEIEEVTR RNLKLLADVEEEIRRVHEKTRRLL ETVLRRAT (SEQ ID NO: 27146) | 2plus1_Key_Cterm_5421 | EKAIRDVA KEIRDRLK ELEEEIEE VTRRNLKL LADVEEEI RRVHEKTR RLLETVLR RAT (SEQ ID NO: 27147) |
| 2plus1_Cage_Cterm_5432 | DEIRKVVKEITDLLKASNDKNRKV VEEIRDLLRKSKKLADELVERLRA LVEDLRRRIDKSGDKETAEDIVRR IIEELKRILKEIEDLARRINREIE RLVEEVERDNRDVNRAIEELLKDI ARRGGSEDLKRVEERAREVSRRNE ESMRRVKEDADRVSEANKEVLDRV REEVKRLIEEVRETLR (SEQ ID NO: 27148) | 2plus1_Key_Cterm_5432 | SEDLKRVE ERAREVSR RNEESMRR VKEDADRV SEANKEVL DRVREEVK RLIEEVRE TLR (SEQ ID NO: 27149) |
| 2plus1_Cage_Cterm_5435 | STAETVAEEVERVLKHSDDLIKEV EDVNRRVEEEIKRVIRELEEEENER LVAEVRKGVKGEILAEIEKRLADN SEKVREVAERAKKLLEENTARVKD ILRESRKLVDLLDEVRGTGSEEA AREIIKRLREVNKRTKEKLDELIK HSEEVLERVKRLIDELRKHSEEVL EDLRRRAK (SEQ ID NO: 27150) | 2plus1_Key_Cterm_5435 | EEAAREII KRLREVNK RTKEKLDE LIKHSEEV LERVKRLI DELRKHSE EVLEDLRR RAK (SEQ ID NO: 27151) |
| 2plus1_Cage_Cterm_5439 | SRVEEIIEDLRRLLEEIRKENEDS IRRSKELLDRVKEINDTIIAELER LLKDIEKEVREKGSESEEVKKALR AVLEELEKLLRRVAEINEEVLRRN SKLVEEDERRNREVLKELARLVEE LIREIGDEDKARKVAEVAEKVLRD IDKLDRESKEAFRATNEEIAKLDE DTARVAERVKKAIEDLAK (SEQ ID NO: 27154) | 2plus1_Key_Cterm_5439 | EDKARKVA EVAEKVLR DIDKLDRE SKEAFRAT NEEIAKLD EDTARVAE RVKKAIED LAK (SEQ ID NO: 27155) |
| 2plus1_Cage_Cterm_5447 | SEADDVLKKLAETVKRIIERLKKL TDDSRRLVEEVHRRNDKLSKESAE AVRKAEERGIDEKDVRKLLEDLKK KSEEVAERNKRILDTLREISKRAE DEVRKVLKELEKTLKELEDRRPDS EELSAEVKKLLDEVRKALARHKDE NDKLLKEIEDSLRRHKEENDRLLE KLKESTR (SEQ ID NO: 27156) | 2plus1_Key_Cterm_5447 | EELSAEVK KLLDEVRK ALARHKDE NDKLLKEI EDSLRRHK EENDRLLE KLKESTR (SEQ ID NO: 27157) |

TABLE 4-continued

| Cage Name | Cage Sequence | Key Name | Key Sequence |
|---|---|---|---|
| 2plus1_Cage_Cterm_5456 | SAEELLREVAELVKRVDEDLRRLL EEVRASNEEVIRRLEEILKRIEEE NRKVVEELRRGGVSEDLVRESKRL VDESRRVIEKLVKESADSVERTRE TVDRLREELKRLVEEIAKMVKGGS SEETVKRLLDELRELLERLKRTIE ELLKRNRDLLADAEEKARRLLEEN RKLLKAARDTAT (SEQ ID NO: 27158) | 2plus1_Key_Cterm_5465 | EETVKRLL DELRELLE RLKRTIEE LLKRNRDL LADAEEKA RRLLEENR KLLKAARD TAT (SEQ ID NO: 27159) |
| 2plus1_Cage_Nterm_2406 | SEVDEVVKEVEDLVRRNEELVEEV VRRVEKVVTDDRRLVEEVVREIRK IVKDVEDLARKLDKEELKRVLDEM RERIERLLEKLRRHSKKLDDELKR LLEELREHSRRVEKRLEDLLKELR ERGVDEKVLRKLEKVIREVRERST RALRKVEEVIRRVREESERALRDL ERVVKEVEKRMREAAR (SEQ ID NO:27162) | 2plus1_Key_Nterm_2406 | SEVDEVVK EVEDLVRR NEELVEEV VRRVEKVV TDDRRLVE EVVREIRK IVKDVEDL ARK (SEQ ID NO: 27163) |
| 2plus1_Cage_Nterm_5406 | DREREVKKRLDEVRERIERLLRRV EEESRRVAEEIRRLIEEVRRRNKK VTEEIRELLKGLKDKEEVRRVLER LRKLNAESDELLERILERLRRLVE ATNRLVKAIIEELRRLVEKIVREV PDSEELREELKKLERKIEKVAKEI HDHDKEVTERLEDLLRRITEHARK SDREIEETAR (SEQ ID NO: 27164) | 2plus1_Key_Nterm_5406 | DREREVKK RLDEVRER IERLLRRV EEESRRVA EEIRRLIE EVRRRNKK VTEEIREL LKGL (SEQ ID NO: 27165) |
| 2plus1_Cage_Nterm_5409 | SEAEELLKRLEDRAEEILRRLEEI LRTSRKLAEDVLRELEKLLRESER RIREVLEELRGIKDKKELEDVIRE VEKELDESLERSRELLKDVLKKLD DNLKESERLVEDIDRELAKILEDL KKAGVPKEVVDEIKRIVDEVRERL KRIVDENAKIVEDARRALEKIVKE NEEILRRLKKELRELRK (SEQ ID NO: 27166) | 2plus1_Key_Nterm_5409 | SEAEELLK RLEDRAEE ILRRLEEI LRTSRKLA EDVLRELE KLLRESER RIREVLEE LRGI (SEQ ID NO: 27167) |
| 3plus_Cage_529_GFP11_Cterm | SEAEDLEELIKELAELLKDVIRKL EKINRRLVKILEDIIRRLKEISKE AEEELRKGTVEDKDILRDLERRLR EILEESDRLLEELKRRLEEILRKS KELLRRLEEVLREILKRAEEVKRS NLPKEELIKEIVKLLEELLRVIEK ILEDNIRLLEELVEVIKEILEKHL RLLEELVRVIERILREVGKDKDEA ERRDHMVLHEYVNAAGITEEVKRR LEEELTRLRETHKKIEKELREALK RVRDRST (SEQ ID NO: 27178) | 3plus_Key_Cterm_529 | KDEAERRR RELKDKLD RLREEHEE VKRRLEEE LTRLRETH KKIEKELR EALKRVRD RST (SEQ ID NO: 27179) |
| 3plus1_Cage_Cterm_500 | SEKEELKRLLDKLLKELKRLSDEL KATIDKILKILKEVSEEVKRTADE LLDAIRRGGVDEEVLREIKREIEE IEKKLRKVNKEIEDEIREIKKKLD EVDDKITKEVEKIKEALDKGGVDA KEVIKALKEILKEHADVFEDVLRR LKEIIKRHRDVVKEVLEELRKILE KVAEVLKRQGRSEDELRKVEEDLK RLEDKLKKLLEDYEKKVRELEETL DDLLRKYEETLRRLEKELEEAER (SEQ ID NO: 27184) | 3plus1_Key_Cterm_500 | EDELRKVE EDLKRLED KLKKLLED YEKKVREL EETLDDLL RKYEETLR RLEKELEE AER (SEQ ID NO: 27185) |
| 3plus1_Cage_Cterm_510 | SEKEELLKLIKRVIELLKRVLEEH LRLVEDVIRRLKELLDSNEKIVRE VIEDLKRLLDEVRGDKEELDRIKE KLEEVLERYKRRLEEIKRDLERML EDYKRELKRIEEDLRRVLEEVERI | 3plus1_Key_Cterm_510 | EDLLRKAK KVITEVRE KLKRNLED VRRVIEDV KRKSARIL |

TABLE 4-continued

| Cage Name | Cage Sequence | Key Name | Key Sequence |
|---|---|---|---|
| | ATRGEGPAEALIDKLRKILERALR ELDKLSKKLDELLKKVLEELEKSN REIDKLLKDVLRRVEEGGASEDLL RKAKKVITEVREKLKRNLEDVRRV IEDVKRKSARILEEARRLIEEVER ELEKIRK (SEQ ID NO: 27190) | | EEARRLIE EVERELEK IRK (SEQ ID NO: 27191) |
| 3plus1_Cage_528_GFP11_Cterm | SEAEDLEELIKELAELLKDVIRKL EKINRRLVKILEDIIRRLKEISKE AEEELRKGTVEDKDILRDLERRLR EILEESDRLLEELKRRLEEILRKS KELLRRLEEVLREILKRAEEVKRS NLPKEELIKEIVKLLEELLRVIEK ILEDNIRLLEELVEVIKEILEKHL RLLEELVRVIERILREVGRDHMVL HEYVNAAGITLDRLREEHEEVKRR LEEELTRLRETHKKIEKELREALK RVRDRST (SEQ ID NO: 27192) | 3plus1_Key_Cterm_528 | KDEAERRR RELKDKLD RLREEHEE VKRRLEEE LTRLRETH KKIEKELR EALKRVRD RST (SEQ ID NO: 27193) |
| 3plus1_Cage_528_GFP11_Cterm | SEAEDLEELIKELAELLKDVIRKL EKINRRLVKILEDIIRRLKEISKE AEEELRKGTVEDKDILRDLERRLR EILEESDRLLEELKRRLEEILRKS KELLRRLEEVLREILKRAEEVKRS NLPKEELIKEIVKLLEELLRVIEK ILEDNIRLLEELVEVIKEILEKHL RLLEELVRVIERILREVGKDKRDH MVLHEYVNAAGITLREEHEEVKRR LEEELTRLRETHKKIEKELREALK RVRDRST (SEQ ID NO: 27194) | 3plus1_Key_Cterm_528 | KDEAERRR RELKDKLD RLREEHEE VKRRLEEE LTRLRETH KKIEKELR EALKRVRD RST (SEQ ID NO: 27195) |
| 3plus1_Cage_528_GFP11_Cterm | SEAEDLEELIKELAELLKDVIRKL EKINRRLVKILEDIIRRLKEISKE AEEELRKGTVEDKDILRDLERRLR EILEESDRLLEELKRRLEEILRKS KELLRRLEEVLREILKRAEEVKRS NLPKEELIKEIVKLLEELLRVIEK ILEDNIRLLEELVEVIKEILEKHL RLLEELVRVIERILREVGKDKDEA ERDHMVLHEYVNAAGITHEEVKRR LEEELTRLRETHKKIEKELREALK RVRDRST (SEQ ID NO: 27196) | 3plus1_Key_Cterm_528 | KDEAERRR RELKDKLD RLREEHEE VKRRLEEE LTRLRETH KKIEKELR EALKRVRD RST (SEQ ID NO: 27197) |
| 3plus1_Cage_529_GFP11_Cterm | SEAEDLEELIKELAELLKDVIRKL EKINRRLVKILEDIIRRLKEISKE AEEELRKGTVEDKDILRDLERRLR EILEESDRLLEELKRRLEEILRKS KELLRRLEEVLREILKRAEEVKRS NLPKEELIKEIVKLLEELLRVIEK ILEDNIRLLEELVEVIKEILEKHL RLLEELVRVIERILREVGKRDHMV LHEYVNAAGITDRLREEHEEVKRR LEEELTRLRETHKKIEKELREALK RVRDRST (SEQ ID NO: 27198) | 3plus1_Key_Cterm_529 | KDEAERRR RELKDKLD RLREEHEE VKRRLEEE LTRLRETH KKIEKELR EALKRVRD RST (SEQ ID NO: 27199) |
| 3plus1_Cage_529_GFP11_Cterm | SEAEDLEELIKELAELLKDVIRKL EKINRRLVKILEDIIRRLKEISKE AEEELRKGTVEDKDILRDLERRLR EILEESDRLLEELKRRLEEILRKS KELLRRLEEVLREILKRAEEVKRS NLPKEELIKEIVKLLEELLRVIEK ILEDNIRLLEELVEVIKEILEKHL RLLEELVRVIERILREVGKDRDHM VLHEYVNAAGITRLREEHEEVKRR LEEELTRLRETHKKIEKELREALK RVRDRST (SEQ ID NO: 27200) | 3plus1_Key_Cterm_529 | KDEAERRR RELKDKLD RLREEHEE VKRRLEEE LTRLRETH KKIEKELR EALKRVRD RST (SEQ ID NO: 27201) |
| 3plus1_Cage_529_GFP11_Cterm | SEAEDLEELIKELAELLKDVIRKL EKINRRLVKILEDIIRRLKEISKE AEEELRKGTVEDKDILRDLERRLR EILEESDRLLEELKRRLEEILRKS | 3plus1_Key_Cterm_529 | KDEAERRR RELKDKLD RLREEHEE VKRRLEEE |

TABLE 4-continued

| Cage Name | Cage Sequence | Key Name | Key Sequence |
|---|---|---|---|
| | KELLRRLEEVLREILKRAEEVKRS NLPKEELIKEIVKLLEELLRVIEK ILEDNIRLLEELVEVIKEILEKHL RLLEELVRVIERILREVGKDKDRD HMVLHEYVNAAGITREEHEEVKRR LEEELTRLRETHKKIEKELREALK RVRDRST (SEQ ID NO: 27202) | | LTRLRETH KKIEKELR EALKRVRD RST (SEQ ID NO: 27203) |
| 3plus1_Cage_534_GFP11_Cterm | DEDRIIEEIARLLEELLRELLELI KKLIETNRRLNEEHERAVRELARL LEELLDRLVKKGISDEKLKRIRER LKRALDDLERLHREINKRLEDLVR ELEKLVREILKELKDALEELRRAS ARAGGEEVLRRLEEIVKKLLDLVR RILERLKEIHKDNVRLLRELNERL TRIVEDLVRLIREILREAGVDERD HMVLHEYVNAAGITIKRLHEDLER KLKESEDELREIEARLEEKIRRLE EKLERKRR (SEQ ID NO: 27206) | 3plus1_Key_Cterm_534 | EKIAEEIE RELEELRR MIKRLHED LERKLKES EDELREIE ARLEEKIR RLEEKLER KRR (SEQ ID NO: 27207) |
| 3plus1_Cage_534_GFP11_Cterm | DEDRIIEEIARLLEELLRELLELI KKLIETNRRLNEEHERAVRELARL LEELLDRLVKKGISDEKLKRIRER LKRALDDLERLHREINKRLEDLVR ELEKLVREILKELKDALEELRRAS ARAGGEEVLRRLEEIVKKLLDLVR RILERLKEIHKDNVRLLRELNERL TRIVEDLVRLIREILREAGVDEKI RDHMVLHEYVNAAGITRLHEDLER KLKESEDELREIEARLEEKIRRLE EKLERKRR (SEQ ID NO: 27208) | 3plus1_Key_Cterm_534 | EKIAEEIE RELEELRR MIKRLHED LERKLKES EDELREIE ARLEEKIR RLEEKLER KRR (SEQ ID NO: 27209) |
| 3plus1_Cage_534_GFP11_Cterm | DEDRIIEEIARLLEELLRELLELI KKLIETNRRLNEEHERAVRELARL LEELLDRLVKKGISDEKLKRIRER LKRALDDLERLHREINKRLEDLVR ELEKLVREILKELKDALEELRRAS ARAGGEEVLRRLEEIVKKLLDLVR RILERLKEIHKDNVRLLRELNERL TRIVEDLVRLIREILREAGVDEKI AEEIERDHMVLHEYVNAAGITLER KLKESEDELREIEARLEEKIRRLE EKLERKRR (SEQ ID NO: 27210) | 3plus1_Key_Cterm_534 | EKIAEEIE RELEELRR MIKRLHED LERKLKES EDELREIE ARLEEKIR RLEEKLER KRR (SEQ ID NO: 27211) |
| 3plus1_Cage_Cterm_539 | SEKEKLLKESEEEVRRLRRTLEEL LRKYREVLERLRKELREIEERVRD VVRRLKEVLDRKGLDIDTIIKEVE DLLKTVLDRLRELLDKIRRLTKEA IEVVREIIERIVRHAERVKDELRK EGGDKEKLDRVDRLIKENTRHLKE ILDRIEDLVRRSEKKLRDIIREVR RLIEELRKKAEEIKKGPDERLVKT LIEDVEAVIKRILELITRVAEDNE RVLERIIRELTDNLERHLKIVREI VK(SEQ ID NO: 27212) | 3plus1_Key_Cterm_539 | ERLVKTLI EDVEAVIK RILELITR VAEDNERV LERIIREL TDNLERHL KIVREIVK (SEQ ID NO: 27213) |
| 3plus1_Cage_Cterm_548 | DKAEVLREALKLLKDLLEELIKIH EESLKRILDLIDTLVKVHEDALRA LKELLERSGLDERELRKVERMATE SLRTIAKLKEELRDLARRSLEKLR EDLKRVDDTLRKVEEKVRRTGPSE ELIEELIRTIEKLLKEIVRINEEV LKAVRELLKTLLKLSEDVVRRIEE ILRKGGVPEEIDRELKRVVEELRR LHEEIKERLDDVARRSEEELRRII KKLKEVVKEIRKKLK (SEQ ID NO: 27214) | 3plus1_Key_Cterm_548 | EEIDRELK RVVEELRR LHEEIKER LDDVARRS EEELRRII KKLKEVVK EIRKKLK (SEQ ID NO: 27215) |
| 3plus1_Cage_Cterm_556 | SERELIERWLELHKEILRLIRELV ERLLKLHREILDTIKKLIRELLEL LEDIARKLGLDKEAKDELREIAKR VEDKLEKLERESRKVEEDLKRKLK ELTDESDTVEKRVRDVVRRGTQSR | 3plus1_Key_Cterm_556 | DDERRTLT ELLKRMED ILEKVERT LKKLLDDS ARMAEEVK |

TABLE 4-continued

| Cage Name | Cage Sequence | Key Name | Key Sequence |
|---|---|---|---|
| | EEIAEELLRLDRKLLKAVEELLKE ILDLNKKLLDDVRAILEETRRVLE KLLDRVRRGERTDDERRTLTELLK RMEDILEKVERTLKKLLDDSARMA EEVKKTLKELLERSEKVAEDVRK (SEQ ID NO: 27216) | | KTLKELLE RSEKVAED VRK (SEQ ID NO: 27217) |
| 3plus1_Cage_Cterm_560 | SKKELLEEVVRRAIELLKRHLEKL KRILEEIVRLLEEHLEKVERVLRA ILSLLDDLLRRGGDERAIRTLEDV KRRLREILERLADENAKAIKRLAD LLDKLEKRNKEAIERLEEILEELK RVRRDEELLRVLETLLKIIEDILR ENTKVLEDLLRLVEEILEANLRVV EELLRLAREILTEIVGDEDKLKEI EDELRRLLEELRRLDKAIKDRLRE LKKDLDEANRRIKETLKKLLREVE K(SEQ ID NO: 27218) | 3plus1_Key_Cterm_560 | EDKLKEIED ELRRLLEEL RRLDKAIKD RLRELKKDL DEANRRIKE TLKKLLREV EK (SEQ ID NO: 27219) |
| 3plus1_Cage_568_GFP11_Cterm | KEIEETLKELEDLNREMVETNRRV LEETRRLNKETVDRVKATLDELAK MLKKLVDDVRKGPTSEELKRLLAE LEELLARVVRRVEELLKKSTDLLE RAVKDSADALRRSHEVLKEVASRV KRAKDEGLPREEVLRLLRELLERH AKVLKDIVRVSEKLLREHLKVLRE IVEVLEELLERILKVILDTTRDHM VLHEYVNAAGITKRRLKEVIDRYE DELRKLRKEYKEKIDKYERKLEEI ERRERT (SEQ ID NO: 27220) | 3plus1_Key_Cterm_568 | KAVEELEK ALEEIKRR LKEVIDRY EDELRKLR KEYKEKID KYERKLEE IERRERT (SEQ ID NO: 27221) |
| 3plus1_Cage_568_GFP11_Cterm | KEIEETLKELEDLNREMVETNRRV LEETRRLNKETVDRVKATLDELAK MLKKLVDDVRKGPTSEELKRLLAE LEELLARVVRRVEELLKKSTDLLE RAVKDSADALRRSHEVLKEVASRV KRAKDEGLPREEVLRLLRELLERH AKVLKDIVRVSEKLLREHLKVLRE IVEVLEELLERILKVILDTTGGDR DHMVLHEYVNAAGITLKEVIDRYE DELRKLRKEYKEKIDKYERKLEEI ERRERT (SEQ ID NO: 27222) | 3plus1_Key_Cterm_568 | KAVEELEK ALEEIKRR LKEVIDRY EDELRKLR KEYKEKID KYERKLEE IERRERT (SEQ ID NO: 27223) |
| 3plus1_Cage_Cterm_581 | SALETVKKLLEDSSEKIERIVEED ERVAKESSDRIRRLVEEDKRVADE ILDLIEKIGDTDTLLKLVEEWSRT SKKLLDDVLKLHKDWSDDSRRLLE EILRVHEELIRRVKEILDREGKPE EVVRELEKVLKESLDTLEEIIRRL DEANAATVKRVADVIRELEDINRK VLEEIKRGSDDAEAVIKVIEKLIR ANKRVWDALLKINEDLVRVNKTVW KELLRVNEKLARDLERVVK (SEQ ID NO: 27226) | 3plus1_Key_Cterm_581 | AEAVIKVI EKLIRANK RVWDALLK INEDLVRV NKTVWKEL LRVNEKLA RDLERVVK (SEQ ID NO: 27227) |
| 3plus1_Cage_Cterm_585 | SKEEKLKDDVRAVLEDLDRVLKEL EKLSEDNLRELKRVLDRITDLHRR ILDELRKGIGSEELLRRVEKVLKD NLDLLRKLVEEHKESSERDLKRVE DLVREIKEVLRKLLELEDRGTDIR KIEEEIERLLRKIRKAVEESKDLN RRNSERIEEVARRSEELARRLLKE IRERGDSKAAEDILRVLEKLVKVS REAIKLILELSEHHVRVSTRIARL LLDVARKLAEVIKEAER (SEQ ID NO: 27228) | 3plus1_Key_Cterm_585 | SKAAEDIL RVLEKLVK VSREAIKL ILELSEHH VRVSTRIA RLLLDVAR KLAEVIKE AER (SEQ ID NO: 27229) |
| 3plus1_Cage_Cterm_587 | SEIEDVIRRLRKILEDLERVSEKL LREIKKILDEARRLNEEVIKEIKR VLEDAVRVFRDGSGSKEELAKLVE ELIRELAKLAKEVDEIHKRIVERL | 3plus1_Key_Cterm_587 | IEDLVREV ERLIKRIE DSLRELEK TVRELLKR |

TABLE 4-continued

| Cage Name | Cage Sequence | Key Name | Key Sequence |
|---|---|---|---|
| | KALVEDAERIHRKIVETLEEIVRG VPSEELKRVVEAIVEVIKEHLKVL ADVIRRIIKAIEENAETIKRVLED IVRVLELVLRGEGSIEDLVREVER LIKRIEDSLRELEKTVRELLKRIK EASDKVREDVDRLIKELKEAAD (SEQ ID NO: 27230) | | IKEASDKV REDVDRLI KELKEAAD (SEQ ID NO: 27231) |
| 3plus1_Cage_Cterm_605 | SREELLDRILEAIAKILEDLKRLI DENLARLEEVVRELERIIDRNLKL IREILDELKKGSGSEEILEKIKKV DKELEDLIRRLLKKLEDLIRETER RLREILKRIRDLLKEVKDRDKDLE RLLEVLEEVLRVIAELAKELLDSL RKVLKVVEEVLRLLNEVNKEVLDV IRELAKDGGSDEIIRKLDELLKEV EKVHKEVKDRIRKLLEDHKRSLDE VKKKLERLLERAKEVVEREKK (SEQ ID NO: 27232) | 3plus1_Key_Cterm_605 | DEIIRKLD ELLKEVEK VHKEVKDR IRKLLEDH KRSLDEVK KKLERLLE RAKEVVER EKK (SEQ ID NO: 27233) |
| 3plus1_Cage_Cterm_607 | SEREELLERIKEILKRVKDKLED LKRLKEILEKLKEKADRDLEELRR RIEEVREKLERTGRTDELVKEVLD TVRRNLENLKRLVEDILRKLEENV KNLTDLVREILKLITELIKRLEDG GLPKEVLDALRRVLEKLEELLREI LERLKRSLEAVRKIEELLKELER SLDELRRALERIRKEIGDSETAVR AIIRVLEKHLEAVRRVLEELLKVL AEHLETVRELIERLKRVLEEAIEV VERVAR (SEQ ID NO: 27234) | 3plus1_Key_Cterm_607 | SETAVRAI IRVLEKHL EAVRRVLE ELLKVLAE HLETVREL IERLKRVL EEAIEVVE RVAR (SEQ ID NO: 27235) |
| 3plus1_Cage_611_GFP11_Cterm | SLEEITKRLLELVEENLARHEEIL RELLELAKRLAKEDRDILEEVLKL IEELLKLLEDNGSSEEDLKRLLKE VIEELRAVVKRVKDKWDEVVKRIE DLVKKLKELHDDTLRKLRELVRKI VTDISESGGEAEKVKRVVEKILEL VERLAKVVKESVEKLLEILRELAE VSKRVAEALLRLLEELVRVIRIKD ERDHMVLHEYVNAAGITLLDELEE VHKRVKKELEDIIEENRRVVKRVR DELREIKRELDE (SEQ ID NO: 27238) | 3plus1_Key_Cterm_611 | ERTLREVV RKVLEEAK RLLDELEE VHKRVKKE LEDIIEEN RRVVKRVR DELREIKR ELDE (SEQ ID NO: 27239) |
| 3plus1_Cage_Cterm_632 | SEKELVDDIRRILEEILRLLRSLL EEVIRLLEENEKLVRRHLKTVIDI LRRVAKLLDENGIRTDEADRVLER LEKAHRELLEDYKRALEKIKETLE RVLREAEEVVKKIDDALRKLGGSK EVLKRLLEELLRLVEKIAEEIKRL LSELVRVTEELVRTNKELLEEAVR VIRKEVGDDSLVREVEELIKRLEK HIDDLLKTSRDLVKRVLDLVDEVV KRVEDLVERVKEKIDT (SEQ ID NO: 27240) | 3plus1_Key_Cterm_632 | DSLVREVE ELIKRLEK HIDDLLKT SRDLVKRV LDLVDEVV KRVEDLVE RVKEKIDT (SEQ ID NO: 27241) |
| 3plus1_Cage_646_GFP11_Cterm | DAEEVVKRLADVLRENDETIRKVV EDLVRIAEENDRLWKKLVEDIAEI LRRIVELLRRGGVPEELLDRLAKV VKSIVEKAEKILERLNRVSKAIAE KLKTIVDELNEVSKEIVKRAEDIL RKGKDKETVLRALRTLVKEYADLS KEVLERVERIVREYVKLSDEVVKS LAEIVEELIRIIEDLLRKGNRDHM VLHEYVNAAGITRKLLEDVKKASE DIVREVERIVRELAKRSDEILKKL EDIVEKLRE (SEQ ID NO: 27244) | 3plus1_Key_Cterm_646 | EDVKRALE ELVSRLRK LLEDVKKA SEDIVREV ERIVRELA KRSDEILK KLEDIVEK LRE (SEQ ID NO: 27245) |
| 3plus1_Cage_646_GFP11_Cterm | DAEEVVKRLADVLRENDETIRKVV EDLVRIAEENDRLWKKLVEDIAEI LRRIVELLRRGGVPEELLDRLAKV VKSIVEKAEKILERLNRVSKAIAE KLKTIVDELNEVSKEIVKRAEDIL RKGKDKETVLRALRTLVKEYADLS | 3plus1_Key_Cterm_646 | EDVKRALE ELVSRLRK LLEDVKKA SEDIVREV ERIVRELA KRSDEILK |

TABLE 4-continued

| Cage Name | Cage Sequence | Key Name | Key Sequence |
|---|---|---|---|
| | KEVLERVERIVREYVKLSDEVVKS LAEIVEELIRIIEDLLRKGNLDED RDHMVLHEYVNAAGITEDVKKASE DIVREVERIVRELAKRSDEILKKL EDIVEKLRE (SEQ ID NO: 27246) | | KLEDIVEK LRE (SEQ ID NO: 27247) |
| 3plus1_Cage_646_GFP11_Cterm | DAEEVVKRLADVLRENDETIRKVV EDLVRIAEENDRLWKKLVEDIAEI LRRIVELLRRGGVPEELLDRLAKV VKSIVEKAEKILERLNRVSKAIAE KLKTIVDELNEVSKEIVKRAEDIL RKGKDKETVLRALRTLVKEYADLS KEVLERVERIVREYVKLSDEVVKS LAEIVEELIRIIEDLLRKGNLDED VRDHMVLHEYVNAAGITDVKKASE DIVREVERIVRELAKRSDEILKKL EDIVEKLRE (SEQ ID NO: 27248) | 3plus1_Key_Cterm_646 | EDVKRALE ELVSRLRK LLEDVKKA SEDIVREV ERIVRELA KRSDEILK KLEDIVEK LRE (SEQ ID NO: 27249) |
| 3plus1_Cage_647_GFP11_Cterm | DAEEVVKRLADVLRENDETIRKVV EDLVRIAEENDRLWKKLVEDIAEI LRRIVELLRRGGVPEELLDRLAKV VKSIVEKAEKILERLNRVSKAIAE KLKTIVDELNEVSKEIVKRAEDIL RKGKDKETVLRALRTLVKEYADLS KEVLERVERIVREYVKLSDEVVKS LAEIVEELIRIIEDLLRKGNLRDH MVLHEYVNAAGITKLLEDVKKASE DIVREVERIVRELAKRSDEILKKL EDIVEKLRE (SEQ ID NO: 27250) | 3plus1_Key_Cterm_647 | EDVKRALE ELVSRLRK LLEDVKKA SEDIVREV ERIVRELA KRSDEILK KLEDIVEK LRE (SEQ ID NO: 27251) |
| 3plus1_Cage_647_GFP11_Cterm | DAEEVVKRLADVLRENDETIRKVV EDLVRIAEENDRLWKKLVEDIAEI LRRIVELLRRGGVPEELLDRLAKV VKSIVEKAEKILERLNRVSKAIAE KLKTIVDELNEVSKEIVKRAEDIL RKGKDKETVLRALRTLVKEYADLS KEVLERVERIVREYVKLSDEVVKS LAEIVEELIRIIEDLLRKGNLDED VKRALERDHMVLHEYVNAAGITSE DIVREVERIVRELAKRSDEILKKL EDIVEKLRE (SEQ ID NO: 27252) | 3plus1_Key_Cterm_647 | EDVKRALE ELVSRLRK LLEDVKKA SEDIVREV ERIVRELA KRSDEILK KLEDIVEK LRE (SEQ ID NO: 27253) |
| 3plus1_Cage_Cterm_647 | DAEEVVKRLADVLRENDETIRKVV EDLVRIAEENDRLWKKLVEDIAEI LRRIVELLRRGGVPEELLDRLAKV VKSIVEKAEKILERLNRVSKAIAE KLKTIVDELNEVSKEIVKRAEDIL RKGKDKETVLRALRTLVKEYADLS KEVLERVERIVREYVKLSDEVVKS LAEIVEELIRIIEDLLRKGNLDED VKRALEELVSRLRKLLEDVKKASE DIVREVERIVRELAKRSDEILKKL EDIVEKLRE (SEQ ID NO: 27254) | 3plus1_Key_Cterm_647 | EDVKRALE ELVSRLRK LLEDVKKA SEDIVREV ERIVRELA KRSDEILK KLEDIVEK LRE (SEQ ID NO: 27255) |
| 3plus1_Cage_Cterm_653 | DEEETLRRLLERKVELAKEYLDVS KEVIDRTTKLLDEYLKTSKRIVDA TVELLERGDLGPDELIKRLAEELE RSLRELEEEIKRLKRELEESLKKL KEIIDRLAEEAEKLLAVLKRGEGS EEEALRALASLVRELIEVLRENDE RLRDVLRRLIEALRKNNEILERVL RKLVRAAEERGRDESSREALEEAR RRLEELLRELNEITKDLEAKLEKL LRDLNELTKALEEELKRLLDELKK RTD (SEQ ID NO: 27256) | 3plus1_Key_Cterm_653 | SREALEEA RRRLEELL RELNEITK DLEAKLEK LLRDLNEL TKALEEEL KRLLDELK KRTD (SEQ ID NO: 27257) |
| 3plus1_Cage_Cterm_658 | DEERIIKTLEDINAKLVEDIKRIL DKVAELNERLADAIRKILEETKRI LEATTRKVRKDGEISEELLRRLEE KLRKLLEDLERVLAEHEDESRRIL EEVERLLKRHADASKELLDRARSV | 3plus1_Key_Cterm_658 | KDTLRTVE KLVEDVKR RLDKLLED YKRLIEEV KKELDKLL |

TABLE 4-continued

| Cage Name | Cage Sequence | Key Name | Key Sequence |
|---|---|---|---|
| | ARGVKSDKELVDRLKKLIDDSLES VRELIERLKELLDRLVKSVEDLIR TIKELLDRLVEVLREGVSDKDTLR TVEKLVEDVKRRLDKLLEDYKRLI EEVKKELDKLLKEYEDALREIKKR IDE (SEQ ID NO: 27258) | | KEYEDALR EIKKRIDE (SEQ ID NO: 27259) |
| 3plus1_Cage_Nterm_263 | SLVDELRKSLERNVRVSEEVARRL KEALKRWVDVVRKVVEDLIRLNED VVRVVEKVTVDESAIERVRRIIEE LNRKLDAVLKKNEDLVRRLTELLD KLLEENRRLVEELDEDLKRRGGTE EVIDTILELIERSIERLKRLLDEL LRIVREALKDNKRVADENLKKLKE ILDELRKDGVEDEELKRVLEKAAD LHRRLKDRHRKLLEDLERIIRELK KKLDEVVEENKRSVDELKR (SEQ ID NO: 27262) | 3plus1_Key_Nterm_263 | SLVDELRK SLERNVRV SEEVARRL KEALKRWV DVVRKVVE DLIRLNED VVRVVEKV (SEQ ID NO: 27263) |
| 3plus1_Cage_647_GFP11_Nterm | DAEEVVKRLADVLRENDETIRKVV EDLVRIAEENDRLWRDHMVLHEYV NAAGITLLRRGGVPEELLDRLAKV VKSIVEKAEKILERLNRVSKAIAE KLKTIVDELNEVSKEIVKRAEDIL RKGKDKETVLRALRTLVKEYADLS KEVLERVERIVREYVKLSDEVVKS LAEIVEELIRIIEDLLRKGNLDED VKRALEELVSRLRKLLEDVKKASE DIVREVERIVRELAKRSDEILKKL EDIVEKLRE (SEQ ID NO: 27276) | 3plus1_Key_Nterm_647 | DAEEVVKR LADVLREN DETIRKVV EDLVRIAE ENDRLWKK LVEDIAEI LRRIVELL RRG (SEQ ID NO: 27277) |

As used throughout the present application, the term "polypeptide" is used in its broadest sense to refer to a sequence of subunit amino acids. The polypeptides of the invention may comprise L-amino acids+glycine, D-amino acids+glycine (which are resistant to L-amino acid-specific proteases in vivo), or a combination of D- and L-amino acids+glycine. The polypeptides described herein may be chemically synthesized or recombinantly expressed. The polypeptides may be linked to other compounds to promote an increased half-life in vivo, such as by PEGylation, HESylation, PASylation, glycosylation, or may be produced as an Fc-fusion or in deimmunized variants. Such linkage can be covalent or non-covalent as is understood by those of skill in the art.

In a fifth aspect the disclosure provides nucleic acids encoding the polypeptide of any embodiment or combination of embodiments of each aspect disclosed herein. The nucleic acid sequence may comprise single stranded or double stranded RNA or DNA in genomic or cDNA form, or DNA-RNA hybrids, each of which may include chemically or biochemically modified, non-natural, or derivatized nucleotide bases. Such nucleic acid sequences may comprise additional sequences useful for promoting expression and/or purification of the encoded polypeptide, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the disclosure.

In a sixth aspect, the disclosure provides expression vectors comprising the nucleic acid of any aspect of the disclosure operatively linked to a suitable control sequence. "Expression vector" includes vectors that operatively link a nucleic acid coding region or gene to any control sequences capable of effecting expression of the gene product. "Control sequences" operably linked to the nucleic acid sequences of the disclosure are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The expression vector must be replicable in the host organisms either as an episome or by integration into host chromosomal DNA. In various embodiments, the expression vector may comprise a plasmid, viral-based vector, or any other suitable expression vector.

In a seventh aspect, the disclosure provides host cells that comprise the nucleic acids or expression vectors (i.e.: episomal or chromosomally integrated) disclosed herein, wherein the host cells can be either prokaryotic or eukaryotic. The cells can be transiently or stably engineered to incorporate the expression vector of the disclosure, using techniques including but not limited to bacterial transformations, calcium phosphate co-precipitation, electroporation, or liposome mediated-, DEAE dextran mediated-, polycationic mediated-, or viral mediated transfection. In one embodiment, the recombinant host cells comprise:
- (a) a first nucleic acid encoding the polypeptide of any embodiment or combination of embodiments of the cage polypeptides of aspects 1-3 of the disclosure, operatively linked to a first promoter; and
- (b) a second nucleic acid encoding the polypeptide of any embodiment or combination of embodiments of the key polypeptide of aspect 4 of the disclosure, wherein the key polypeptide is capable of binding to a structural region of the cage polypeptide to induce a conformational change in the cage polypeptide, wherein the second nucleic acid is operatively linked to a second promoter.

The recombinant host cells may comprise a single cage polypeptide encoding nucleic acid and a single key polypeptide encoding nucleic acid, or may comprise a plurality (i.e.: 2, 3, 4, 5, 6, 7, 8, 9, 10, or more) first and second nucleic acids—in one such embodiment, each second nucleic acid may encode a key polypeptide capable of binding to a structural region and inducing a conformational change of a different cage polypeptide encoded by the plurality of first nucleic acids. In another embodiment, each second nucleic acid may encode a key polypeptide capable of binding to a structural region and inducing a conformational change of more than one of the cage polypeptides encoded by the plurality of first nucleic acids.

Thus, in one embodiment the first nucleic acid comprises a plurality of first nucleic acids encoding a plurality of different cage polypeptides. In one such embodiment, the second nucleic acid comprises a plurality of second nucleic acids encoding a plurality of different key polypeptides, wherein the plurality of different key polypeptides comprise one or more key polypeptides that are capable of binding to and inducing a conformational change in only a subset of the plurality of different cage polypeptides. In another such embodiment, the second nucleic acid encodes a single key polypeptide that is capable of binding to and inducing a conformational change in each different cage polypeptide.

In another embodiment, the host cells comprise nucleic acids encoding and/or expression vectors capable of expressing the fusion proteins disclosed herein, wherein the host cells comprise:
- (a) a first nucleic acid encoding a first fusion protein (i.e.: cage polypeptide fused to key polypeptide) linked to a first promoter; and
- (b) a second nucleic acid encoding a second fusion protein operatively linked to a second promoter, wherein:
  - (i) the cage polypeptide encoded by the first nucleic acid is activated by the key polypeptide encoded by the second nucleic acid;
  - (ii) the cage polypeptide encoded by the first nucleic acid is not activated by the key polypeptide encoded by the first nucleic acid;
  - (iii) the cage polypeptide encoded by the second nucleic acid is activated by the key polypeptide encoded by the first nucleic acid; and
  - (iv) the cage polypeptide encoded by the second nucleic acid is not activated by the key polypeptide encoded by the second nucleic acid.

In all these embodiments, the first and/or second nucleic acids may, for example, be in the form of an expression vector. In other embodiments, the first and/or second nucleic acids may be in the form of nucleic acid integrated into the host cell genome.

A method of producing a polypeptide according to the disclosure is an additional part of the disclosure. In one embodiment, the method comprises the steps of (a) culturing a host according to this aspect of the disclosure under conditions conducive to the expression of the polypeptide, and (b) optionally, recovering the expressed polypeptide. The expressed polypeptide can be recovered from the cell free extract or recovered from the culture medium. In another embodiment, the method comprises chemically synthesizing the polypeptides.

In an eight aspect, the disclosure provides kits. In one embodiment, the kits comprise:
- (a) one or more polypeptides of any embodiment or combination of embodiments of aspects 1-3 of the disclosure (i.e.: the cage polypeptides);
- (b) one or more polypeptides of any embodiment or combination of embodiments of aspect 4 of the disclosure (i.e.: the key polypeptides); and
- (c) optionally, one or more fusion proteins of any embodiment disclosed herein.

In another embodiment, the kits comprise:
- (a) a first nucleic acid encoding the cage polypeptide of any embodiment or combination of embodiments of aspects 1-3 of the disclosure;
- (b) a second nucleic acid encoding the key polypeptides of any embodiment or combination of embodiments of aspect 4 of the disclosure; and
- (c) optionally, a third nucleic acid encoding the fusion protein of any embodiment disclosed herein.

In another embodiment, the kit comprises:
- (a) a first expression vector comprising a first nucleic acid encoding the cage polypeptide of any embodiment or combination of embodiments of aspects 1-3 of the disclosure, wherein the first nucleic acid is operatively linked to a first promoter; and
- (b) a second expression vector comprising a second nucleic acid encoding the key polypeptides of any embodiment or combination of embodiments of aspect 4 of the disclosure, wherein the second nucleic acid is operatively linked to a second promoter.

In each of the kit embodiments, the first nucleic acid, the second nucleic acid, the first expression vector, and/or the second expression vector may comprise a single nucleic acid encoding or expression vector capable of expressing the cage or key polypeptide, or may comprise a plurality (i.e.: 2, 3, 4, 5, 6, 7, 8, 9, 10, or more) of first nucleic acids, second nucleic acids, first expression vectors, and/or the second expression vectors. In various such embodiments, each second nucleic acid may encode, or each second expression vector may be capable of expressing, a key polypeptide capable of binding to a structural region and inducing a conformational change of a different cage polypeptide encoded by the plurality of first nucleic acids or capable of being expressed by the plurality of first expression vectors. In other embodiments, each second nucleic acid may encode, or each second expression vector may be capable of expressing, a key polypeptide capable of binding to a structural region and inducing a conformational change of more than one of the cage polypeptides encoded by the plurality of first nucleic acids or capable of being expressed by the plurality of first expression vectors.

In one embodiment, the promoters operatively linked to the cage polypeptide-encoding nucleic acids (first promoters) are different than the promoters operatively linked to the key polypeptide-encoding nucleic acids (second promoters), allowing tunable control of the cage polypeptides and any functional polypeptide domains by controlling expression of the key polypeptide. In other embodiments, the promoters operatively linked to the cage polypeptide-encoding nucleic acids (first promoters) are the same as the promoters operatively linked to the key polypeptide-encoding nucleic acids (second promoters). In other embodiments, the first promoters and/or second promoters may be inducible promoters.

In a ninth aspect, the disclosure provides a LOCKR switch comprising
(a) a cage polypeptide comprising a structural domain and a latch domain further comprising one or more bioactive peptides, wherein the structural domain interacts with the latch domain to prevent activity of the bioactive peptide(s);
(b) an optional key polypeptide that binds to the cage structural domain, thereby displacing the latch domain and activating the bioactive peptide(s); and
(c) optionally, an effector polypeptide(s) that binds to the bioactive peptide(s) when the bioactive peptide(s) is(are) activated.

The cage polypeptides and its structural and latch regions are discussed above, as are bioactive peptides, effector polypeptides, and key polypeptides. Any embodiment of the cage polypeptides, bioactive peptides, and key polypeptides disclosed herein may be used in the LOCKR switches and kits of the disclosure. For example, in one embodiment, the cage polypeptide comprises:
(a) a helical bundle comprising between 2 and 7 alpha-helices; and
(b) amino acid linkers connecting each alpha helix;

In one embodiment, the key polypeptide is present, and may comprise the key polypeptide of any embodiment or combination of embodiments disclosed herein.

In another embodiment, the effector polypeptide is present, and comprises a polypeptide that selectively binds to the bioactive peptide. Any suitable effector polypeptide can be used depending on the bioactive peptide of interest. In various non-limiting embodiments, the effector peptide may comprise Bcl2, GFP1-10, a protease, etc.

The present disclosure also provides a LOCKR switch comprising a cage polypeptide described herein and a key polypeptide. In some aspects, a LOCKR switch comprises (a) a cage polypeptide comprising a structural region and a latch region further comprising one or more bioactive peptides, and (b) a key polypeptide that binds to the cage structural region. In some aspects, a LOCKR switch comprises (a) a cage polypeptide comprising a structural region and a latch region further comprising one or more bioactive peptides, and (b) a key polypeptide that binds to the cage structural region, wherein the one or more bioactive peptides in the latch region bind to or interact with one or more effector polypeptide(s). In other aspects, a LOCKR switch comprises (a) a cage polypeptide comprising a structural region and a latch region further comprising one or more bioactive peptides, wherein the structural region interacts with the latch region to prevent activity of the one or more bioactive peptides; (b) a key polypeptide that binds to the cage structural region, thereby displacing the latch region and activating the one or more bioactive peptides. In some other aspects, the LOCKR further comprises one or more effector polypeptide(s) that bind to the one or more bioactive peptides when the one or more bioactive peptides are activated.

In some aspects, both a latch region and a key polypeptide can bind to or interact with a structural region in the corresponding cage polypeptide. The interaction between a latch region and a structural region in a cage polypeptide can be intramolecular interaction, and the interaction between a key polypeptide and a structural region of the corresponding cage polypeptide can be intermolecular interaction. However, in some aspects, the affinity of the latch region to the structural region of the cage polypeptide is higher than the affinity of the key polypeptide to the structural region of the cage polypeptide in the absence of an effector polypeptide.

In some aspects, the affinity of the latch region to the structural region of the cage polypeptide is at least about 1.5 fold, at least about 2 fold, at least about 3 fold, at least about 4 fold, at least about 5 fold, at least about 6 fold, at least about 7 fold, at least about 8 fold, at least about 9 fold, at least about 10 fold, at least about 11 fold, at least about 12 fold, at least about 13 fold, at least about 14 fold, at least about 15 fold, at least about 16 fold, at least about 17 fold, at least about 18 fold, at least about 19 fold, at least about 20 fold, at least about 21 fold, at least about 22 fold, at least about 23 fold, at least about 24 fold, at least about 25 fold, at least about 26 fold, at least about 27 fold, at least about 28 fold, at least about 29 fold, or at least about 30 fold higher than the affinity of the key polypeptide to the structural region of the cage polypeptide in the absence of an effector polypeptide. In some aspects, the affinity of the latch region to the structural region of the cage polypeptide is at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2.0 fold, at least about 2.1 fold, at least about 2.2 fold, at least about 2.3 fold, at least about 2.4 fold, at least about 2.5 fold, at least about 2.6 fold, at least about 2.7 fold, at least about 2.8 fold, at least about 2.9 fold, or at least about 3.0 fold higher than the affinity of the key polypeptide to the structural region of the cage polypeptide in the absence of an effector polypeptide. In some aspects, the affinity of the latch region to the structural region of the cage polypeptide is at least about 30 fold, at least about 40 fold, at least about 50 fold, at least about 60 fold, at least about 70 fold, at least about 80 fold, at least about 90 fold, at least about 100 fold, at least about 110 fold, at least about 120 fold, at least about 130 fold, at least about 140 fold, at least about 150 fold, at least about 160 fold, at least about 170 fold, at least about 180 fold, at least about 190 fold, at least about 200 fold, at least about 210 fold, at least about 220 fold, at least about 230 fold, at least about 240 fold, at least about 250 fold, at least about 260 fold, at least about 270 fold, at least about 280 fold, at least about 290 fold, at least about 300 fold, e.g., about 30 fold to about 300 fold, e.g., about 100 fold to about 300 fold, about 50 fold to about 100 fold, higher than the affinity of the key polypeptide to the structural region of the cage polypeptide in the absence of an effector polypeptide.

In other embodiments, the intramolecular Latch-Cage affinity is higher than the intermolecular Key-Cage affinity, and in the presence of the Effector protein, the intermolecular Key-Cage affinity is higher than the intramolecular Latch-Cage affinity. As a result, the function of the bioactive peptide is dependent on the presence of Cage, Key, and Effector protein.

In certain embodiments, the intermolecular Key-Cage interaction may outcompete the Latch-Cage interaction in the absence of Effector protein. In the absence of Key, the Latch-Cage affinity is higher than the Latch-Effector protein affinity (via binding of the Bioactive peptide to the Effector protein), and in the presence of Key, the Latch-Effector protein affinity (via binding of the Bioactive peptide to the Effector protein) is higher than the Latch-Cage affinity. As a result, the function of the bioactive peptide is dependent on the presence of Cage, Key, and Effector protein.

Figure 8:
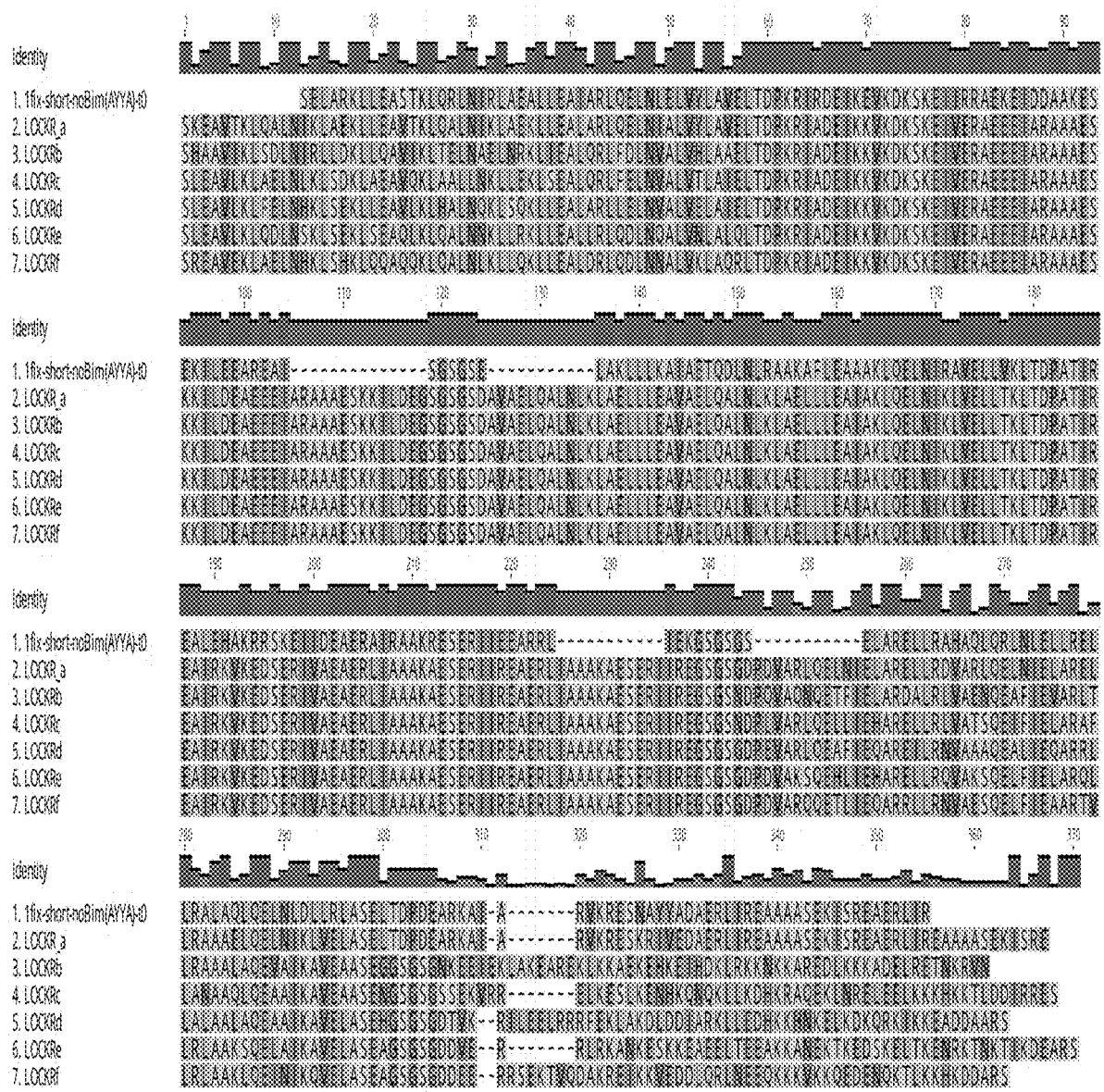
FIG. 8: Multiple sequence alignment (MSA) comparing the original LOCKR_a Cage scaffold design to its asymmetrized (1fix-short -noBim(AYYA)-t0) and orthogonal (LOCKRb-f) design counterparts. Only 150 (40.8%) of the sites are identical across the MSA, with a pairwise % identity of 69.4%. The Latch regions (the C-terminal region starting at position labeled 311 in this MSA) have very little sequence identity/similarity. (from top to bottom SEQ ID NOs: 17, 39, 7, 8, 9, 10, 11)
Figure 9:
FIG. 9: Superposition of the crystal structure (white) of 1fix-short-noBim(AYYA)-t0 (FIG. 4B) onto the x-ray crystal structure of the base scaffold 5L6HC3_1[5] (dark) used to make LOCKRa (FIG. 1) demonstrates that the asymmetrizing mutations (variable positions shown in FIG. 8 MSA) do not affect the three-dimensional structure of the protein. The backbone RMSD between the two proteins is 0.85 Angstroms (from superposing of all backbone atoms between chains A).

As disclosed herein, the cage polypeptides can be used together with the key polypeptides by using the cage polypeptides to sequester a bioactive peptide in the latch region, where it remains inactive until the key polypeptide displaces the latch through competitive intermolecular binding that induces conformational change, exposing the encoded bioactive peptide or domain and activating the system (see FIG. 1). The combined use of the cage and key polypeptides is described in more detail herein in the examples that follow, and is referred to as a LOCKR switch. LOCKR stands for Latching Orthogonal Cage-Key pRotiens; each LOCKR design consists of a cage polypeptide and a key polypeptide, which are two separate polypeptide chains. Orthogonal LOCKR design (see FIG. 3) are denoted by lowercase letter subscripts: LOCKR$_a$ consists of Cage$_a$ and Key$_a$, and LOCKR$_b$ consists of Cage$_b$ and Key$_b$, etc. such that Cage$_a$ is only activated by Key$_a$, and Cage$_b$ is only activated by Key$_b$, etc. Prefixes in the polypeptide and LOCKR names denote the functional group that is encoded and controlled by the LOCKR switch. For example, BimLOCKR refers to designed switches that encode the Bim peptide, and GFP11-LOCKR refers to designed switches that encode GFP11 (the 11th strand of GFP). See FIG. 8 for a sequence alignment comparing the original LOCKR_a Cage scaffold design to its asymmetrized (1fix-short -noBim(AYYA)-t0) and orthogonal (LOCKRb-f) design counterparts.

In another embodiment, the nomenclature for the cage is identified by 1fix-short and 1fix-latch, indicating similar, yet distinct, embodiments of Cage$_a$ as defined above. They are all activated by Key$_a$. The functional group encoded in the latch is identified by the third portion of the name while the suffix indicates the presence of a toehold. For example, 1fix-short-Bim-t0 encodes Bim on the 1fix-short scaffold with no toehold. In another example, 1fix-latch Mad1SID T0 2 indicates that the 1fix-latch scaffold was used to encode Mad1SID with no residues. The suffix 2 indicates that there are two versions where the functional sequence is encoded in different locations on the latch region.

In one embodiment of the eighth and ninth aspects of the disclosure, the one or more cage polypeptide and the one or more key polypeptide comprise at least one cage polypeptide and at least one key polypeptide in the same row of Tables 1, 2, 3, and/or 4. As will be understood by those of skill in the art based on the teachings herein, such kits may include multiple (i.e.: 2, 3, 4, 5, 6, 7, 8, 9, 10, 20, 50, 100, or more) cage and key polypeptide pairs that can be used together as a LOCKR switch.

In one embodiment of the kits or switches disclosed herein, the one or more cage polypeptide and the one or more key polypeptide comprise at least one cage polypeptide and at least one key polypeptide having an amino acid sequence having at least 45%, 50%, 55%, 60%, 65%, 70%, 75%, 80%, 85%, 90%, 91%, 92%, 93%, 94%, 95%, 96%, 97%, 98%, 99%, or 100% sequence identity along its length to a cage polypeptide and a key polypeptide, respectively, in the same row of Table 1, 2, 3 and/or 4.

In a tenth aspect, the disclosure provides use of the polypeptides, kits, and/or LOCKR switches disclosed herein to sequester bioactive peptide in the cage polypeptide, holding them in an inactive ("off") state, until combined with the key polypeptide to induce a conformational change that activates ("on") the bioactive peptide. Details of exemplary such uses and methods are disclosed throughout.

In one embodiment of the kits or switches disclosed herein, the one or more cage polypeptide and the one or more key polypeptide comprise at least one cage polypeptide and at least one key polypeptide having an amino acid sequence having at least 45%, 50%, 55%, 60%, 65%, 70%, 75%, 80%, 85%, 90%, 91%, 92%, 93%, 94%, 95%, 96%, 97%, 98%, 99%, or 100% sequence identity along its length to a cage polypeptide and a key polypeptide, respectively, in the same row of Table 1, 2, 3, and/or 4.

In another embodiment of the eighth and ninth aspects of the disclosure, the one or more cage polypeptide and the one or more key polypeptide comprise at least one cage polypeptide and at least one key polypeptide that are matched by identification numbers in the naming conventions used herein. As noted above, orthogonal LOCKR designs (see FIG. 3) are denoted by lowercase letter subscripts: LOCKR$_a$ consists of Cage$_a$ and Key$_a$, and LOCKR$_b$ consists of Cage$_b$ and Key$_b$, etc. such that Cage$_a$ is only activated by Key$_a$, and Cage$_b$ is only activated by Key$_b$, etc. Prefixes in the polypeptide and LOCKR names denote the functional group that is encoded and controlled by the LOCKR switch. In one embodiment, all 3plus1 (3+1) and 2plus1 (2+1) cage and key polypeptides disclosed herein are matched by identification numbers.

In some embodiments the cage and key polypeptide names include the prefix 2plus1 or 3plus1 defines the helix architecture with the first number defining the number of helices in the structural region, with the second number defining the number of helices in the latch region. The Nterm or Cterm suffix defines if the latch on the cage component of the kit encompasses the N or C terminus respectively, as is denoted by brackets [ ]. The Nterm versus Cterm and numerical suffix corresponds to the same suffix on the key with which it is activated from. For example, cage 2plus1 Cage Cterm 2406 (SEQ ID NO:27126) is activated by 2plus2 Key Cterm 2406 (SEQ ID NO:27127).

EXAMPLES

Summary:

We have developed a general approach to design novel protein switches that can sequester bioactive peptides and/or binding domains, holding them in an inactive ("off") state, until combined with a second designed polypeptide called the Key, which induces a conformational change that activates ("on") the bioactive peptide or binding domain.

Nomenclature and Structural Features that Define LOCKR Switches:

- LOCKR stands for Latching Orthogonal Cage-Key pRotiens; each LOCKR design consists of a Cage protein and a Key protein, which are two separate polypeptide chains.
- The Cage encodes the sequestered bioactive peptide or binding domain in a region of the Cage scaffold denoted as the Latch. The general strategy is to optimize the position of the encoded peptide or binding domain for maximum burial of the functional residues that need to be sequestered, simultaneously optimizing for burial of hydrophobic residues, and for solvent exposure/compensatory hydrogen bonds of polar residues.
- The Key displaces the Latch through competitive intermolecular binding that induces conformational change, exposing the encoded bioactive peptide or domain and activating the system (FIG. 1).
- Orthogonal LOCKR designs (FIG. 3) are denoted by lowercase letter subscripts: LOCKR$_a$ consists of Cage$_a$ and Key$_a$, and LOCKR$_b$ consists of Cage$_b$ and Key$_b$, etc. such that Cage$_a$ is only activated by Key$_a$, and Cage$_b$ is only activated by Key$_b$, etc.

Prefixes denote the functional group that is encoded and controlled by the LOCKR switch. For example, Bim-LOCKR refers to designed switches that encode the Bim peptide, and GFP11-LOCKR refers to designed switches that encode GFP11 (the 11$^{th}$ strand of GFP).

Toehold: The dynamic range of LOCKR activation by Key can be tuned by truncating the Latch length, simultaneously weakening the Cage-Latch interaction and opening an exposed region on the Cage that the Key can bind to as a "toehold" (FIG. 2. LOCKR can also be tuned in a similar manner by designing mutations into the Latch that weaken the Cage-Latch interaction (FIGS. 1-2, FIG. 10). The length of the toehold is included as a suffix to the design name: For example "-t0" means no toehold, and "-t9" means a toehold of 9 residues (i.e. Latch truncated by 9 residues).

If the term "Lock" is used in reference to a single polypeptide chain (not in reference to the LOCKR acronym), it is assumed to be synonymous with "Cage".

These designs comprise the first ever de novo designed proteins that can undergo conformational switching in response to protein binding. They are modular in that they can encode bioactive peptides of all three types of secondary structure in an inactive conformation: alpha helix, beta strand, loop, and are tunable in that their responsiveness can be tuned over a large dynamic range by varying length (length of Cage scaffold and/or Latch Toehold), and/or mutating residues in the Cage-Latch interface. Designed LOCKR switches can be used to control the activity of a wide range of functional peptides. The ability to harness these biological functions with tight, inducible control is useful, for example, in engineering cells (inducible activation of function, engineering complex logic behavior and circuits), developing sensors, developing inducible protein-based therapeutics, and creating new biomaterials.

Design of LOCKR Switches

We set out to design de novo switchable protein systems guided by the following general considerations. First, the free energy tuning required to achieve maximal dynamic range upon addition of the switch-triggering input is more straightforward in a system governed by competition between inter- and intra-molecular interactions at the same site rather than at distant sites (as is common in allosteric biological systems). Second, a stable protein framework with an extended binding surface available for the competing interactions has advantages over a framework that only becomes ordered upon binding, as the former is more programmable and less likely to engage in off-target interactions. These features are described by the abstract system depicted in FIG. 1a, which undergoes thermodynamically-driven switching between a binding incompetent and a binding competent state. A latch (blue) contains a peptide sequence (orange) that can bind a target (yellow) unless blocked by intramolecular interactions to a cage (cyan); a more tightly binding key (magenta) outcompetes the latch allowing the peptide to bind target. The behavior of such a system is governed by the binding equilibrium constants for the individual subreactions (FIG. 1a): $K_{open}$, the dissociation of latch from cage; $K_{LT}$, the binding of latch to target; and $K_m$, the binding of key to cage. Solution of this set of equations shows that when the latch-cage interaction is too weak (red and orange curves), the system is leaky and the fold induction by key is low, while when the latch-cage interaction is too strong (purple curve), the system is only partially activated, even at high key concentrations. The latch-cage interaction affinity that gives optimal switching (FIG. 1b, blue curve left, green curve right) is a function of the latch-target binding affinity. We used this model to guide design of an optimally switchable protein system, as described in the following sections.

LOCKR Design Strategy

To design such a switchable system, we chose structural features amenable to tuning of the affinities of the cage-latch and cage-key interactions over a wide dynamic range. Alpha helices have advantages over beta strands because inter-helical interfaces are dominated by sidechain-sidechain interactions, which can be more readily tuned than the cooperative backbone hydrogen bonding necessary for beta sheets. To allow fine control over the relative affinities of the cage-latch and cage-key interactions, we chose to design interfaces containing buried hydrogen bond networks: as illustrated by Watson Crick base pairing, considerable specificity can be obtained with relatively minor changes in the positions of hydrogen bond donors and acceptors[4,5]. We selected as a starting point a designed homo-trimer of α-helical hairpins with hydrogen bond network-mediated subunit-subunit interaction specificity (5L6HC3_1)[5]. By designing short unstructured loops connecting the subunits, we generated monomeric protein frameworks with five or six helices and 40 residues per helix (FIG. 1c). In the five-helix framework, there is an open binding site for a sixth helix added in trans, whereas this site is filled by a sixth helix in cis in the six-helix framework.

Figure 1C:
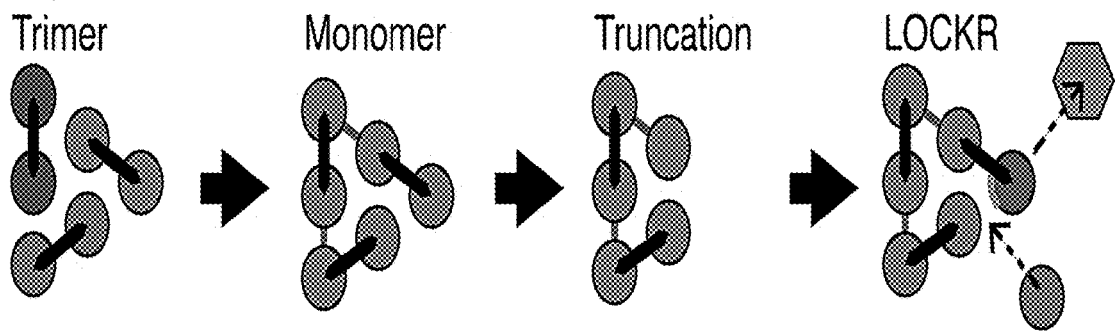
Figure 1D:
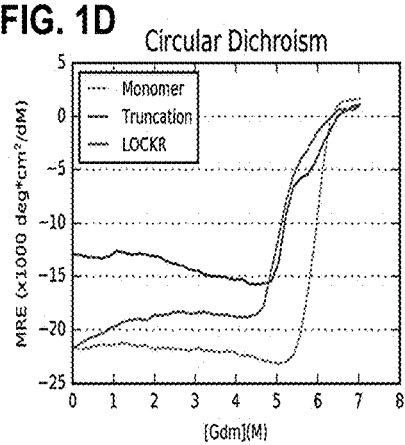
Figure 1E:
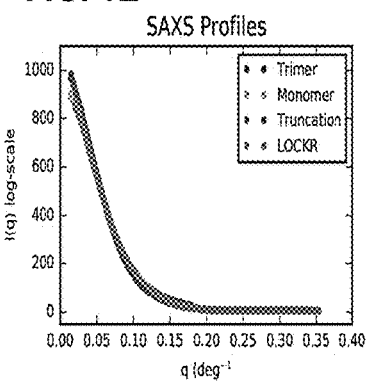
Figure 1F:
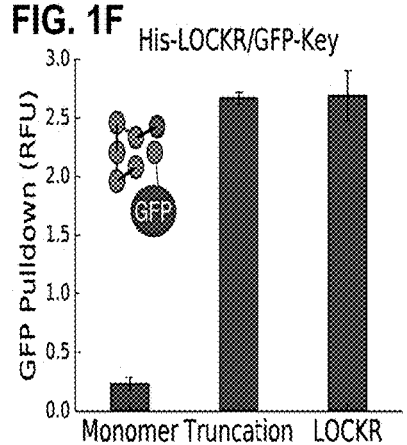

The five helix (cage) and six helix (cage plus latch) designs were soluble when recombinantly expressed in E. coli, and the purified proteins were largely monomeric by size-exclusion chromatography with multi-angle light scattering, and very thermostable, remaining folded at upwards of 95° C. and 5 M guanidine hydrochloride (FIG. 1d). Small-angle X-ray scattering (SAXS) spectra were in close agreement to the design models and previous of the original trimers (FIG. 1e), suggesting that the structure was not altered by the loops. The five-helix framework, but not the six-helix framework, bound the sixth helix fused to GFP in a pull-down assay (FIG. 1f); the latter result is expected since if the interfaces are otherwise identical, the intramolecular interaction $K_{open}$, should outcompete its intermolecular counterpart, $K_m$, because of the reduced entropic cost of formation of intramolecular interactions. To tune $K_{open}$, we screened destabilizing mutations in the latch (large hydrophobics to alanine or serine, and alanine residues to larger hydrophobics or serine) and using the GFP pull-down assay, identified mutants with a range of affinities for the key. A double mutant, V223S/I238S, bound key as strongly as the five-helix cage without the latch (FIG. 1e, 10); the two serines likely weaken the cage-latch interaction because of the desolvation penalty associated with burying the side-chain hydroxyls, and because they decrease the helical propensity of the latch. SAXS and CD spectra indicate that in the absence of key, V223S,I238S is a well-folded six-helix bundle with structure similar to the original monomer (FIG. 1d). We call this cage-latch-key system LOCKR, for Latching Orthogonal Cage-Key pRoteins.

Figure 2A:
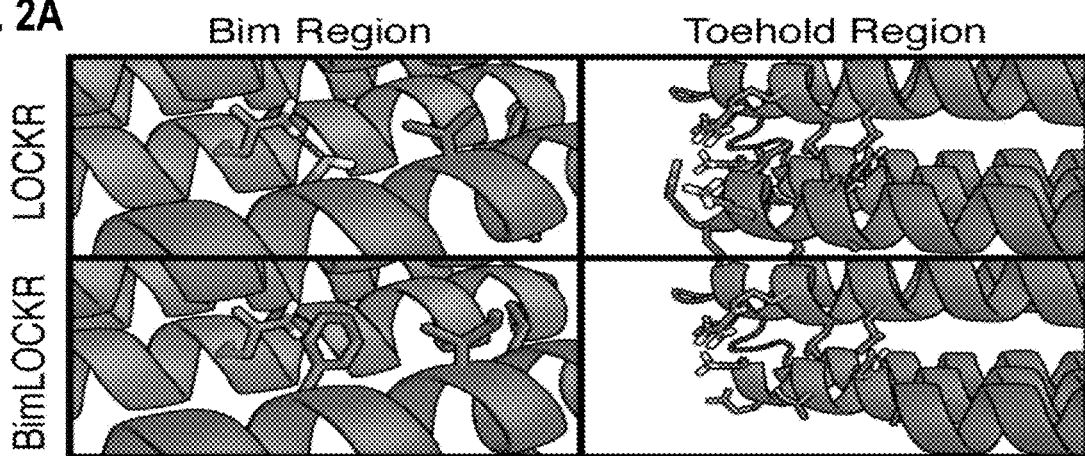
FIG. 2A-2D: BimLOCKR design and activity.
Figure 2B:
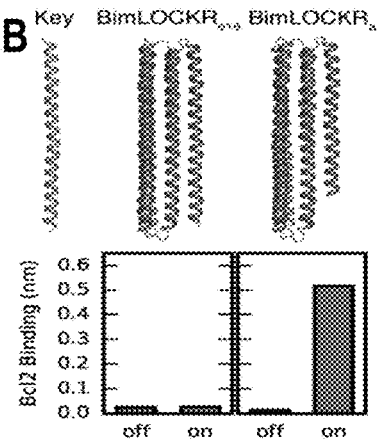
Figure 2C:
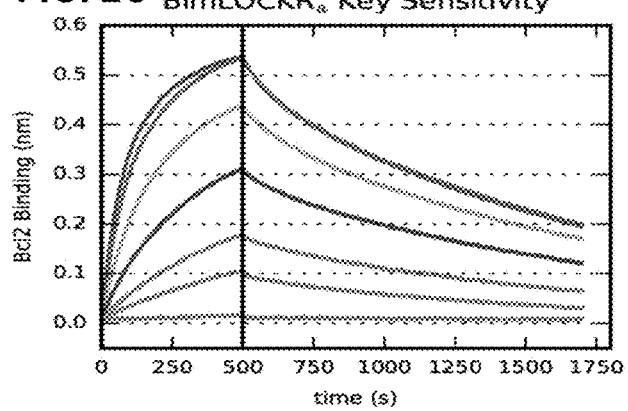
Figure 2D:
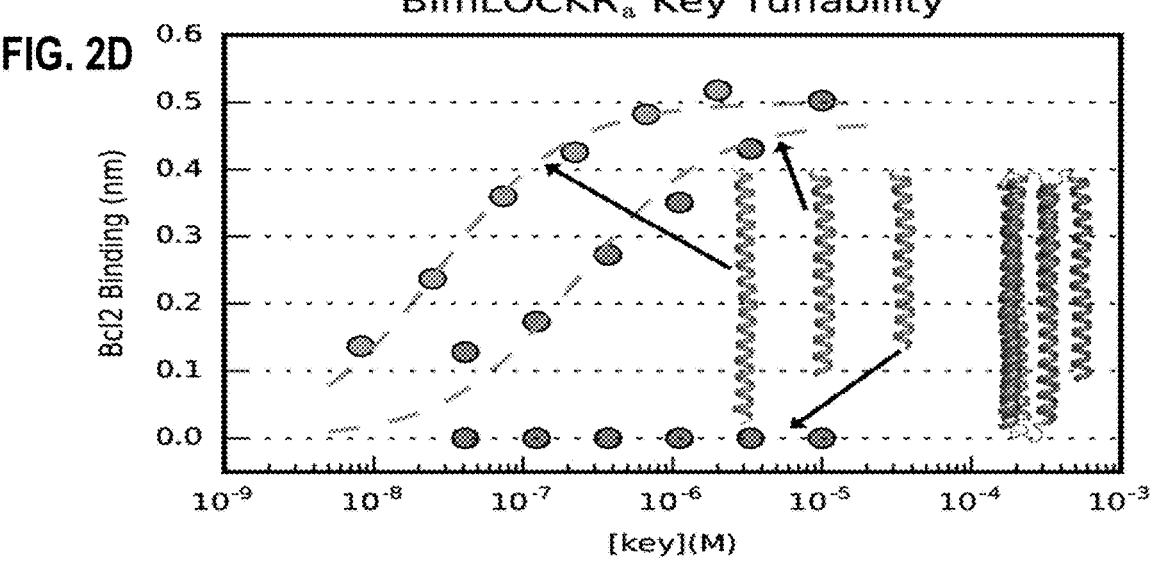
Figure 4A:
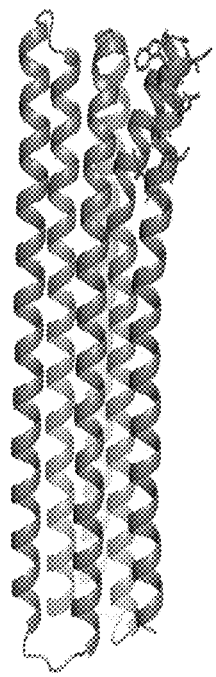
FIG. 4A-4B: Experimentally determined x-ray crystal structures of asymmetrized LOCKR switch designs.
Figure 4B:
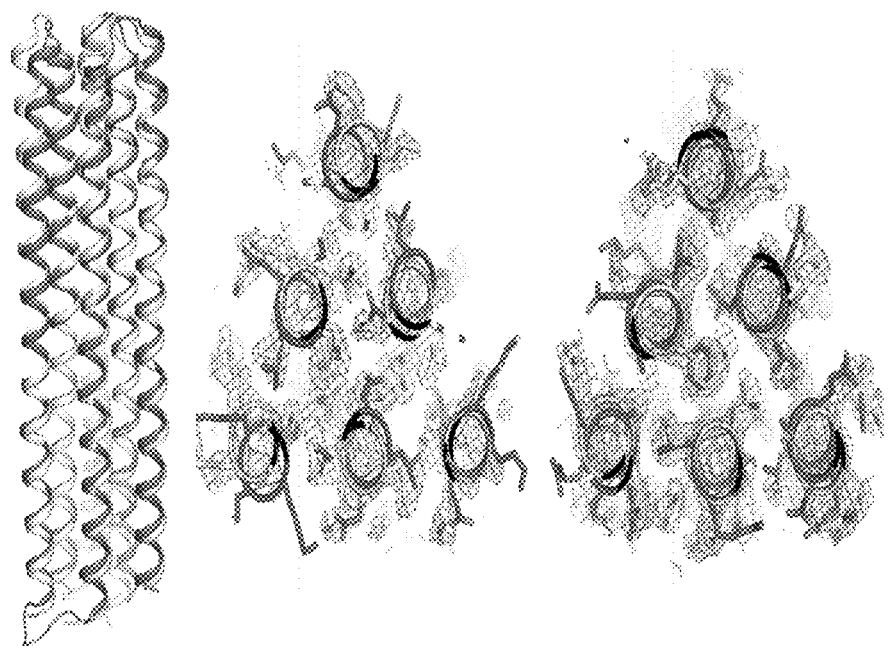
Figure 5A:
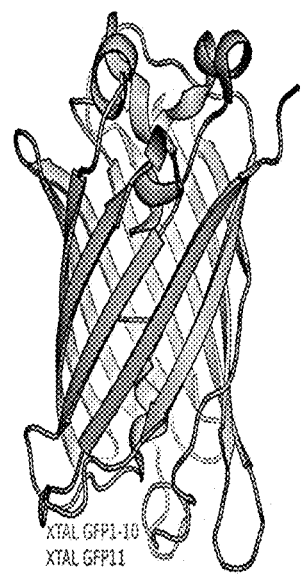
FIG. 5A-5D: LOCKR switch that can prevent split GFP11 from complementing GFP1-10 in the absence of Key.
Figure 5B:
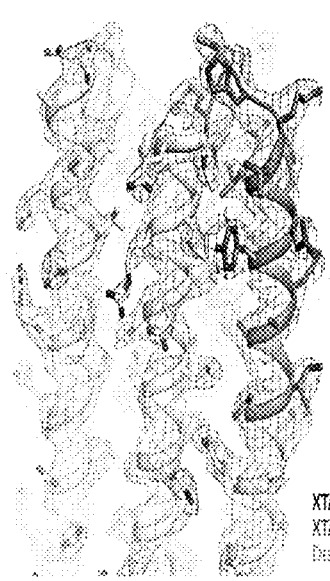
Figure 5C:
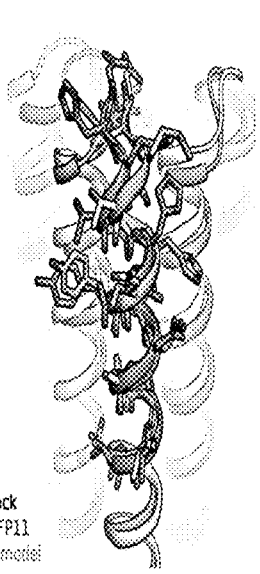
Figure 5D:
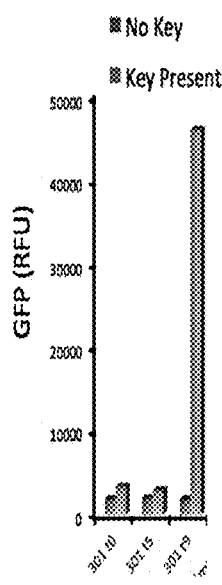
Figure 6A:
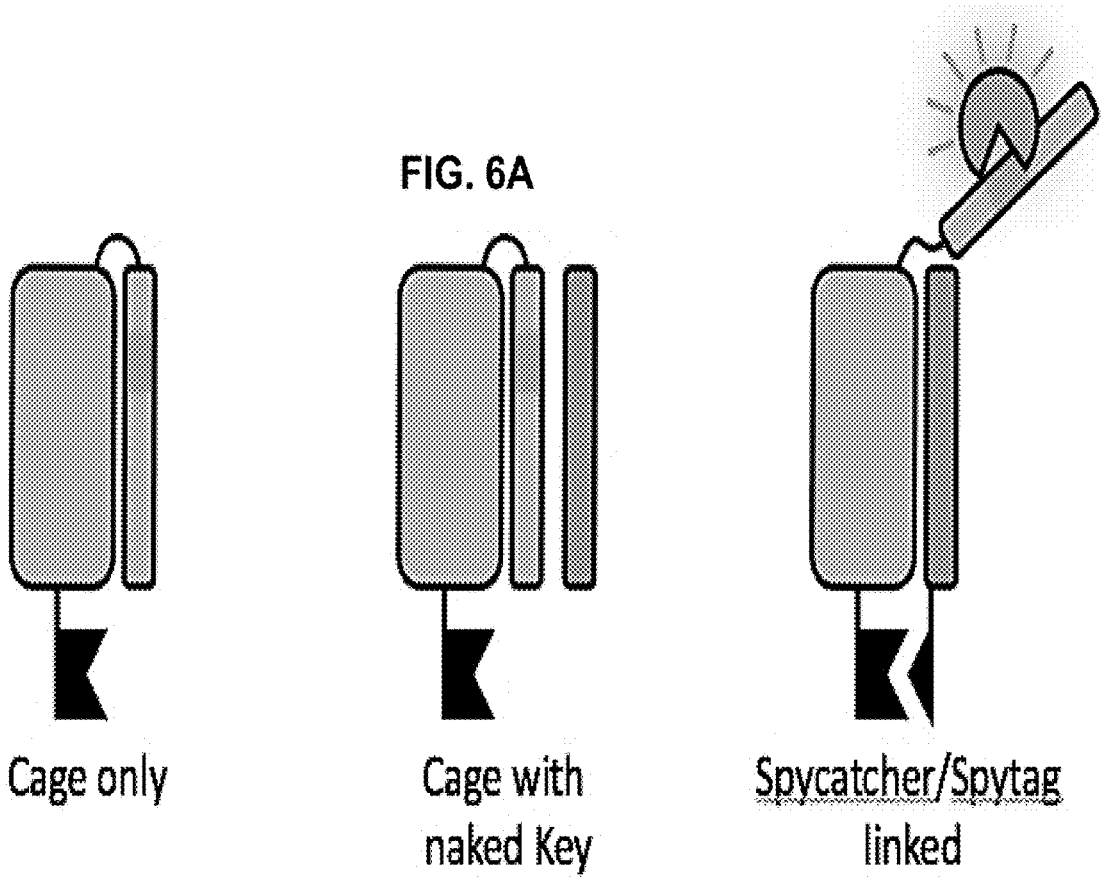
FIG. 6A-6C: Designed GFP11-LOCKR switch from FIG. 4, tuned to be colocalization-dependent.
Figure 6B:
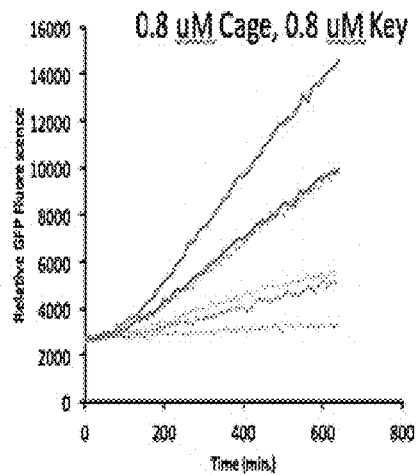
Figure 6C:
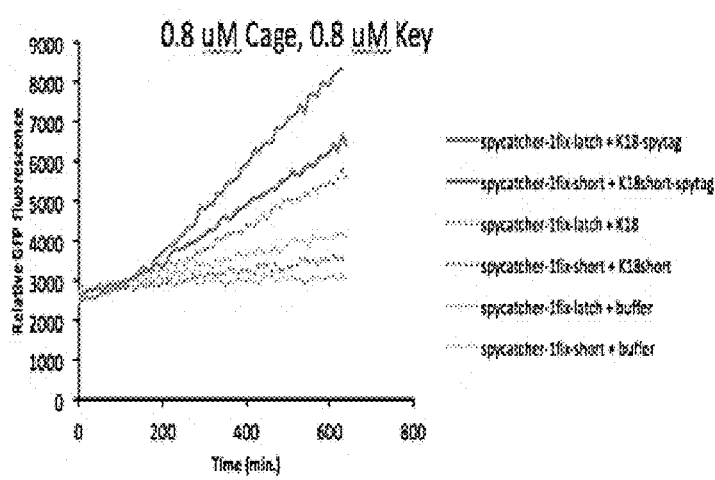

Controlling Bim-Bcl2 Binding, and Tuning the Dynamic Range of Activation:

To install function into LOCKR, we selected the Bim-Bcl2 interaction central to apoptosis as a model system, seeking to cage Bim such that binding to Bcl2 only occurred in the presence of key. We designed constructs with two possible Bim-related sequences designed onto the latch: a designed Bcl2-binding peptide (aBcl2LOCKR) or just the Bim residues crucial for Bcl2 binding (pBimLOCKR). Each has a different affinity for Bcl2, allowing us to sample a range of $K_{LT}$ values in the initial series of designs. Bim-related sequences were grafted onto the latch by sampling different helical registers such that residues involved in binding to Bcl2 are sequestered in the cage-latch interface (data not shown), optimizing for the burial of hydrophobic residues and surface exposure of polar residues. $K_{open}$ can be tuned by non-optimal interactions between the cage and Bim residues or by changing the length of the latch (FIG. 2a). Initial designs were tested for binding to Bcl2 by bio-layer interferometry, and were either showed little Bcl2 binding even in the presence of key, or Bcl2 binding even in the absence of key. The range of $K_{open}$ and $K_{CK}$ values accessible with this system was evidently not matched to $K_{LT}$ in this case: the key Tuning for Co-Localization Dependence FIGS. 1-2 demonstrate that the dynamic range of LOCKR activation can be predictively tuned, suggesting that the system can be modulated to respond only when the Cage and Key are colocalized, which would be advantageous for a wide range of functions. Using the GFP11-LOCKR from FIG. 4, we demonstrated that this is indeed the case, and that that designed LOCKR switches can be tuned to be colocalization dependent using Spycatcher™/Spytag™ fusions (FIG. 6). Spycatcher™ covalently fuses to Spytag™; when Spycatcher™ fuse Cage was mixed with its Spytag™-fused Key, it showed significantly more fluorescence that when mixed with its Key that was not fused to Spytag™ (FIG. 6).

Caged Intein LOCKR Switches

Figure 7:
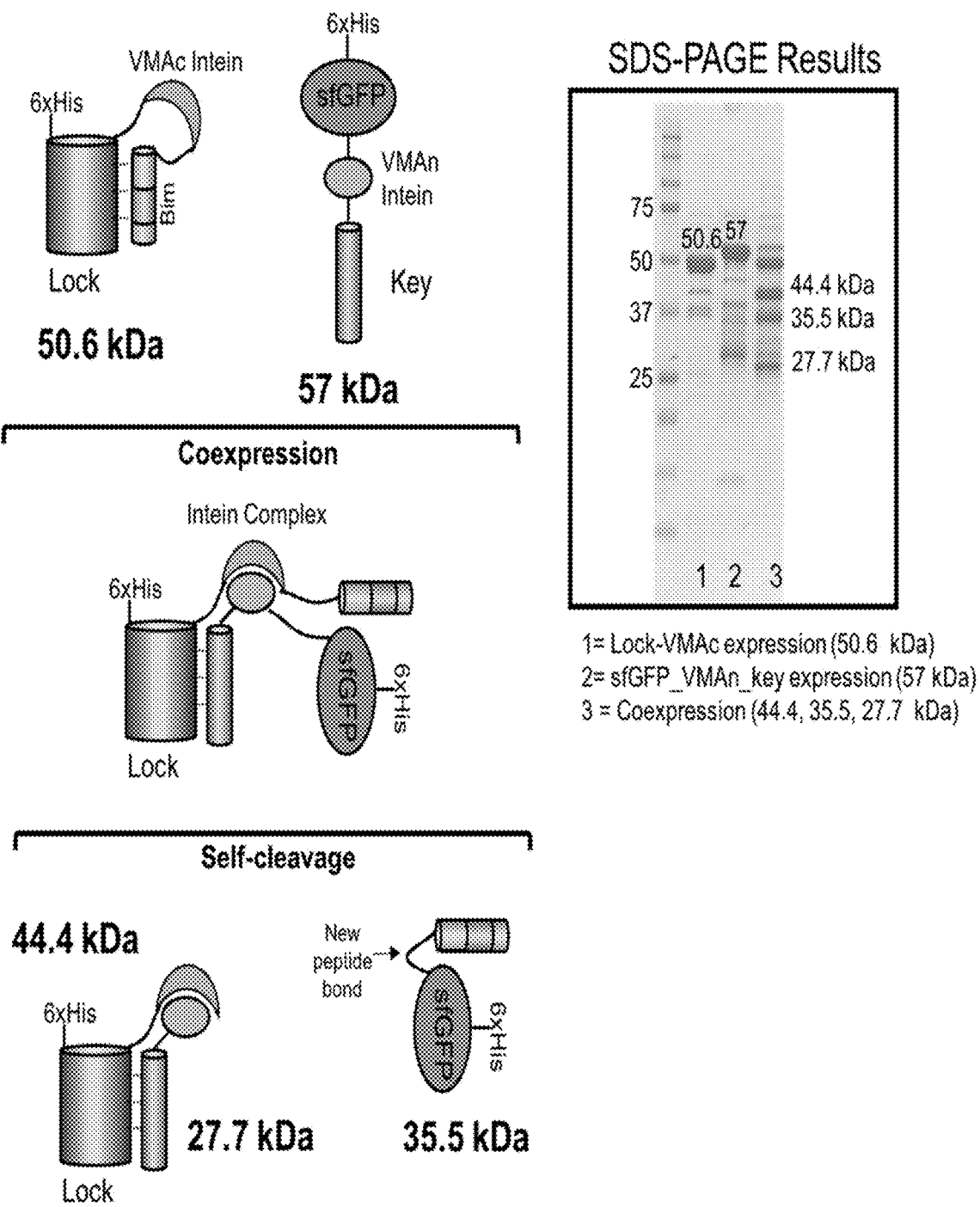
FIG. 7: Caged Intein LOCKR switches. Designed LOCKR switch with Cage component encoding the VMAc Intein shows successful activation when mixed with designed Key fused to sfGFP and VMAn Intein. The SDS-PAGE shows successful VMAc-VMAn reaction, with bands corresponding to the correct molecular weight of the expected spliced protein products.

Designed LOCKR switch, with Cage component encoding the VMAc Intein, shows successful activation when mixed with designed Key fused to sfGFP and VMAn Intein (FIG. 7). The SDS-PAGE shows successful VMAc-VMAn reaction, with bands corresponding to the correct molecular weight of the expected spliced protein products (FIG. 7).

Large-Scale High-Throughput Design of LOCKR Switches

The original LOCKR switch design (FIGS. 1-2) was built starting from a de novo designed symmetric homotrimer, 5L6HC3_1, which contains 6 helices[5]. We reasoned we should be make smaller LOCKR switches, consisting of 3 or 4 helices. Using everything that we learned from the testing and experimental validation of the original LOCKR switch, we created a computational pipeline to automate the design of thousands of new LOCKR switch scaffolds from scratch by exhaustively sampling Crick helical parameters[4,9]. These 2plus1 and 3plus1 LOCKR switches have smaller payload than the original designs (advantageous for cell engineering efforts), and due to lack of symmetry, are likely to be well-behaved and not aggregation-prone. (See Methods section for details of computational design and experimental testing).

strepLOCKR (STREPII-LOCKR)

Using the new 2+1 and 3+1 LOCKR scaffolds from the large-scale high-throughput design, we designed and tested new LOCKR scaffolds that encode and control the STREPII sequence, (N)WSHPQFEK (SEQ ID NO:63) (see Methods section for details). The designs (FIG. 13A) sequester the STREPII tag as compared to a positive control (FIG. 13B) and can be activated in the presence of Key (FIG. 13C-D), as determined by biolayerinterferometry (Octet) data.

The data in FIG. 12 demonstrate caging of the PAH2 domain of the mSin3A transcriptional repressor. See the figure legend for details.

Figure 14:
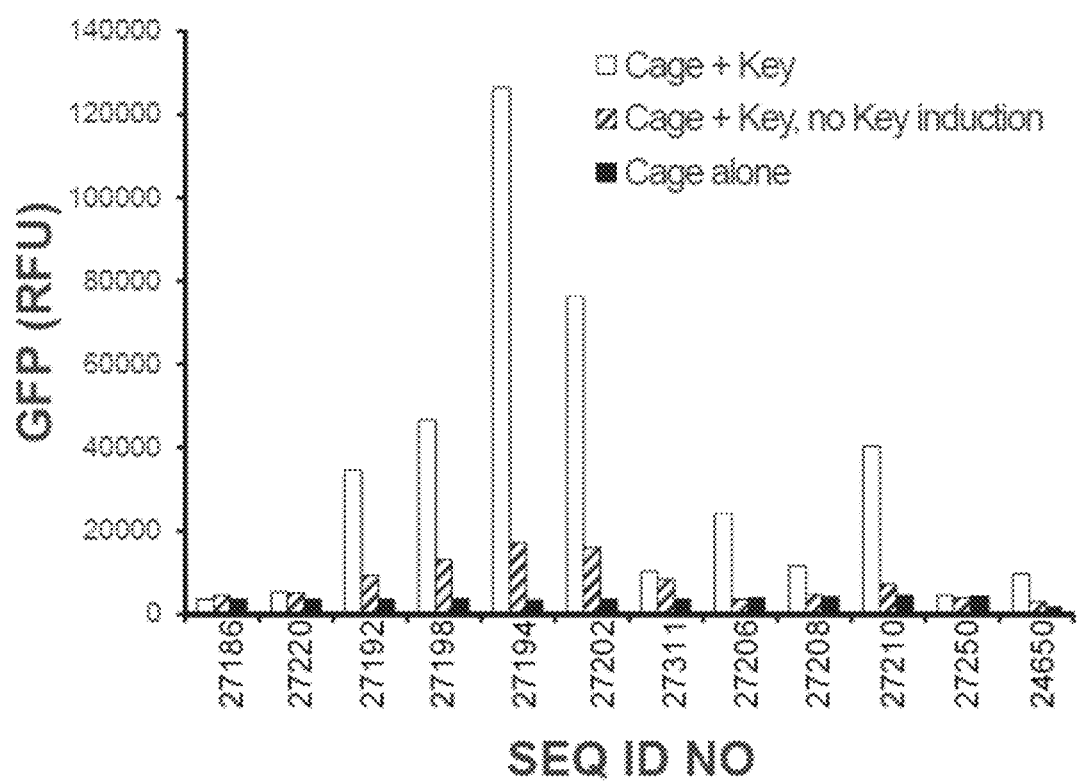
FIG. 14: 3plus1 LOCKR switches activate GFP fluorescence in response to expression of Key. LOCKR switches were designed in which 3plus1 Cages were used to sequester strand 11 of GFP (GFP11) in an inactive conformation, thereby preventing reconstitution of split GFP (comprised of GFP1-10 and GFP11), resulting in fluorescence. Expression plasmids were prepared for inducibly expressing the Cage (p15a origin of replication, spectinomycin resistance, arabinose-inducible promoter controlling expression of GFP1-10 and LOCKR-Caged GFP11) and Key (colE1 origin of replication, kanamycin resistance, and IPTG-inducible promoter). Chemically competent *E. coli* Stellar cells (Takarabio) were transformed according to manufacturer's protocols either with the Cage plasmid alone or with both the Cage and Key plasmids. These transformations were grown overnight at 37 C in liquid LB media supplemented with spectinomycin (Cage alone) or spectinomycin+kanamycin (Cage and Key). The resulting cultures were diluted ¹⁄₁₀₀ into fresh LB media supplemented with appropriate antibiotics and either arabinose only (induce expression of Cage and GFP1-10) or both arabinose and IPTG (induce expression of Cage, GFP1-10, and Key), then allowed to grow at 37 C for 16 hours. 200 uL of each expression culture was washed once in 200 uL PBS, resuspended in 200 uL PBS, and transferred to a black-walled 96-well plate. GFP fluorescence was evaluated on a Biotek Synergy H1MF plate reader (excitation/emission 479/520 nm). Fluorescence was minimal for Cage alone, confirming that LOCKR proteins prevented activation of split GFP in the absence of Key. Induction of Key expression resulted in a large increase in fluorescence for SEQ ID NOs 27192, 27198, 27194, 27202, 27206, and 27210. These results demonstrate that the 3plus1 LOCKR architecture is able to control the function of bioactive peptide GFP11.

The data in FIG. 14 demonstrate 3plus1 LOCKR switches activating GFP fluorescence in response to expression of key. See the figure legend for details Discussion Here we demonstrate the power of the LOCKR platform by caging protein-protein interactions that can be inducibly activated by key. We show in vitro data caging the Bim peptide from binding its family members, GFP strand11 from completing the truncated 1-10 construct, and an anti-StrepTag™II antibody from binding caged StrepTag™II. The modularity and hyperstability of de novo designed proteins enables tuning of switch activation over a broad dynamic range by tuning the strength of the competing cage-key and cage-latch interfaces. Using this approach, we can now design switches beyond these proof-of-concept designs to cage peptides for more complex applications. LOCKR is useful for controlling native signaling networks, and in general for controlling biological function through fully synthetic networks of de novo signaling molecules.

LOCKR brings to proteins the modularity of DNA switching technology, but with advantages of being able to control, and be coupled to, the wide range of biochemical functions that can be carried out by proteins and bioactive peptides (which are much more diverse and wide ranging than nucleic acids).

Methods

PCR Mutagenesis and Isothermal Assembly

All primers for mutagenesis were ordered from Integrated DNA Technologies (IDT). Mutagenic primers were designed to anneal >18 bp on either side of the site for mutagenesis with the desired mutation encoded in the primer. PCR was used to create fragments upstream and downstream of the mutation site with >20 bp overlap with the desired pET vector. The resulting amplicons were isothermally assembled into either pET21b, pET28b, or pET29b restriction digested with XhoI and NdeI and transformed into chemically competent E. coli XL1-Blue cells. Monoclonal colonies were sequenced with Sanger sequencing. Sequence verified plasmid was purified using Qiagen miniprep kit and transformed into chemically competent E. coli BL21(DE3)Star, BL21(DE3)Star-pLysS cells (Invitrogen), or Lemo21(DE3) cells (NEB) for protein expression.

Synthetic Gene Construction

Synthetic genes were ordered from Genscript Inc. (Piscataway, NJ, USA) and delivered in pET 28b+, pET21b+, or pET29b+E. coli expression vectors, inserted at the NdeI and XhoI sites of each vector. For pET28b+constructs, synthesized DNA was cloned in frame with the N-terminal hexahistidine tag and thrombin cleavage site and a stop codon was added at the C-terminus. For pET21b+constructs, a stop codon was added at the C-terminus such that the protein was expressed with no hexahistidine tag. For pET29b+constructs, the synthesized DNA was cloned in frame with the C-terminal hexahistidine tag. Plasmids were transformed into chemically competent E. coli BL21(DE3)Star, BL21 (DE3)Star-pLysS cells (Invitrogen), or Lemo21(DE3) cells (NEB) for protein expression.

Bacterial Protein Expression and Purification

Starter cultures were grown in Lysogeny Broth (LB) or Terrific™ Broth II (TBII) overnight in the presence of 50 µg/mL carbenicillin (pET21b+) or 30 µg/mL (for LB) to 60 µg/mL (for TBII) kanamycin (pET28b+ and pET29b+). Starter cultures were used to inoculate 500 mL of Studier TBM-5052 autoinduction media containing antibiotic and grown at 37° C. for 24 hours. Cells were harvested by centrifugation at 4000 rcf for 20 minutes at 4° C. and resuspended in lysis buffer (20 mM Tris, 300 mM NaCl, 20 mM Imidazole, pH 8.0 at room temperature), then lysed by microfluidization in the presence of 1 mM PMSF. Lysates were cleared by centrifugation at 24,000 rcf for at least 30 minutes at 4° C. Supernatant was applied to Ni-NTA (Qiagen) columns pre-equilibrated in lysis buffer. The column was washed twice with 15 column volumes (CV) of wash buffer (20 mM Tris, 300 mM NaCl, 40 mM Imidazole, pH 8.0 at room temperature), followed by 15 CV of high-salt wash buffer (20 mM Tris, 1M NaCl, 40 mM Imidazole, pH 8.0 at room temperature) then 15 CV of wash buffer. Protein was eluted with 20 mM Tris, 300 mM NaCl, 250 mM Imidazole, pH 8.0 at room temperature. Proteins were further purified by gel filtration using FPLC and a Superdex™ 75 Increase 10/300 GL (GE) size exclusion column, pooling fractions containing monomeric protein.

Size-Exclusion Chromatography, Multi-Angle Light Scattering (SEC-MALS)

SEC-MALS experiments used a Superdex™ 75 Increase 10/300 GL (GE) size exclusion column connected to a miniDAWN™ TREOS multi-angle static light scattering and an Optilab T-rEX™ (refractometer with Extended range) detector (Wyatt Technology Corporation, Santa Barbara CA, USA). Protein samples were injected at concentrations of 3-5 mg/mL in TBS (pH 8.0). Data was analyzed using ASTRA™ (Wyatt Technologies) software to estimate the weight average molar mass (Mw) of eluted species, as well as the number average molar mass (Mn) to assess monodispersity by polydispersity index (PDI)=Mw/Mn.

Circular Dichroism (CD) Measurements

CD wavelength scans (260 to 195 nm) and temperature melts (25 to 95 C) were measured using an AVIV model 420 CD spectrometer. Temperature melts monitored absorption signal at 222 nm and were carried out at a heating rate of 4° C./min. Protein samples were at 0.3 mg/mL in PBS pH 7.4 in a 0.1 cm cuvette. Guanidinium chloride (GdmCl) titrations were performed on the same spectrometer with an automated titration apparatus in PBS pH 7.4 at 25 C, monitored at 222 nm with protein sample at 0.03 mg/mL in a 1 cm cuvette with stir bar. Each titration consisted of at least 40 evenly distributed concentration points with one minute mixing time for each step. Titrant solution consisted of the same concentration of protein in PBS+GdmCl. GdmCl concentration was determined by refractive index.

Small Angle X-Ray Scattering (SAXS)

Samples were exchanged into SAXS buffer (20 mM Tris, 150 mM NaCl, 2% glycerol, pH 8.0 at room temperature) via gel filtration. Scattering measurements were performed at the SIBYLS™ 12.3.1 beamline at the Advanced Light Source. The X-ray wavelength ($\lambda$) was 1.27 Å and the sample-to-detector distance of the Mar165 detector was 1.5 m, corresponding to a scattering vector q ($q=4\pi*\sin(\theta/\lambda)$ where $2\theta$ is the scattering angle) range of 0.01 to 0.59 Å$^{-1}$. Data sets were collected using 34 0.2 second exposures over a period of 7 seconds at 11 keV with protein at a concentration of 6 mg/mL. Data were also collected at a concentration of 3 mg/mL to determine concentration-dependence; all presented data was collected at the higher concentration as no concentration-dependent aggregation was observed. Data from 32 exposures was averaged separately over the Gunier, Parod, and Wide-q regions depending on signal quality over each region and frame. The averages were analyzed using the ScÅtter software package to analyze data and report statistics. FoXS was used to compare design models to experimental scattering profiles and calculate quality of fit (X) values. The hexahistidine tags and thrombin cleavage sites on the N-terminii of LOCKR proteins were modeled using Rosetta Remodel™ so that the design sequence matched that of the experimentally tested protein. To capture conformational flexibility of these residues, 100 independent models were generated, clustered, and the cluster center of the largest cluster was selected as a representative model for FoXS fitting without bias.

GFP Pulldown Assay

His-tagged LOCKR was expressed per the above protocol from pET28b+ while the key was expressed fused to superfolder GFP (sfGFP) without a his-tag in pET21b+. The his-tagged LOCKR was purified to completion and dialyzed into TBS (20 mM Tris, 150 mM NaCl, pH 8.0 at room temperature); the key-GFP remained as lysate for this assay. 100 µL LOCKR at >1 uM was applied to a 96-well black Pierce® Nickel Coated Plate (ThermoFisher) and incubated at room temperature for 1 hour. Sample was discarded from the plate and washed 3× with 200 µL TBST (TBS+0.05% Tween-20). 100 µL of lysate containing key-GFP was added to each well and incubated at room temperature for 1 hour. Sample was discarded from the plate and washed 3× with 200 µL TBST (TBS+0.05% Tween-20). The plate was washed 1× with TBS, and 100 µL of TBS was added to each well. sfGFP fluorescence was measured on a Molecular Devices SpectraMax™ M5 plate reader or BioTek Synergy Neo2 plate reader; fluorescence was measured at 485 nm excitation and 530 nm emission, with a bandwidth of 20 nm for excitation and emission.

Bio-Layer Interferometry (BLI)

BLI measurements were made on an Octet® RED96 System (ForteBio) with streptavidin (SA) coated biosensors and all analysis was performed within ForteBio Data Analysis Software version 9.0.0.10. Assays were performed with protein diluted into HBS-EP+ Buffer from GE (10 mM HEPES, 150 mM NaCl, 3 mM EDTA, 0.05% v/v Surfactant P20, 0.5% non-fat dry milk, pH7.4 at room temperature). Biotinylated Bcl2 was loaded onto the SA tips to a threshold of 0.5 nm programmed into the machine's protocol. Baseline was obtained by dipping the loaded biosensors into HBS-EP+ buffer; association kinetics were observed by dipping into wells containing defined concentrations of LOCKR and key, then dissociation kinetics were observed by dipping into the buffer used to obtain the baseline. Kinetic constants and response at equilibrium were computed by fitting a 1:1 binding model.

Thermodynamic LOCKR Model

The thermodynamic model in FIG. 1a illustrates three free parameters for five equillibrea. This defines three equations that relate the concentrations of all species (open or closed Switch, Key, Target, Switch-Key, Switch-Target, and Switch-Key-Target) at equilibrium.

$$K_{open}=[Switch_{open}]/[Switch_{closed}]$$

$$K_{CK}=[Switch_{open}][Key]/[Switch\text{-}Key]=[Switch\text{-}Target][Key]/[Switch\text{-}Key\text{-}Target]$$

$$K_{LT}=[Switch\text{-}Key][Target]/[Switch\text{-}Key\text{-}Target]=[Switch_{open}][Target]/[Switch\text{-}Target]$$

The total amount of each component (Switch, Key, and Target) is also constant and constrains the values of each species at equilibrium. This introduces the following equations to the model.

$$[Switch]_{total}=[Switch_{open}]+[Switch_{closed}]+[Switch\text{-}Key]+[Switch\text{-}Target]+[Switch\text{-}Key\text{-}Target]$$

$$[Key]_{total}=[Key]+[Switch\text{-}Key]+[Switch\text{-}Key\text{-}Target]$$

$$[Target]_{total}=[Target]+[Switch\text{-}Target]+[Switch\text{-}Key\text{-}Target]$$

These six equations were fed into sympy.nsolve( ) to find solutions given the six constants (three equilibrium constants, three total concentrations). Fraction bound was extracted from this solution and plotted for the corresponding figures.

Grafting Functional Sequence onto LOCKR Using Rosetta

Models of functional LOCKRs were made by grafting bioactive sequences onto the latch were designed using Rosetta™ XML to sample grafts starting at every helical register on the latch. This protocol uses two Rosetta movers, SimpleThreadingMover to change the amino acid sequence on the latch, and FastRelax™ with default settings to find the lowest energy structure given the functional mutations. Designs were selected by eye in PyMol™ 2.0 and high quality grafts had important binding residues interacting with the cage and minimized the number of buried unsatisfied hydrogen bonding residues.

Rosetta Design of Orthogonal LOCKR

Redesign of LOCKR$_a$ to orthogonal cage-key pairs using was carried out using Rosetta with scorefunction beta_nov16. We extracted a model of the five-helix cage from the extended LOCKR model and used the Rosetta™ BundleGridSampler module to generate an ensemble of backbones for new latch geometries. The BundleGridSampler generates backbone geometry based on the Crick mathematical expressions for a coiled-coil, and allows efficient, parallel sampling of a regular grid of coiled-coil expression parameter values, which correspond to a continuum of peptide backbone conformations. For each parametrically-generated latch conformation sampled, Rosetta™ residue selectors specified the interface of the cage and latch for design of hydrogen bonding networks (HBNet) followed by Rosetta™ sidechain design. Residues were selected for design through Rosetta residue selectors by selecting the interface of the latch and cage via the InterfaceByVector residue selector. This residue selection was passed into both HBNet and sidechain design to strictly design the switching interface while leaving the cage with its original LOCKR sequence. Hydrogen Bond networks were designed using HBNetStapleInterface on the residues selected at the interface. The output contained designs with two or three hydrogen bond networks which span the three helices that make up the interface. All output from HBNet was then designed using PackRotamersMover to place residues at the interface while maintaining the hydrogen bond networks. Two rounds of design were done. The first used beta_soft to aggressively pack the interface with potentially clashing rotamers while optimizing the interaction energy at the interface, then the structure was minimized using beta to resolve potential clashing atoms according to the full Rosetta score function. The final round of design placed rotamers with the full beta Rosetta score function to finally optimize the interactions across the cage-latch interface.

Candidate orthogonal LOCKR designs were selected based on lacking unsatisfied buried hydrogen bonding residues, the count of alanine residues as a proxy for packing quality, and sequence dissimilarity as a metric to find polar/hydrophobic patterns dissimilar enough to be orthogonal. Unsatisfied hydrogen bonding atoms were filtered out using the BuriedUnsatHbonds filter allowing no unsatisfied polar atoms according to the filter's metrics. Packing quality was determined by counting alanine residues at the interface because high alanine count means poor interdigitation of residues. A maximum of 15 alanine residues were allowed in the entire three helix interface. Pairwise sequence dissimilarity of every designed latch was scored with BLOSUM62 by aligning sequences using the Bio.pairwise2 package from BioPython as shown in seq_alignment.py. Alignment was performed disallowing gaps within the sequence through large opening and extension penalties which is analogous to a structural alignment of two helices to find the most similar superposition based on hydrophobic-polar patterning. Each score was subtracted from the maximum score to convert scores into a distance metric; the most diverse sequences has the lowest BLOSUM62 score which converts to the largest distance. The sequences were then clustered using HeirClust_fromRMSD.py and clustered with a cutoff of 170, resulting in 13 clusters. The center of each cluster was picked by maximizing distance between the 13 centers selected. The 13 candidates were then filtered by eye in PyMol™ 2.0 for unsatisfied hydrogen bonding atoms and qualitative packing quality. The five best designs by these three metrics were ordered as LOCKR$_{b-f}$.

Asymmetrized LOCKR Switches

The original LOCKR$_a$ switch was redesigned using Rosetta™ with HBNet; residues known to be important for LOCKR function were kept fixed, and remaining residues were optimized to preserve hydrophobic packing while introducing sequence diversity that minimized the number of repeating amino acid sequences and motifs. Synthetic DNA coding for the designs was obtained as described previously and designs were expressed, purified, and biophysically characterized as described previously. Crystallization trials were set up as described in the next section.

X-Ray Crystallography

Crystallization of Protein Samples

Purified protein samples were concentrated to 12-50 mg/ml in 20 mM Tris pH 8.0 and 100 mM NaCl. Samples were screened with a 5-position deck Mosquito crystal (ttplabtech) with an active humidity chamber, utilizing the following crystallization screens: JCSG+(Qiagen), JCSG Core I-IV (Qiagen), PEG/Ion (Hampton Research), and Morpheus (Molecular Dimensions). The optimal conditions for crystallization of the different designs were found as follows:

1-fix-short-BIM-t0: 0.1M Tris pH 8.5, 5% (w/v) PEG 8000, 20% (v/v) PEG 300, 10% (v/v) Glycerol (no cryo needed)

1fix-short-GFP-t0: 0.2M Sodium chloride, 0.1M Sodium cacodylate pH 6.5, 2.0M Ammonium sulfate (plus 20% glycerol for cryo)

1fix-short-noBim(AYYA)-t0: 0.2M di-Sodium tartrate, 20% (w/v) PEG 3350 (no cryo added)

X-Ray Data Collection and Structure Determination

The crystals of the designed proteins were looped and placed in the corresponding reservoir solution, containing 20% (v/v) glycerol if the reservoir solution did not contain cryoprotectant, and flash-frozen in liquid nitrogen. The X-ray data sets were collected at the Advanced Light Source at Lawrence Berkeley National Laboratory with beamlines 8.2.1 and 8.2.2. Data sets were indexed and scaled using either XDS[35] or HKL2000[36]. Initial models were generated by the molecular-replacement method with the program PHASER™[37] within the Phenix™ software suite[38], using the design models as the initial search models. Efforts were made to reduce model bias through refinement with simulated annealing using Phenix.refine, or, if the resolution was sufficient, by using Phenix.autobuild[40] with rebuild-in-place set to false, simulated annealing and prime-and-switch phasing. Iterative rounds of manual building in COOT and refinement in Phenix™ were used to produce the final models. Due to the high degree of self-similarity inherit in coiled-coil-like proteins, datasets for the reported structures suffered from a high degree of pseudo translational non-crystallographic symmetry, as report by Phenix.Xtriage™, which complicated structure refinement and may explain the higher than expected R values reported. RMSDs of bond lengths, angles and dihedrals from ideal geometries were calculated with Phenix™. The overall quality of all final models was assessed using the program MOLPROBITY™.

gfpLOCKR: (GFP11-LOCKR) Switch Design and Characterization

Using the asymmetrized LOCKR$_a$ design scaffold, the 11$^{th}$ strand of GFP was encoded into the Latch sequence of the Cage as described in the section above "Grafting Functional Sequence onto LOCKR using Rosetta™", and synthetic genes coding for the designed proteins obtained as described above. Proteins were purified and biophysically characterized as described above. To test for induction of fluorescence upon addition of Key, the proteins were mixed by pipetting and immediately assayed in a black 96-well plate using a Biotek Synergy Neo2 plate reader to monitor relative GFP fluorescence (Ex: 488, Em: 508, 10 minutes between reads). Cage leakiness was evaluated by measuring GFP fluorescence over time in the absence of Key In Vitro Co-Localization-Dependent Switching with gfpLOCKR (GFP11-LOCKR)

The GfpLOCKR Cage was cloned with SpyCatcher™ fused to its N-terminus via a floppy linker, the gfpLOCKR Key was cloned with SpyTag™ fused to its C-terminus via a floppy linker, and GFP1-10 was cloned into its own pET21 vector. These proteins were expressed in E. coli Lemo21 cells with Studier's autoinduction media overnight at 18 C. After expression, the producer cells were harvested by centrifugation and lysed by microfluidizer. The desired proteins were purified from clarified lysates by Ni-NTA affinity chromatography and quantitated by $A_{280}$ on a nanodrop. Proteins were diluted to final concentrations in PBS (GFP1-10: 1.9 uM in all samples; Cage: 1.5 uM, 0.8 uM, 0.4 uM, 0.2 uM, 0.094 uM; Key: 1.5 uM, 0.8 uM, 0.4 uM, 0.2 uM, 0.094 uM) and pooled as follows: SpyCatcher™-Cage alone (no Key), SpyCatcher™-Cage with naked Key (no SpyTag™), and SpyCatcher-Cage with SpyTag-Key. The proteins were mixed by pipetting and immediately assayed in a black 96-well plate using a Biotek Synergy Neo2 plate reader to monitor relative GFP fluorescence (Ex: 488, Em: 508, 10 minutes between reads). Cage leakiness was evaluated by measuring GFP fluorescence over time in the absence of Key. Co-localization dependence was confirmed by showing that SpyTag™-Key activated GFP fluorescence faster than did naked Key.

Caged Intein LOCKR Switches

The VMAc intein sequence was designed to be encoded into the Latch of $LOCKR_a$. The VMAn intein sequence was fused to $Key_a$. Constructs were cloned and purified as previous LOCKR designs described above. Intein activity (splicing) was assessed by SDS-PAGE.

Large-Scale High-Throughput Design of LOCKR Switches

The computational pipeline to design of thousands of new LOCKR switch scaffolds from scratch is as follows: backbones were exhaustively sampled using Crick helical parameters for 3-helix bundles (denoted 2plus1 or 2+1 because of a 2-helix scaffold plus 1-helix latch) and 4-helix bundles (denoted 3plus1 or 3+1 because of 3-helices plus 1-helix latch); parameters sampled include z-offset (−1.51, 0 and 1.51), helical phase every 10 degrees between 0 and 100, and superhelical radii for each helix ranging from 5-10 angstroms from the central superhelical axis (z-axis); based on the success of the original LOCKR design, we focused on designs with straight helices and no supercoiling (superhelical twist fixed to 0.0). Each generated helix is 58 residues in length; Rosetta loop closure methods were used to add loops connecting all helices into a single polypeptide chain (Cage scaffold). Seuqence and sidechain design was carried out using HBNet, MC-HBNet, and RosettaDesign™. Additional designs were generated by truncating the helical bundles into shorter scaffolds, making versions with the Latch as either the N-terminal or C-terminal helix, and by trying different toehold lengths (truncations of Latch helix that end in a polar residue and remove at least one or two hydrophobic packing residues from the original design). Designs were selected based on computational methods learned from iterative testing and design of previous LOCKR scaffolds and HBNet helical bundles: important metrics include secondary structure shape complementarity (ss_sc)>0.65 (best designs had ss_sc>0.7); RosettaHoles™ filter in regions surrounding hydrogen bond networks to eliminate designs with large cavities adjacent to hydrogen bond networks in the core of the scaffolds; designs were required to have at least 2 distinct hydrogen bond networks that spanned all helices of the design model (i.e. each helix must contribute at least one amino acid sidechain to the network); the number of Ile, Leu, and Val residues, and number of contacts made by these amino acid types, as compared to Ala (smaller amino acid) also serves as a proxy that correlates well with designs that have tight, interdigitated hydrophobic packing, which is important for generating a stable protein scaffold.

strepLOCKR (STREPII-LOCKR) Computational Design:

LOCKR switches encoding the STREPII tag, (N)WSHPQFEK (SEQ ID NO:63), were designed using the 2plus1 and 3plus1 switches from the large-scale high-throughput LOCKR design set. This sequence is difficult to encode because of the Pro (which kinks alpha helices) and the Trp and His, which if buried must likely participate in hydrogen bonds. To address these issues, rather than sampling all helical residues, the large-scale design set was mined to find LOCKR scaffolds that already contained Trp (W), His (H) already pre-organized into hydrogen bond networks of the designs. Designs with pre-organized Phe (F) were also considered.

strepLOCKR (STREPII-LOCKR) Experimental Testing:

The purified proteins were tested for their ability to sequester the STREPII sequence in absence of Key, and activate in presence of Key using biolayerinterferometry (Octet® RED96 System, PALL ForteBio): THE™ NWSHPQFEK (SEQ ID NO:63) Tag Antibody (mAb mouse, Genscript A01732-200) was loaded onto Anti-Mouse IgG Fc Capture (AMC) Biosensors (PALL ForteBio); tips were preconditioned by cycling between Glycine pH 1.65 and Octet assay buffer: HBS-EP+ Buffer from GE (10 mM HEPES, 150 mM NaCl, 3 mM EDTA, 0.05% v/v Surfactant P20, 0.5% non-fat dry milk, pH7.4 at room temperature). Protein samples were diluted into Octet assay buffer, keeping dilution factors consistent as to minimize noise. The antibody-loaded tips were reused up to 8 times using the recommended regeneration protocol of cycling between Glycine pH 1.65 and Octet assay buffer (minimal loss in loading was observed when the tips were preconditions, and a signal threshold was set to ensure consistent loading of the tips each time).

The THE™ NWSHPQFEK (SEQ ID NO:63) Tag Antibody (mAb mouse, Genscript A01732-200) was used at a concentration of 5 ug/mL in Octet assay buffer; stocks of antibody were made up to 0.5 mg/mL with 400 ul mqH2O, aliquoted and stored at −80 C, thawed immediately before use.

Purification of Proteins from Bacterial Preps not Already Described Above:

Starter cultures were grown at 37° C. in either Luria-Bertani (LB) medium overnight, or in Terrific Broth for 8 hours, in the presence of 50 μg/ml carbenicillin (pET21-NESG) or 50 μg/ml kanamycin (pET-28b+). Starter cultures were used to inoculate 500 mL of LB (induced with 0.2 mM IPTG at OD600 of ~0.6-0.9) or Studier auto-induction media containing antibiotic. Cultures were expressed overnight at 18° C. (many designs were also later expressed at 37° C. for 4 hours with no noticeable difference in yield). Cells were harvested by centrifugation for 15 minutes at 5000 rcf 4° C. and resuspended in lysis buffer (20 mM Tris, 300 mM NaCl, 20 mM Imidazole, pH 8.0 at room temperature), then lysed by sonication in presence of lysozyme, DNAse, and EDTA-free cocktail protease inhibitor (Roche) or 1 mM PMSF. Lysates were cleared by centrifugation at 4° C. 18,000 rpm for at least 30 minutes and applied to Ni-NTA (Qiagen) columns pre-equilibrated in lysis buffer. The column was washed three times with 5 column volumes (CV) of wash buffer (20 mM Tris, 300 mM NaCl, 40 mM Imidazole, pH 8.0 at room temperature), followed by 3-5 CV of high-salt wash buffer (20 mM Tris, 1 M NaCl, 40 mM Imidazole, pH 8.0 at room temperature), and then 5 CV of wash buffer. Protein was eluted with 20 mM Tris, 300 mM NaCl, 250 mM Imidazole, pH 8.0 at room temperature. No reducing agents were added, as none of the designed proteins contained cysteines.

REFERENCES

1. Huang, P.-S., Boyken, S. E. & Baker, D. The coming of age of de novo protein design. *Nature* 537, 320-327 (2016).
2. Joh, N. H. et al. De novo design of a transmembrane $Zn^{2+}$-transporting four-helix bundle. *Science* 346, 1520-1524 (2014).
3. Davey, J. A., Damry, A. M., Goto, N. K. & Chica, R. A. Rational design of proteins that exchange on functional timescales. *Nat. Chem. Biol.* 13, 1280-1285 (2017).
4. Huang, P.-S. et al. High thermodynamic stability of parametrically designed helical bundles. *Science* 346, 481-485 (2014).
5. Boyken, S. E. et al. De novo design of protein homo-oligomers with modular hydrogen-bond network-mediated specificity. *Science* 352, 680-687 (2016).
6. Berger, S. et al. Computationally designed high specificity inhibitors delineate the roles of BCL2 family proteins in cancer. *Elife* 5, 1422 (2016).
7. Leaver-Fay, A. et al. ROSETTA3: an object-oriented software suite for the simulation and design of macromolecules. *Meth Enzymol* 487, 545-574 (2011).
8. Kuhlman, B. & Baker, D. Native protein sequences are close to optimal for their structures. *Proc Natl Acad Sci USA* 97, 10383-10388 (2000).
9. Crick, F. H. C. The packing of [alpha]-helices: simple coiled-coils. Acta Cryst (1953). Q6, 689-697 [doi: 10.1107/S0365110X53001964]6, 1-9 (1953).
10. Glantz, S. T. et al. Functional and topological diversity of LOV domain photoreceptors. *Proc Natl Acad Sci USA* 113, E1442-51 (2016).
11. Dueber, J. E., Mirsky, E. A. & Lim, W. A. Engineering synthetic signaling proteins with ultrasensitive input/output control. 25, 660-662 (2007).
12. Dueber, J. E., Yeh, B. J., Chak, K. & Lim, W. A. Reprogramming control of an allosteric signaling switch through modular recombination. *Science* 301, 1904-1908 (2003).
13. Huang, P.-S. et al. RosettaRemodel: A Generalized Framework for Flexible Backbone Protein Design. *PLoS ONE* 6, e24109 (2011).
14. Schneidman-Duhovny, D., Hammel, M. & Sali, A. FoXS: a web server for rapid computation and fitting of SAXS profiles. *Nucleic Acids Res* 38, W540-4 (2010).
15. Maguire, J. B., Boyken, S. E., Baker, D. & Kuhlman, B. Rapid Sampling of Hydrogen Bond Networks for Computational Protein Design. *J. Chem. Theory Comput* 14, 2751-2760 (2018).

SEQUENCE LISTING

The patent contains a lengthy sequence listing. A copy of the sequence listing is available in electronic form from the USPTO web site (https://seqdata.uspto.gov/?pageRequest=docDetail&DocID=US12304927B2). An electronic copy of the sequence listing will also be available from the USPTO upon request and payment of the fee set forth in 37 CFR 1.19(b)(3).

We claim:

1. A LOCKR switch comprising
   (a) a cage polypeptide comprising
      the amino acid sequence of SEQ ID NO: 27194, wherein the C-terminal 60 amino acids are optional and may be present or may be deleted; and
   (b) a key polypeptide comprising the amino acid sequence of SEQ ID NO: 27195.

2. The LOCKR switch of claim 1, wherein the cage polypeptide and the key polypeptide are present in a single fusion protein.

3. A pharmaceutical composition comprising the LOCKR switch of claim 1 and a pharmaceutically acceptable carrier.

4. A host cell comprising the LOCKR switch of claim 1.

5. The LOCKR switch of claim 1, wherein the cage polypeptide further comprises one or more peptides fused to the cage polypeptide.

6. A pharmaceutical composition comprising the LOCKR switch of claim 5 and a pharmaceutically acceptable carrier.

7. A host cell comprising the LOCKR switch of claim 5.

8. A nucleic acid encoding a LOCKR switch comprising
   (a) a nucleic acid encoding the cage polypeptide as recited in claim 1; and
   (b) a nucleic acid encoding the key polypeptide as recited in claim 1.

9. A pharmaceutical composition comprising the nucleic acid encoding a LOCKR switch of claim 8 and a pharmaceutically acceptable carrier.

10. A host cell comprising the nucleic acid encoding a LOCKR switch of claim 8.

\* \* \* \* \*